US006949559B2

(12) United States Patent
Trova

(10) Patent No.: US 6,949,559 B2
(45) Date of Patent: Sep. 27, 2005

(54) NITROGEN SUBSTITUTED BIARYL PURINE DERIVATIVES AS POTENT ANTIPROLIFERATIVE AGENTS

(75) Inventor: Michael Peter Trova, Schenectady, NY (US)

(73) Assignee: AMR Technology, Inc., Manchester Center, VT (US)

( * ) Notice: Subject to any disclaimer, the term of this patent is extended or adjusted under 35 U.S.C. 154(b) by 86 days.

(21) Appl. No.: 10/680,832

(22) Filed: Oct. 7, 2003

(65) Prior Publication Data

US 2004/0077666 A1 Apr. 22, 2004

Related U.S. Application Data

(63) Continuation of application No. 09/950,543, filed on Sep. 11, 2001, now Pat. No. 6,667,311.

(51) Int. Cl.[7] ................... C07D 473/22; C07D 473/16; C07D 473/18; A61K 31/52; A61K 31/522

(52) U.S. Cl. .............................. 514/263.2; 514/263.21; 544/276; 544/277

(58) Field of Search ................................ 544/276, 277; 514/263.21, 263.2

(56) References Cited

U.S. PATENT DOCUMENTS

| 5,282,824 A | 2/1994 | Gianturco |
| 5,866,702 A | 2/1999 | Mackman et al. |
| 6,316,456 B1 | 11/2001 | Meijer et al. |
| 6,413,974 B1 | 7/2002 | Dumont et al. |
| 6,479,487 B1 | 11/2002 | Dumont et al. |
| 6,627,633 B2 | 9/2003 | Trova |
| 2002/0032327 A1 | 3/2002 | Lum et al. |
| 2002/0035252 A1 | 3/2002 | Lum et al. |
| 2002/0091263 A1 | 7/2002 | Trova |
| 2003/0092909 A1 | 5/2003 | Trova |

FOREIGN PATENT DOCUMENTS

| FR | 2 741 881 A | 6/1997 |
| FR | 2 793 794 A1 | 11/2000 |
| JP | 11222435 A | 8/1999 |
| WO | WO 98/05335 | 2/1998 |
| WO | WO 99/07705 | 2/1999 |
| WO | WO 99/43675 | 9/1999 |
| WO | WO 99/43676 | 9/1999 |
| WO | WO 00/55161 | 9/2000 |

OTHER PUBLICATIONS

Schow et al., "Synthesis and Activity of 2,6,9-Trisubstituted Purines," *Bioorganic & Medicinal Chemistry Letters* 7(210):2697-2703 (1997).
Imbach et al., "2,6,9-Trisubstituted Purines: Optimization Towards Highly Potent and Selective CDK1 Inhibitors," *Bioorganic & Medicinal Chemistry Letters* 9:91-96 (1999).
Legraverend et al., "Synthesis and in vitro Evaluation of Novel 2,6,9-Trisubstituted Purines Acting as Cyclin-Dependent Kinase Inhibitors," *Bioorganic & Medicinal Chemistry* 7:1281-1293 (1999).
Pérez-Roger et al., "Inhibition of Cellular Proliferation by Drug Targeting of Cyclin-Dependent Kinases," *Current Pharmaceutical Biotechnology*, 1:107-116 (2000).
Gray et al., "ATP-Site Directed Inhibitors of Cyclin-Dependent Kinases," *Current Medicinal Chemistry*, 6:859-875 (1999).
Brooks et al., "The Cell Cycle and Drug Discovery: The Promise and the Hope," *DDT*, 4(10):455-464 (1999).

(Continued)

*Primary Examiner*—Mark L. Berch
(74) *Attorney, Agent, or Firm*—Nixon Peabody LLP

(57) ABSTRACT

The compounds of the present invention are 2,6,9-trisubstituted purine derivatives which are inhibitors of cyclin/cdk complexes. The compounds of the current invention also are potent inhibitors of human cellular proliferation. As such, the compounds of the present invention constitute pharmaceutical compositions with a pharmaceutically acceptable carrier. Such compounds are useful in treating a disorder mediated by elevated levels of cell proliferation in a mammal compared to a healthy mammal by administering to such mammal an effective amount of the compound. Examples of the compounds of the present invention are represented by the following chemical structures:

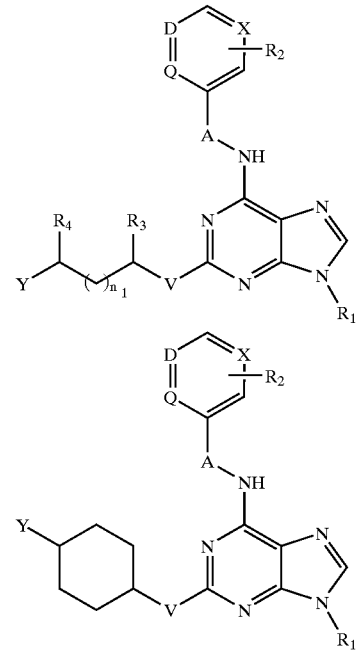

with X, Y, D, Q, V, A, $R_1$, $R_2$, $R_3$, $R_4$, and $n_1$ defined herein.

13 Claims, No Drawings

OTHER PUBLICATIONS

Coleman et al., "Chemical Inhibitors of Cyclin–Dependent Kinases," in Plattner, ed., *Annual Reports in Medicinal Chemistry,* Academic Press, Inc., 32:171–179 (1997).

Mani et al., "Cyclin–Dependent Kinase Inhibitors: Novel Anticancer Agents," *Exp. Opin. Invest. Drugs,* 9(8):1849–1870 (2000).

Fischer et al., "Inhibitors of Cyclin–Dependent Kinases as Anti–Cancer Therapeutics," *Current Medicinal Chemistry,* 7:1213–1245 (2000).

Stedman, *Stedman's Medical Dictionary,* 26th Ed., Williams & Wilkins, Baltimore, Maryland, pp. 1534, 1673 (1995).

Mattsson et al., "Current Concepts in Restenosis Following Balloon Angioplasty," *Trends Cardiovasc. Med.,* 5(5):200–204 (1995).

Nikol et al., "Regulation of Smooth Muscle Cell Proliferation and its Possible Role in Preventing Restenosis Post–Angioplasty," *Wien Klin Wochenschr,* 107(13):379–389 (1995).

American Heart Association "Stenosis and Restenosis of Coronary Arteries," http://americanheartassociation.com/Heart_and_Stroke_A_Z_Guide/sten.html (2001).

Green et al., *Protective Groups in Organic Synthesis* (Second Edition), pp. 318–319 and 331–332 (1991).

NITROGEN SUBSTITUTED BIARYL PURINE DERIVATIVES AS POTENT ANTIPROLIFERATIVE AGENTS

This application is a continuation of U.S. patent application Ser. No. 09/950,543, filed Sep. 11, 2001, now U.S. Pat. No. 6,667,311, which is hereby incorporated by reference in its entirety.

FIELD OF THE INVENTION

The present invention relates to compounds that are shown to be potent cyclin/cyclin dependent kinase (cdk) inhibitors. Compounds with these properties are shown to be potent inhibitors of cell growth and proliferation. Such compounds can be used to treat the following conditions in mammals: rheumatoid arthritis, lupus, type 1 diabetes, multiple sclerosis, cancer, restenosis, gout and other proliferative diseases involving elevated levels of cell proliferation compared to healthy mammals. Compounds of the present invention which are biaryl substituted purine derivatives are shown to be potent antiproliferative agents against a number of human transformed cell lines, and also inhibitors of human cyclin/cdk kinase complexes.

BACKGROUND OF THE INVENTION

Cellular Proliferation and Cancer.

The disruption of external or internal regulation of cellular growth can lead to uncontrolled proliferation and in cancer, tumor formation. This loss of control can occur at many levels and, indeed, does occur at multiple levels in most tumors. Further, although tumor cells can no longer control their own proliferation, they still must use the same basic cellular machinery employed by normal cells to drive their growth and replication.

Cyclin Dependent Kinases and Cell Cycle Regulation.

Progression of the normal cell cycle from the G1 to S phase, and from the G2 phase to M phase is dependent on cdks (Sherr, C. J., *Science* 274:1672–1677 (1996)). Like other kinases, cdks regulate molecular events in the cell by facilitating the transfer of the terminal phosphate of adenosine triphosphate (ATP) to a substrate protein. Isolated cdks require association with a second subunit, called cyclins (Desai et al., *Mol. Cell. Biol.,* 15:345–350 (1995)). Cyclins cause conformational changes at the cdk active site, allowing ATP access and interaction with the substrate protein. The balance between its rates of synthesis and degradation controls the level of each cyclin at any point in the cycle (Elledge, S. J., et al., *Biochim. Biophys. Acta,* 1377:M61–M70 (1998)). The influences of cyclin/cdk activity on the cell cycle and cellular transformation are summarized in Table 1.

Abnormal Cyclin/cdk Activity in Cancer.

In a normal cell, interlocking pathways respond to the cell's external environment and internal checkpoints monitor conditions within the cell to control the activity of cyclin/cdk complexes. A reasonable hypothesis is that the disruption of normal control of cyclin/cdk activity may result in uncontrolled proliferation. This hypothesis appears to hold in a number of tumor types in which cyclins are expressed at elevated levels (Table 1). Mutations in the genes encoding negative regulators (proteins) of cyclin/cdk activity are also found in tumors (Larsen, C.-J., *Prog. Cell Cycle Res.,* 3:109–124 (1997)); (Kamb, A., *Trends in Genetics,* 11:136–140 (1995)). Members of the Cip family of cdk inhibitors form a ternary complex with the cyclin/cdk and require binding to cyclinA, cyclinE, or cyclinD (Hall, M., et al., *Oncogene,* 11:1581–1588 (1995)). In contrast, Ink family members form a binary complex with cdk4 or cdk6 and prevent binding to cyclinD (Parry, D.; et al., *EMBO J.,* 14:503–511 (1995)).

TABLE 1

Associations Among Cyclins and Cancers

| Cyclin | Cell Cycle Role | Associated cdk | Cancer |
| --- | --- | --- | --- |
| A | S, G2 to M | cdk1, cdk2 | hepatocellular carcinoma (Wang, J.; et al., Oncogene 8: 1653–1656 (1992)) |
| B1/B2 | G2 to M | cdk1 | none yet defined |
| D1 | G1 | cdk4, cdk6 | parathyroid adenoma (Motokura, T., et al., Nature, 350: 512–515 (1991)) centrocytic B cell lymphoma (Withers, D. A., et al., Mol. Cell. Biol., 11: 4846–4853 (1991)) esophageal carcinoma (Jiang, W., et al., Cancer Res., 52: 2980–2983 (1992)) breast cancer (Dickson, C., et al., Cancer Lett., 90: 43–50 (1995)) squamous cell carcinoma (Bartkova, J., et al., Cancer Res., 55: 949–956 (1995)) hepatocellular carcinoma (Nishida, N., et al., Cancer Res., 54: 3107–3110 (1994)) |
| D2 | G1 | cdk4, cdk6 | colorectal carcinoma (Leach, F. S., et al., Cancer Res., 53: 1986–1989 (1993)) |
| E | G1 to S | cdk2 | breast cancer (Keytomarsi, K., et al., Cancer Res., 54: 380–385 (1994)) gastric carcinoma (Akama, Y.; et al., Jap. J. Cancer Res., 86: 617–621 (1995)) colorectal carcinoma (Kitihara, K.; et al., Int. J. Cancer, 62: 25–28 (1995)) |

Inhibitors of Cyclin/cdk Complexes as Potential Anticancer Agents.

Tumors with elevated cyclin/cdk activity, whether from the over expression of cyclins or the loss of an endogenous cdk inhibitor, are prime targets for potential therapies based on small molecule cyclin/cdk inhibitors. In fact, several small molecule inhibitors of cyclin/cdks are reported (Meijer, L., et al., "Progress in Cell Cycle Research," Plenum Press: New York, 351–363 (1995)) and appear to bind at the ATP site of the kinase. Some information is known about small molecule inhibitors of other kinases, such as PKC (serine kinase) (Murray, K. J. et al., "Ann. Rep. Med. Chem.," J. Bristol, Ed., Academic Press, Inc.: New York, Chapter 26 (1994)) and tyrosine kinases (Fantl, W. J., et al., Ann. Rev. Biochem., 62:453 (1993); Burke, T. R., Drugs of the Future, 17:119–1131 (1992); Dobrusin, E. M. et al., "Ann. Rep. Med. Chem," J. Bristol, Ed., Academic Press Inc.: New York, Chapter 18 (1992); Spence, P., Curr. Opin. Ther. Patents, 3:3 (1993)). A number of known inhibitors were obtained from commercial sources or were synthesized by literature procedures.

Purine Compounds as Cyclin/cdk Inhibitors.

There are several reports of 2,6-diamino substituted purine derivatives as cyclin/cdk inhibitors and as inhibitors of cellular proliferation. Among those are reports by U.S. Pat. No. 5,583,137 to Coe, et al., olomoucine (Vesely, J., et al., Eur. J. Biochem., 224:771–786 (1994)), roscovitine (Meijer, L., Eur. J. Biochem., 243:527–536 (1997)), WO 97/16452 to Zimmerman, Imbach, P., et al., Bioorg. Med. Chem. Lett., 9:91–96 (1999), Norman, T. C., et al., J. Amer. Chem. Soc., 118:7430–7431 (1996), Gray, N. S., et al., Tetrahedron Lett., 38:1161–1164 (1997), Gray, N. S., et al., Science, 281:533–538 (1998), WO 98/05335 to Lum, et al., Schow, S. R., et al., Bioorg. Med. Chem. Lett, 7:2697–2702 (1997), U.S. Pat. No. 5,886,702 to Mackman, et al., Nugiel, D. A., et al., J. Org. Chem., 62:201–203 (1997), and Fiorini, M. T. et al., Tetrahedron Lett., 39:1827–1830 (1998). Many of these reported compounds are shown to inhibit cyclin/cdk complexes and have modest cellular proliferation inhibition properties.

The compounds of the present invention are shown to have far superior biological activities as cyclin/cdk complex inhibitors as well as inhibitors of cellular proliferation compared to those previously reported. In fact, the art (e.g., Fiorini, M. T. et al., Tetrahedron Lett., 39:1827–1830 (1998)) teaches away from compounds of this invention, claiming lack of cellular proliferation inhibition.

SUMMARY OF THE INVENTION

The compounds of the present invention are 2,6,9-trisubstituted purine derivatives which are inhibitors of cyclin/cdk complexes. The compounds of the current invention also are potent inhibitors of human cellular proliferation. As such, the compounds of the present invention constitute pharmaceutical compositions with a pharmaceutically acceptable carrier. Such compounds are useful in treating conditions in a mammal mediated by elevated levels of cell proliferation compared to a healthy mammal by administering to such mammal an effective amount of the compound.

In one embodiment, the compounds of the present invention are represented by the chemical structure found in Formula I

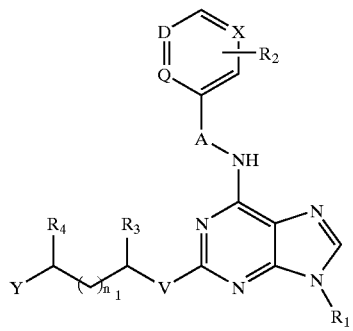

Formula I wherein:
$R_1$ are the same or different and independently selected from the group consisting of:
  H;
  $C_1$–$C_6$-straight chain alkyl;
  $C_2$–$C_6$-straight alkenyl chain;
  $C_3$–$C_6$-branched alkyl chain;
  $C_3$–$C_6$-branched alkenyl chain;
  $C_3$–$C_7$-cycloalkyl;
  $CH_2$—($C_3$–$C_7$-cycloalkyl);
  $CH_2CF_3$;
  $CH_2CH_2CF_3$; and
  $CH(CF_3)_2$;
the combination of X, D, and Q are either:
  D=Q=N, and X=CH; or
  D=X=N, and Q=CH; or
  Q=X=N, and D=CH; or
  Q=N, and D=X=CH;
V=NH;
  O;
  S; or
  $CH_2$;
$R_2$=phenyl;
  substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
  1-naphthyl;
  2-naphthyl;
  heterocycles selected from the group consisting of:
    2-pyridyl;
    3-pyridyl;
    4-pyridyl;
    2-pyrimidyl;
    4-pyrimidyl;
    5-pyrimidyl;
    thiophene-2-yl;
    thiophene-3-yl;
    2-furanyl;
    3-furanyl;
    oxazol-2-yl;
    oxazol-4-yl;
    oxazol-5-yl;
    thiazol-2-yl;
    thiazol-4-yl;
    thiazol-5-yl;

imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;

$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n$Ph; and
$(CH_2)_n$-substituted phenyl, wherein the phenyl substituents are as defined above in $R_2$;

$R_4$=H;
$C_1$–$C_4$-straight chain alkyl; or
$C_3$–$C_4$-branched chain alkyl;

$R_3$ and $R_4$ can be linked together by a carbon chain to form with intervening atoms a 5–8-membered saturated or unsaturated ring;

$n_1$=0–3;
$n$=0–3;
A=$CH_2$;
$(CH_2)_2$;
$(CH_2)_3$;
$OCH_2CH_2$; or
$CHCH_3$;

Y=H;
$OR_1$;
$N(R_1)_2$;
$N(R_1)C(O)R_3$;
$N(R_1)C(O)R_5$;
$N(R_1)C(O)CH(R_6)NH_2$;
$N(R_1)SO_2R_3$;
$N(R_1)C(O)NHR_3$; or
$N(R_1)C(O)OR_6$;

$R_5$=$C_3$–$C_7$-cycloalkyl;
$R_6$=$C_1$–$C_4$-straight chain alkyl;
$C_3$–$C_4$-branched chain alkyl;
$C_2$–$C_4$-alkenyl chain;
$(CH_2)_n$Ph; or
$(CH_2)_n$-substituted phenyl, wherein the phenyl substituents are as defined above in $R_2$;
or a pharmaceutically acceptable salt thereof.

Another aspect of the present invention is directed to a compound of the following formula:

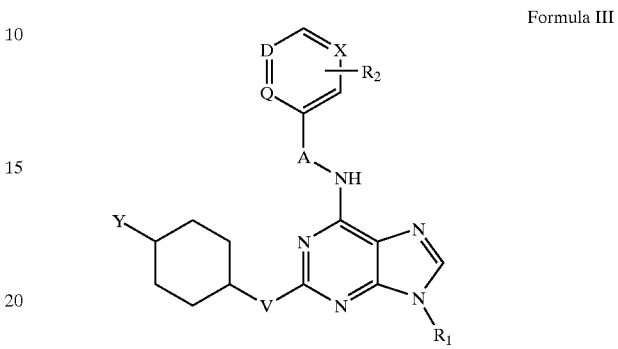

Formula III wherein:
$R_1$ are the same or different and independently selected from the group consisting of:
H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—($C_3$–$C_7$-cycloalkyl);
$CH_2CF_3$;
$CH_2CH_2CF_3$; and
$CH(CF_3)_2$;

the combination of X, D, and Q are either:
D=Q=N, and X=CH; or
D=X=N, and Q=CH; or
Q=X=N, and D=CH; or
Q=N, and D=X=CH;

V=NH;
O;
S; or
$CH_2$;

$R_2$=phenyl;
substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
1-naphthyl;
2-naphthyl;
heterocycles selected from the group consisting of:
2-pyridyl;
3-pyridyl;
4-pyridyl;
2-pyrimidyl;
4-pyrimidyl;
5-pyrimidyl;
thiophene-2-yl;
thiophene-3-yl;

2-furanyl;
3-furanyl;
oxazol-2-yl;
oxazol-4-yl;
oxazol-5-yl;
thiazol-2-yl;
thiazol-4-yl;
thiazol-5-yl;
imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;
n=0–3;
A=$CH_2$;
$(CH_2)_2$;
$(CH_2)_3$;
$OCH_2CH_2$; or
$CHCH_3$;
Y=H;
$OR_1$;
$N(R_1)_2$;
$N(R_1)C(O)R_3$;
$N(R_1)C(O)R_5$;
$N(R_1)C(O)CH(R_6)NH_2$;
$N(R_1)SO_2R_3$;
$N(R_1)C(O)NHR_3$; or
$N(R_1)C(O)OR_6$;
$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n$Ph; and
$(CH_2)_n$-substituted phenyl, wherein the phenyl substituents are as defined above in $R_2$;
$R_5$=$C_3$–$C_7$-cycloalkyl;
$R_6$=$C_1$–$C_4$-straight chain alkyl;
$C_3$–$C_4$-branched chain alkyl; or
$C_2$–$C_4$-alkenyl chain;
or a pharmaceutically acceptable salt thereof.

The present invention is also directed to a process for preparation of a purine derivative compound of the formula:

Formula I wherein:
$R_1$ are the same or different and independently selected from the group consisting of:
H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—($C_3$–$C_7$-cycloalkyl);
$CH_2CF_3$;
$CH_2CH_2CF_3$; and
$CH(CF_3)_2$;
the combination of X, D, and Q are either:
D=Q=N, and X=CH; or
D=X=N, and Q=CH; or
Q=—X=N, and D=CH; or
Q=N, and D=X=CH;
V=NH;
O;
S; or
$CH_2$;
$R_2$=phenyl;
substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
1-naphthyl;
2-naphthyl;
heterocycles selected from the group consisting of:
2-pyridyl;
3-pyridyl;
4-pyridyl;
2-pyrimidyl;
4-pyrimidyl;
5-pyrimidyl;
thiophene-2-yl;
thiophene-3-yl;
2-furanyl;
3-furanyl;
oxazol-2-yl;
oxazol-4-yl;

oxazol-5-yl;
thiazol-2-yl;
thiazol-4-yl;
thiazol-5-yl;
imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n Ph$; and
$(CH_2)_n$-substituted phenyl, wherein the phenyl substituents are as defined above in $R_2$;
$R_4$=H;
$C_1$–$C_4$-straight chain alkyl; or
$C_3$–$C_4$-branched chain alkyl;
$R_3$ and $R_4$ can be linked together by a carbon chain to form with intervening atoms a 5–8-membered saturated or unsaturated ring;
$n_1$=0–3;
n=0–3;
A=$CH_2$;
$(CH_2)_2$;
$(CH_2)_3$;
$OCH_2CH_2$; or
$CHCH_3$;
Y=H;
$OR_1$;
$N(R_1)_2$;
$N(R_1)C(O)R_3$;
$N(R_1)C(O)R_5$;
$N(R_1)C(O)CH(R_6)NH_2$;
$N(R_1)SO_2R_3$;
$N(R_1)C(O)NHR_3$; or
$N(R_1)C(O)OR_6$;
$R_5$=$C_3$–$C_7$-cycloalkyl;
$R_6$=$C_1$–$C_4$-straight chain alkyl;
$C_3$–$C_4$-branched chain alkyl;
$C_2$–$C_4$-alkenyl chain;
$(CH_2)_n Ph$; or
$(CH_2)_n$-substituted phenyl, wherein the phenyl substituents are as defined above in $R_2$;
or a pharmaceutically acceptable salt thereof, said process comprising:
reacting a first intermediate compound of the formula:

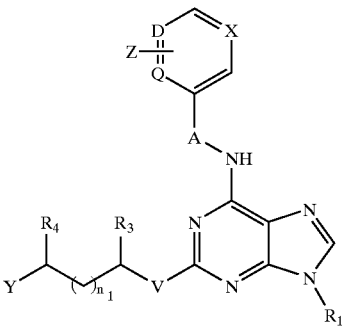

Formula IX where Z=Br or I
with a compound of the formula: $R_2$—$B(OH)_2$, $R_2$—$Sn(n-Bu)_3$, or $R_2$—$Sn(Me)_3$, or mixtures thereof, under conditions effective to form the purine derivative compound.

Another aspect of the present invention is directed to a process for preparation of a purine derivative compound of the formula:

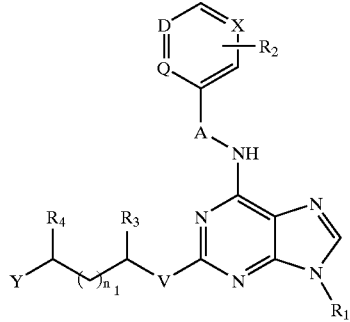

Formula I wherein:
$R_1$ are the same or different and independently selected from the group consisting of:
H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—$(C_3$–$C_7$-cycloalkyl);
$CH_2CF_3$;
$CH_2CH_2CF_3$; and
$CH(CF_3)_2$;

the combination of X, D, and Q are either:
  D=Q=N, and X=CH; or
  D=X=N, and Q=CH; or
  Q=X=N, and D=CH; or
  Q=N, and D=X=CH;
V=NH;
  O;
  S; or
  $CH_2$;
$R_2$=phenyl;
  substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
  1-naphthyl;
  2-naphthyl;
  heterocycles selected from the group consisting of:
    2-pyridyl;
    3-pyridyl;
    4-pyridyl;
    2-pyrimidyl;
    4-pyrimidyl;
    5-pyrimidyl;
    thiophene-2-yl;
    thiophene-3-yl;
    2-furanyl;
    3-furanyl;
    oxazol-2-yl;
    oxazol-4-yl;
    oxazol-5-yl;
    thiazol-2-yl;
    thiazol-4-yl;
    thiazol-5-yl;
    imidazol-2-yl;
    imidazol-4-yl;
    pyrazol-3-yl;
    pyrazol-4-yl;
    isoxazol-3-yl;
    isoxazol-4-yl;
    isoxazol-5-yl;
    isothiazol-3-yl;
    isothiazol-4-yl;
    isothiazol-5-yl;
    1,3,4-thiadiazol-2-yl;
    benzo[b]furan-2-yl;
    benzo[b]thiophene-2-yl;
    2-pyrrolyl;
    3-pyrrolyl;
    1,3,5-triazin-2-yl;
    pyrazin-2-yl;
    pyridazin-3-yl;
    pyridazin-4-yl;
    2-quinolinyl;
    3-quinolinyl;
    4-quinolinyl;
    1-isoquinolinyl;
    3-isoquinolinyl; and
    4-isoquinolinyl; or
  substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
  H;
  $C_1$–$C_4$-straight chain alkyl;
  $C_3$–$C_4$-branched chain alkyl;
  $C_2$–$C_4$-alkenyl chain;
  $(CH_2)_n$Ph; and
  $(CH_2)_n$-substituted phenyl, wherein the phenyl substituents are as defined above in $R_2$;
$R_4$=H;
  $C_1$–$C_4$-straight chain alkyl; or
  $C_3$–$C_4$-branched chain alkyl;
$R_3$ and $R_4$ can be linked together by a carbon chain to form with intervening atoms a 5–8-membered saturated or unsaturated ring;
$n_1$=0–3;
n=0–3;
A=$CH_2$;
  $(CH_2)_2$;
  $(CH_2)_3$;
  $OCH_2CH_2$; or
  $CHCH_3$;
Y=H;
  $OR_1$;
  $N(R_1)_2$;
  $N(R_1)C(O)R_3$;
  $N(R_1)C(O)R_5$;
  $N(R_1)C(O)CH(R_6)NH_2$;
  $N(R_1)SO_2R_3$;
  $N(R_1)C(O)NHR_3$; or
  $N(R_1)C(O)OR_6$;
$R_5$=$C_3$–$C_7$-cycloalkyl;
$R_6$=$C_1$–$C_4$-straight chain alkyl;
  $C_3$–$C_4$-branched chain alkyl;
  $C_2$–$C_4$-alkenyl chain;
  $(CH_2)_n$Ph; or
  $(CH_2)_n$-substituted phenyl, wherein the phenyl substituents are as defined above in $R_2$;
or a pharmaceutically acceptable salt thereof, said process comprising:
reacting a first intermediate compound of the formula:

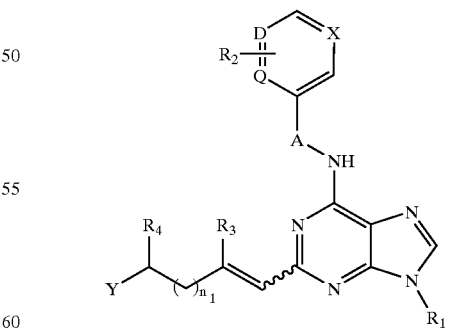

Formula XV under reductive or hydrogenation conditions effective to form the purine derivative compound.

Another aspect of the present invention is directed to a process for preparation of a purine derivative compound of the formula:

Formula I wherein:
R₁ are the same or different and independently selected from the group consisting of:
  H;
  $C_1$–$C_6$-straight chain alkyl;
  $C_2$–$C_6$-straight alkenyl chain;
  $C_3$–$C_6$-branched alkyl chain;
  $C_3$–$C_6$-branched alkenyl chain;
  $C_3$–$C_7$-cycloalkyl;
  $CH_2$—($C_3$–$C_7$-cycloalkyl);
  $CH_2CF_3$;
  $CH_2CH_2CF_3$; and
  $CH(CF_3)_2$;
the combination of X, D, and Q are either:
  D=Q=N, and X=CH; or
  D=X=N, and Q=CH; or
  Q=X=N, and D=CH; or
  Q=N, and D=X=CH;
V=NH;
  O;
  S; or
  $CH_2$;
R₂=phenyl;
  substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
  1-naphthyl;
  2-naphthyl;
  heterocycles selected from the group consisting of:
    2-pyridyl;
    3-pyridyl;
    4-pyridyl;
    2-pyrimidyl;
    4-pyrimidyl;
    5-pyrimidyl;
    thiophene-2-yl;
    thiophene-3-yl;
    2-furanyl;
    3-furanyl;
    oxazol-2-yl;
    oxazol-4-yl;
    oxazol-5-yl;
    thiazol-2-yl;
    thiazol-4-yl;
    thiazol-5-yl;
    imidazol-2-yl;
    imidazol-4-yl;
    pyrazol-3-yl;
    pyrazol-4-yl;
    isoxazol-3-yl;
    isoxazol-4-yl;
    isoxazol-5-yl;
    isothiazol-3-yl;
    isothiazol-4-yl;
    isothiazol-5-yl;
    1,3,4-thiadiazol-2-yl;
    benzo[b]furan-2-yl;
    benzo[b]thiophene-2-yl;
    2-pyrrolyl;
    3-pyrrolyl;
    1,3,5-triazin-2-yl;
    pyrazin-2-yl;
    pyridazin-3-yl;
    pyridazin-4-yl;
    2-quinolinyl;
    3-quinolinyl;
    4-quinolinyl;
    1-isoquinolinyl;
    3-isoquinolinyl; and
    4-isoquinolinyl; or
  substituted heterocycle, wherein the substituents (1–2 in number) are in any position and are independently selected from the group consisting of Br, Cl, F, $R_1$, and $C(O)CH_3$;
R₃ are the same or different and independently selected from the group consisting of:
  H;
  $C_1$–$C_4$-straight chain alkyl;
  $C_3$–$C_4$-branched chain alkyl;
  $C_2$–$C_4$-alkenyl chain;
  $(CH_2)_n$Ph; and
  $(CH_2)_n$-substituted phenyl, wherein the phenyl substituents are as defined above in $R_2$;
$R_4$=H;
  $C_1$–$C_4$-straight chain alkyl; or
  $C_3$–$C_4$-branched chain alkyl;
$R_3$ and $R_4$ can be linked together by a carbon chain to form with intervening atoms a 5–8-membered saturated or unsaturated ring;
$n_1$=0–3;
$n$=0–3;
A=$CH_2$;
  $(CH_2)_2$;
  $(CH_2)_3$;
  $OCH_2CH_2$; or
  $CHCH_3$;
Y=H;
  $OR_1$;
  $N(R_1)_2$;
  $N(R_1)C(O)R_3$;
  $N(R_1)C(O)R_5$;
  $N(R_1)C(O)CH(R_6)NH_2$;
  $N(R_1)SO_2R_3$;
  $N(R_1)C(O)NHR_3$; or
  $N(R_1)C(O)OR_6$;
$R_5$=$C_3$–$C_7$-cycloalkyl;
$R_6$=$C_1$–$C_4$-straight chain alkyl;
  $C_3$–$C_4$-branched chain alkyl;

$C_2$–$C_4$-alkenyl chain;
$(CH_2)_n$Ph; or
$(CH_2)_n$-substituted phenyl, wherein the phenyl substituents are as defined above in $R_2$;
or a pharmaceutically acceptable salt thereof, said process comprising:
reacting a first intermediate compound of the formula:

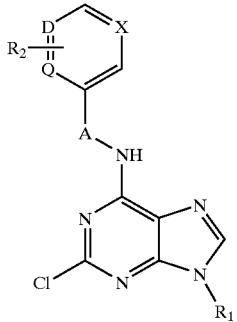

Formula XIV with a compound of the formula:

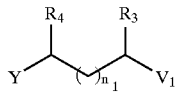

Formula VIII where $V_1$=$NH_2$;
OH; or
SH;
under conditions effective to form the purine derivative compound.

Another aspect of the present invention is directed to a process for preparation of a purine derivative compound of the formula:

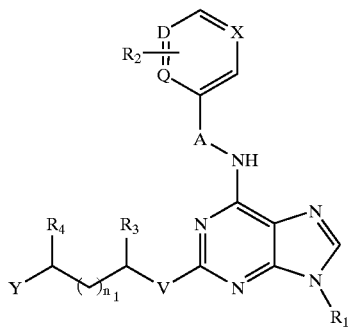

Formula XX wherein:
$R_1$ are the same or different and independently selected from the group consisting of:
H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—($C_3$–$C_7$-cycloalkyl);
$CH_2CF_3$;
$CH_2CH_2CF_3$; and
$CH(CF_3)_2$;
the combination of X, D, and Q are either:
D=Q=N and X=CH; or
D=X=N and Q=CH; or
Q=X=N and D=CH; or
Q=N and D=X=CH;
V=NH;
O;
S; or
$CH_2$;
$R_2$=phenyl;
substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
1-naphthyl;
2-naphthyl;
heterocycles selected from the group consisting of:
2-pyridyl;
3-pyridyl;
4-pyridyl;
2-pyrimidyl;
4-pyrimidyl;
5-pyrimidyl;
thiophene-2-yl;
thiophene-3-yl;
2-furanyl;
3-furanyl;
oxazol-2-yl;
oxazol-4-yl;
oxazol-5-yl;
thiazol-2-yl;
thiazol-4-yl;
thiazol-5-yl;
imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;

R$_3$ are the same or different and independently selected from the group consisting of:
H;
C$_1$–C$_4$-straight chain alkyl;
C$_3$–C$_4$-branched chain alkyl;
C$_2$–C$_4$-alkenyl chain;
(CH$_2$)$_n$Ph; and
(CH$_2$)$_n$-substituted phenyl, wherein the phenyl substituents are as defined above in R$_2$;
R$_4$=H;
C$_1$–C$_4$-straight chain alkyl; or
C$_3$–C$_4$-branched chain alkyl;
R$_3$ and R$_4$ can be linked together by a carbon chain to form with intervening atoms a 5–8-membered saturated or unsaturated ring;
n$_1$=0–3;
n=0–3;
A=CH$_2$;
(CH$_2$)$_2$;
(CH$_2$)$_3$;
OCH$_2$CH$_2$; or
CHCH$_3$;
Y=NR$_1$C(O)R$_3$;
NR$_1$C(O)R$_5$;
NR$_1$ SO$_2$R$_3$;
NR$_1$C(O)NHR$_3$; or
NR$_1$C(O)OR$_6$
R$_5$=C$_3$–C$_7$-cycloalkyl;
R$_6$=C$_1$–C$_4$-straight chain alkyl;
C$_3$–C$_4$-branched chain alkyl;
C$_2$–C$_4$-alkenyl chain;
(CH$_2$)$_n$Ph; or
(CH$_2$)$_n$-substituted phenyl, wherein the phenyl substituents are as defined above in R$_2$;
or a pharmaceutically acceptable salt thereof;
said process comprising:
reacting a first intermediate compound having the same formula as the purine derivative compound except that Y=NHR$_1$, with R$_3$COCl or R$_5$COCl or R$_3$SO$_2$Cl or R$_3$NCO or R$_6$OC(O)Cl under conditions effective to form the purine derivative compound.

Yet another aspect of the present invention is directed to a process for preparation of a purine derivative compound of the formula:

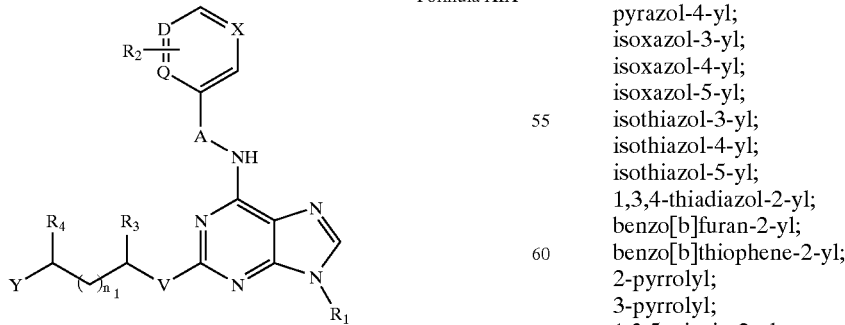

Formula XIX wherein:
R$_1$ are the same or different and independently selected from the group consisting of:
H;
C$_1$–C$_6$-straight chain alkyl;
C$_2$–C$_6$-straight alkenyl chain;
C$_3$–C$_6$-branched alkyl chain;
C$_3$–C$_6$-branched alkenyl chain;
C$_3$–C$_7$-cycloalkyl;
CH$_2$—(C$_3$–C$_7$-cycloalkyl);
CH$_2$CF$_3$;
CH$_2$CH$_2$CF$_3$; and
CH(CF$_3$)$_2$;
the combination of X, D, and Q are either:
D=Q=N and X=CH; or
D=X=N and Q=CH; or
Q=X=N and D=CH; or
Q=N and D=X=CH;
V=NH;
O;
S; or
CH$_2$;
R$_2$=phenyl;
substituted phenyl, wherein the substituents (1–2 in number) are in any position and are independently selected from the group consisting of R$_1$, OR$_1$, SR$_1$, S(O)R$_1$, S(O$_2$)R$_1$, NHR$_1$, NO$_2$, OC(O)CH$_3$, NHC(O)CH$_3$, F, Cl, Br, CF$_3$, C(O)R$_1$, C(O)NHR$_1$, phenyl, and C(O)NHCHR$_1$CH$_2$OH;
1-naphthyl;
2-naphthyl;
heterocycles selected from the group consisting of:
2-pyridyl;
3-pyridyl;
4-pyridyl;
2-pyrimidyl;
4-pyrimidyl;
5-pyrimidyl;
thiophene-2-yl;
thiophene-3-yl;
2-furanyl;
3-furanyl;
oxazol-2-yl;
oxazol-4-yl;
oxazol-5-yl;
thiazol-2-yl;
thiazol-4-yl;
thiazol-5-yl;
imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;

3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n Ph$; and
$(CH_2)_n$-substituted phenyl, wherein the phenyl substituents are as defined above in $R_2$;
$R_4$=H;
$C_1$–$C_4$-straight chain alkyl; or
$C_3$–$C_4$-branched chain alkyl;
$R_3$ and $R_4$ can be linked together by a carbon chain to form with intervening atoms a 5–8-membered saturated or unsaturated ring;
$n_1$=0–3;
n=0–3;
A=$CH_2$;
$(CH_2)_2$;
$(CH_2)_3$;
$OCH_2CH_2$; or
$CHCH_3$;
Y=$NHC(O)CH(R_6)NH_2$;
$R_5$=$C_3$–$C_7$-cycloalkyl;
$R_6$=$C_1$–$C_4$-straight chain alkyl;
$C_3$–$C_4$-branched chain alkyl;
$C_2$–$C_4$-alkenyl chain;
$(CH_2)_n Ph$; or
$(CH_2)_n$-substituted phenyl, wherein the phenyl substituents are as defined above in $R_2$;
or a pharmaceutically acceptable salt thereof;
said process comprising:
reacting a first intermediate compound having the same formula as the purine derivative compound except that Y is $NH_2$, with a compound of the formula: PNHCH($R_6$)$CO_2H$ under conditions effective to form the purine derivative compound after a suitable deprotection strategy,
wherein
P=$C(O)OtBu$;
$C(O)OCH_2Ph$;
Fmoc
Benzyl; or
Alloc.

The compounds of the present invention, as described in Formula I, show significantly improved growth inhibition of human transformed cell lines and/or cyclin/cdk inhibition relative to compounds of the prior art. These compounds have been demonstrated to be potent growth inhibitors in dozens of human transformed cell lines. Olomoucine, a structurally related purine derivative, is a poor human transformed cell growth inhibition agent with $GI_{50}$ values in the 20,000–100,000 nM range over 60-transformed cell lines. By contrast, the compounds of the present invention demonstrate $GI_{50}$ values over 60-transformed cell lines in the <10–25,000 nM range, preferably in the <10–100 nM range over 60-transformed cell lines, and, most preferably, <10 nM across 60-human transformed cell lines. This finding is unexpected from the prior art, which specifically teaches that compounds of the present invention would not be potent human transformed cell line growth inhibitors.

The $R_2$ group in Formula I imparts unexpected and significant improvement in growth inhibition in human transformed cell lines, while substitution of various groups at $R_3$ and $R_4$ found in Formula I impart important features that contribute to cyclin/cdk inhibition and growth inhibition of human transformed cell lines. Specifically, the combination of the $R_2$ group and the substitutions within $R_3$ and $R_4$ result in compounds with superior biological activity. Compounds which are cyclin/cdk inhibitors and/or human transformed cell line growth inhibitors have utility in treating human proliferative cellular disorders.

DETAILED DESCRIPTION OF THE INVENTION

The compounds of the present invention are represented by the chemical structure found in Formula I.

Formula I wherein:
$R_1$ are the same or different and independently selected from the group consisting of:
H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—($C_3$–$C_7$-cycloalkyl);
$CH_2CF_3$;
$CH_2CH_2CF_3$; and
$CH(CF_3)_2$;
the combination of X, D, and Q are either:
D=Q=N, and X=CH; or
D=X=N, and Q=CH; or
Q=X=N, and D=CH; or
Q=N, and D=X=CH;
V=NH;
O;
S; or
$CH_2$;
$R_2$=phenyl;
substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
1-naphthyl;
2-naphthyl;
heterocycles selected from the group consisting of:
  2-pyridyl;
  3-pyridyl;
  4-pyridyl;
  2-pyrimidyl;
  4-pyrimidyl;
  5-pyrimidyl;
  thiophene-2-yl;
  thiophene-3-yl;
  2-furanyl;
  3-furanyl;
  oxazol-2-yl;
  oxazol-4-yl;
  oxazol-5-yl;
  thiazol-2-yl;
  thiazol-4-yl;
  thiazol-5-yl;
  imidazol-2-yl;
  imidazol-4-yl;
  pyrazol-3-yl;
  pyrazol-4-yl;
  isoxazol-3-yl;
  isoxazol-4-yl;
  isoxazol-5-yl;
  isothiazol-3-yl;
  isothiazol-4-yl;
  isothiazol-5-yl;
  1,3,4-thiadiazol-2-yl;
  benzo[b]furan-2-yl;
  benzo[b]thiophene-2-yl;
  2-pyrrolyl;
  3-pyrrolyl;
  1,3,5-triazin-2-yl;
  pyrazin-2-yl;
  pyridazin-3-yl;
  pyridazin-4-yl;
  2-quinolinyl;
  3-quinolinyl;
  4-quinolinyl;
  1-isoquinolinyl;
  3-isoquinolinyl; and
  4-isoquinolinyl; or
substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
  H;
  $C_1$–$C_4$-straight chain alkyl;
  $C_3$–$C_4$-branched chain alkyl;
  $C_2$–$C_4$-alkenyl chain;
  $(CH_2)_n$Ph; and
  $(CH_2)_n$-substituted phenyl, wherein the phenyl substituents are as defined above in $R_2$;
$R_4$=H;
  $C_1$–$C_4$-straight chain alkyl; or
  $C_3$–$C_4$-branched chain alkyl;
$R_3$ and $R_4$ can be linked together by a carbon chain to form with intervening atoms a 5–8-membered saturated or unsaturated ring;

$n_1$=0–3;
$n$=0–3;
A=$CH_2$;
  $(CH_2)_2$;
  $(CH_2)_3$;
  $OCH_2CH_2$; or
  $CHCH_3$;
Y=H;
  $OR_1$;
  $N(R_1)_2$;
  $N(R_1)C(O)R_3$;
  $N(R_1)C(O)R_5$;
  $N(R_1)C(O)CH(R_6)NH_2$;
  $N(R_1)SO_2R_3$;
  $N(R_1)C(O)NHR_3$; or
  $N(R_1)C(O)OR_6$;
$R_5$=$C_3$–$C_7$-cycloalkyl;
$R_6$=$C_1$–$C_4$-straight chain alkyl;
  $C_3$–$C_4$-branched chain alkyl;
  $C_2$–$C_4$-alkenyl chain;
  $(CH_2)_n$Ph; or
  $(CH_2)_n$-substituted phenyl, wherein the phenyl substituents are as defined above in $R_2$;
or a pharmaceutically acceptable salt thereof.

More preferably, the compounds of the current invention are represented by the chemical structure found in Formula III.

Formula III wherein:
$R_1$ are the same or different and independently selected from the group consisting of:
  H;
  $C_1$–$C_6$-straight chain alkyl;
  $C_2$–$C_6$-straight alkenyl chain;
  $C_3$–$C_6$-branched alkyl chain;
  $C_3$–$C_6$-branched alkenyl chain;
  $C_3$–$C_7$-cycloalkyl;
  $CH_2$—($C_3$–$C_7$-cycloalkyl);
  $CH_2CF_3$;
  $CH_2CH_2CF_3$; and
  $CH(CF_3)_2$;
the combination of X, D, and Q are either:
  D=Q=N, and X=CH; or
  D=X=N, and Q=CH; or
  Q=X=N, and D=CH; or
  Q=N, and D=X=CH;

V=NH;
O;
S; or
$CH_2$;
$R_2$=phenyl;
  substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
1-naphthyl;
2-naphthyl;
heterocycles selected from the group consisting of:
  2-pyridyl;
  3-pyridyl;
  4-pyridyl;
  2-pyrimidyl;
  4-pyrimidyl;
  5-pyrimidyl;
  thiophene-2-yl;
  thiophene-3-yl;
  2-furanyl;
  3-furanyl;
  oxazol-2-yl;
  oxazol-4-yl;
  oxazol-5-yl;
  thiazol-2-yl;
  thiazol-4-yl;
  thiazol-5-yl;
  imidazol-2-yl;
  imidazol-4-yl;
  pyrazol-3-yl;
  pyrazol-4-yl;
  isoxazol-3-yl;
  isoxazol-4-yl;
  isoxazol-5-yl;
  isothiazol-3-yl;
  isothiazol-4-yl;
  isothiazol-5-yl;
  1,3,4-thiadiazol-2-yl;
  benzo[b]furan-2-yl;
  benzo[b]thiophene-2-yl;
  2-pyrrolyl;
  3-pyrrolyl;
  1,3,5-triazin-2-yl;
  pyrazin-2-yl;
  pyridazin-3-yl;
  pyridazin-4-yl;
  2-quinolinyl;
  3-quinolinyl;
  4-quinolinyl;
  1-isoquinolinyl;
  3-isoquinolinyl; and
  4-isoquinolinyl; or
substituted heterocycle, wherein the substituents (1–2 in number) are in any position and are independently selected from the group consisting of Br, Cl, F, $R_1$, and $C(O)CH_3$;
n=0–3;
A=$CH_2$;
  $(CH_2)_2$;
  $(CH_2)_3$;
  $OCH_2CH_2$; or
  $CHCH_3$;

Y=H;
  $OR_1$;
  $N(R_1)_2$;
  $N(R_1)C(O)R_3$;
  $N(R_1)C(O)R_5$;
  $N(R_1)C(O)CH(R_6)NH_2$;
  $N(R_1)SO_2R_3$;
  $N(R_1)C(O)NHR_3$; or
  $N(R_1)C(O)OR_6$;
$R_3$ are the same or different and independently selected from the group consisting of:
  H;
  $C_1$–$C_4$-straight chain alkyl;
  $C_3$–$C_4$-branched chain alkyl;
  $C_2$–$C_4$-alkenyl chain;
  $(CH_2)_n$Ph; and
  $(CH_2)_n$-substituted phenyl, wherein the phenyl substituents are as defined above in $R_2$;
$R_5$=$C_3$–$C_7$-cycloalkyl;
$R_6$=$C_1$–$C_4$-straight chain alkyl;
  $C_3$–$C_4$-branched chain alkyl; or
  $C_2$–$C_4$-alkenyl chain;
or a pharmaceutically acceptable salt thereof.

In another embodiment, the present invention is directed to a method of treating a mammal with a disorder mediated by elevated levels of cellular proliferation comprising administering a therapeutically effective amount of the compound of the present invention to the mammal under conditions effective to treat the disorder mediated by elevated levels of cell proliferation.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

Based on the results obtained in the standard pharmacological test procedures described below, the compounds of the present invention are useful as antineoplastic agents. More particularly, the compounds of the present invention are useful for inhibiting the growth of neoplastic cells, causing cell death of neoplastic cells, and eradicating neoplastic cells. The compounds of the present invention are, therefore, useful for treating solid tumors, including sarcomas and carcinomas, such as astrocytomas, prostate cancer, breast cancer, small cell lung cancer, and ovarian cancer, leukemias, lymphomas, adult T-cell leukemia/lymphoma, and other neoplastic disease states.

In addition to the utilities described above, many of the compounds of the present invention are useful in the preparation of other compounds.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

General Synthetic Schemes

The compounds of the present invention can be prepared by conventional methods of organic synthesis practiced by those skilled in the art. The general reaction sequences outlined below are general methods useful for preparing the compounds of the present invention and are not meant to be limiting in scope or utility.

Reaction of 2,6-dichloropurine (Formula IV) with various amines of Formula V, many of which are commercially available or prepared by literature methods or modifications of literature methods, in the presence of a polar solvent, such as ethanol, provides purines of Formula VI (General Flowsheet I, infra). Reaction of purines of Formula VI with alkyl halides ($R_1$-Z) in the presence of a base such as potassium carbonate provides N1-alkylated purines of Formula VII. Chloride displacement of N1-alkylated purines of Formula VII with amines, thiols or alcohols of structure Formula VIII, either in neat solution or in an inert solvent such as ethanol or butanol, with or without a base such as sodium hydride as appropriate, at an appropriate temperature provides purines of Formula IX (V=NH, O, S). Transition metal-mediated cross-coupling reaction of purines of Formula IX with boronic acid ($R_2$—$B(OH)_2$) or tin reagents ($R_2$—$Sn(n-Bu)_3$ or $R_2$—$SnMe_3$) provides purines of Formula X (V=NH, O, S). If in Formula X (Y=$NH_2$), then subsequent reaction of Formula X (Y=$NH_2$) with acid chloride ($R_3COCl$), or sulfonyl chloride ($R_3SO_2Cl$), or isocyanate ($R_3NCO$), or chloroformate ($ClC(O)OR_6$) reagents provides purines of Formula XI wherein Y=$NHC(O)R_3$, $NHSO_2R_3$, or $NHC(O)NHR_3$, or $NHC(O)OR_6$, respectively. On the other hand, if in Formula X, Y already is $OR_1$ or $NHC(O)R_3$ or $NHSO_2R_3$ or $NHC(O)NHR_3$ or $NHC(O)OR_6$, as a result of what Y started out as in Formula VIII, then this last step is unnecessary.

Reaction of purines of Formula VII, with alkenyl tin reagents of Formula XII, which are prepared by conventional methods described in the literature, in the presence of a transition metal catalyst, such as Pd(0), provides purines of Formula XIII (General Flowsheet II, infra). Subsequent reaction of purines of Formula XIII with boronic acid ($R_2$—$B(OH)_2$) or tin reagents ($R_2$—$Sn(n-Bu)_3$ or $R_2$—$SnMe_3$) in the presence of a transition metal catalyst, such as Pd(0), provides purines of Formula XV. Alternatively, by switching the order of reactions dependent on the precise reactivity of the purine of Formula VII, reaction of purines of Formula VII with boronic acid ($R_2$—$B(OH)_2$) or tin reagents ($R_2$—$Sn(n-Bu)_3$ or $R_2$—$SnMe_3$) in the presence of a transition metal catalyst, such as Pd(0), provides purines of Formula XIV. Subsequent reaction of purines of Formula XIV, with alkenyl tin reagents of Formula XII, which are prepared by conventional methods described in the literature, in the presence of a transition metal catalyst, such as Pd(0), provides purines of Formula XV. Finally reduction of the olefin within Formula XV provides purines of Formula X (V=$CH_2$).

Definitions of the groups include:

Z=Br;

I;

V=$NH_2$;

OH;

SH;

$R_1$ are the same or different and independently selected from:
- H;
- $C_1$–$C_6$-straight chain alkyl;
- $C_2$–$C_6$-straight alkenyl chain;
- $C_3$–$C_6$-branched alkyl chain;
- $C_3$–$C_6$-branched alkenyl chain;
- $C_3$–$C_7$-cycloalkyl;
- $CH_2$—($C_3$–$C_7$-cycloalkyl);
- $CH_2CF_3$;
- $CH_2CH_2CF_3$;
- $CH(CF_3)_2$;

the combination of X, D, and Q are selected from:
- D=Q=N, and X=CH;
- D=X=N, and Q=CH;
- Q=X=N, and D=CH;
- Q=N, and D=X=CH;

V=NH;
- O;
- S;
- $CH_2$;

$R_2$ can be in any position on the ring and selected from:
- phenyl;
- substituted phenyl, wherein the substituents (1–2 in number) are in any position and are independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;
- 1-naphthyl;
- 2-naphthyl;
- heterocycles including:
  - 2-pyridyl;
  - 3-pyridyl;
  - 4-pyridyl;
  - 2-pyrimidyl;
  - 4-pyrimidyl;
  - 5-pyrimidyl;
  - thiophene-2-yl;
  - thiophene-3-yl;
  - 2-furanyl;
  - 3-furanyl;
  - oxazol-2-yl;
  - oxazol-4-yl;
  - oxazol-5-yl;
  - thiazol-2-yl;
  - thiazol-4-yl;
  - thiazol-5-yl;
  - imidazol-2-yl;
  - imidazol-4-yl;
  - pyrazol-3-yl;
  - pyrazol-4-yl;
  - isoxazol-3-yl;
  - isoxazol-4-yl;
  - isoxazol-5-yl;
  - isothiazol-3-yl;
  - isothiazol-4-yl;
  - isothiazol-5-yl;
  - 1,3,4-thiadiazol-2-yl;
  - benzo[b]furan-2-yl;
  - benzo[b]thiophene-2-yl;
  - 2-pyrrolyl;
  - 3-pyrrolyl;
  - 1,3,5-triazin-2-yl;
  - pyrazin-2-yl;
  - pyridazin-3-yl;
  - pyridazin-4-yl;
  - 2-quinolinyl;
  - 3-quinolinyl;
  - 4-quinolinyl;
  - 1-isoquinolinyl;
  - 3-isoquinolinyl;
  - 4-isoquinolinyl;
- substituted heterocycle, wherein the substituents (1–2 in number) are in any position and are independently selected from Br, Cl, F, $R_1$, $C(O)CH_3$;

$R_3$ are the same or different and independently selected from:
- H;
- $C_1$–$C_4$-straight chain alkyl;
- $C_3$–$C_4$-branched chain alkyl;
- $C_2$–$C_4$-alkenyl chain;
- $(CH_2)_n$Ph;
- $(CH_2)_n$-substituted phenyl, wherein the phenyl substituents are as defined above in $R_2$;

$R_4$=H;
- $C_1$–$C_4$-straight chain alkyl;
- $C_3$–$C_4$-branched chain alkyl;

$R_3$ and $R_4$ can be linked together by a carbon chain to form a 5–8-membered saturated or unsaturated ring;

$n_1$=0–3;
n=0–3;
A=($CH_2$);
- $(CH_2)_2$;
- $(CH_2)_3$;
- ($OCH_2CH_2$);
- ($CHCH_3$);

Y=H;
- $OR_1$;
- $N(R_1)_2$;
- $N(R_1)C(O)R_3$;
- $N(R_1)C(O)R_5$;
- $N(R_1)C(O)CH(R_6)NH_2$;
- $N(R_1)SO_2R_3$;
- $N(R_1)C(O)NHR_3$;
- $N(R_1)C(O)OR_6$;

$R_5$=$C_3$–$C_7$-cycloalkyl;
$R_6$=$C_1$–$C_4$-straight chain alkyl;
- $C_3$–$C_4$-branched chain alkyl;
- $C_2$–$C_4$-alkenyl chain;
- $(CH_2)_n$Ph;
- $(CH_2)_n$-substituted phenyl, wherein the phenyl substituents are as defined above in $R_2$.

General Flowsheet I
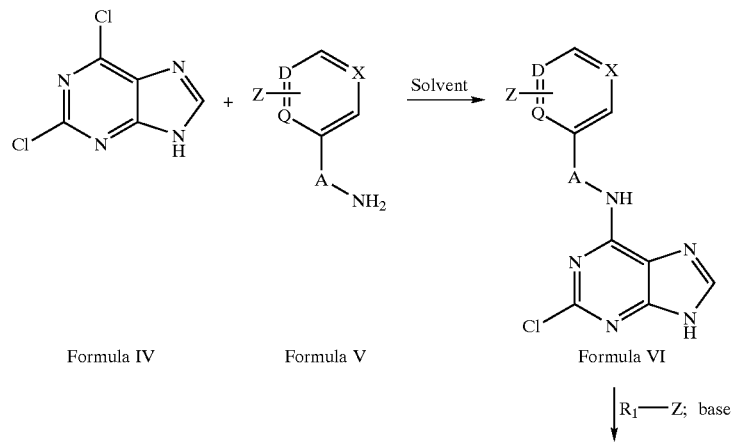
Formula IV        Formula V        Formula VI
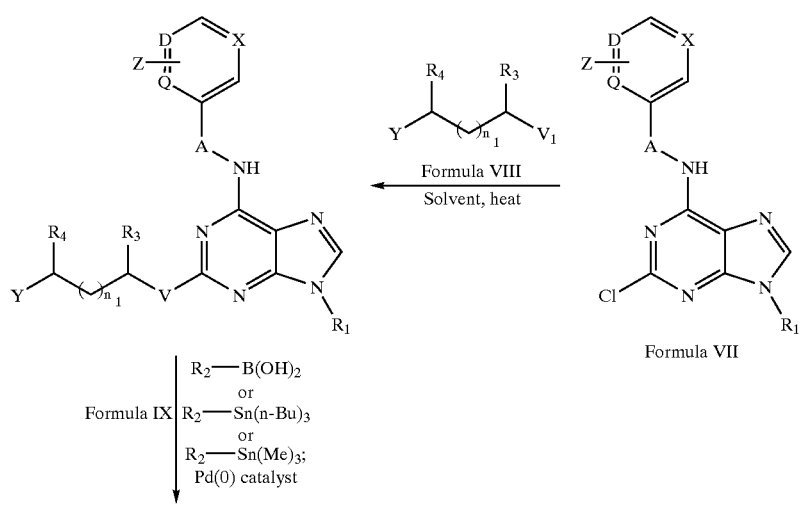
Formula VII
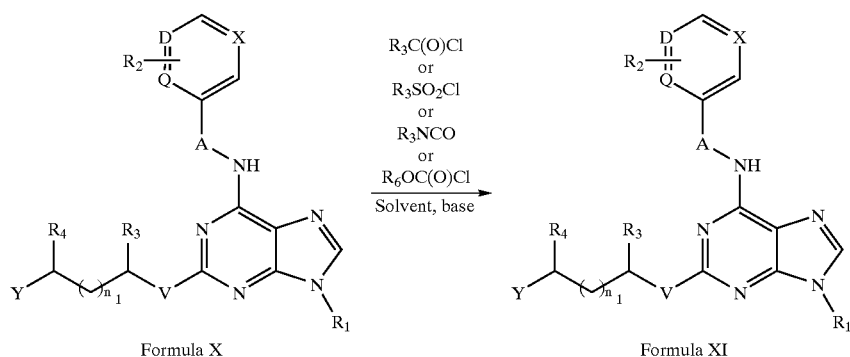
Formula X        Formula XI General Flowsheet II
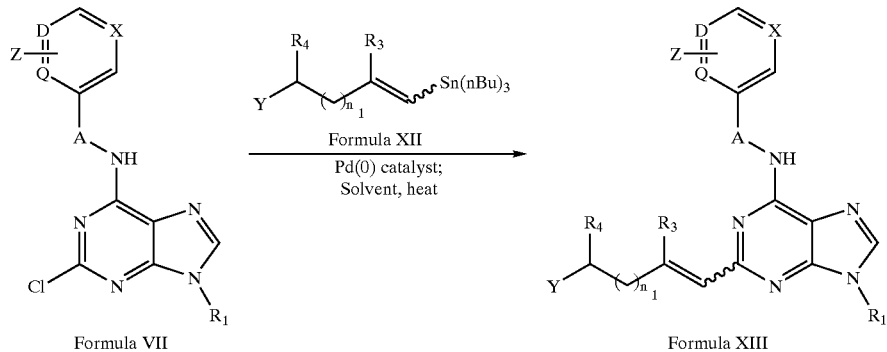
Formula VII
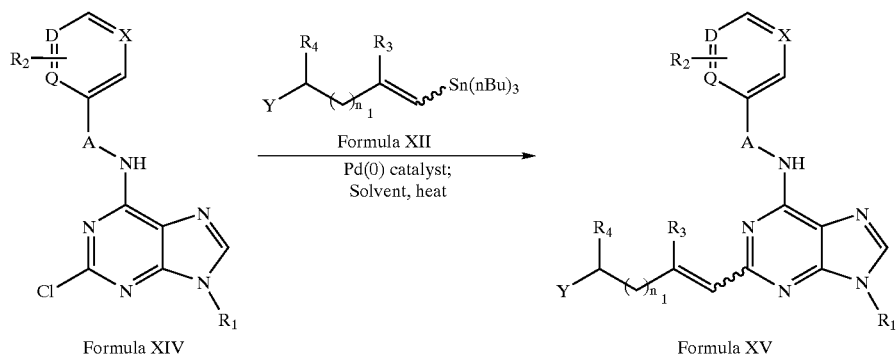
Formula XIV
Formula XV
Hydrogenate
Solvent
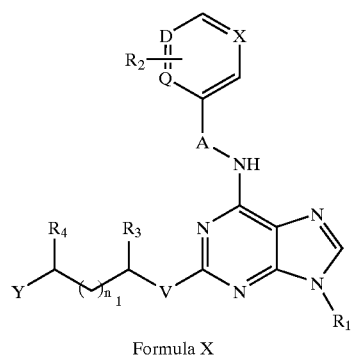
Formula X Additional, general non-limiting syntheses of compounds of the present invention of Formula X and Formula XI are shown below in General Flowsheet III.

priate temperature provides purines of Formula X (V=NH, O, S). If in Formula X (Y=NH$_2$), then subsequent reaction of Formula X (Y=NH$_2$) with acid chloride (R$_3$COCl), or sulfonyl chloride (R$_3$SO$_2$Cl), or isocyanate (R$_3$NCO), or chloroformate (ClC(O)OR$_6$) reagents provides purines of Formula XI wherein Y=NHC(O)R$_3$, NHSO$_2$R$_3$, or NHC(O)NHR$_3$, or NHC(O)OR$_6$, respectively. On the other hand, if in Formula X, Y already is OR$_1$ or NHC(O)R$_3$ or NHSO$_2$R$_3$ or NHC(O)NHR$_3$ or NHC(O)OR$_6$, as a result of what Y started out as in Formula VIII, then this last step is unnecessary.

Definitions of the groups include:

Z=Br;
  I;
V$_1$=NH$_2$;
  OH;
  SH;
R$_1$ are the same or different and independently selected from:

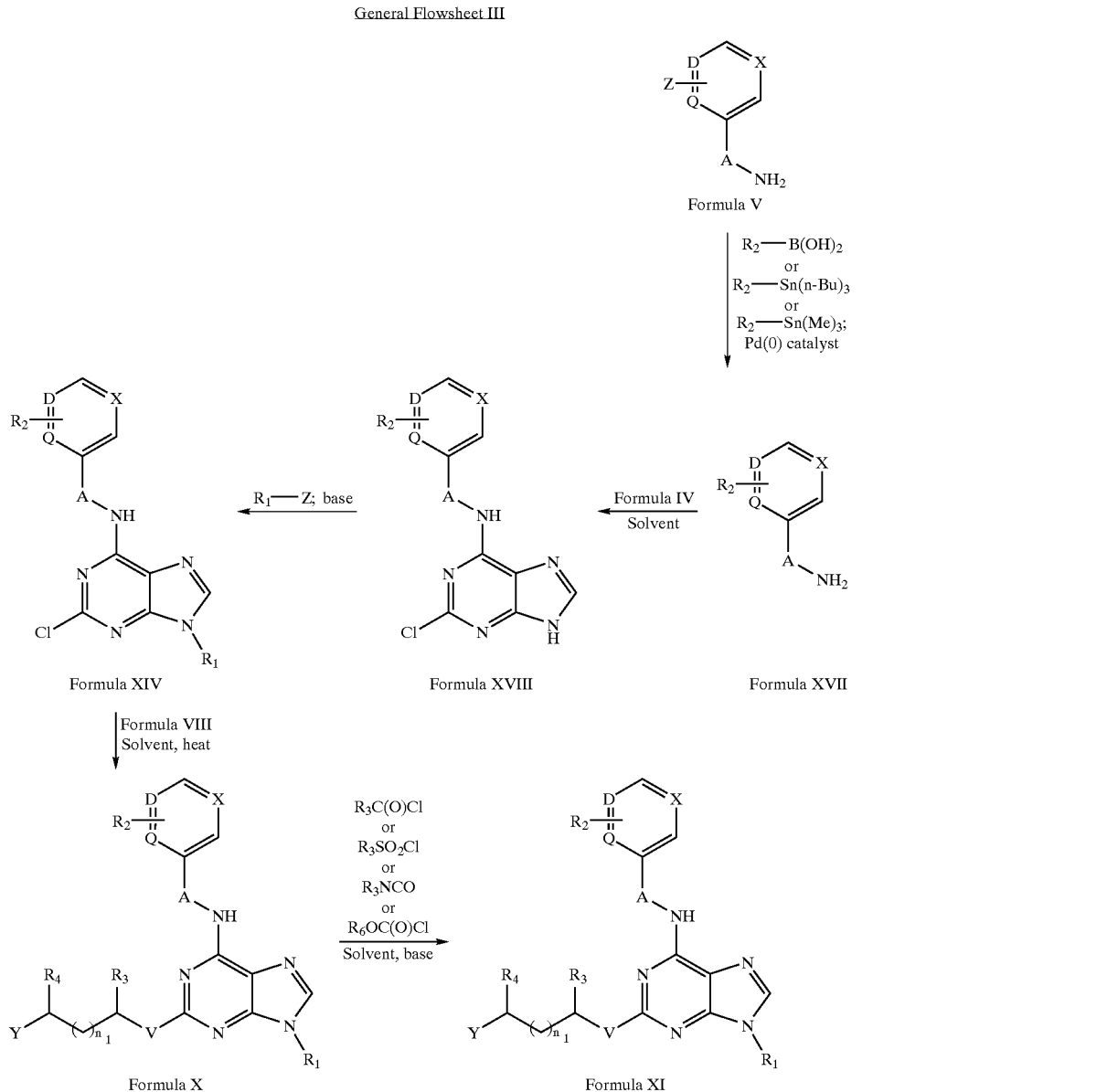

General Flowsheet III

Reaction of various amines of Formula V, many of which are commercially available or prepared by literature methods or modifications of literature methods, with boronic acid (R$_2$—B(OH)$_2$) or tin reagents (R$_2$—Sn(n-Bu)$_3$) or (R$_2$—SnMe$_3$) in the presence of a transition metal catalyst, such as Pd(0), provides biaryl amines of Formula XVII. Reaction of 2,6-dichloropurine (Formula IV) with various amines of Formula XVII, in the presence of a polar solvent, such as ethanol, provides purines of Formula XVIII. Reaction of purines of Formula XVIII with alkyl halides (R$_1$-Z) in the presence of a base such as potassium carbonate provides N1-alkylated purines of Formula XIV. Chloride displacement of N1-alkylated purines of Formula XIV with amines, thiols or alcohols of Formula VIII, either in neat solution or in an inert solvent such as ethanol or butanol, with or without a base such as sodium hydride as appropriate, at an appro- H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—($C_3$–$C_7$-cycloalkyl);
$CH_2CF_3$;
$CH_2CH_2CF_3$;
$CH(CF_3)_2$;
the combination of X, D, and Q are selected from:
  D=Q=N, and X=CH;
  D=X=N, and Q=CH;
  Q=X=N, and D=CH;
  Q=N, and D=X=CH;
V=NH;
  O;
  S;
  $CH_2$;
$R_2$ can be in any position on the ring and selected from:
  phenyl;
  substituted phenyl, wherein the substituents (1–2 in number) are in any position and are independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;
  1-naphthyl;
  2-naphthyl;
  heterocycles including:
    2-pyridyl;
    3-pyridyl;
    4-pyridyl;
    2-pyrimidyl;
    4-pyrimidyl;
    5-pyrimidyl;
    thiophene-2-yl;
    thiophene-3-yl;
    2-furanyl;
    3-furanyl;
    oxazol-2-yl;
    oxazol-4-yl;
    oxazol-5-yl;
    thiazol-2-yl;
    thiazol-4-yl;
    thiazol-5-yl;
    imidazol-2-yl;
    imidazol-4-yl;
    pyrazol-3-yl;
    pyrazol-4-yl;
    isoxazol-3-yl;
    isoxazol-4-yl;
    isoxazol-5-yl;
    isothiazol-3-yl;
    isothiazol-4-yl;
    isothiazol-5-yl;
    1,3,4-thiadiazol-2-yl;
    benzo[b]furan-2-yl;
    benzo[b]thiophene-2-yl;
    2-pyrrolyl;
    3-pyrrolyl;
    1,3,5-triazin-2-yl;
    pyrazin-2-yl;
    pyridazin-3-yl;
    pyridazin-4-yl;
    2-quinolinyl;
    3-quinolinyl;
    4-quinolinyl;
    1-isoquinolinyl;
    3-isoquinolinyl;
    4-isoquinolinyl;
  substituted heterocycle, wherein the substituents (1–2 in number) are in any position and are independently selected from Br, Cl, F, $R_1$, $C(O)CH_3$;
$R_3$ are the same or different and independently selected from:
  H;
  $C_1$–$C_4$-straight chain alkyl;
  $C_3$–$C_4$-branched chain alkyl;
  $C_2$–$C_4$-alkenyl chain;
  $(CH_2)_n$Ph;
  $(CH_2)_n$-substituted phenyl, wherein the phenyl substituents are as defined above in $R_2$;
$R_4$=H;
  $C_1$–$C_4$-straight chain alkyl;
  $C_3$–$C_4$-branched chain alkyl;
$R_3$ and $R_4$ can be linked together by a carbon chain to form a 5–8-membered saturated or unsaturated ring;
$n_1$=0–3;
n=0–3;
A=($CH_2$);
  $(CH_2)_2$;
  $(CH_2)_3$;
  ($OCH_2CH_2$);
  ($CHCH_3$);
Y=H;
  $OR_1$;
  $N(R_1)_2$;
  $N(R_1)C(O)R_3$;
  $N(R_1)C(O)R_5$;
  $N(R_1)C(O)CH(R_6)NH_2$;
  $N(R_1)SO_2R_3$;
  $N(R_1)C(O)NHR_3$;
  $N(R_1)C(O)OR_6$;
$R_5$=$C_3$–$C_7$-cycloalkyl;
$R_6$=$C_1$–$C_4$-straight chain alkyl;
  $C_3$–$C_4$-branched chain alkyl;
  $C_2$–$C_4$-alkenyl chain;
  $(CH_2)_n$Ph;
  $(CH_2)_n$-substituted phenyl, wherein the phenyl substituents are as defined above in $R_2$.

Additional, general non-limiting syntheses of compounds of the present invention of Formula XVI, Formula XVII and Formula XVIII are shown below in General Flowsheet IV.

General Flowsheet IV

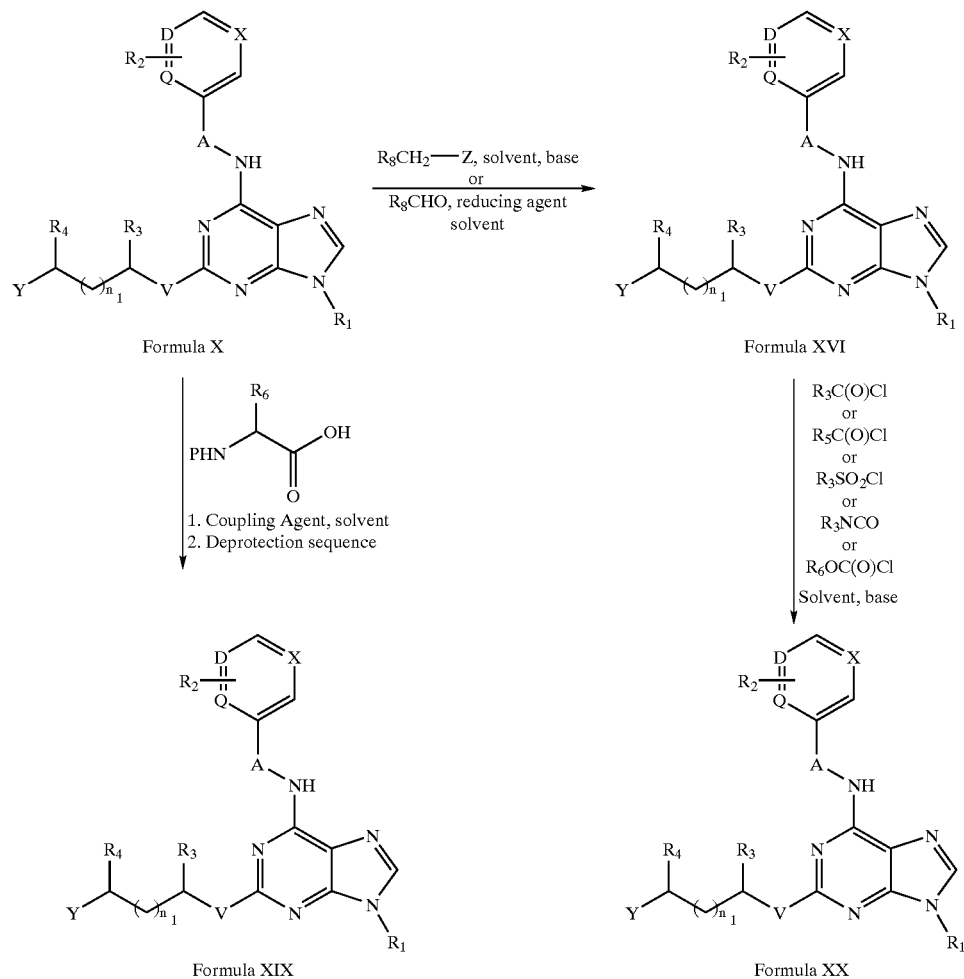

If in Formula X (Y=NH$_2$), then subsequent reaction of Formula X (Y=NH$_2$) with alkyl halide (R$_8$CH$_2$Z), an appropriate base, and a solvent; or reaction of Formula X (Y=NH$_2$) with aldehyde (R$_8$CHO) in the presence of a solvent and a suitable reducing agent provides purines of Formula XVI wherein Y=NHR$_1$, or N(R$_1$)$_2$. On the other hand, if in Formula X, Y already is NHR$_1$, or N(R$_1$)$_2$, as a result of what Y started out as in Formula X, then this last step is unnecessary. If in Formula XVI (Y=NHR$_1$), then subsequent reaction of Formula XVI (Y=NHR$_1$) with acid chloride (R$_3$COCl), or sulfonyl chloride (R$_3$SO$_2$Cl), or isocyanate (R$_3$NCO), or chloroformate (ClC(O)OR$_6$) reagents provides purines of Formula XX wherein Y=NR$_1$C(O)R$_3$, or NR$_1$C(O)R$_5$, or NR$_1$SO$_2$R$_3$, or NR$_1$C(O)NHR$_3$, or NR$_1$C(O)OR$_6$, respectively. On the other hand, if in Formula XVI, Y already is NR$_1$C(O)R$_3$, or NR$_1$C(O)R$_5$, or NR$_1$SO$_2$R$_3$, or NR$_1$C(O)NHR$_3$, or NR$_1$C(O)OR$_6$, as a result of what started out as in Formula XVI, then this last step is unnecessary.

If in Formula X (Y=NH$_2$), then subsequent reaction of Formula X (Y=NH$_2$) with acid (PNHCH(R$_6$)CO$_2$H), in a suitable solvent in the presence of an appropriate coupling agent provides a purine derivative; which upon suitable deprotection provides purines of Formula XIX wherein Y=NHC(O)CH(R$_6$)NH$_2$. On the other hand, if in Formula X, Y already is NHC(O)CH(R$_6$)NH$_2$, as a result of what Y started out as in Formula X, then this last step is unnecessary.

Definitions of the groups include:

Z=Br;

I;

P=C(O)OtBu;

C(O)OCH$_2$Ph;

Fmoc;

Benzyl;

Alloc;

R$_1$ are the same or different and independently selected from:

H;

C$_1$–C$_6$-straight chain alkyl;

C$_2$–C$_6$-straight alkenyl chain;

C$_3$–C$_6$-branched alkyl chain;

C$_3$–C$_6$-branched alkenyl chain;

C$_3$–C$_7$-cycloalkyl;

CH$_2$—(C$_3$–C$_7$-cycloalkyl);

CH$_2$CF$_3$;

CH$_2$CH$_2$CF$_3$;

CH(CF$_3$)$_2$;

the combination of X, D, and Q are selected from:
  D=Q=N, and X=CH;
  D=X=N, and Q=CH;
  Q=X=N, and D=CH;
  Q=N, and D=X=CH;
V=NH;
  O;
  S;
  $CH_2$;
$R_2$ can be in any position on the ring and selected from:
  phenyl;
  substituted phenyl, wherein the substituents (1–2 in number) are in any position and are independently selected from $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, $C(O)NHCHR_1CH_2OH$;
  1-naphthyl;
  2-naphthyl;
  heterocycles including:
    2-pyridyl;
    3-pyridyl;
    4-pyridyl;
    2-pyrimidyl;
    4-pyrimidyl;
    5-pyrimidyl;
    thiophene-2-yl;
    thiophene-3-yl;
    2-furanyl;
    3-furanyl;
    oxazol-2-yl;
    oxazol-4-yl;
    oxazol-5-yl;
    thiazol-2-yl;
    thiazol-4-yl;
    thiazol-5-yl;
    imidazol-2-yl;
    imidazol-4-yl;
    pyrazol-3-yl;
    pyrazol-4-yl;
    isoxazol-3-yl;
    isoxazol-4-yl;
    isoxazol-5-yl;
    isothiazol-3-yl;
    isothiazol-4-yl;
    isothiazol-5-yl;
    1,3,4-thiadiazol-2-yl;
    benzo[b]furan-2-yl;
    benzo[b]thiophene-2-yl;
    2-pyrrolyl;
    3-pyrrolyl;
    1,3,5-triazin-2-yl;
    pyrazin-2-yl;
    pyridazin-3-yl;
    pyridazin-4-yl;
    2-quinolinyl;
    3-quinolinyl;
    4-quinolinyl;
    1-isoquinolinyl;
    3-isoquinolinyl;
    4-isoquinolinyl;
  substituted heterocycle, wherein the substituents (1–2 in number) are in any position and are independently selected from Br, Cl, F, $R_1$, $C(O)CH_3$;
$R_3$ are the same or different and independently selected from:
  H;
  $C_1$–$C_4$-straight chain alkyl;
  $C_3$–$C_4$-branched chain alkyl;
  $C_2$–$C_4$-alkenyl chain;
  $(CH_2)_n$Ph;
  $(CH_2)_n$-substituted phenyl, wherein the phenyl substituents are as defined above in $R_2$;
$R_4$=H;
  $C_1$–$C_4$-straight chain alkyl;
  $C_3$–$C_4$-branched chain alkyl;
$R_3$ and $R_4$ can be linked together by a carbon chain to form a 5–8-membered saturated or unsaturated ring;
$n_1$=0–3;
n=0–3;
A=$(CH_2)$;
  $(CH_2)_2$;
  $(CH_2)_3$;
  $(OCH_2CH_2)$;
  $(CHCH_3)$;
Y=H;
  $OR_1$;
  $N(R_1)_2$;
  $N(R_1)C(O)R_3$;
  $N(R_1)C(O)R_5$;
  $N(R_1)C(O)CH(R_6)NH_2$;
  $N(R_1)SO_2R_3$;
  $N(R_1)C(O)NHR_3$;
  $N(R_1)C(O)OR_6$;
$R_5$=$C_3$–$C_7$-cycloalkyl;
$R_6$=$C_1$–$C_4$-straight chain alkyl;
  $C_3$–$C_4$-branched chain alkyl;
  $C_2$–$C_4$-alkenyl chain;
  $(CH_2)_n$Ph;
  $(CH_2)_n$-substituted phenyl, wherein the phenyl substituents are as defined above in $R_2$;
$R_8$=$C_1$–$C_5$-straight chain alkyl;
  $C_2$–$C_5$-straight alkenyl chain;
  $C_3$–$C_5$-branched alkyl chain;
  $C_3$–$C_5$-branched alkenyl chain;
  $C_3$–$C_7$-cycloalkyl;
  $CF_3$;
  $CH_2CF_3$.

The synthesis of compound 5 is shown below in Scheme I.
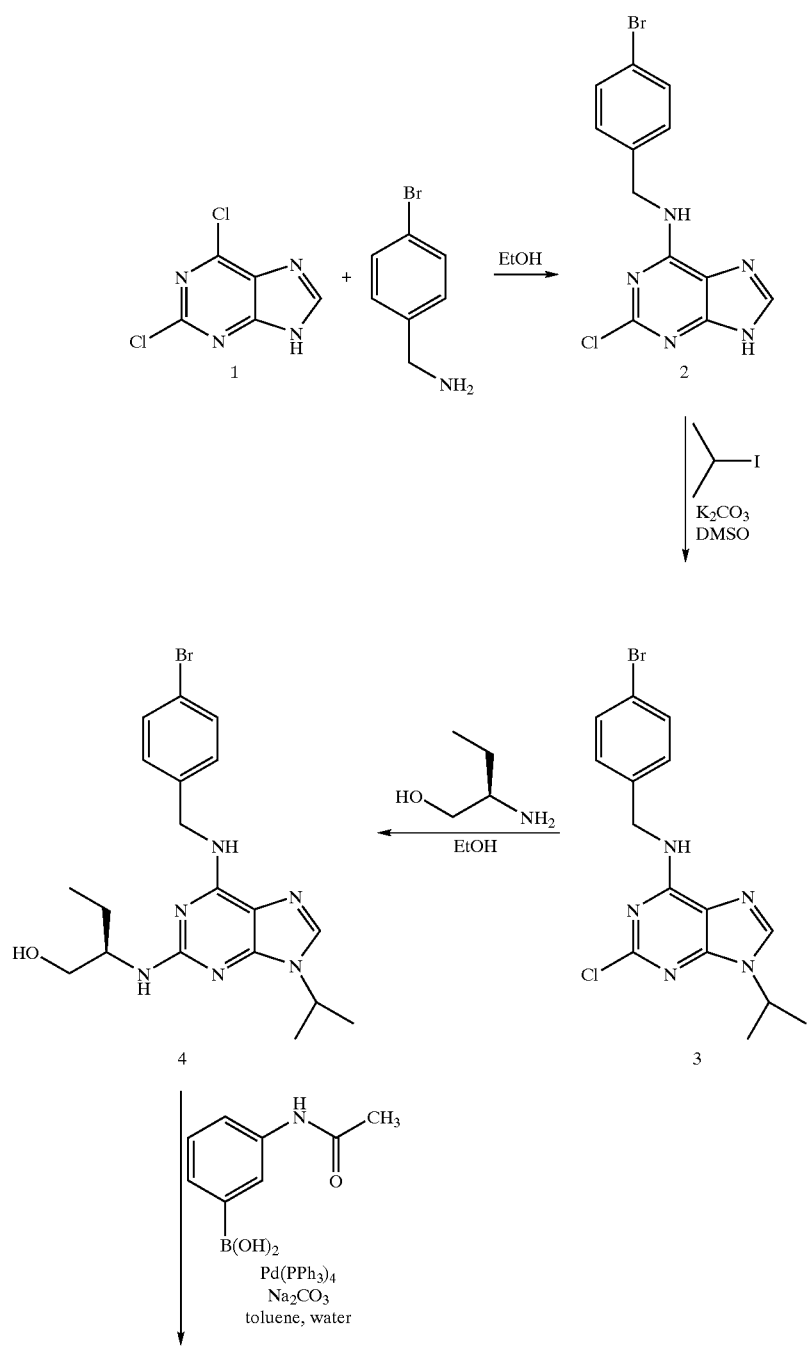

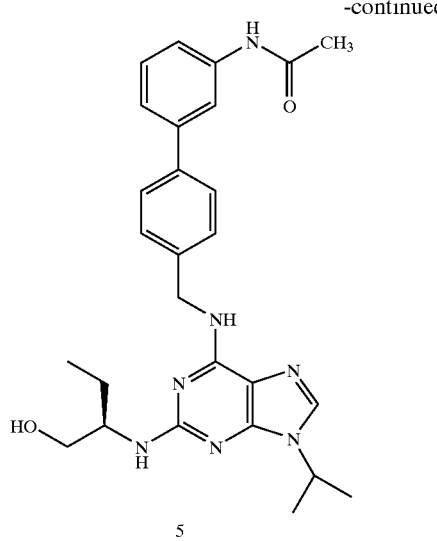
The synthesis of compound 11 is shown below in Scheme II.
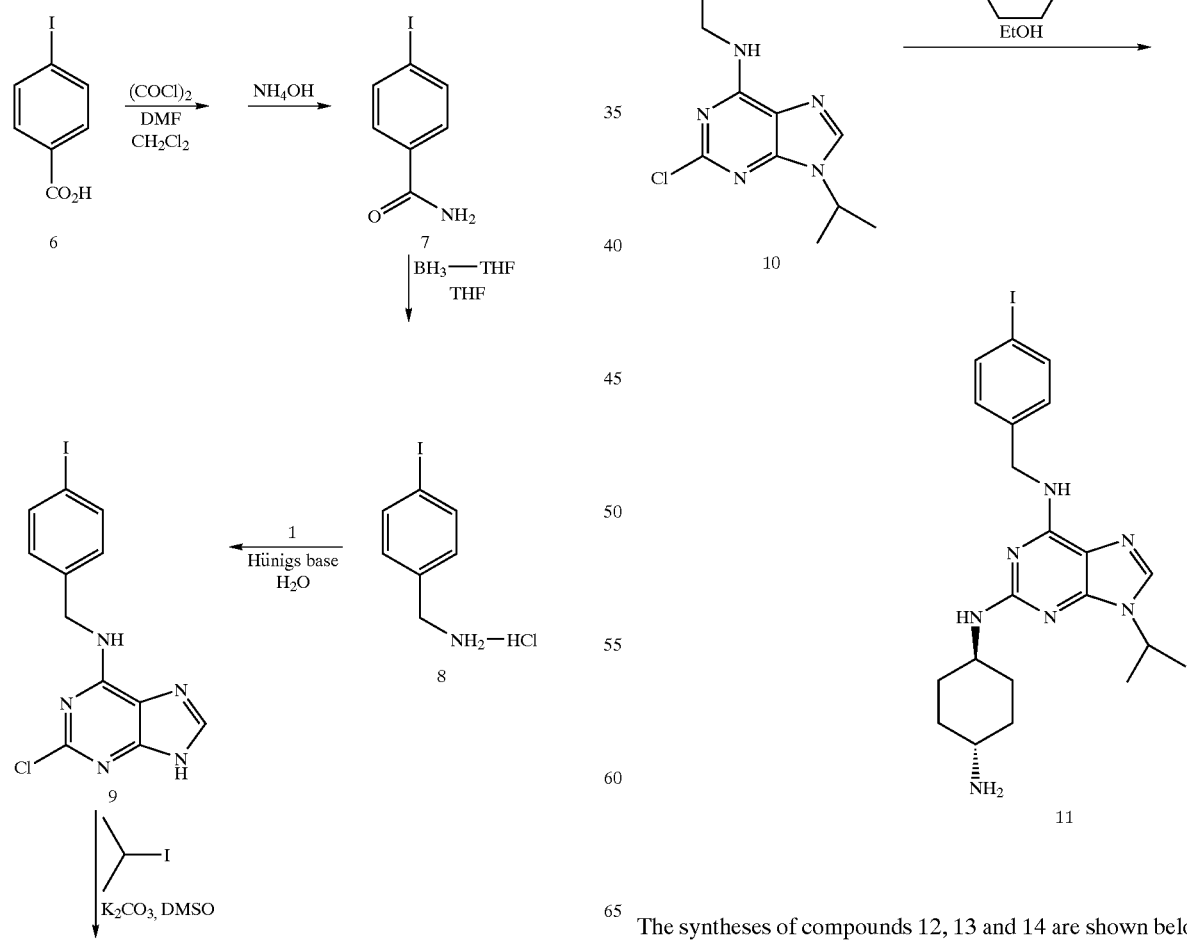
The syntheses of compounds 12, 13 and 14 are shown below in Scheme III.

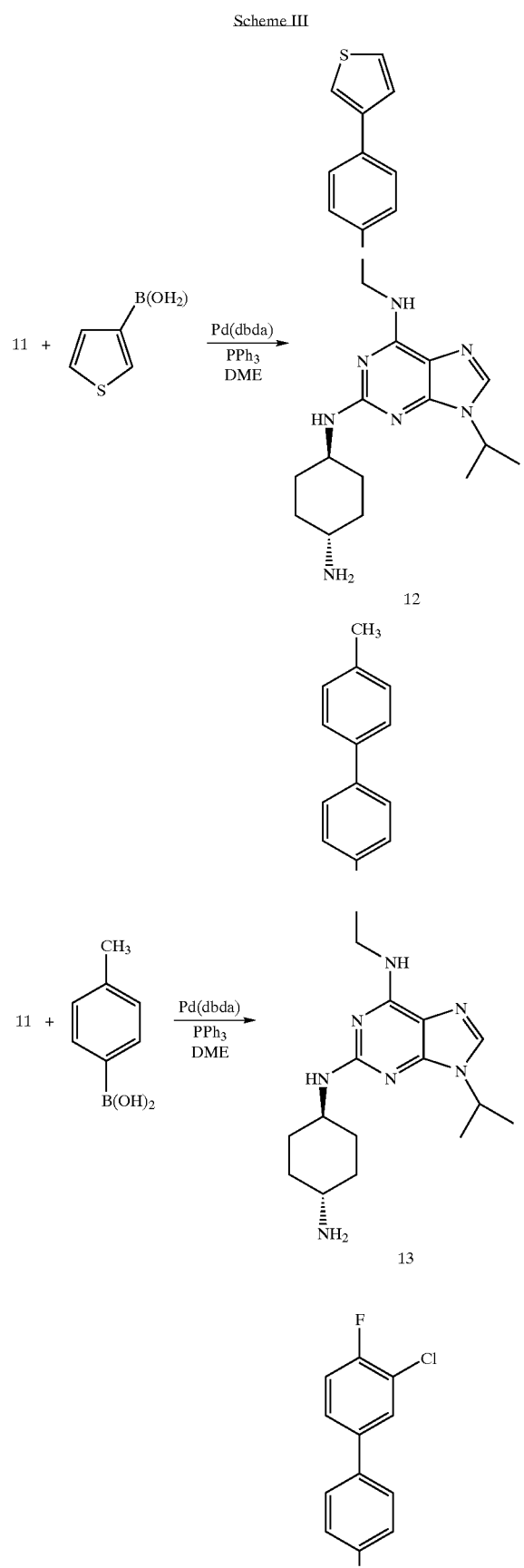
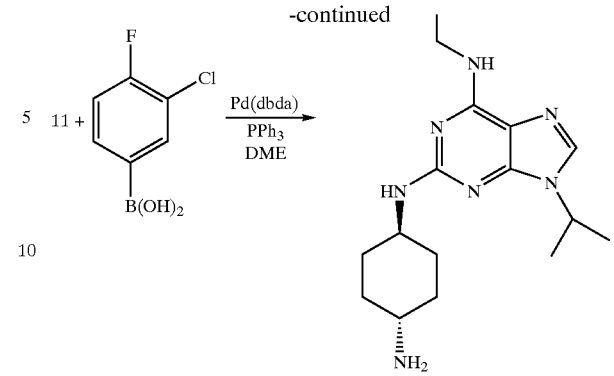
The synthesis of compound 17 is shown below in Scheme IV.
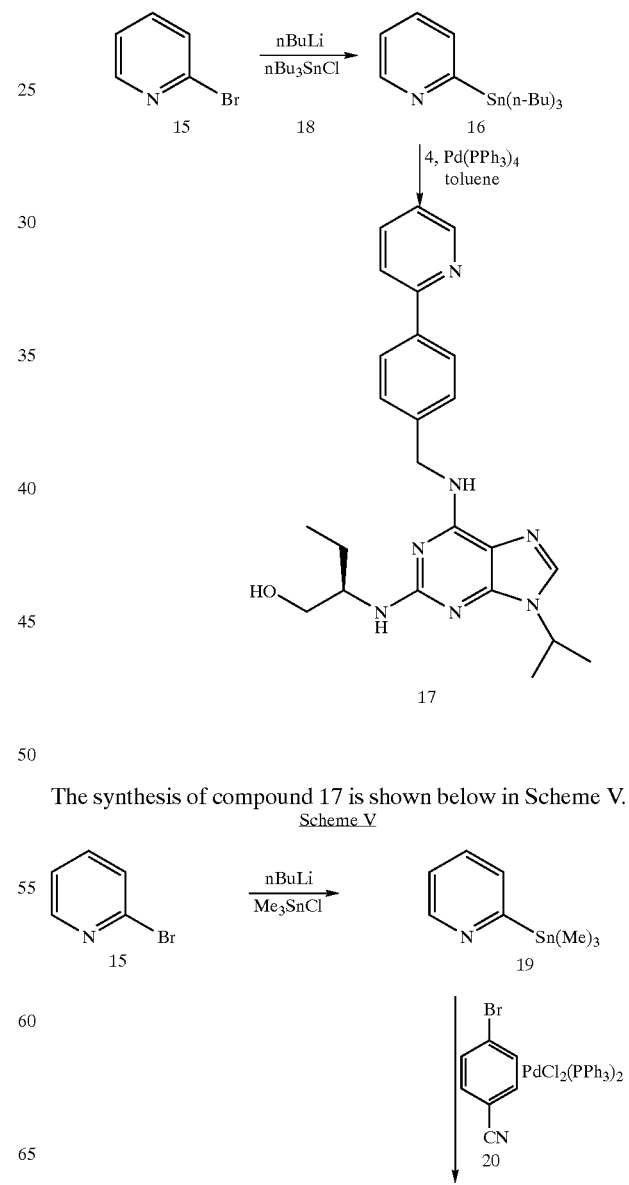
The synthesis of compound 17 is shown below in Scheme V.

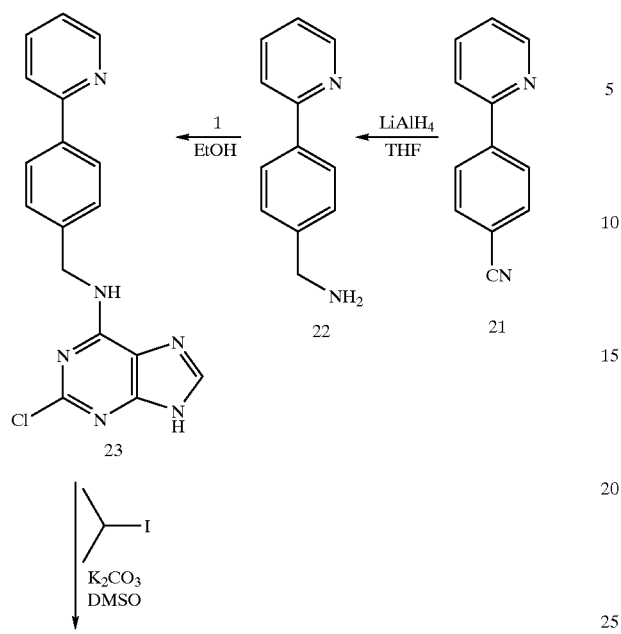
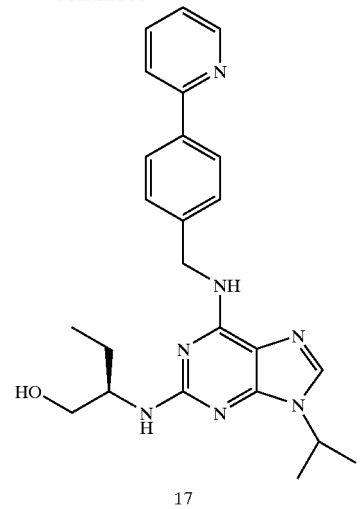
The synthesis of compound 25 is shown below in Scheme VI.
Scheme VI
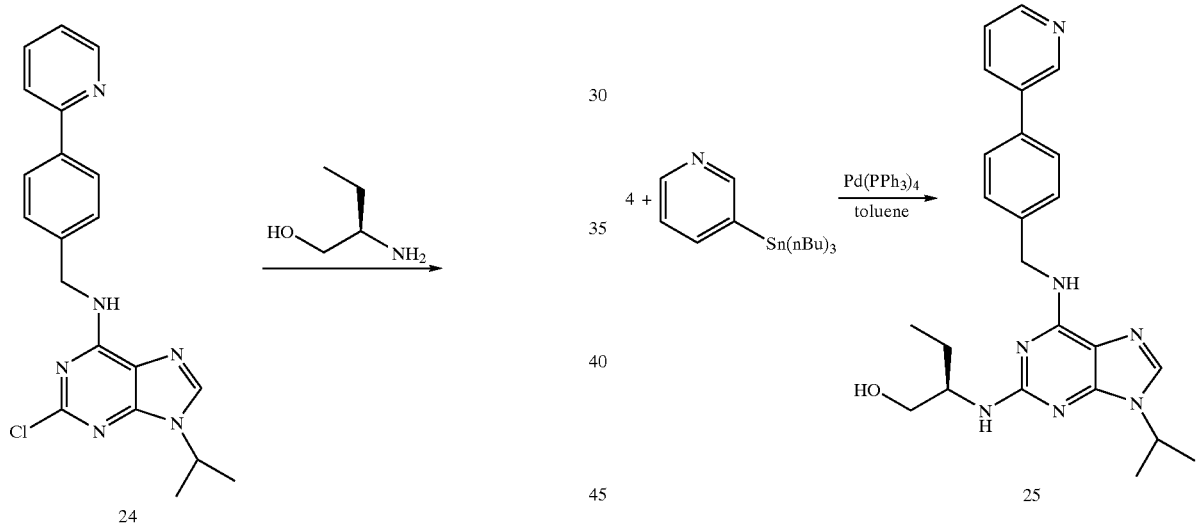
The synthesis of compound 25 is shown below in Scheme VII.
Scheme VII
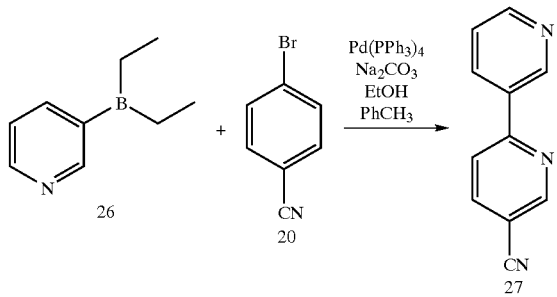

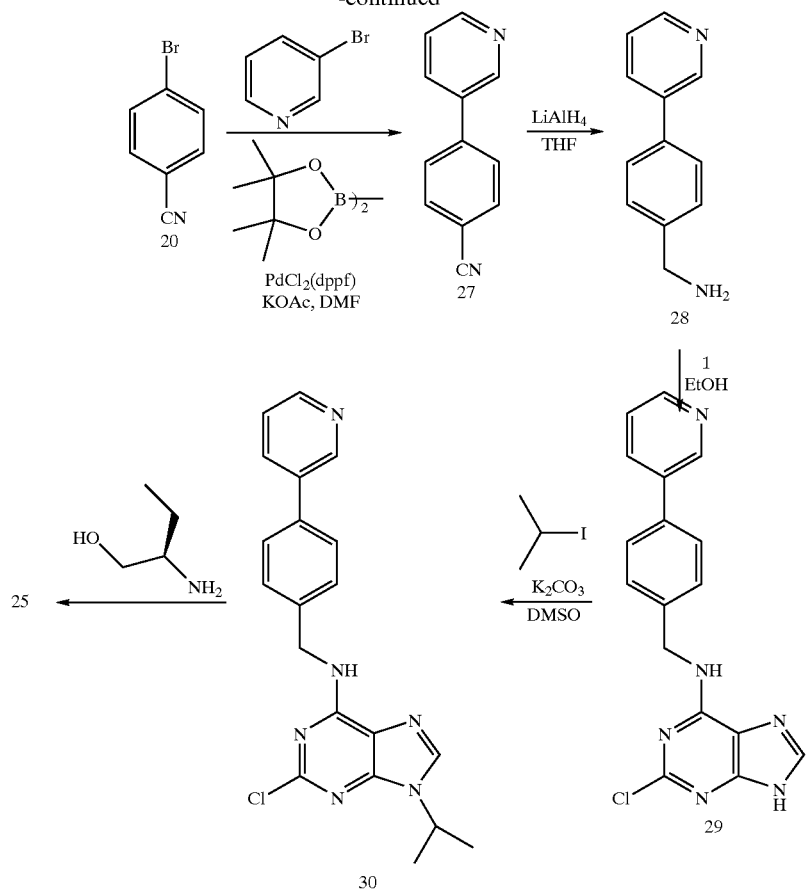
The synthesis of compound 32 is shown below in Scheme VIII.
The syntheses of compounds 33 and 34 are shown below in Scheme IX.
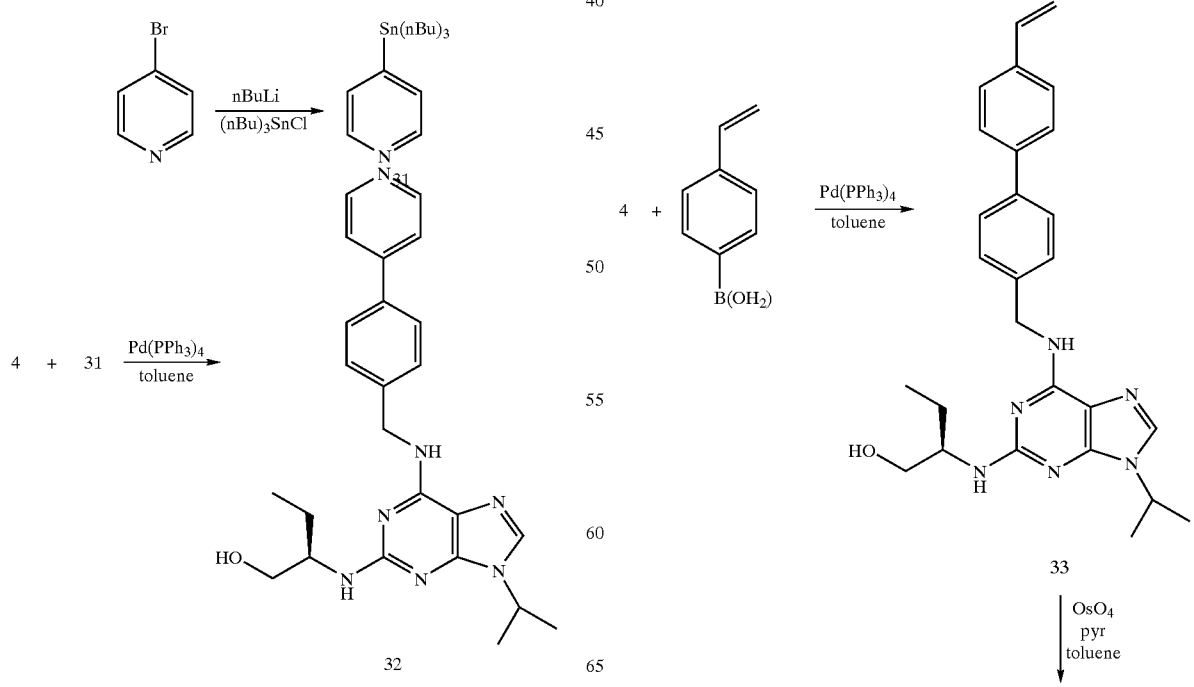

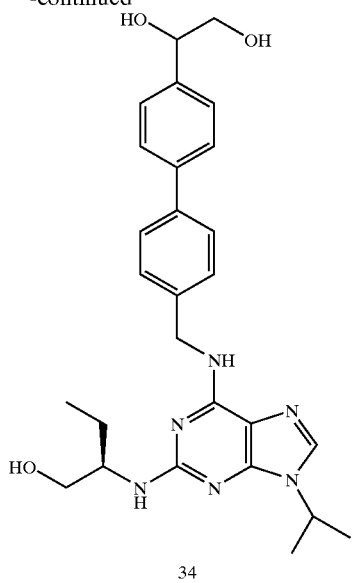
34
The syntheses of compounds 36, 38, and 40 are shown below in Scheme X.
Scheme X
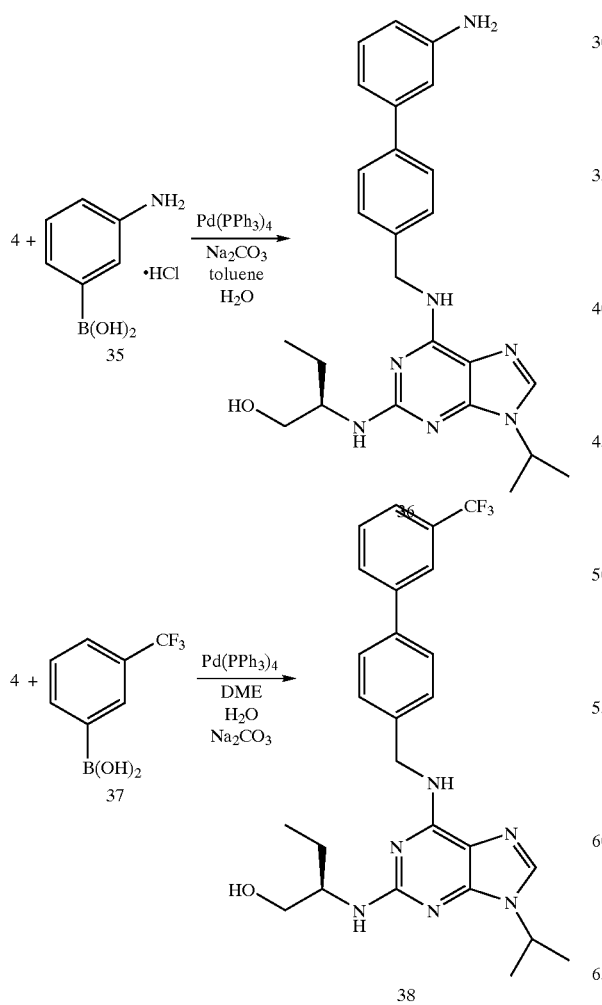
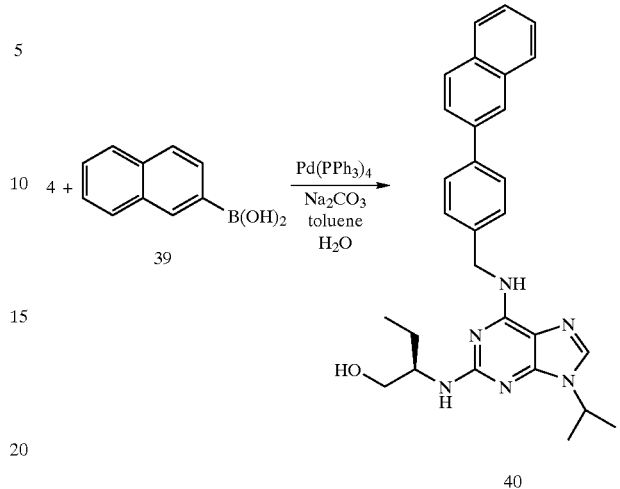
40
The synthesis of compound 43 is shown below in Scheme XI.
Scheme XI
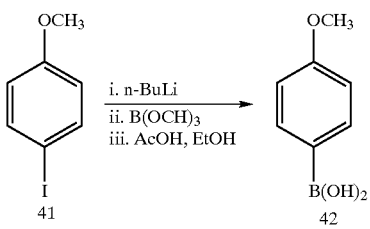
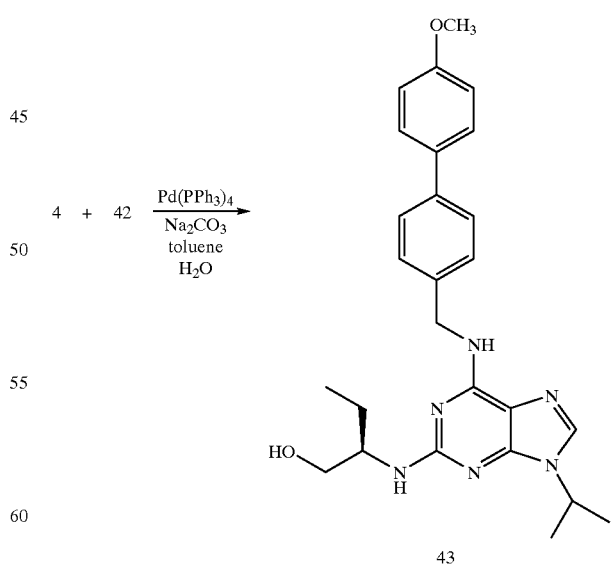
43
The synthesis of compound 46 is shown below in Scheme XII.

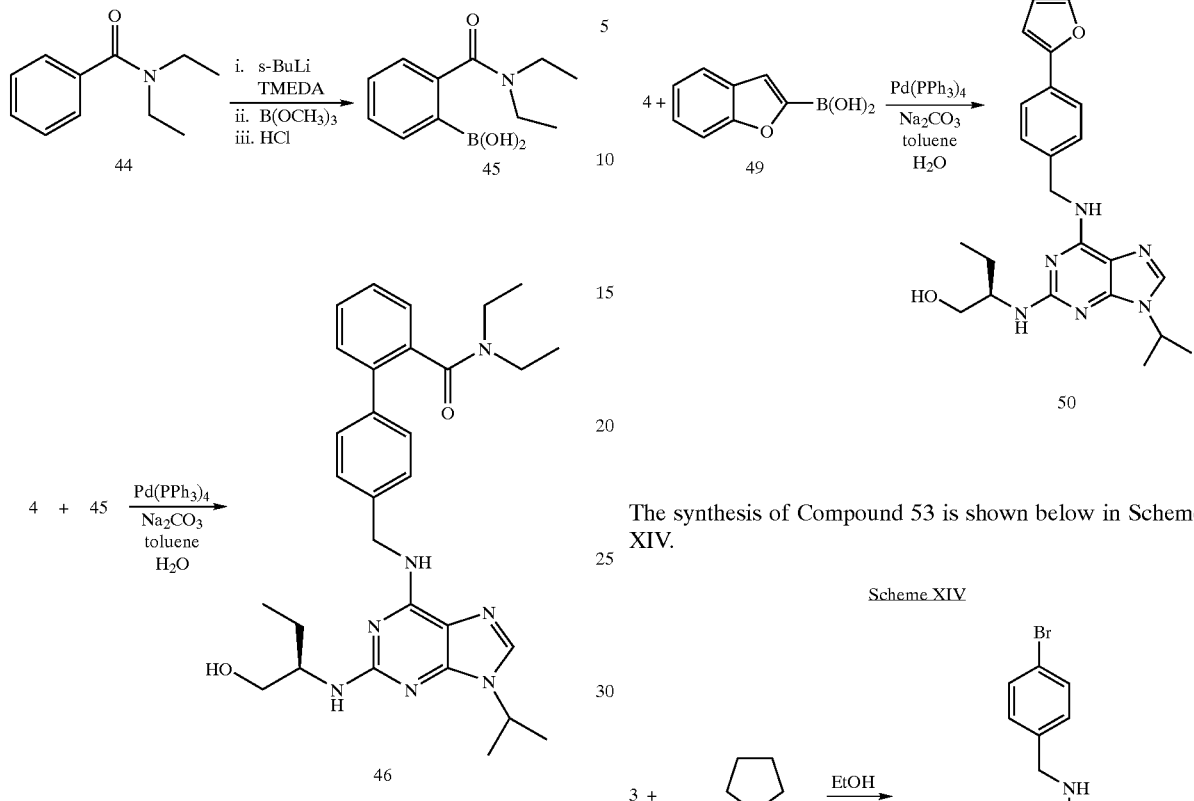
The synthesis of Compound 48 and 50 are shown below in Scheme XIII.
The synthesis of Compound 53 is shown below in Scheme XIV.
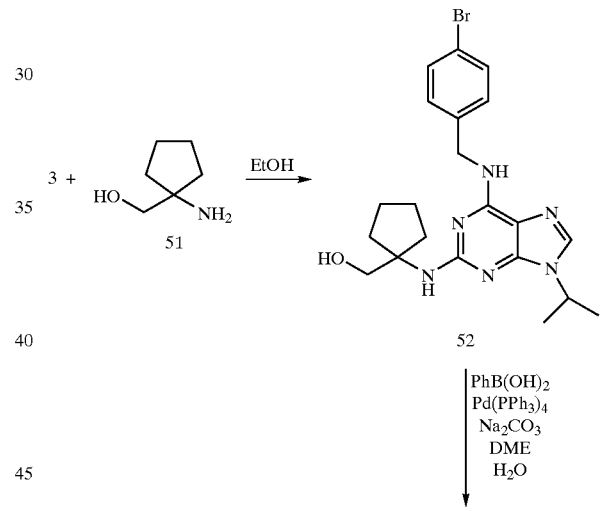
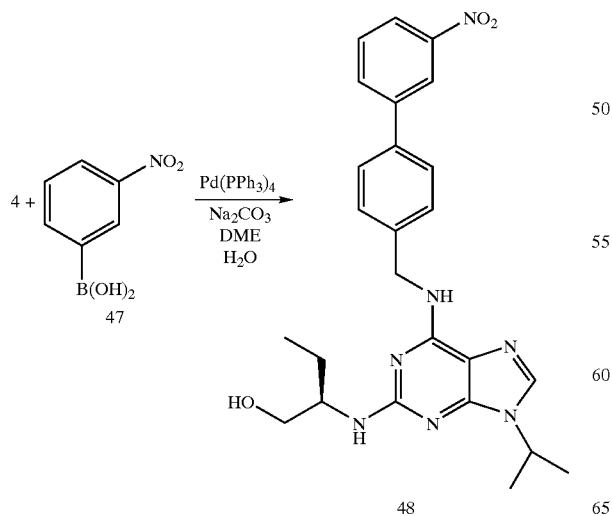

The synthesis of compound 54 is shown below in Scheme XV.
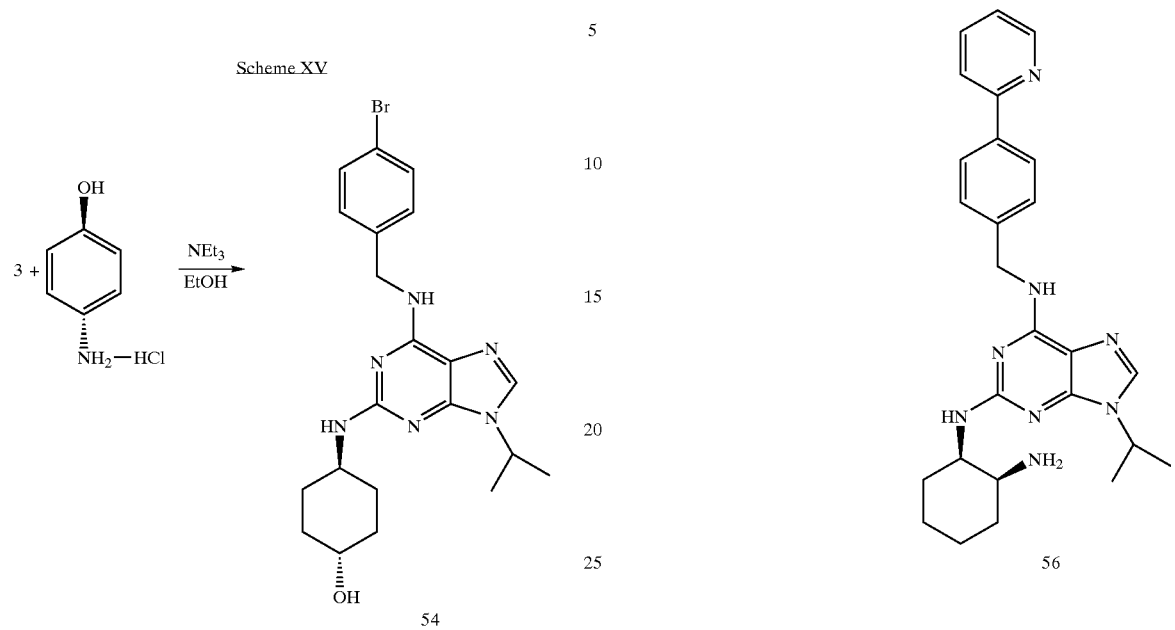
The synthesis of compound 56 is shown below in Scheme XVI.
The synthesis of compound 58 is shown below in Scheme XVII.
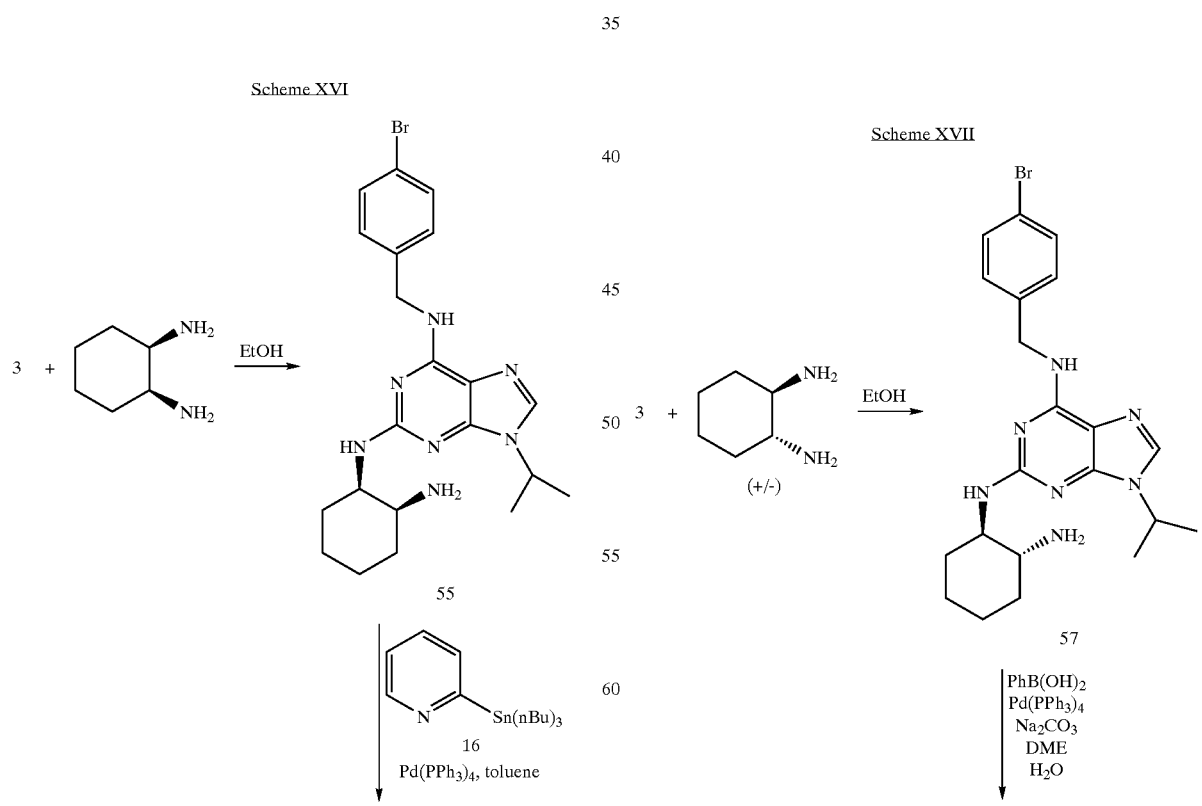

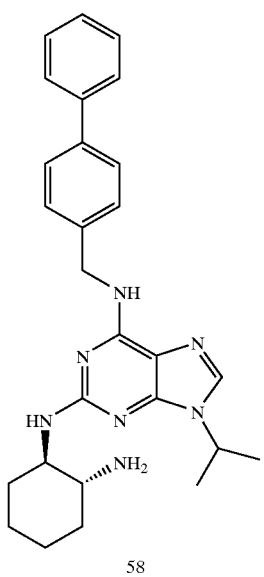
58
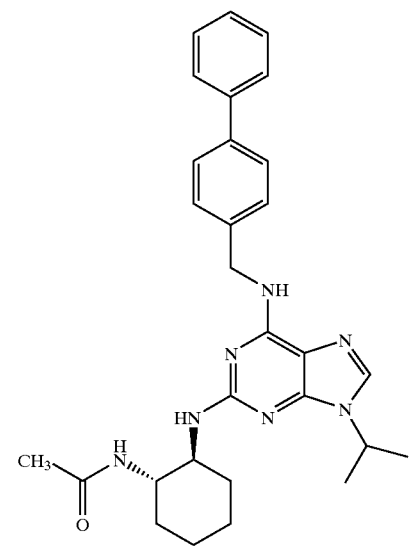
60
The synthesis of compound 60 is shown below in Scheme XVIII.
The syntheses of compounds 61, and 62 are shown below in Scheme XIX.
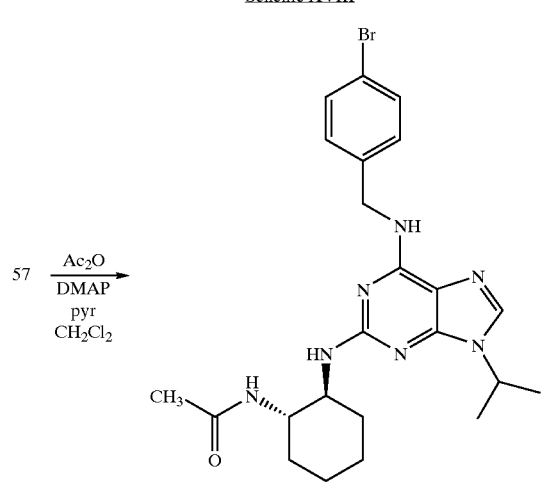
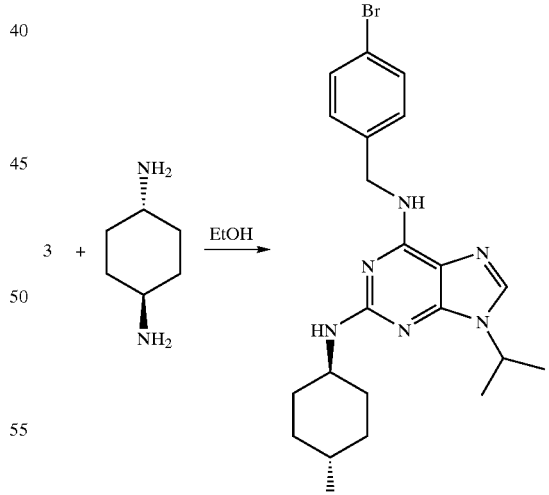

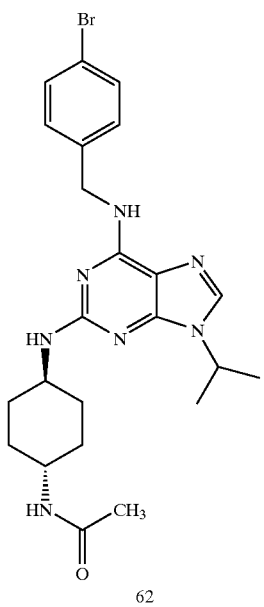
The syntheses of compounds 64, and 65 are shown below in Scheme XX.
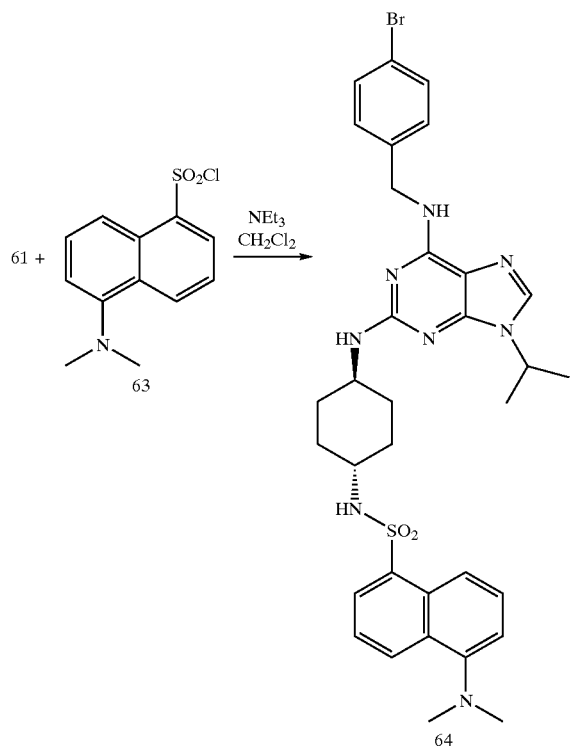
Scheme XX
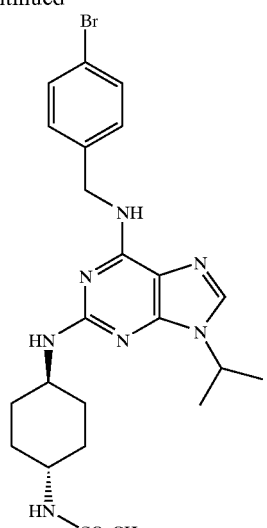
The syntheses of compounds 66, and 67 are shown below in Scheme XXI.
Scheme XXI
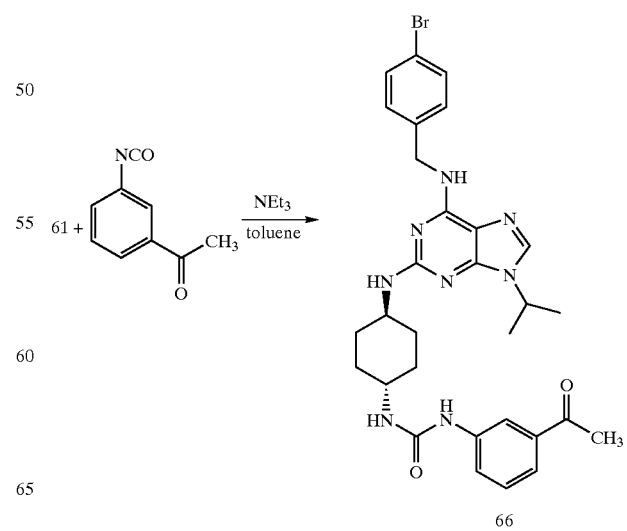

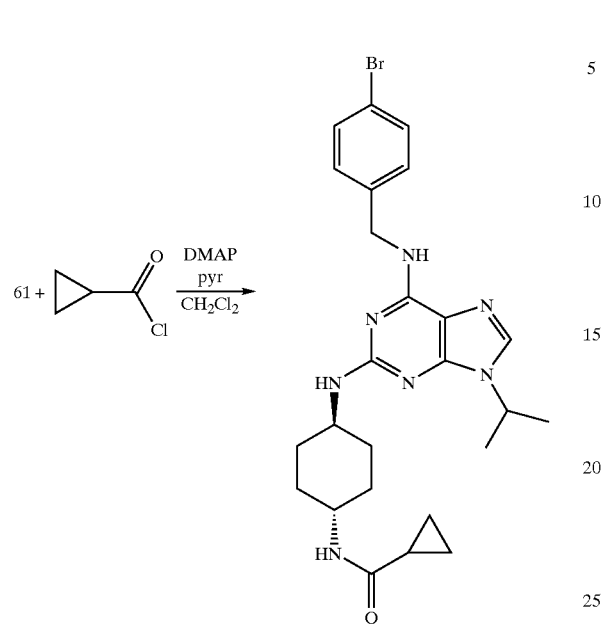
The syntheses of compound 73 is shown below in Scheme XXII.
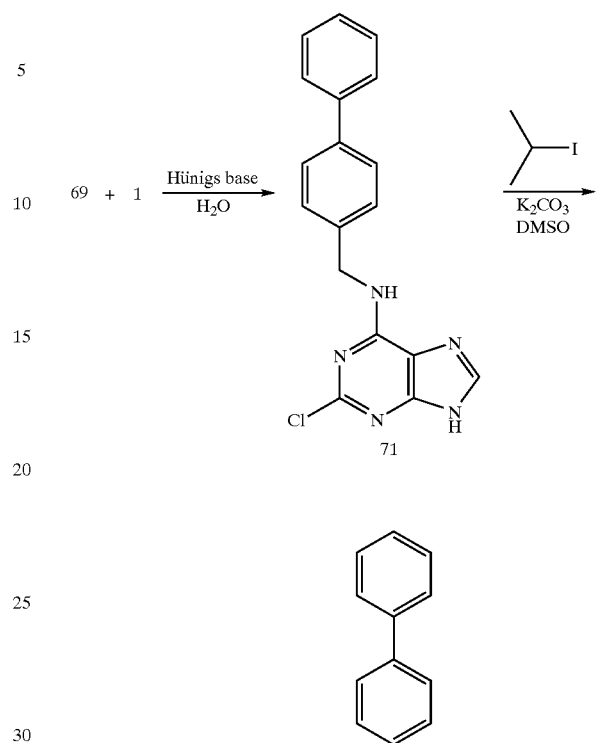
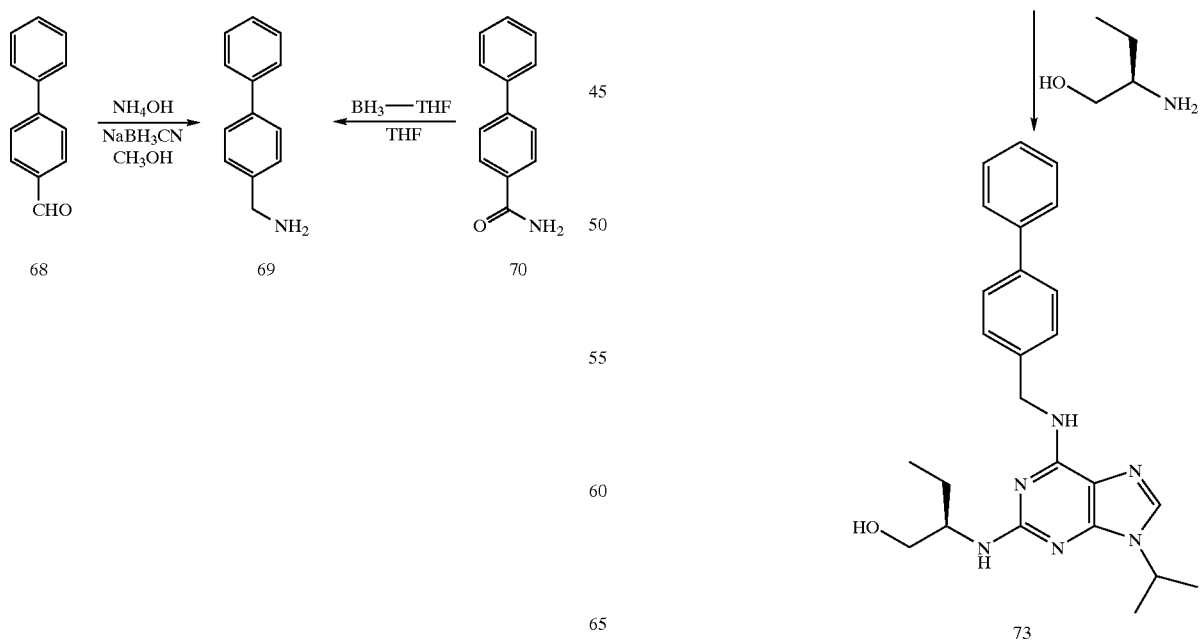

The synthesis of compounds 74, 75, and 76 are shown below in Scheme XXIII.
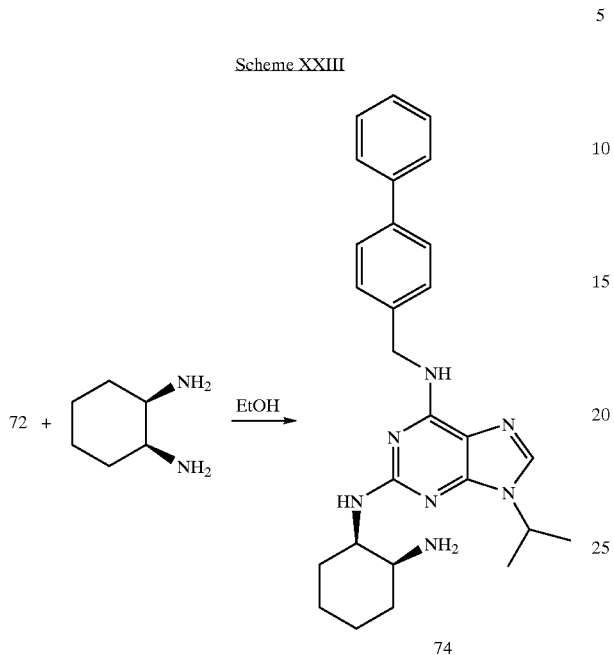
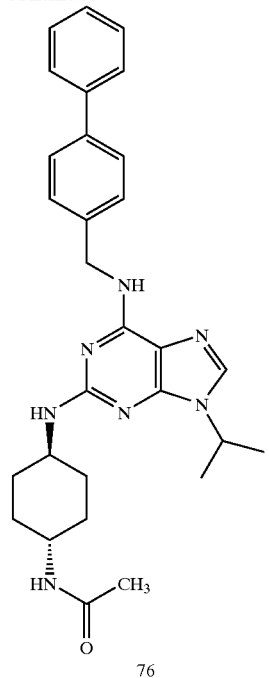
The syntheses of compound 77 is shown below in Scheme XXIV.
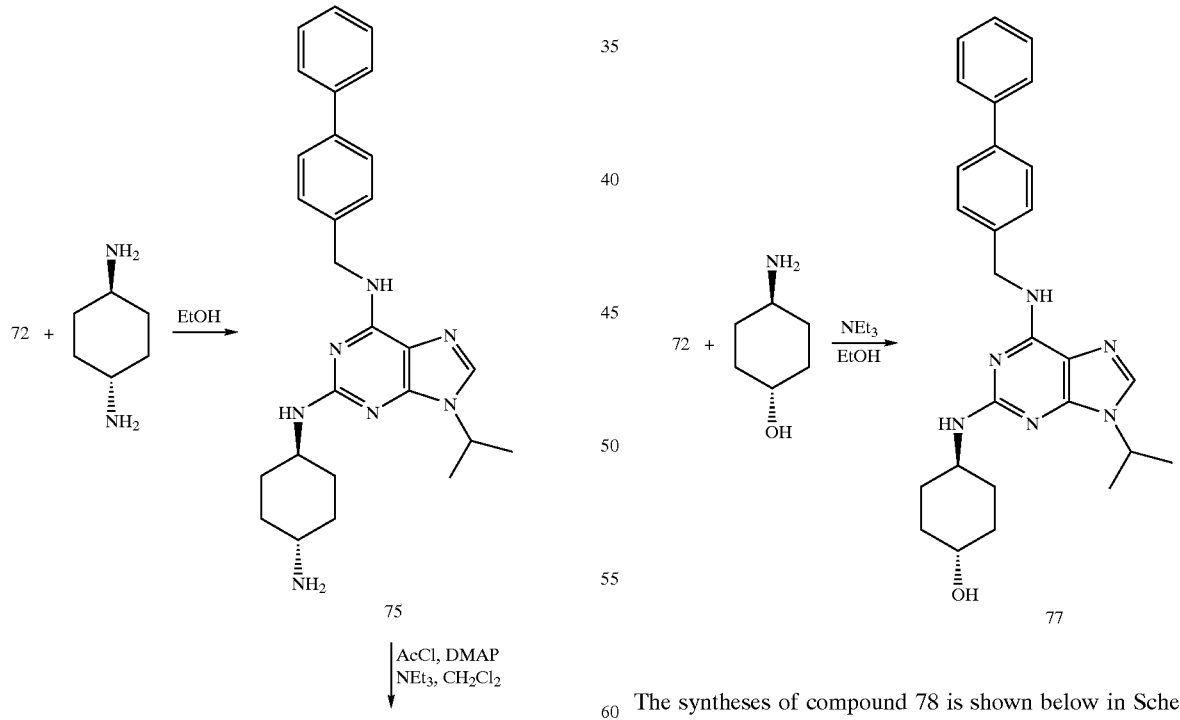
The syntheses of compound 78 is shown below in Scheme XXV.

Scheme XXV
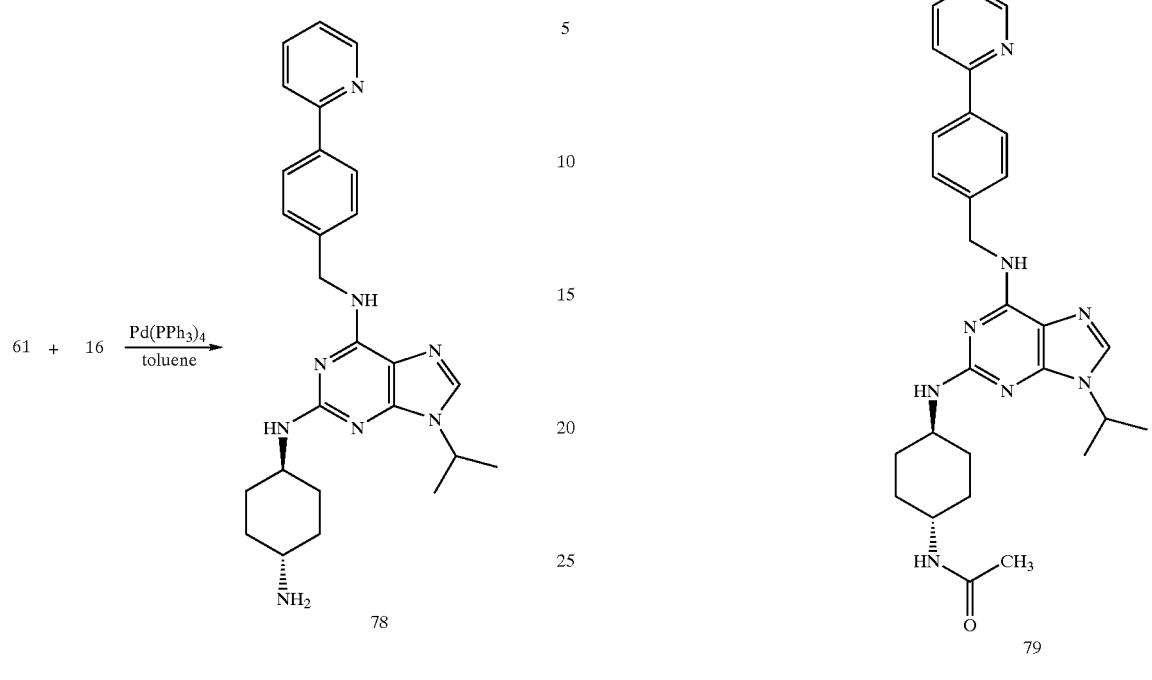
An alternative synthesis of compound 78, and the synthesis of compound 79 are shown below in Scheme XXVI.
The synthesis of compound 80 is shown below in Scheme XXVII.
Scheme XXVI
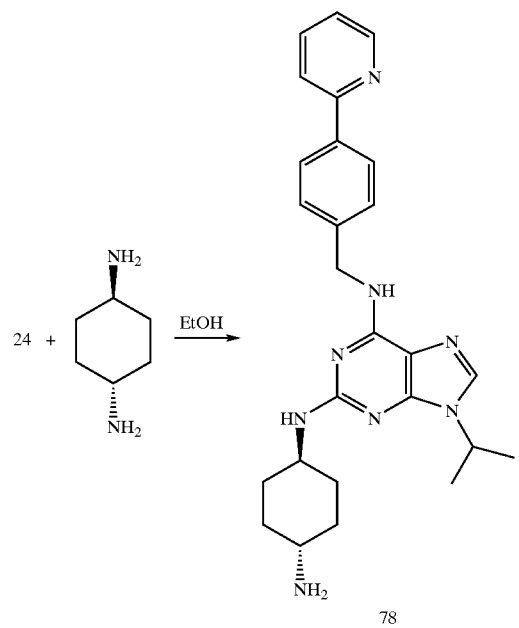
Scheme XXVII
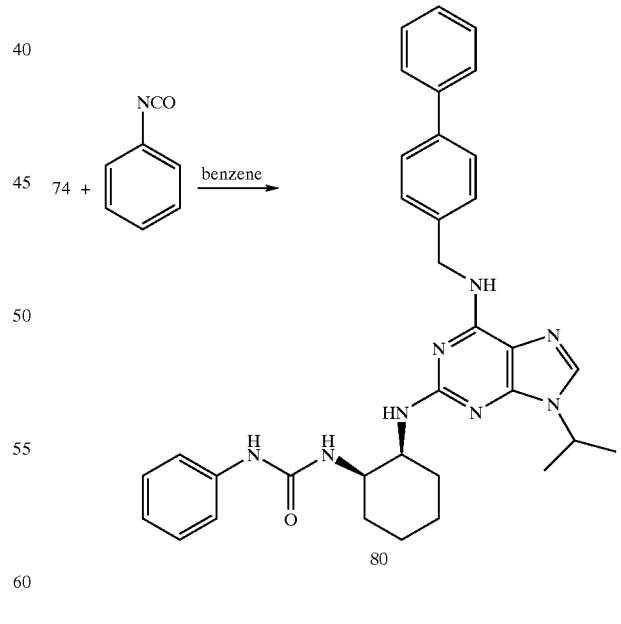
The syntheses of compounds 86, and 87 are shown below in Scheme XXVIII.

Scheme XXVIII
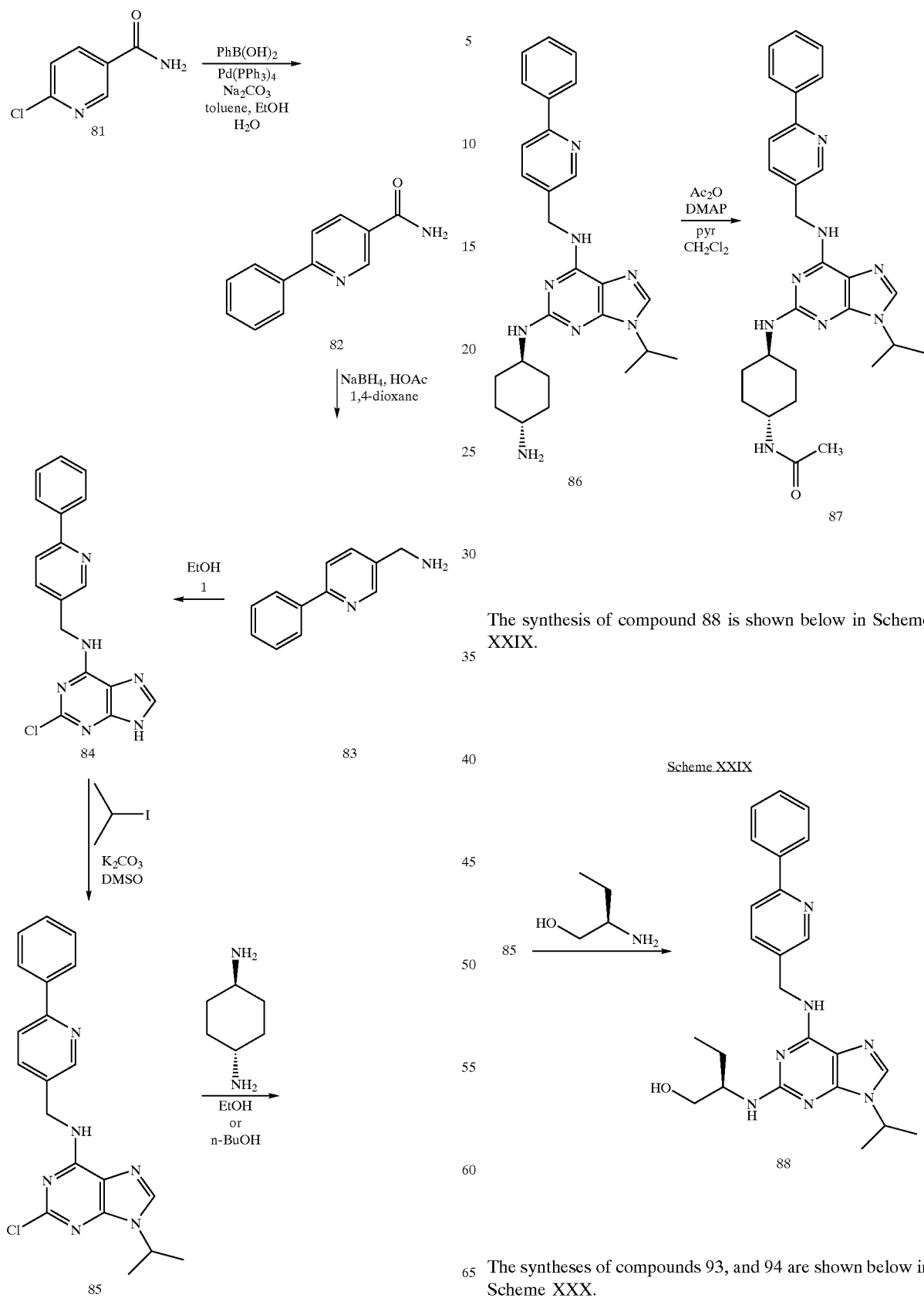
The synthesis of compound 88 is shown below in Scheme XXIX.
Scheme XXIX
The syntheses of compounds 93, and 94 are shown below in Scheme XXX.

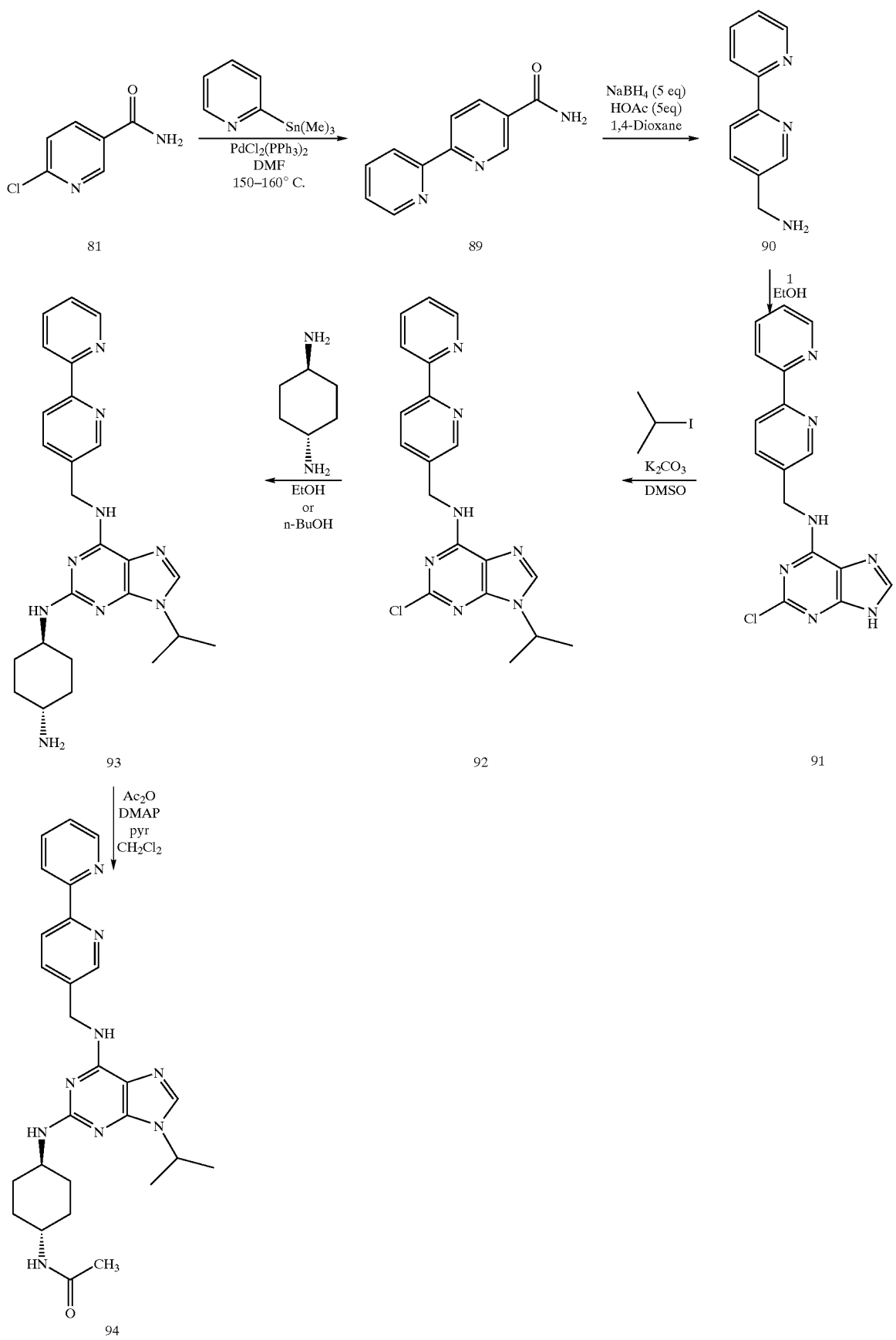
Scheme XXX

The syntheses of compounds 95, and 96 are shown below in Scheme XXXI.
The synthesis of compound 97 is shown below in Scheme XXXII.
The syntheses of compounds 98, and 99 are shown below in Scheme XXXIII.
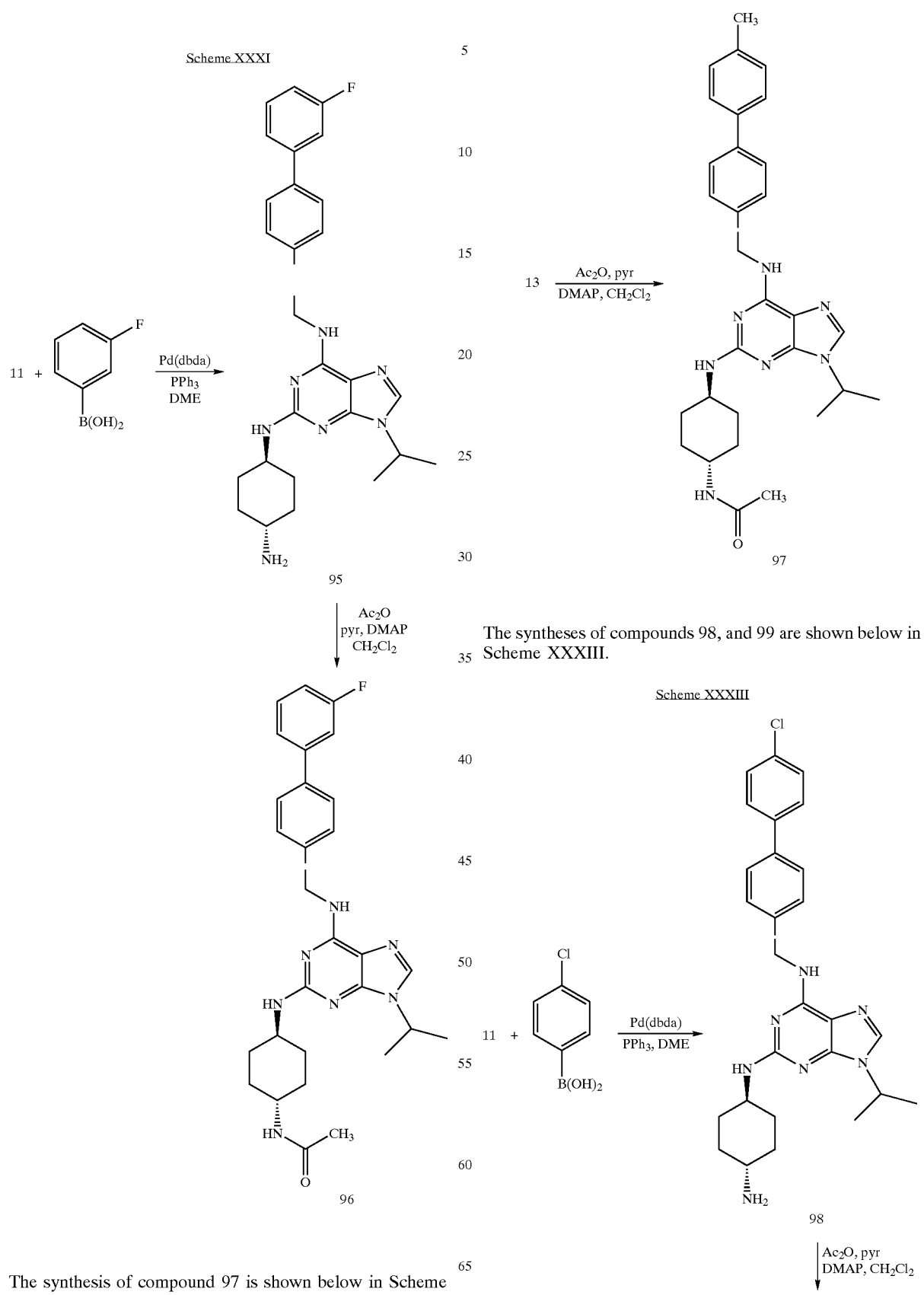

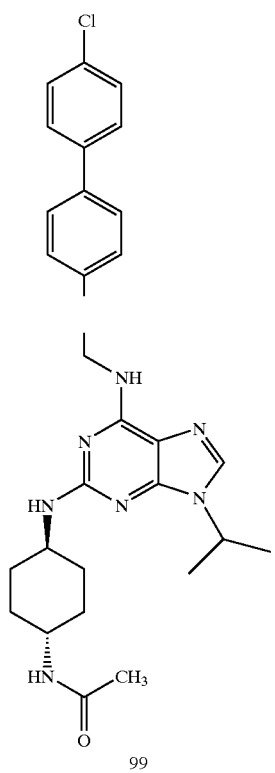
The syntheses of compound 100 is shown below in Scheme XXXIV.
The syntheses of compounds 101, and 102 are shown below in Scheme XXXV.
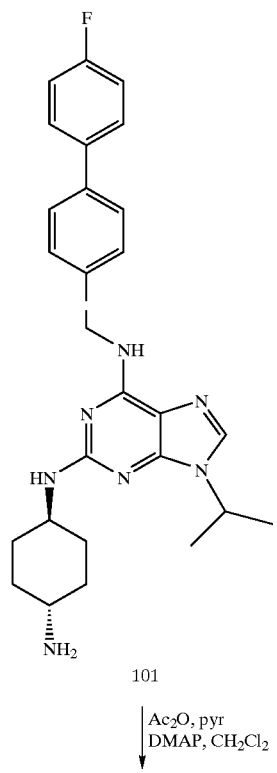
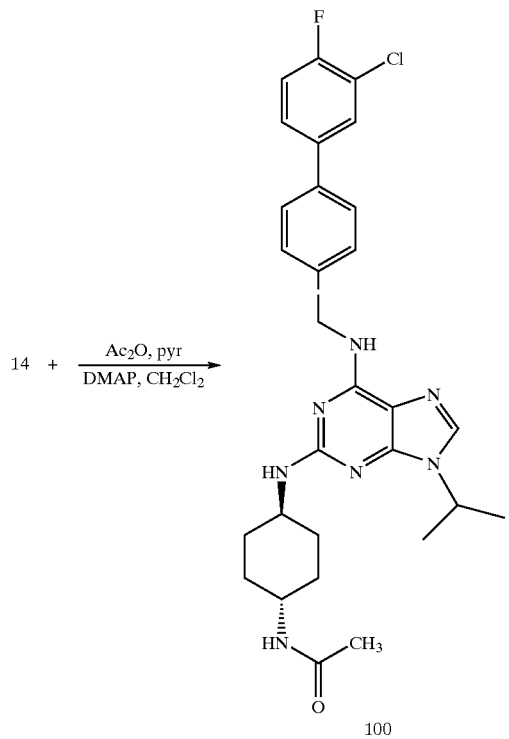
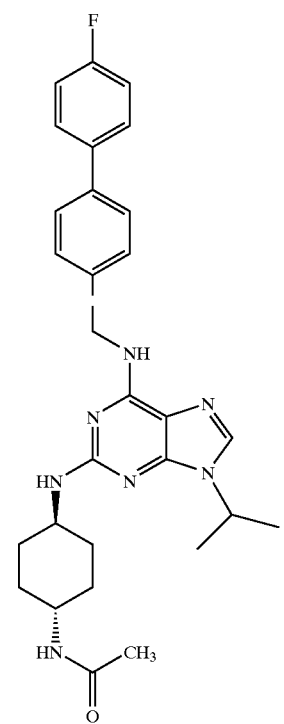
The syntheses of compounds 103, and 104 are shown below in Scheme XXXVI.

The syntheses of compounds 106, 107, and 108 are shown below in Scheme XXXVII.
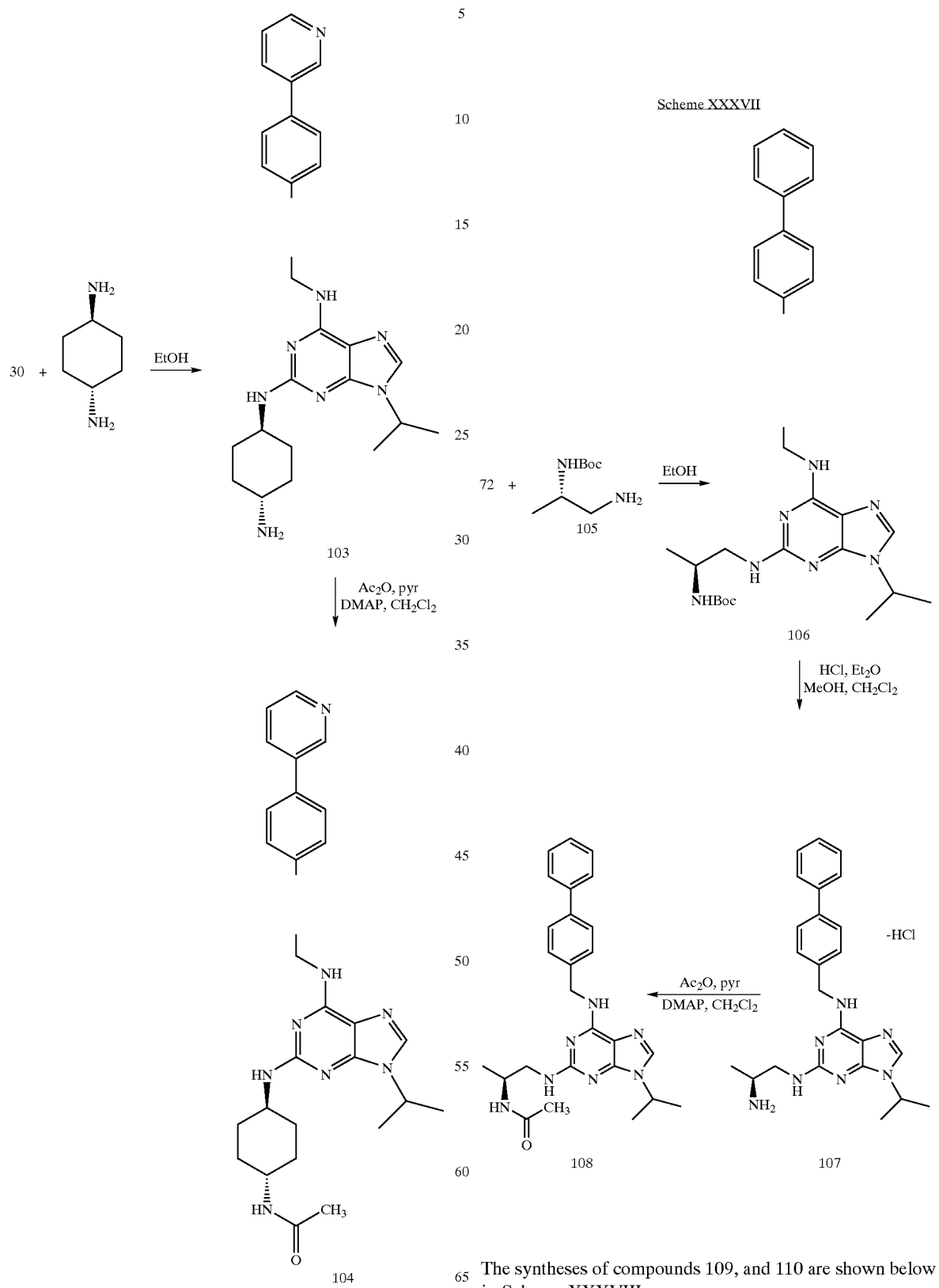
The syntheses of compounds 109, and 110 are shown below in Scheme XXXVIII.

The syntheses of compounds 111, and 112 are shown below in Scheme XXXIX.
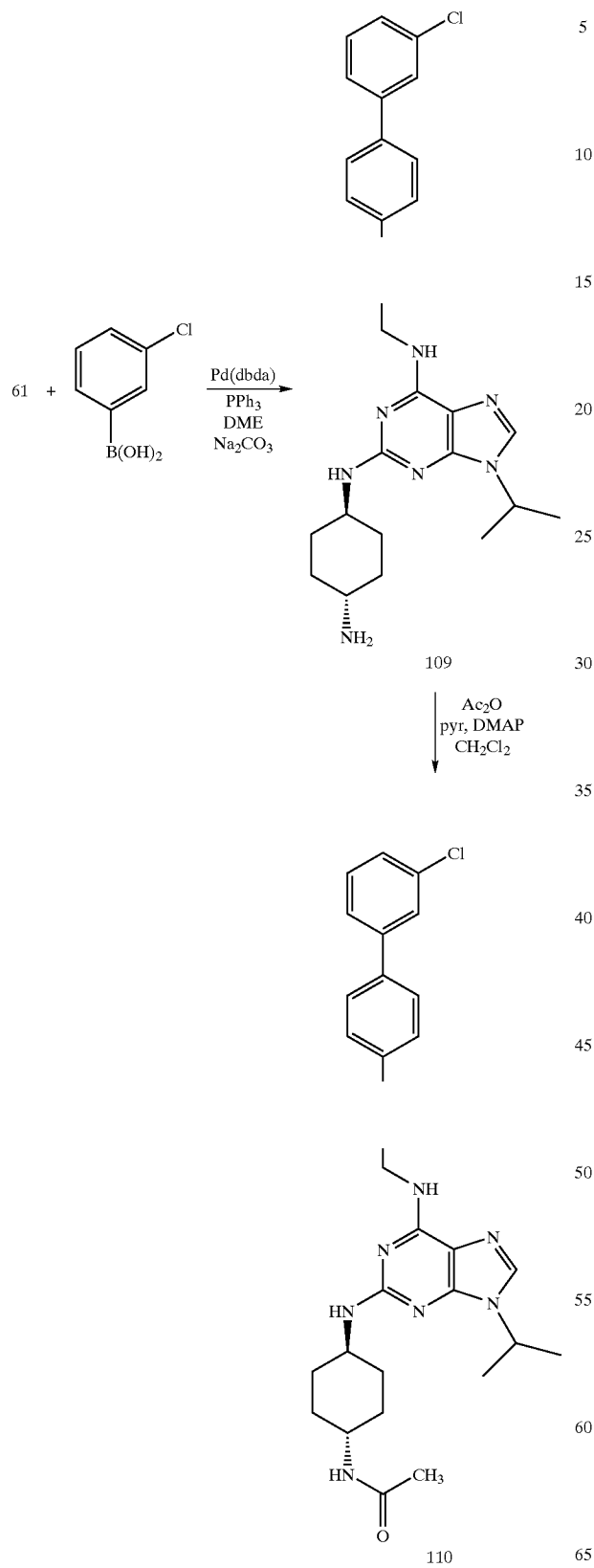
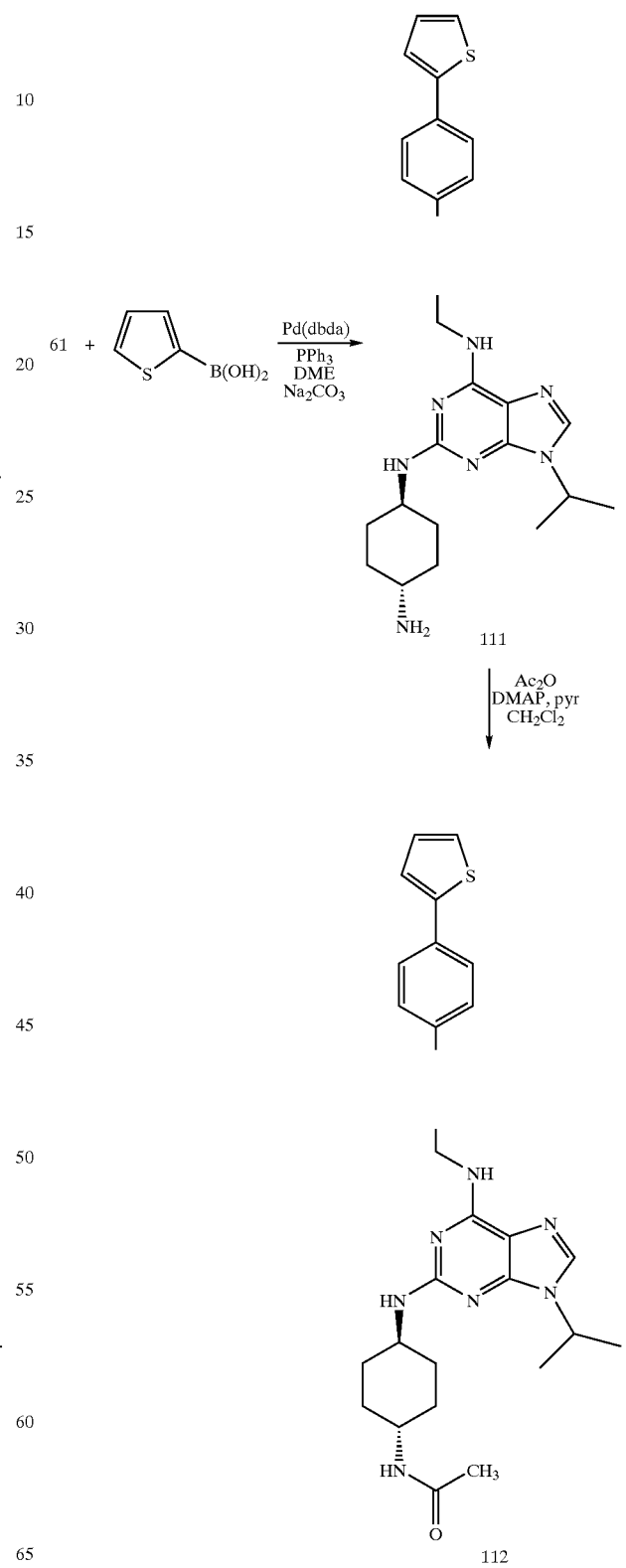

The synthesis of compound 113 is shown below in Scheme XL.
Scheme XL
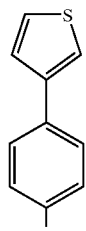
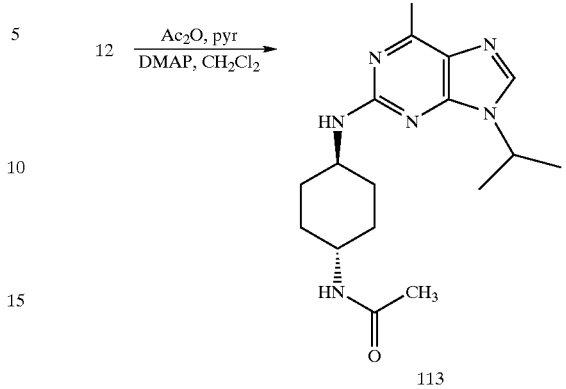
113
The syntheses of compounds 114, 115, 116, and 117 are shown below in Scheme XLI.
Scheme XLI
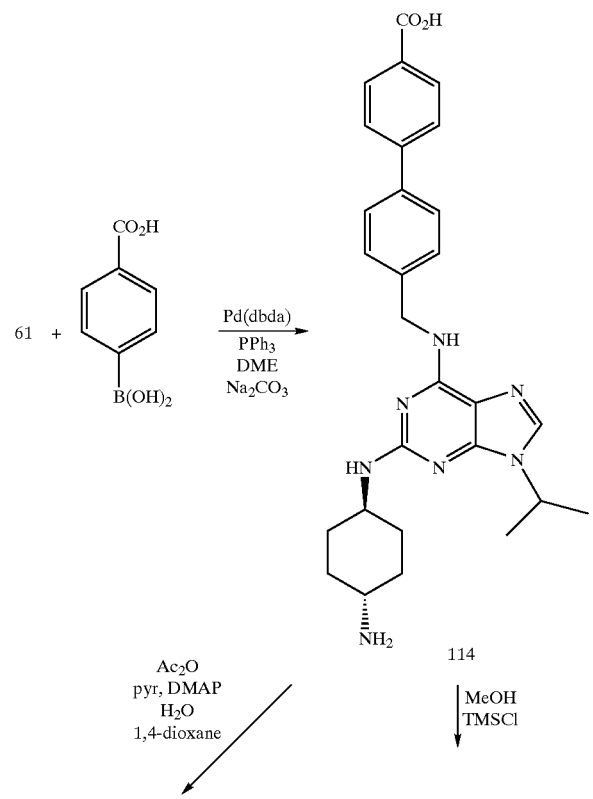

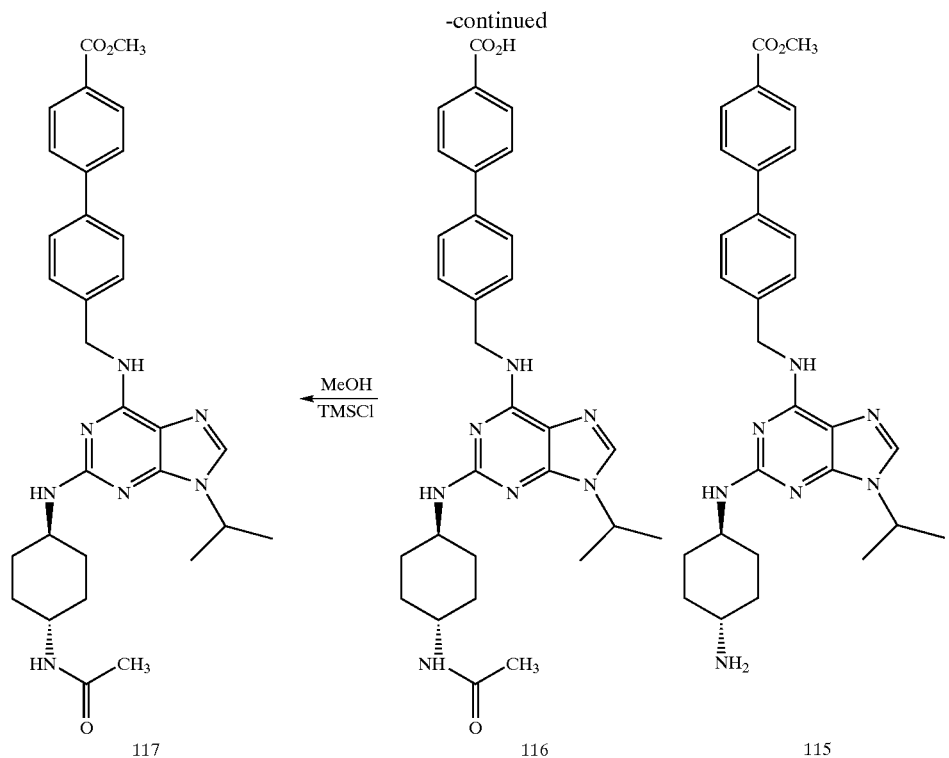
The syntheses of compound 118 is shown below in Scheme XLII.
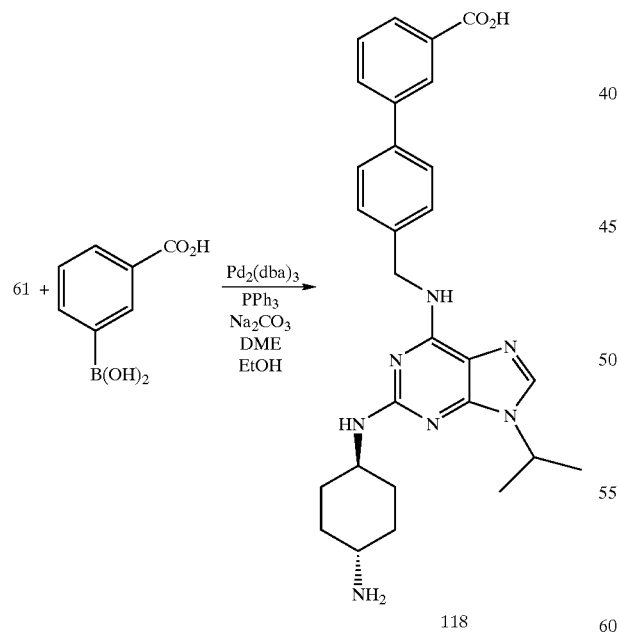
The syntheses of compounds 123 and 124 are shown below in Scheme XLIII.

US 6,949,559 B2
Scheme XLIII
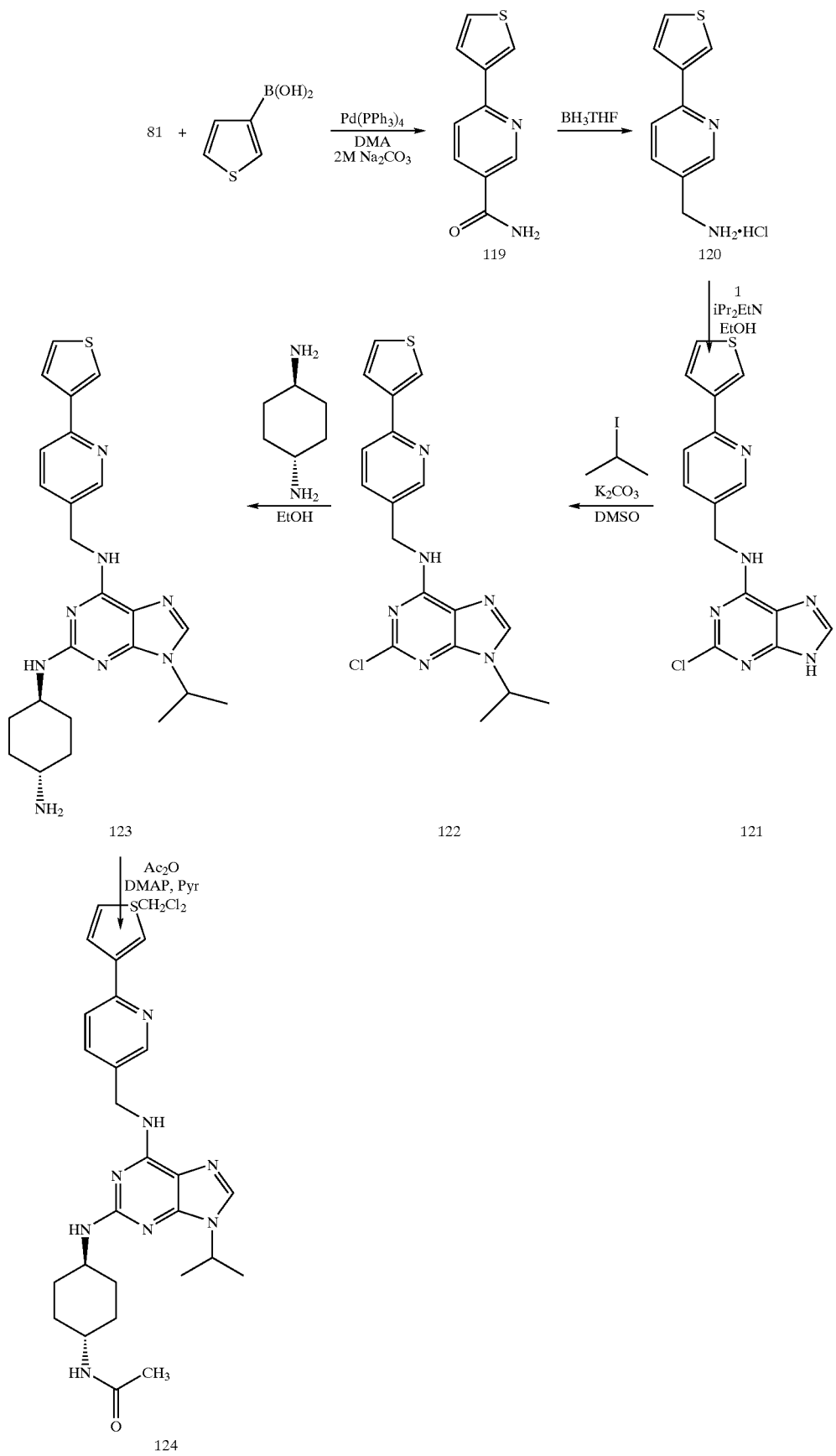

The syntheses of compounds 131 and 132 are shown below in Scheme XLIV.
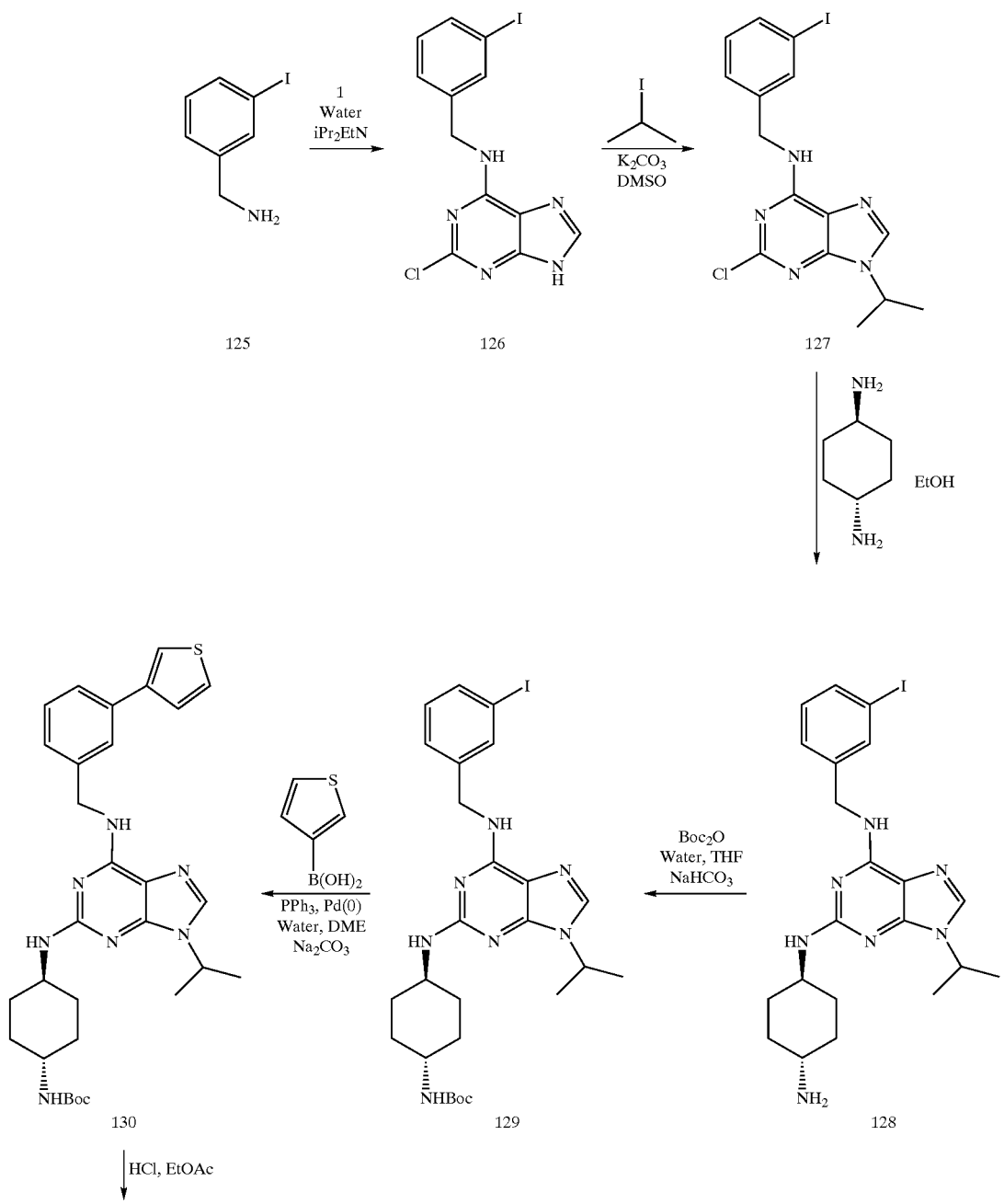
Scheme XLIV -continued
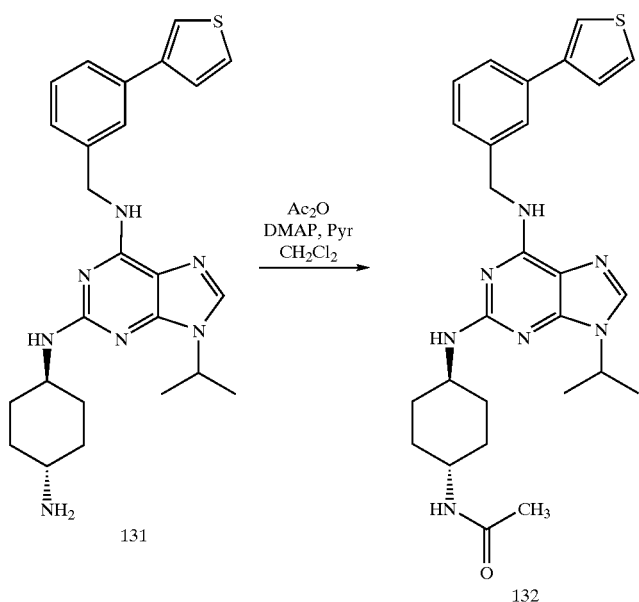
The syntheses of compounds 134 and 135 are shown below in Scheme XLV.
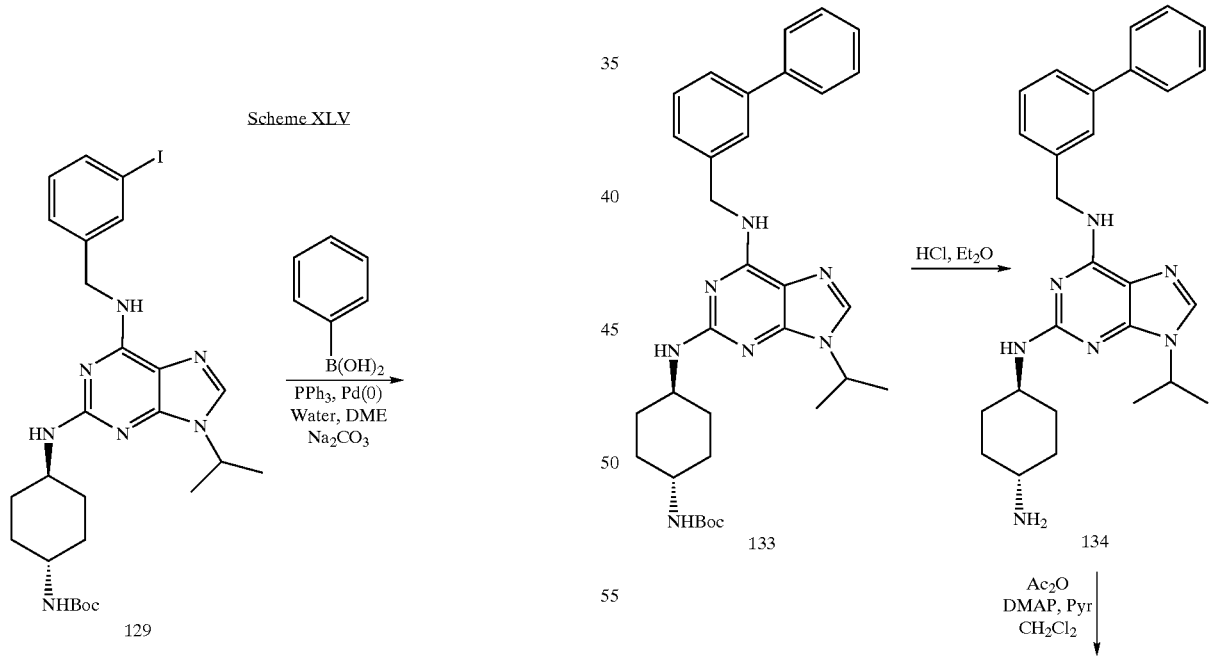

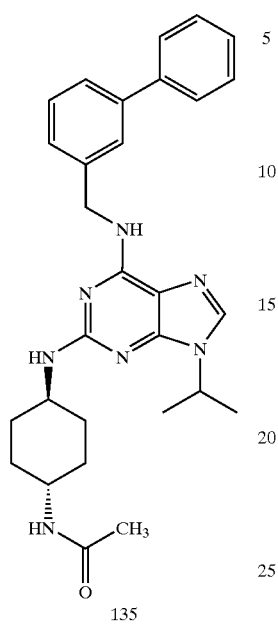
135
The synthesis of compound 137 is shown below in Scheme XLVI.
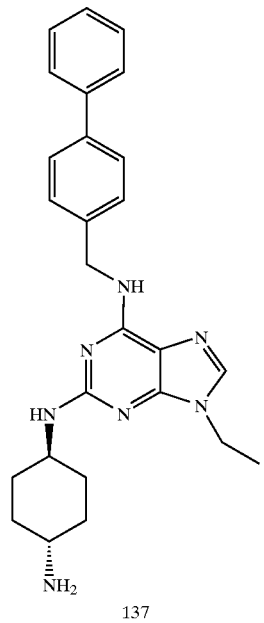
137
The syntheses of compounds 139 and 140 are shown below in Scheme XLVII.
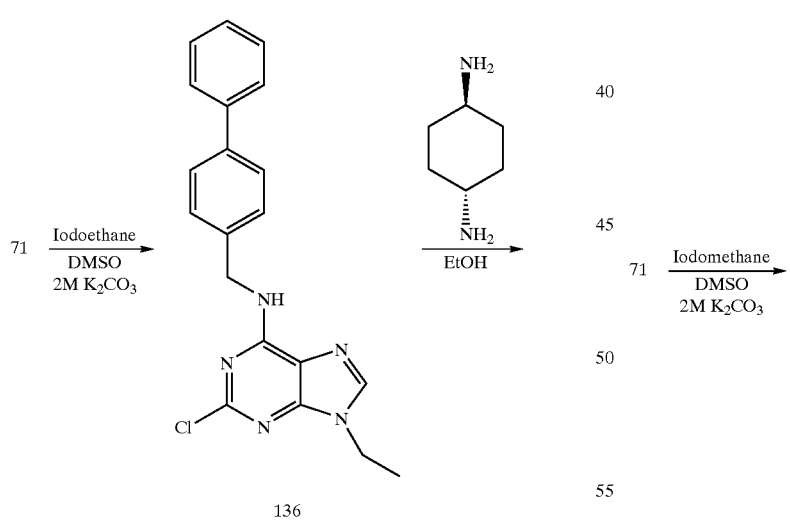
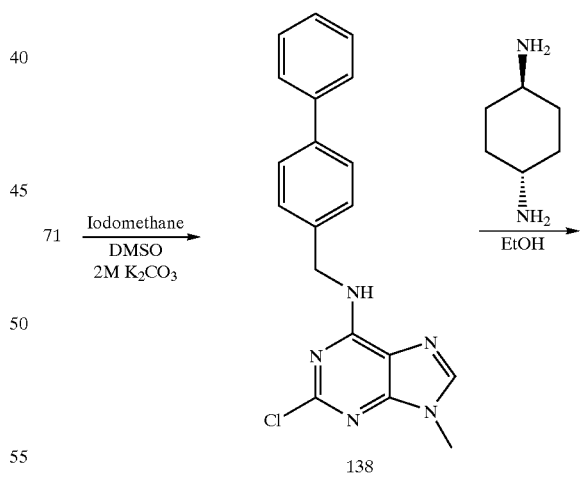

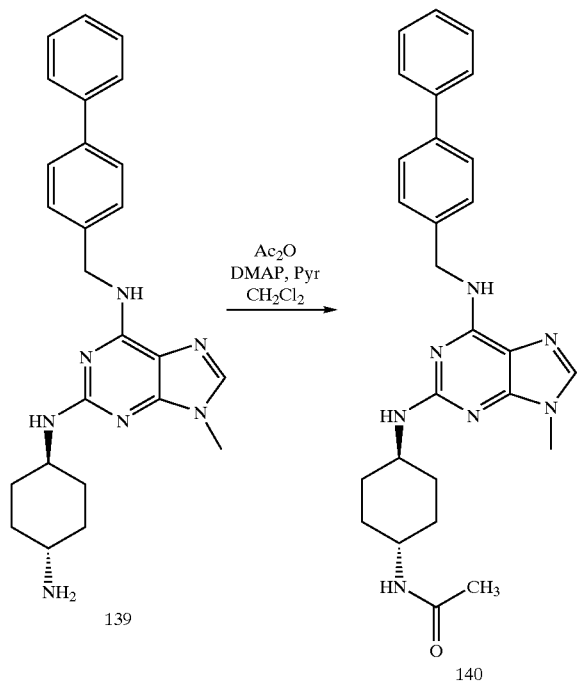
139
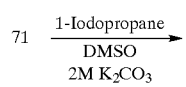
140
The synthesis of compound 142 is shown below in Scheme XLVIII.
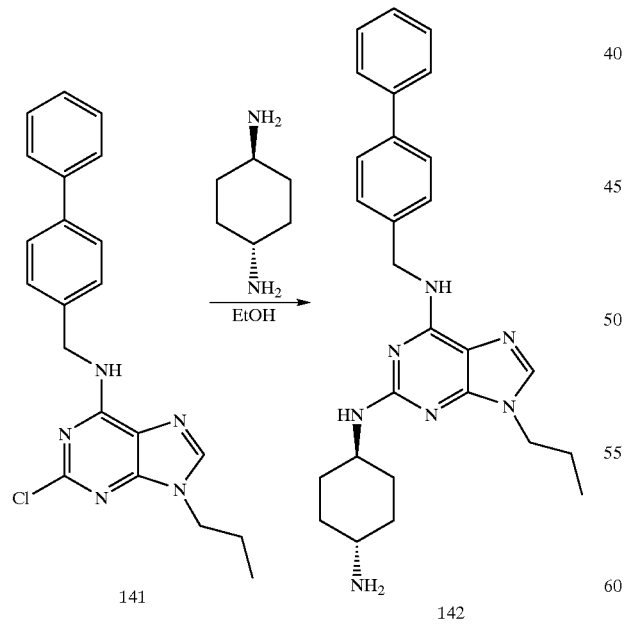
141
142
The synthesis of compound 144 is shown below in Scheme XLIX.
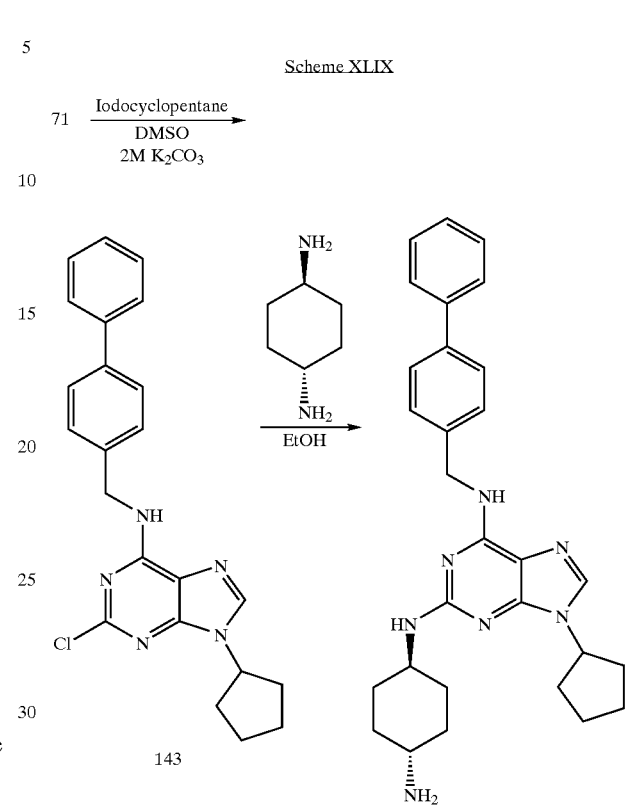
143
144
The synthesis of compound 146 is shown below in Scheme L.
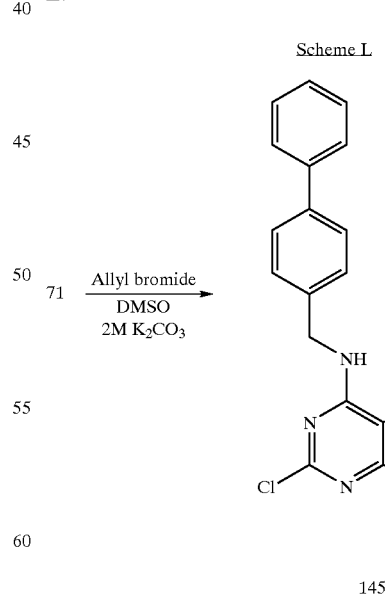
145

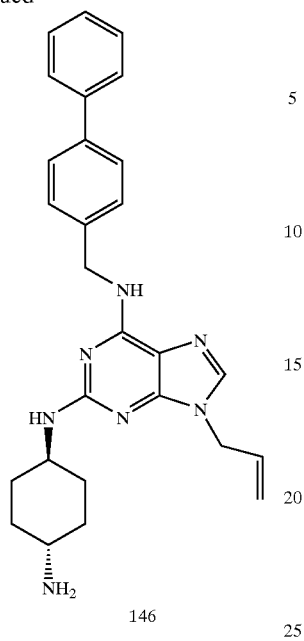
146
The syntheses of compound 148 is shown below in Scheme LI.
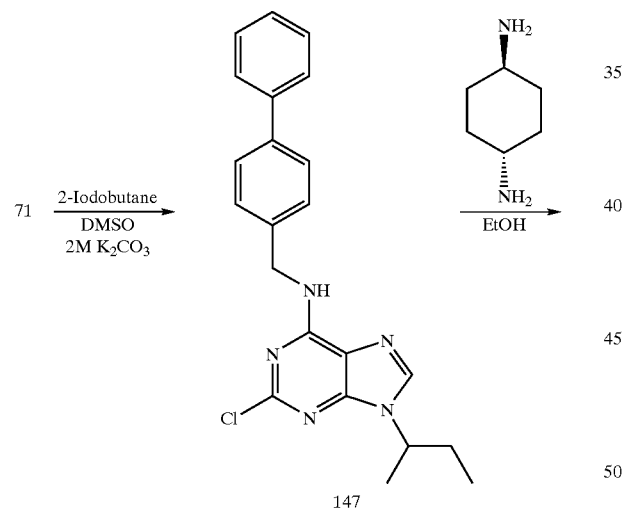
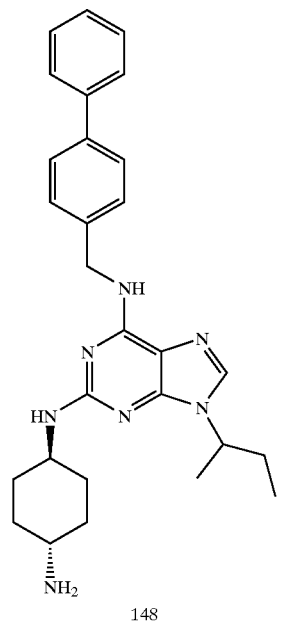
148
The syntheses of compounds 149–152 are shown below in Scheme LII.

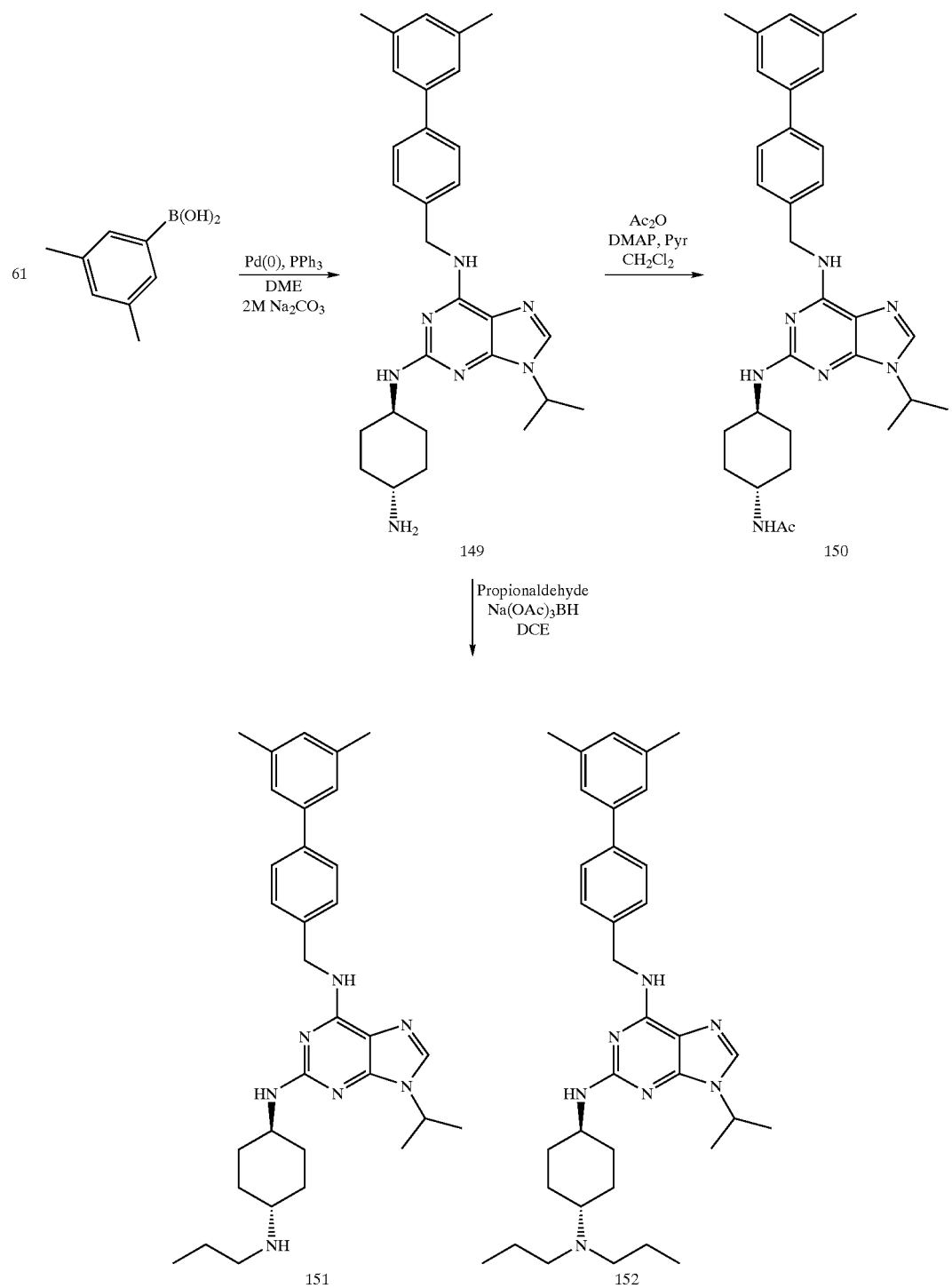

The syntheses of compounds 153–156 are shown below in Scheme LIII.
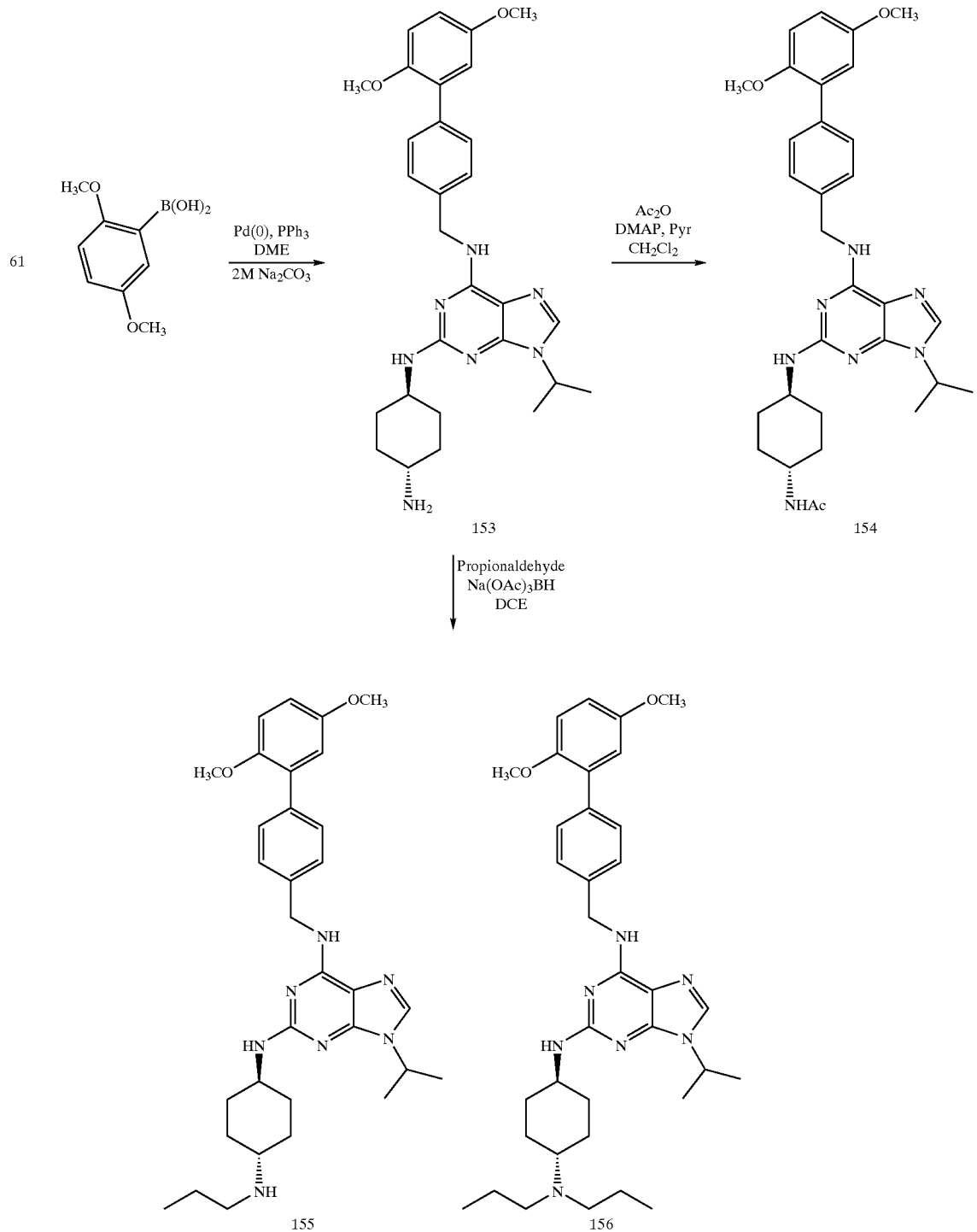

The syntheses of compounds 157–159 are shown below in Scheme LIV.
Scheme LIV
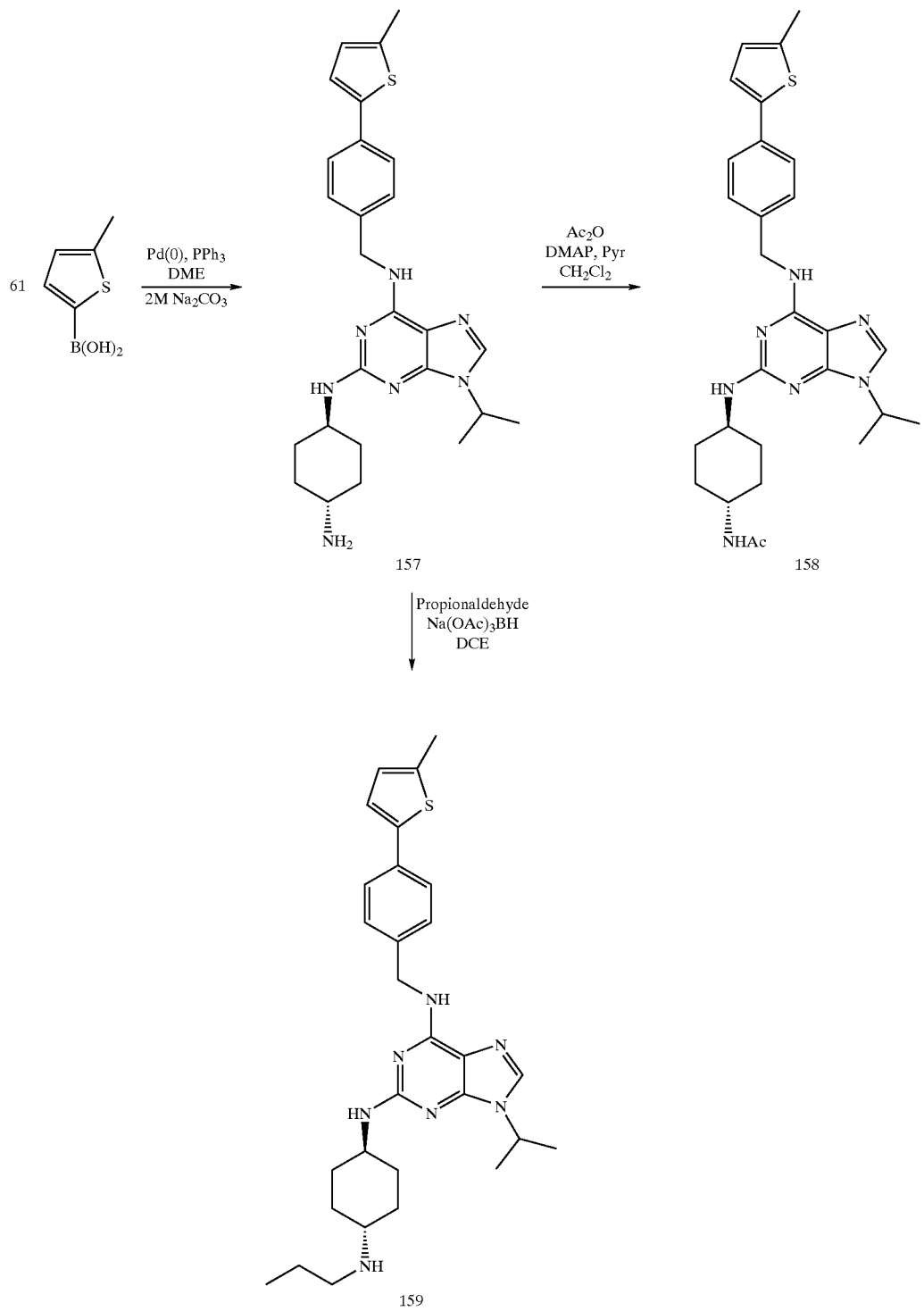

The syntheses of compounds 160–163 are shown below in Scheme LV.
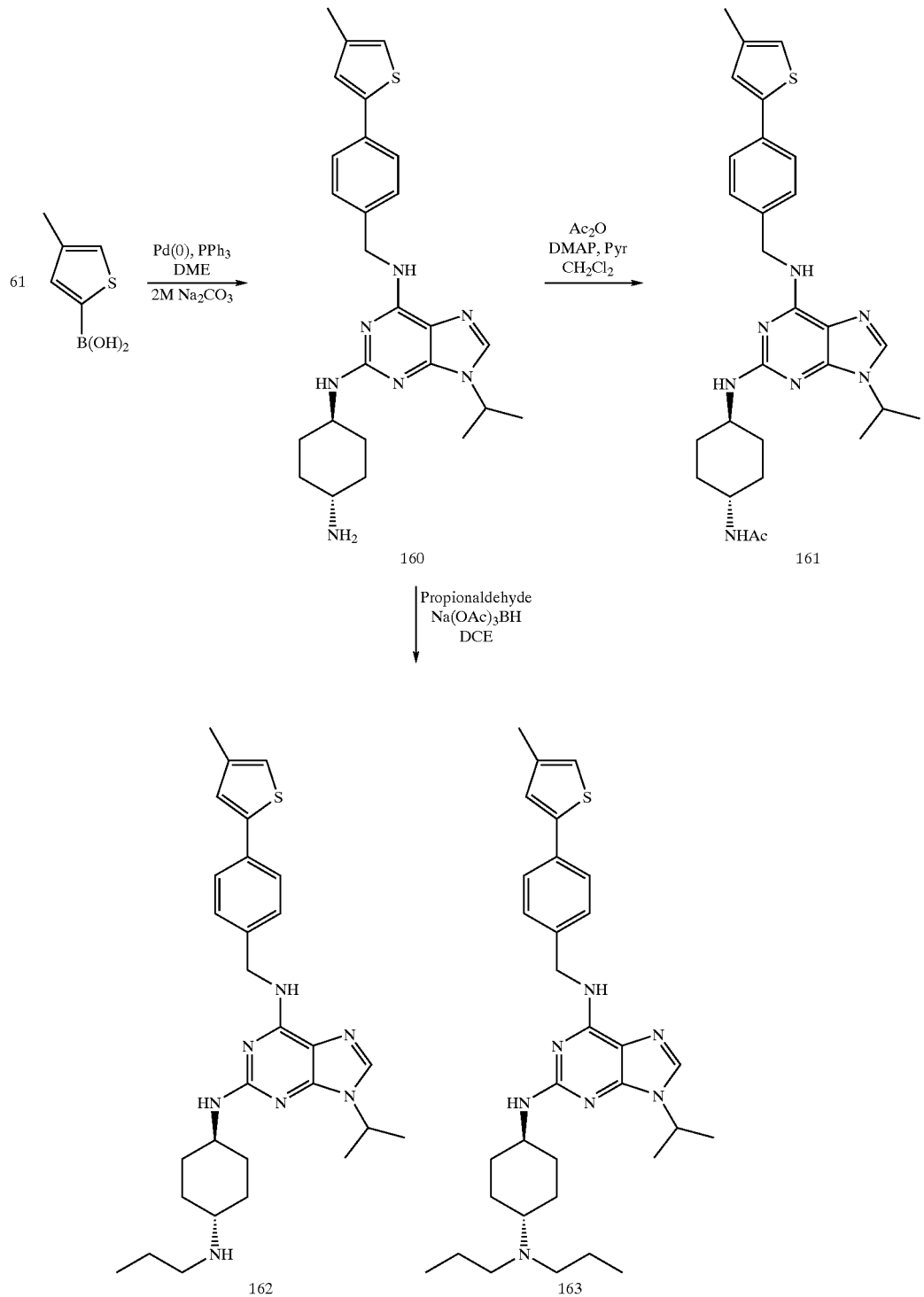

The syntheses of compounds 164–166 are shown below in Scheme LVI.
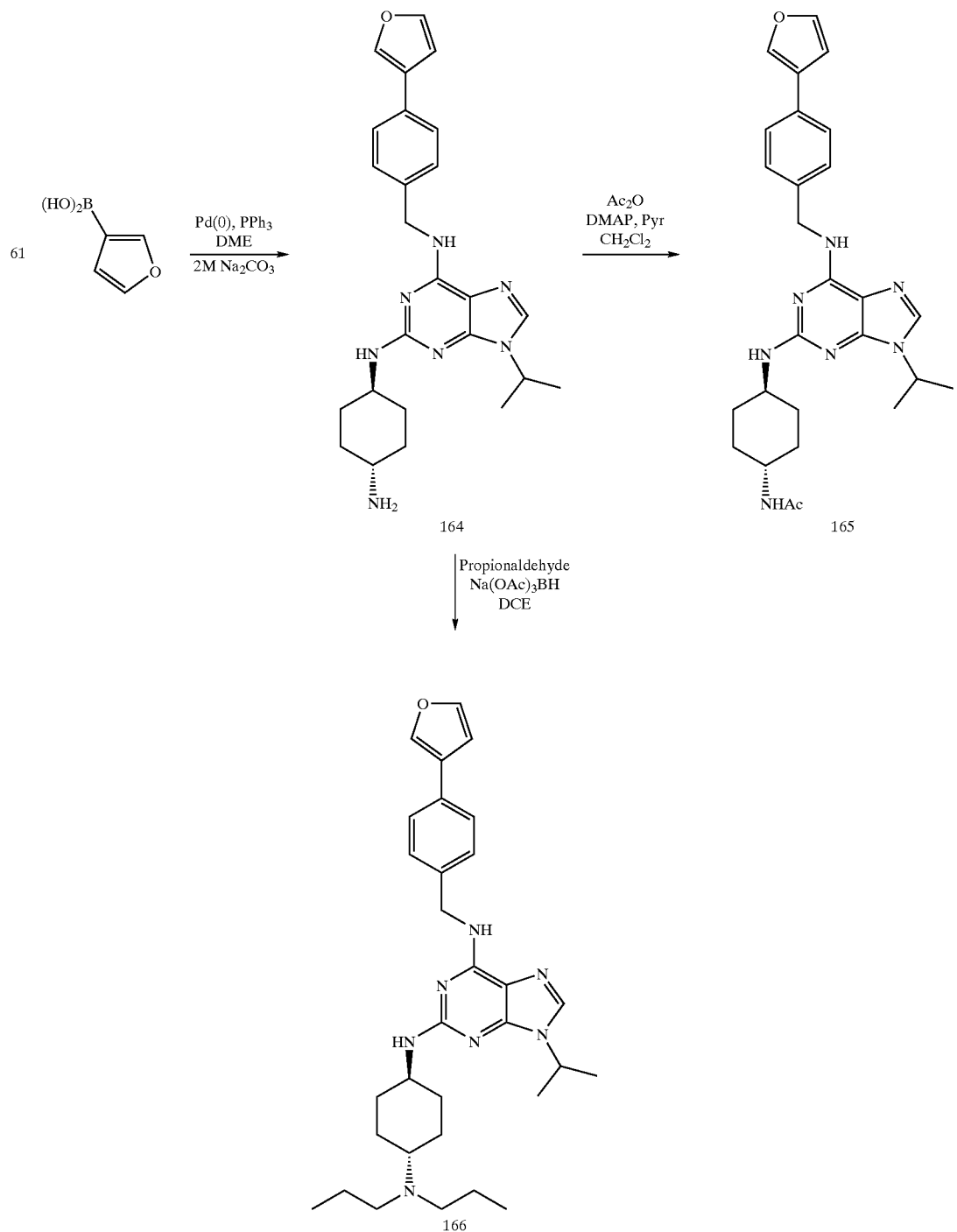

The syntheses of compounds 167–168 are shown below in Scheme LVII.
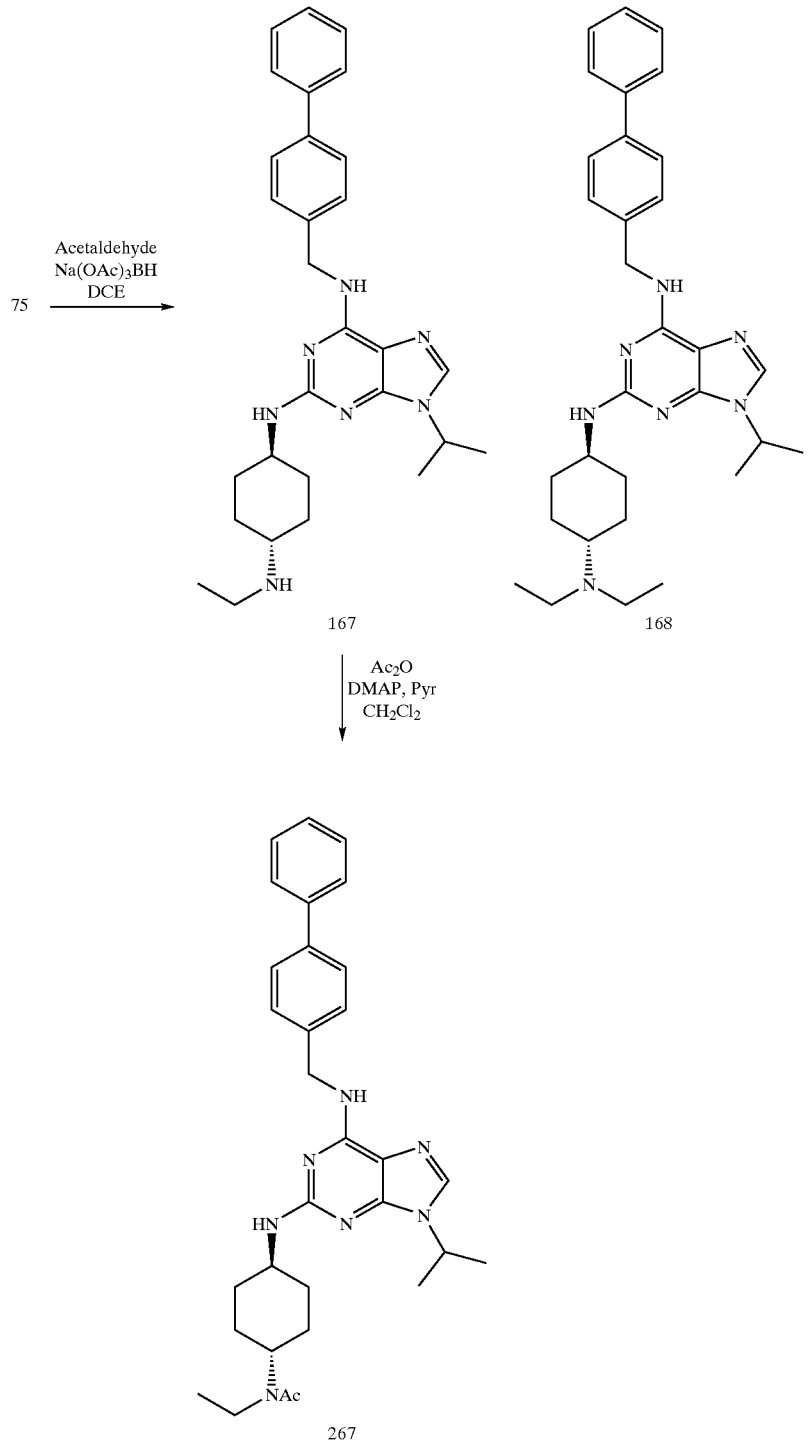

The syntheses of compounds 169–171 are shown below in Scheme LVIII.
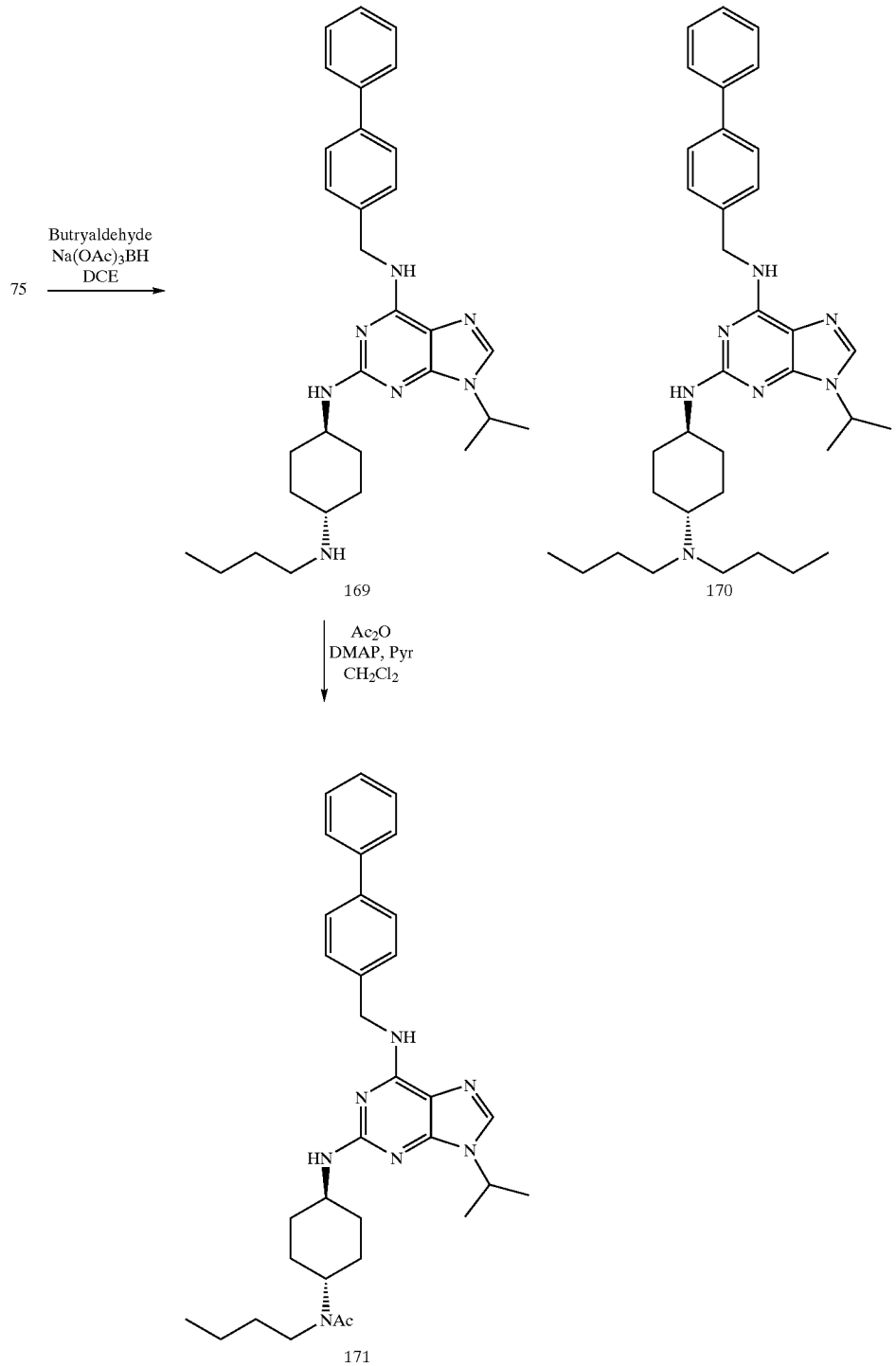

The syntheses of compounds 172–173 are shown below in Scheme LIX.
Scheme LIX
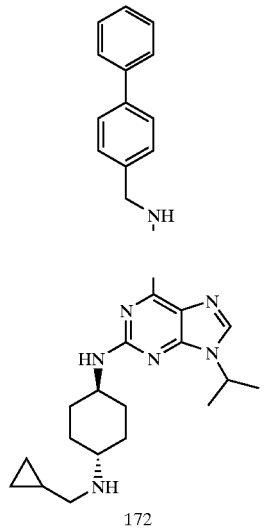
The syntheses of compounds 174–176 are shown below in Scheme LX.
Scheme LX
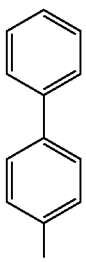
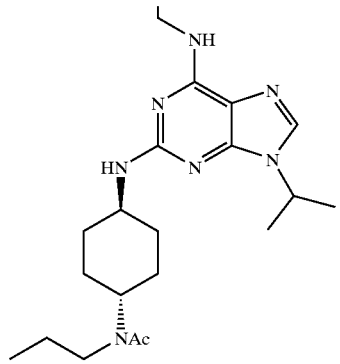
176
The syntheses of compounds 177–178 are shown below in Scheme LXI.
Scheme LXI
The syntheses of compounds 179–180 are shown below in Scheme LXII.

Scheme LXII
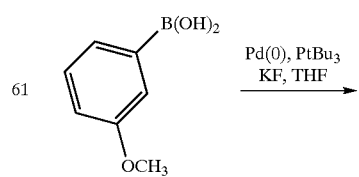
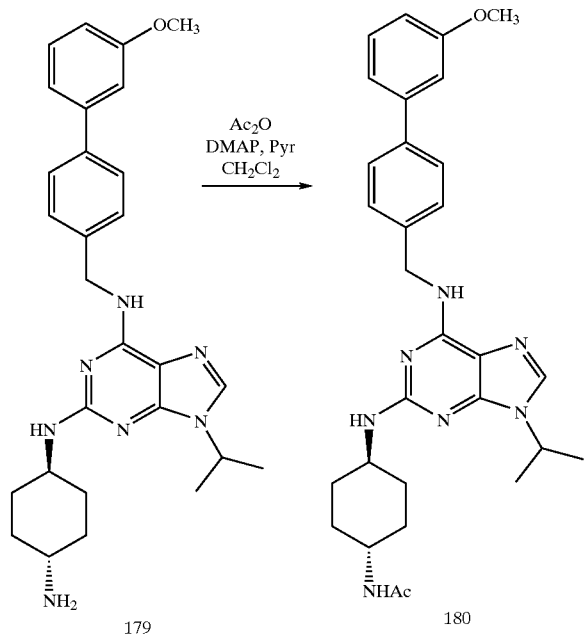
Scheme LXIII
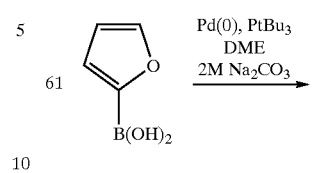
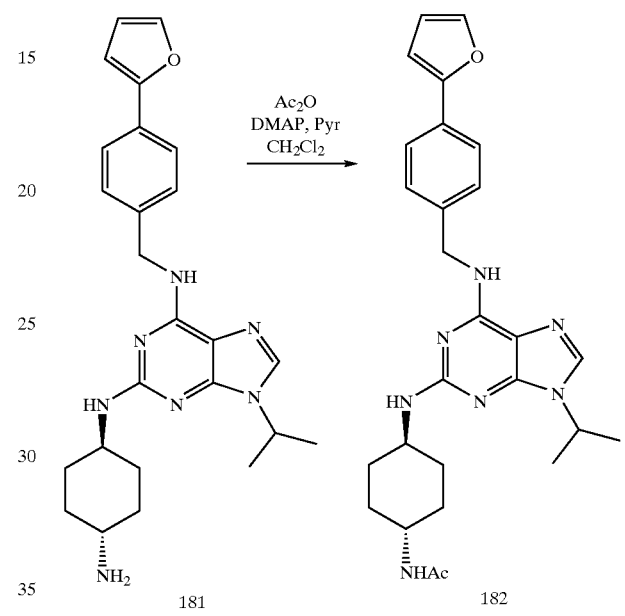
The syntheses of compounds 181–182 are shown below in Scheme LXIII.
The syntheses of compounds 187–188 are shown below in Scheme LXIV.
Scheme LXIV
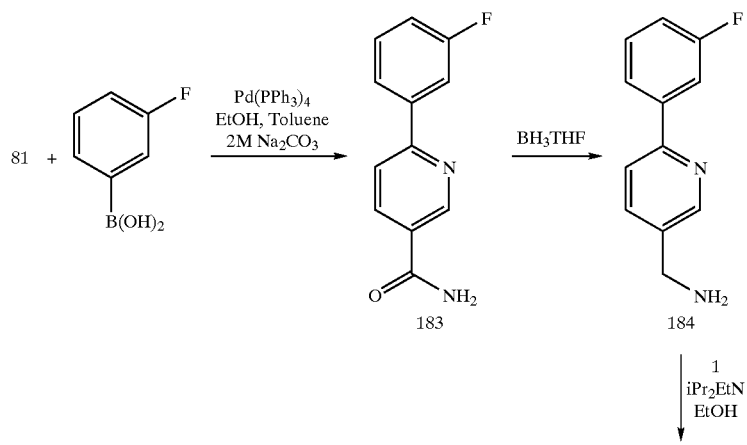

-continued
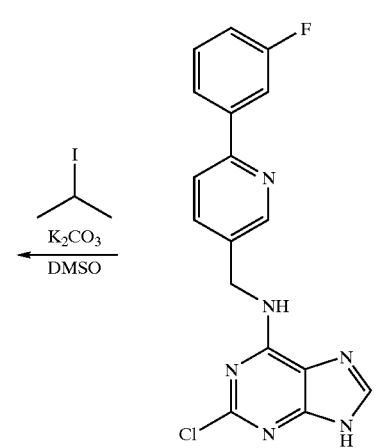
185
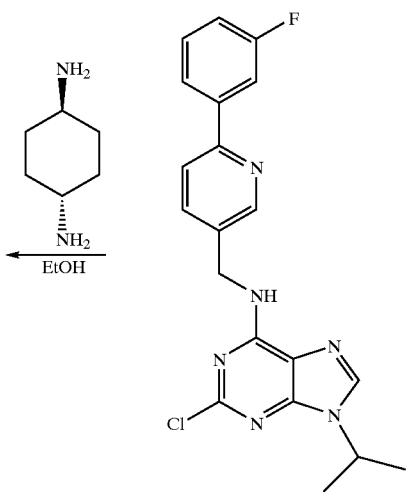
186
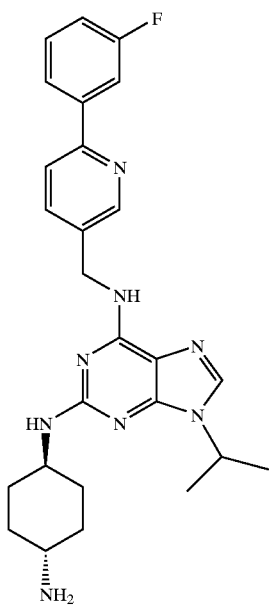
187
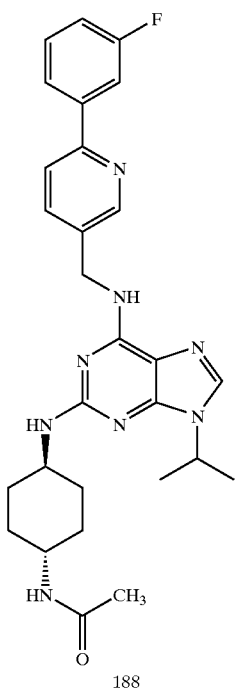
188

The syntheses of compounds 193 and 194 are shown below in Scheme LXV.
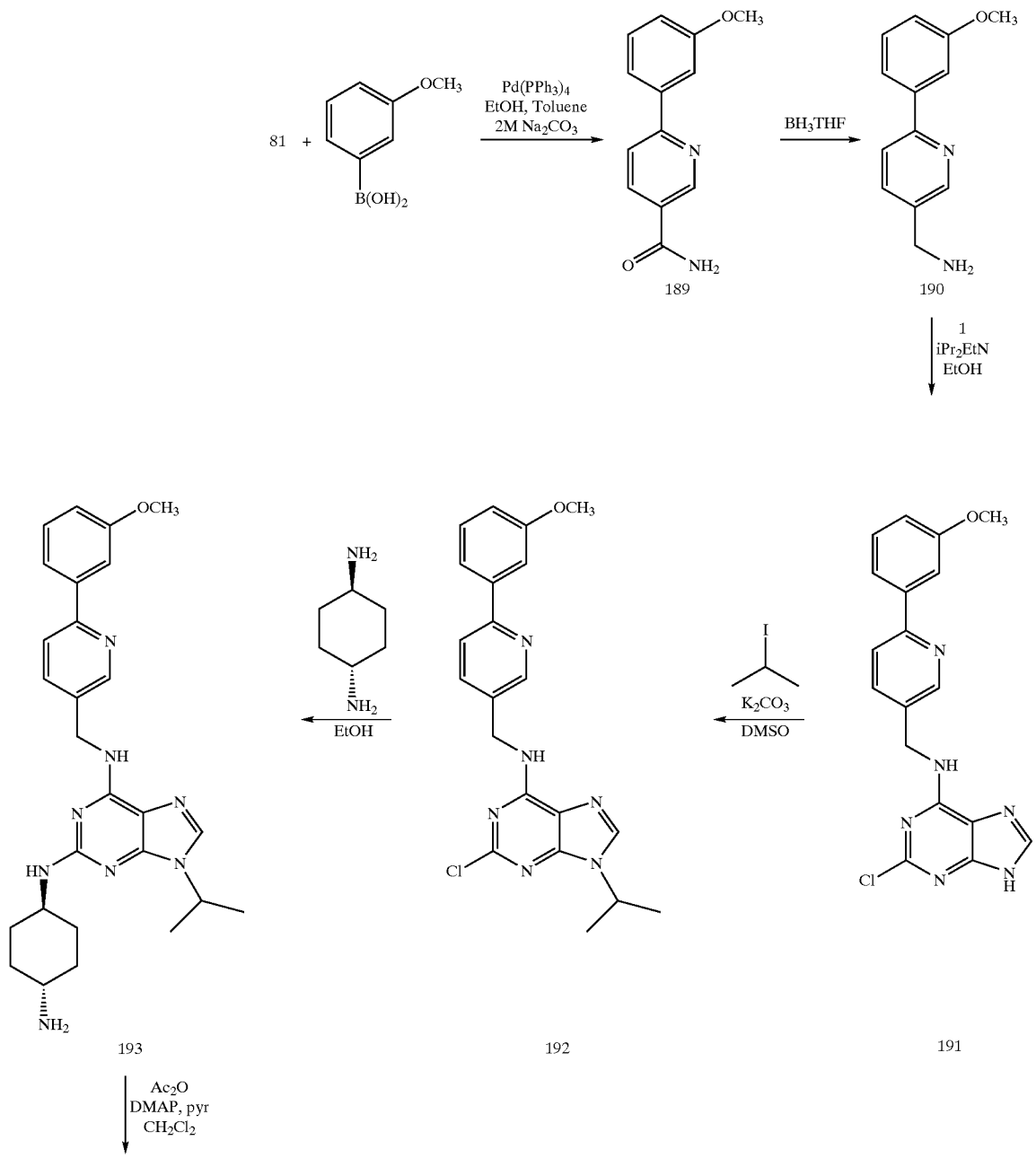

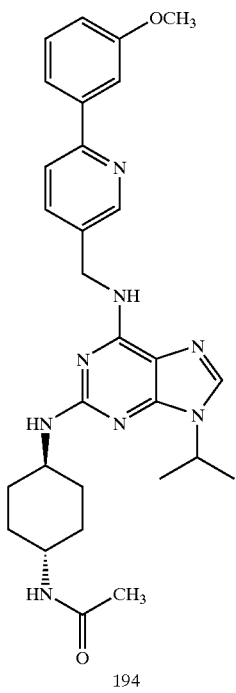
194
The syntheses of compounds 199–200 are shown below in Scheme LXVI.
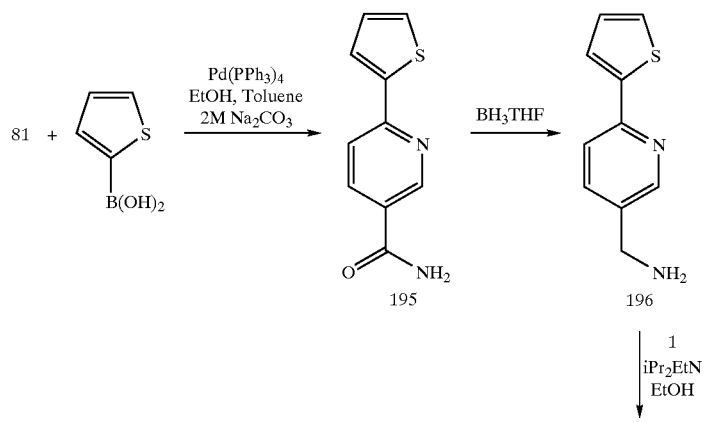

-continued
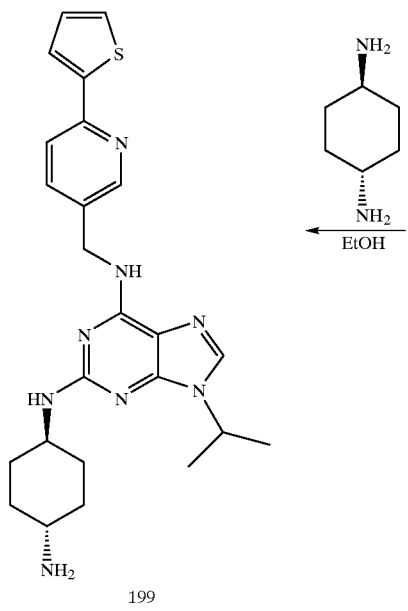 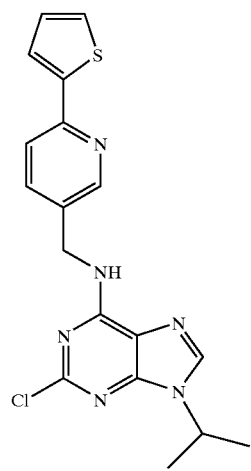 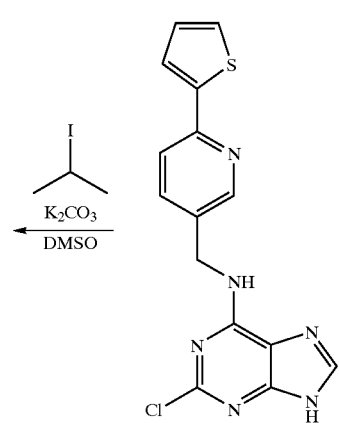
199     198     197
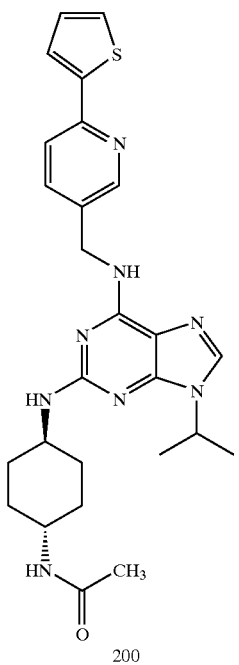
200

The syntheses of compounds 205–206 are shown below in Scheme LXVII.
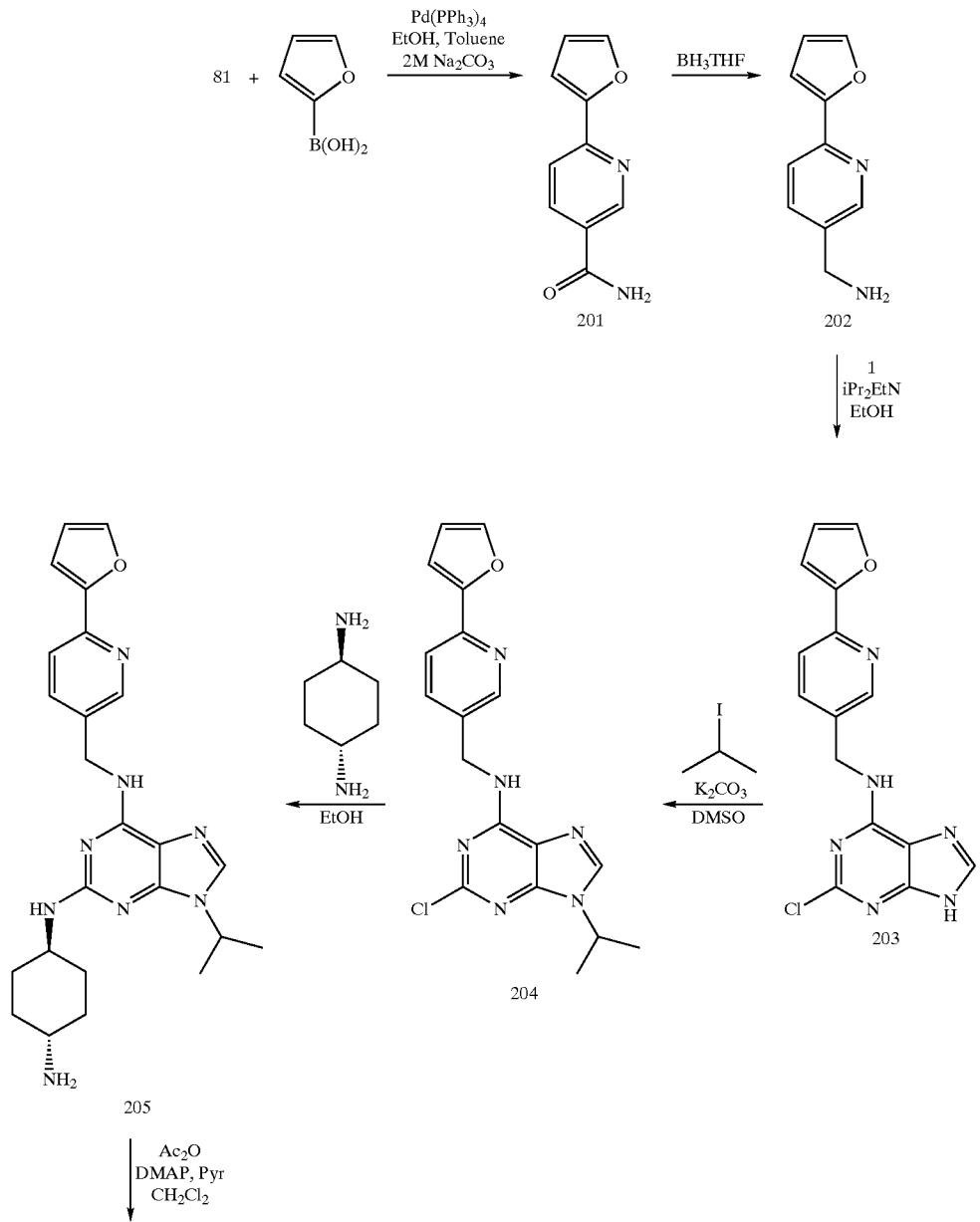

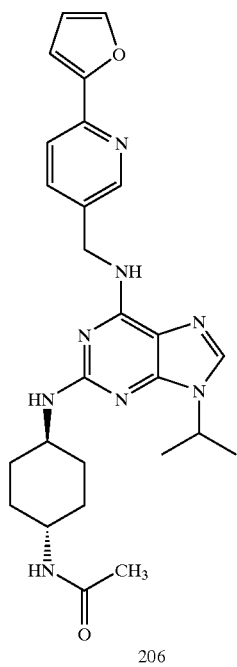
The syntheses of compounds 207–210 are shown below in Scheme LXVIII.
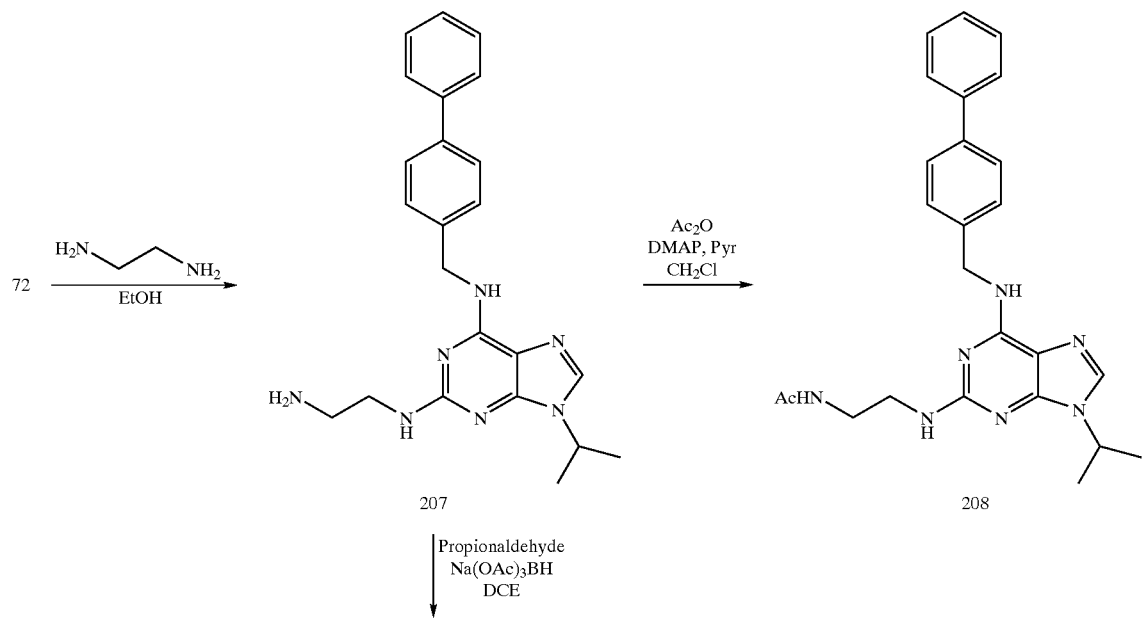

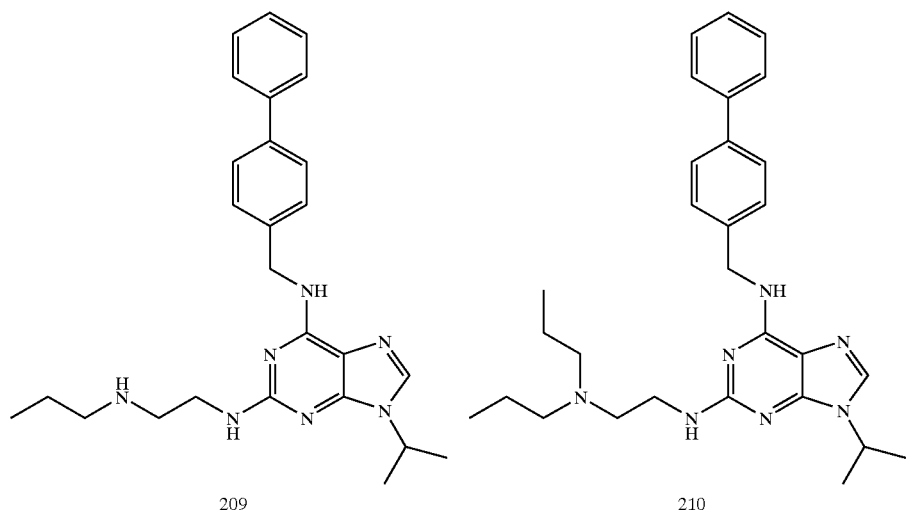
The syntheses of compounds 211–212 are shown below in Scheme LXIX.
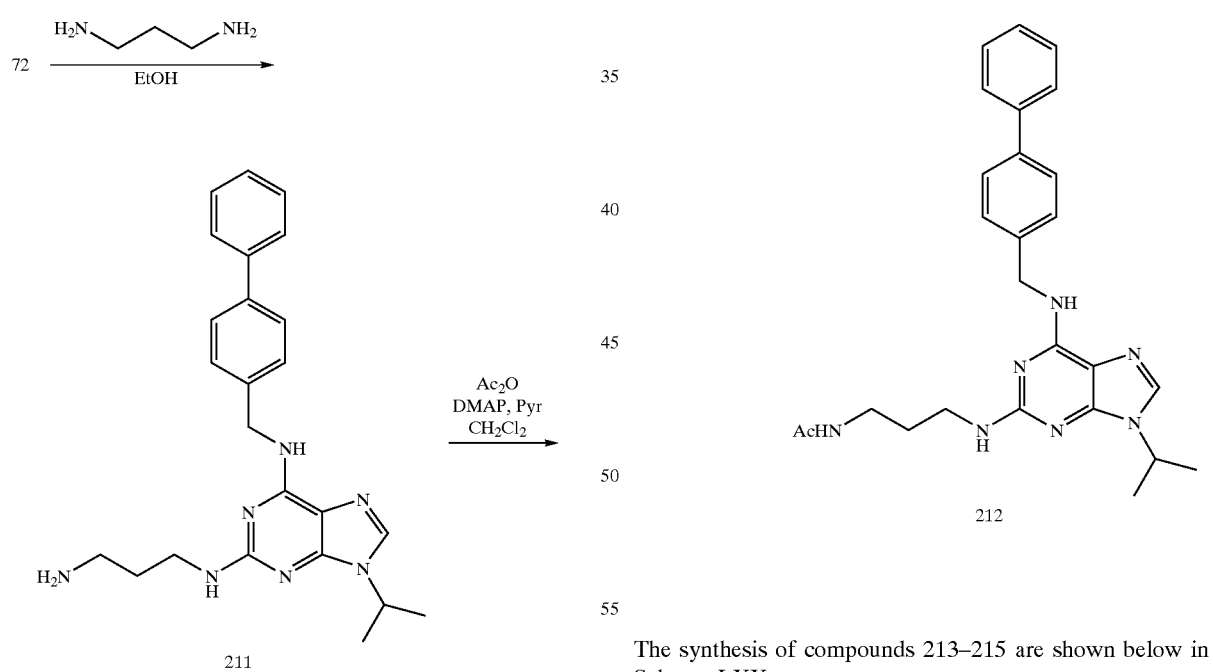
The synthesis of compounds 213–215 are shown below in Scheme LXX.

Scheme LXX
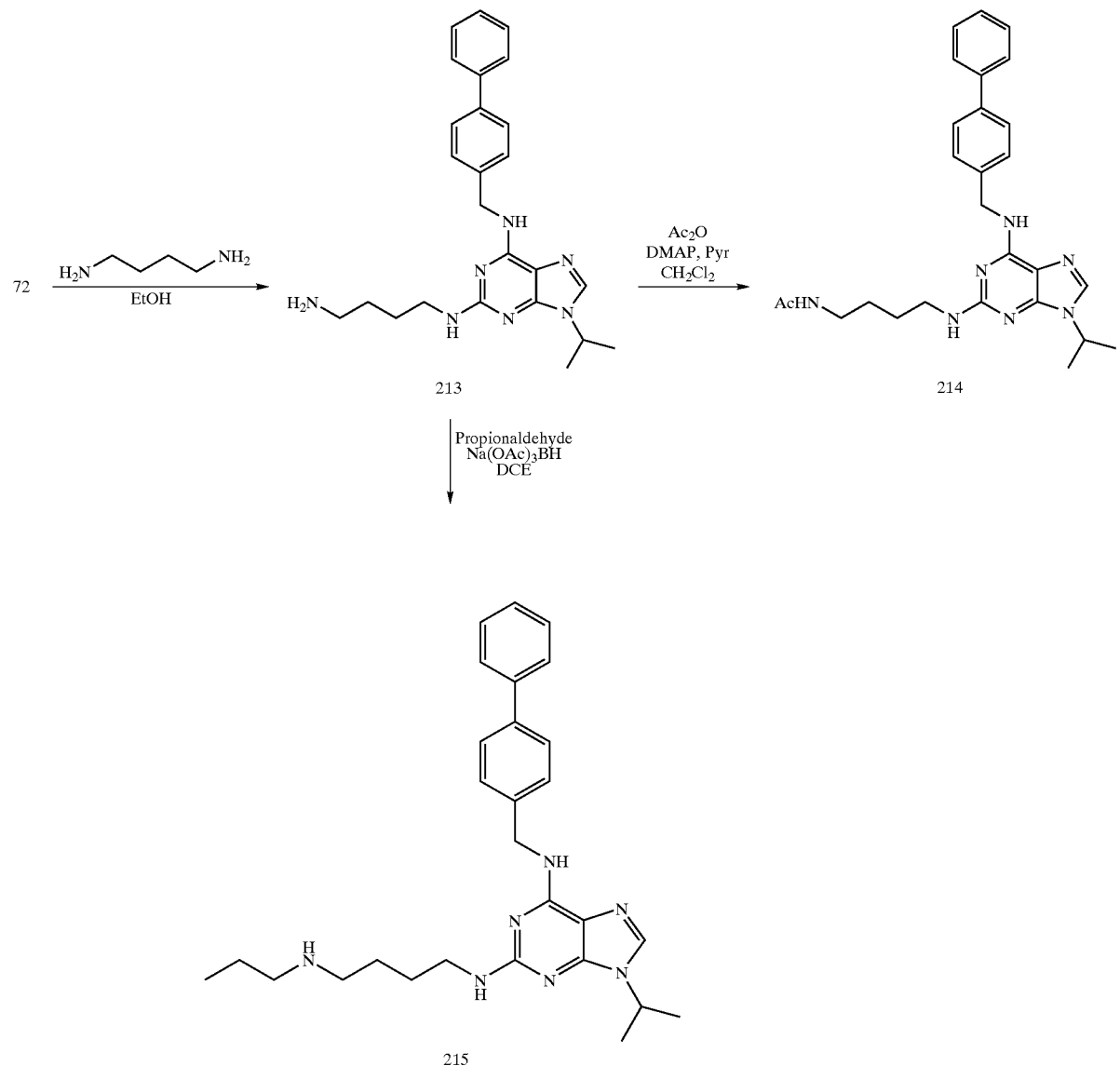

The syntheses of compounds 216–217 are shown below in Scheme LXXI.
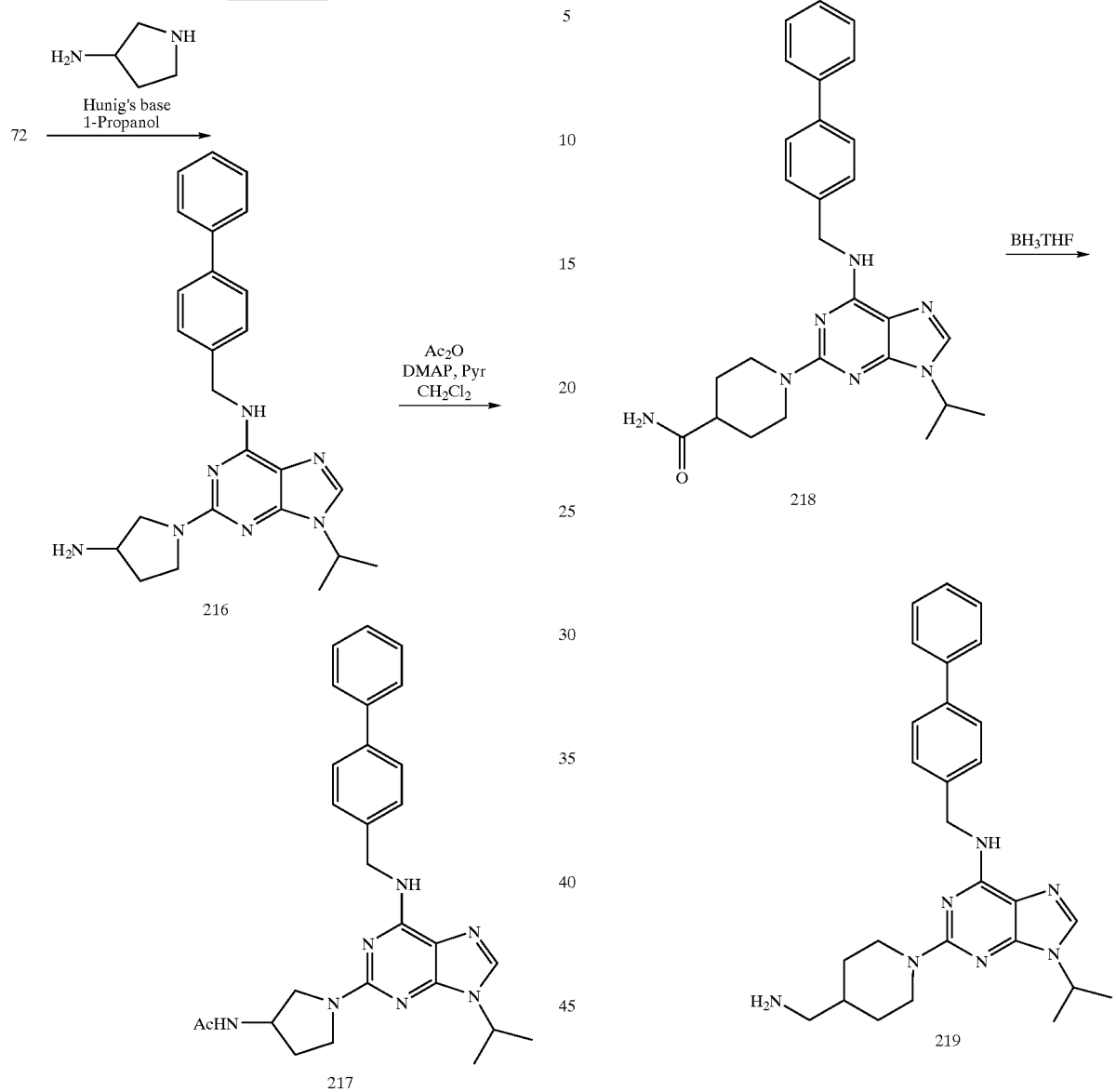
The syntheses of compounds 218–219 are shown below in Scheme LXXII.
The synthesis of compounds 221 is shown below in Scheme LXXIII.
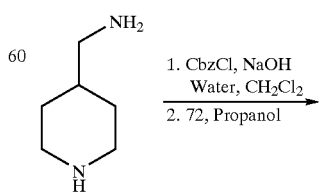

-continued
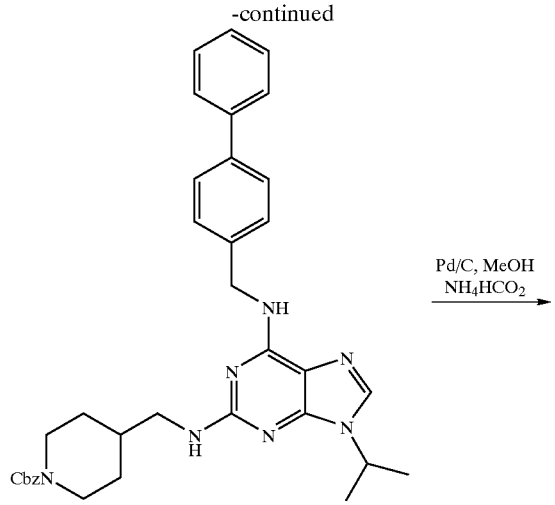
220
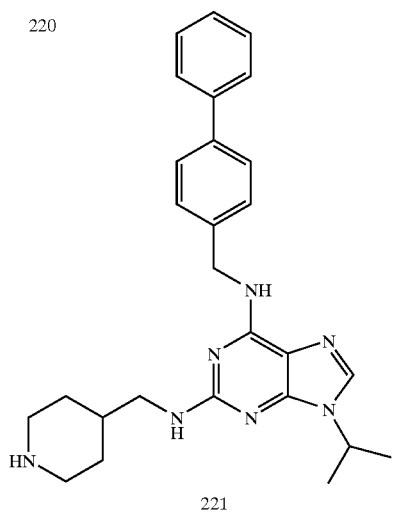
221
The synthesis of compound 222 is shown below in Scheme LXXIV.
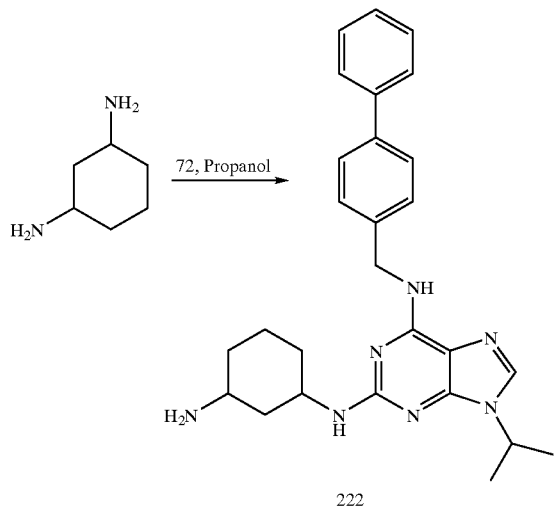
222
The synthesis of compound 223 is shown below in Scheme LXXV.
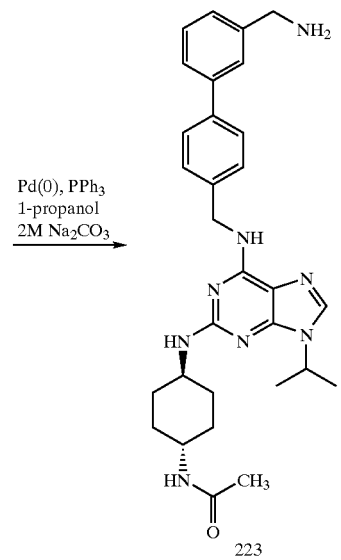
223
The synthesis of compound 224 is shown below in Scheme LXXVI.
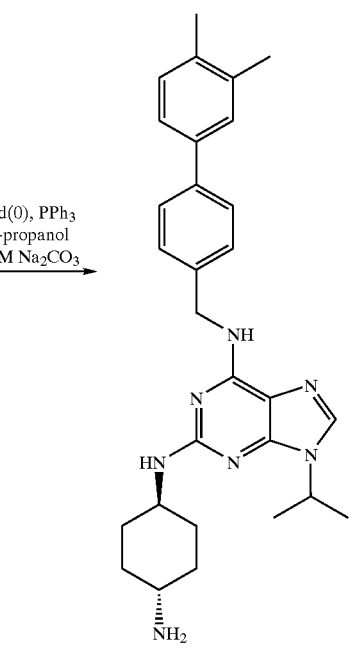
224
The synthesis of compound 229 is shown below in Scheme LXXVII.

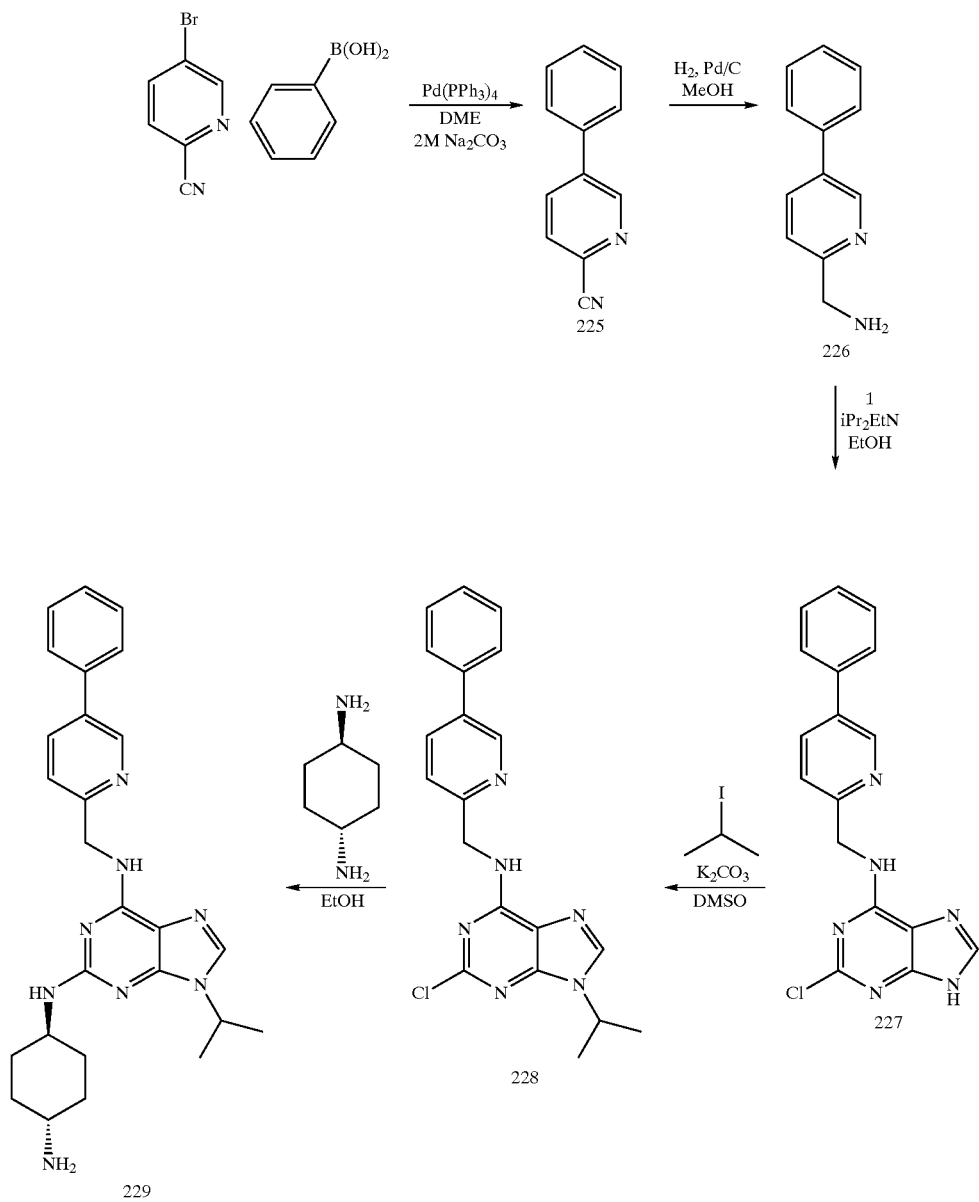

The syntheses of compounds 230–233 are shown below in Scheme LXXVIII.
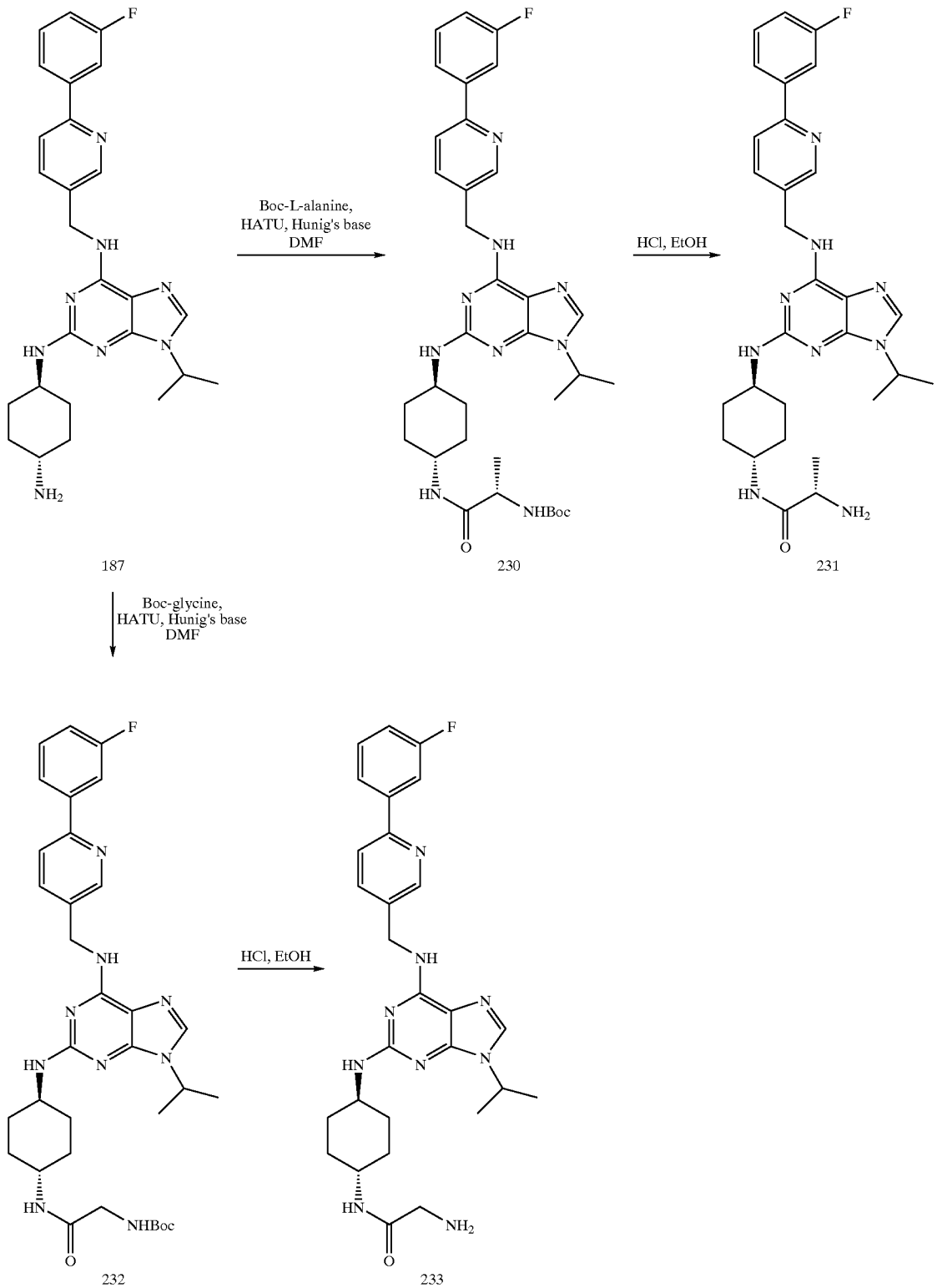

The syntheses of compounds 239–241 are shown below in Scheme LXXIX.
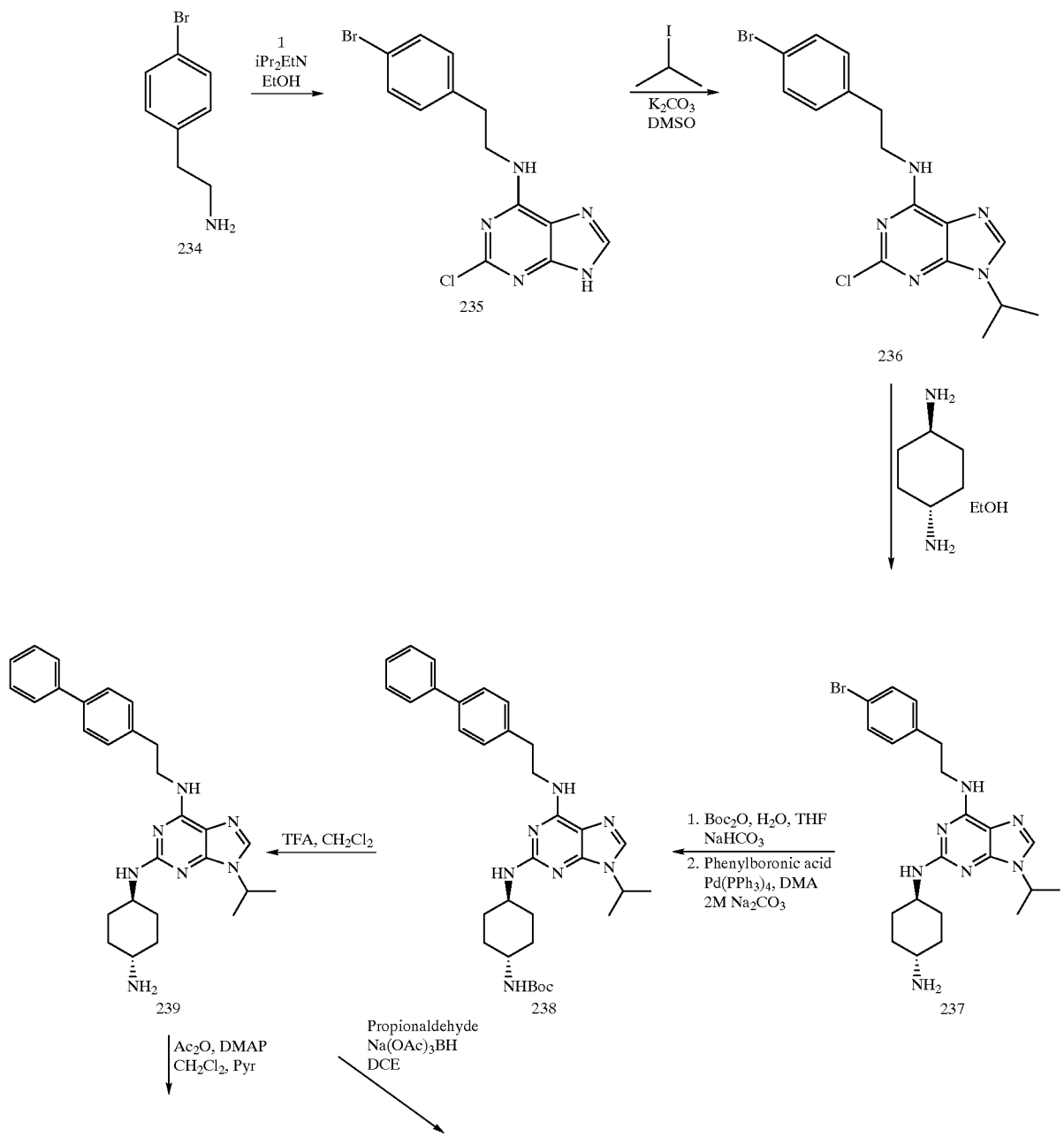

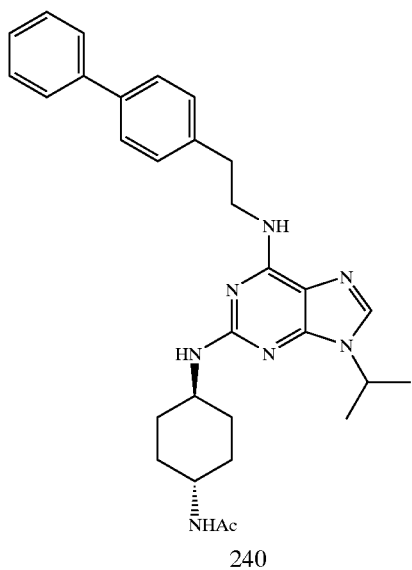
240
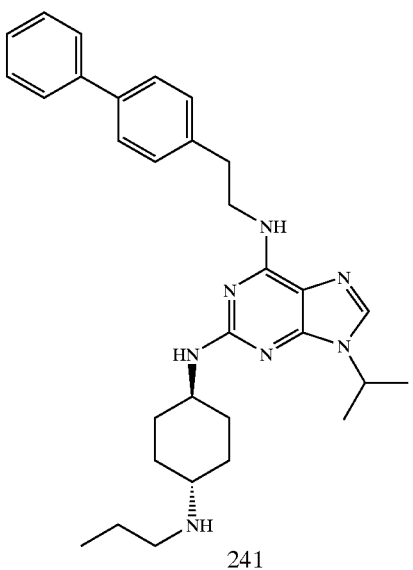
241
The syntheses of compounds 242–243 are shown below in Scheme LXXX.
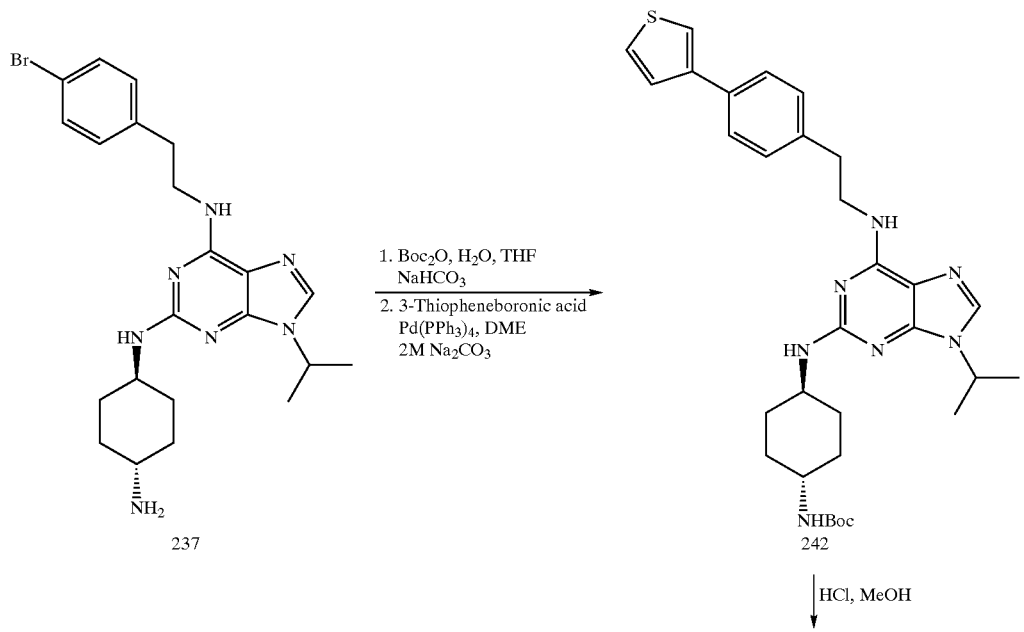

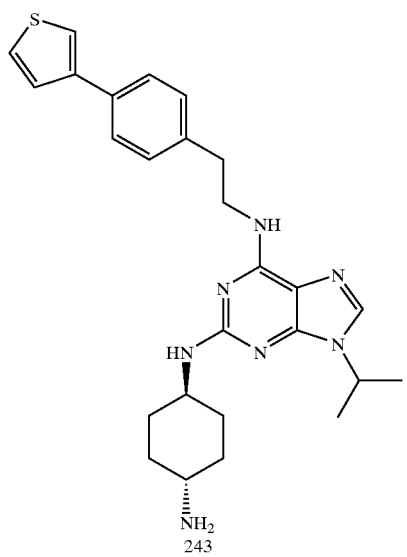
243
The syntheses of compounds 248–250 are shown below in Scheme LXXXI.
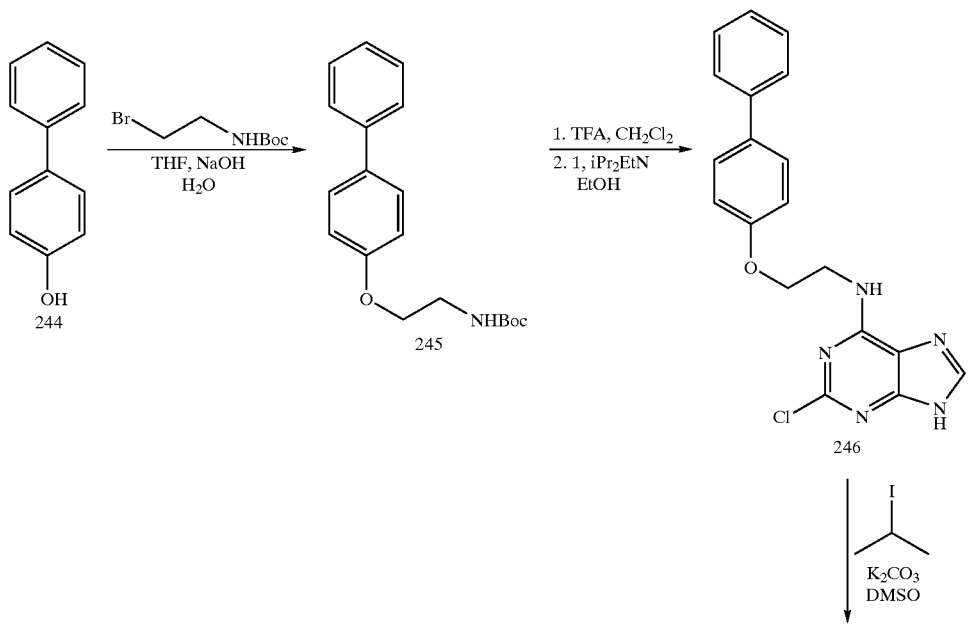

-continued
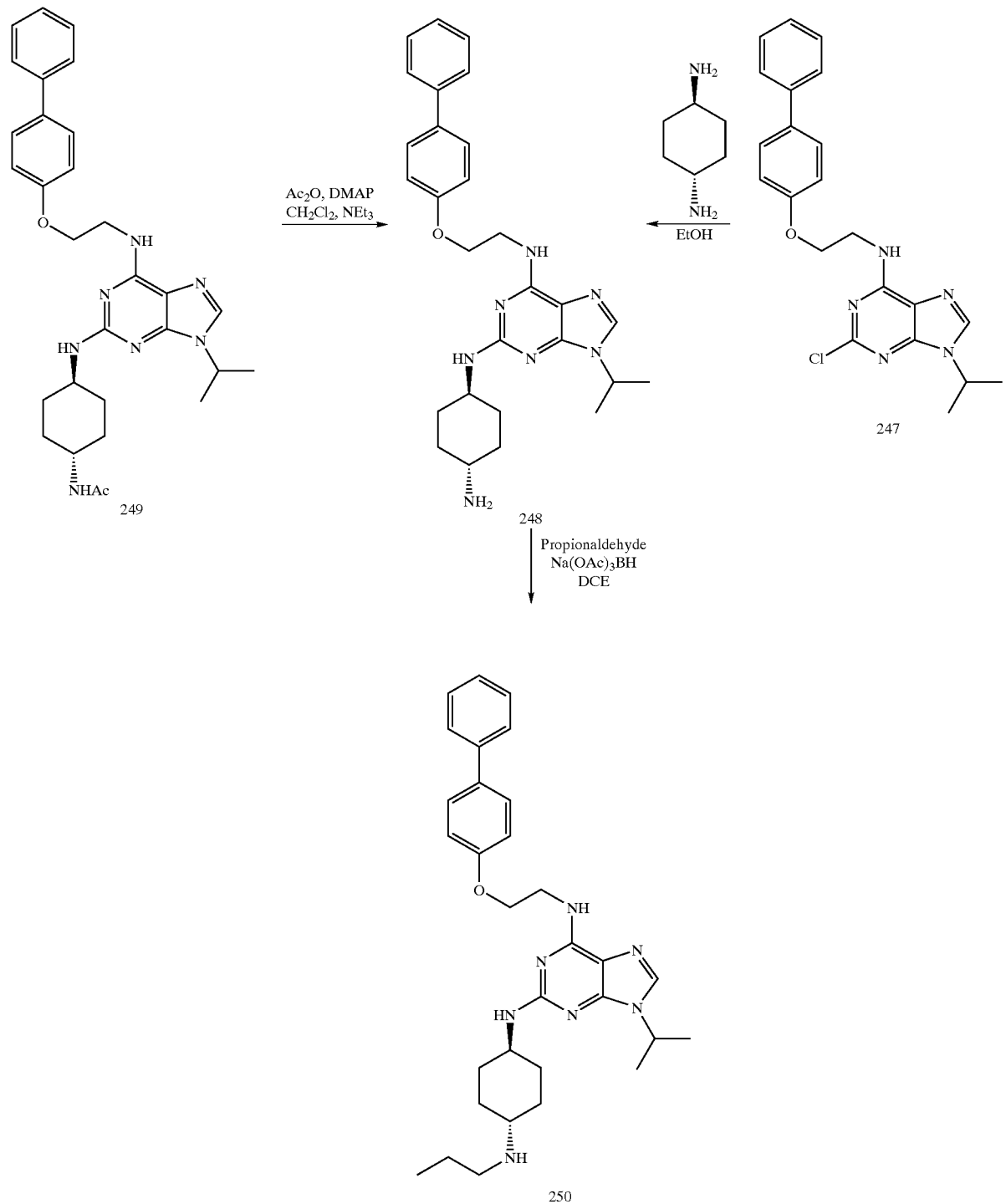

The syntheses of compounds 123 and 124 are shown below in Scheme LXXXII.
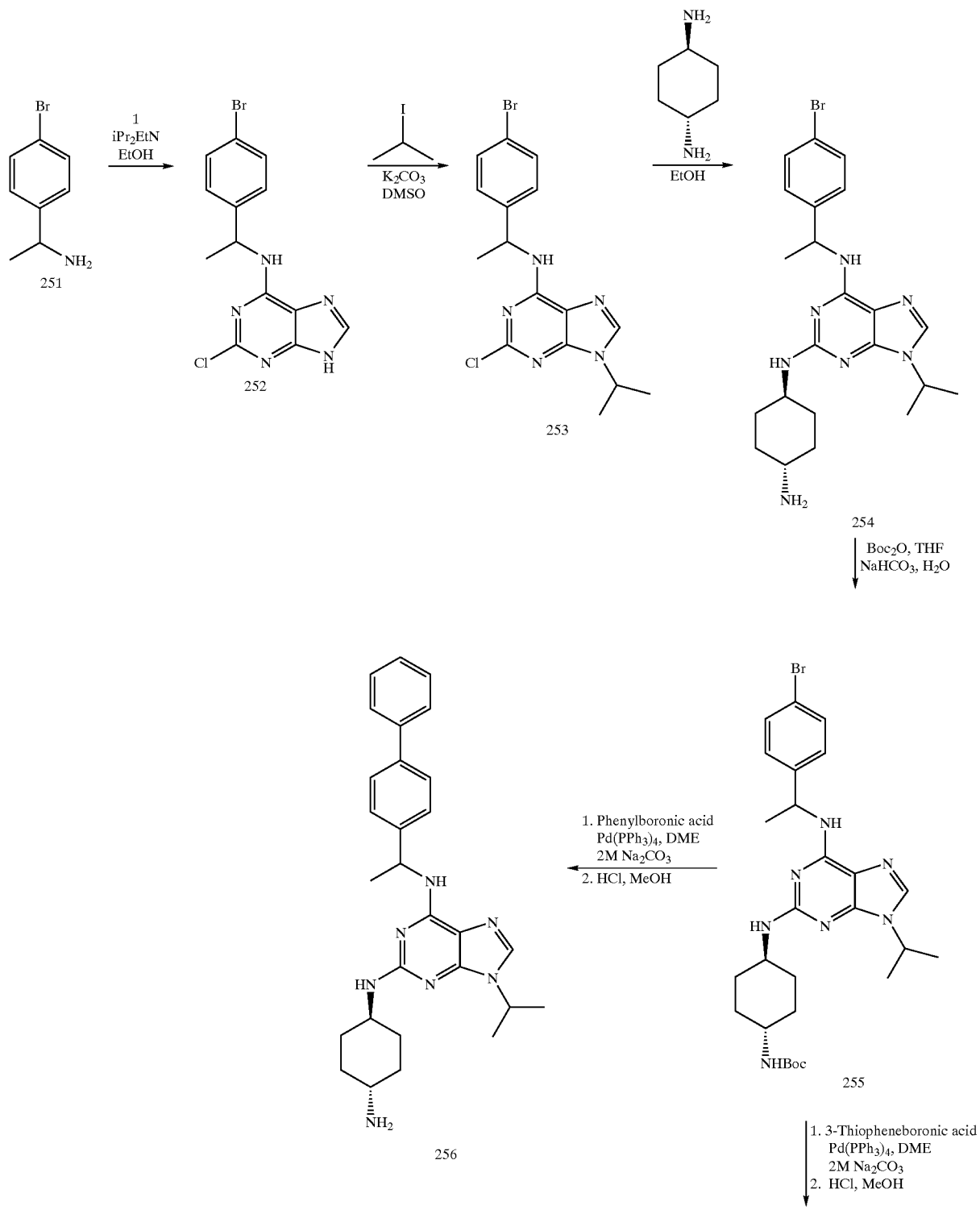

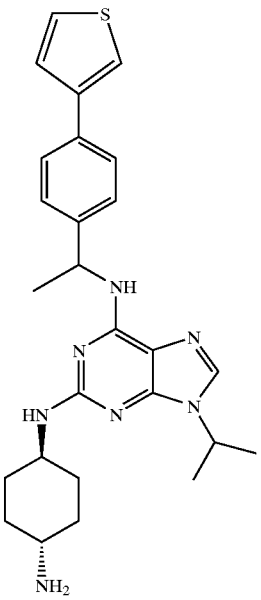
The syntheses of compounds 258–260 are shown below in Scheme LXXXIII.
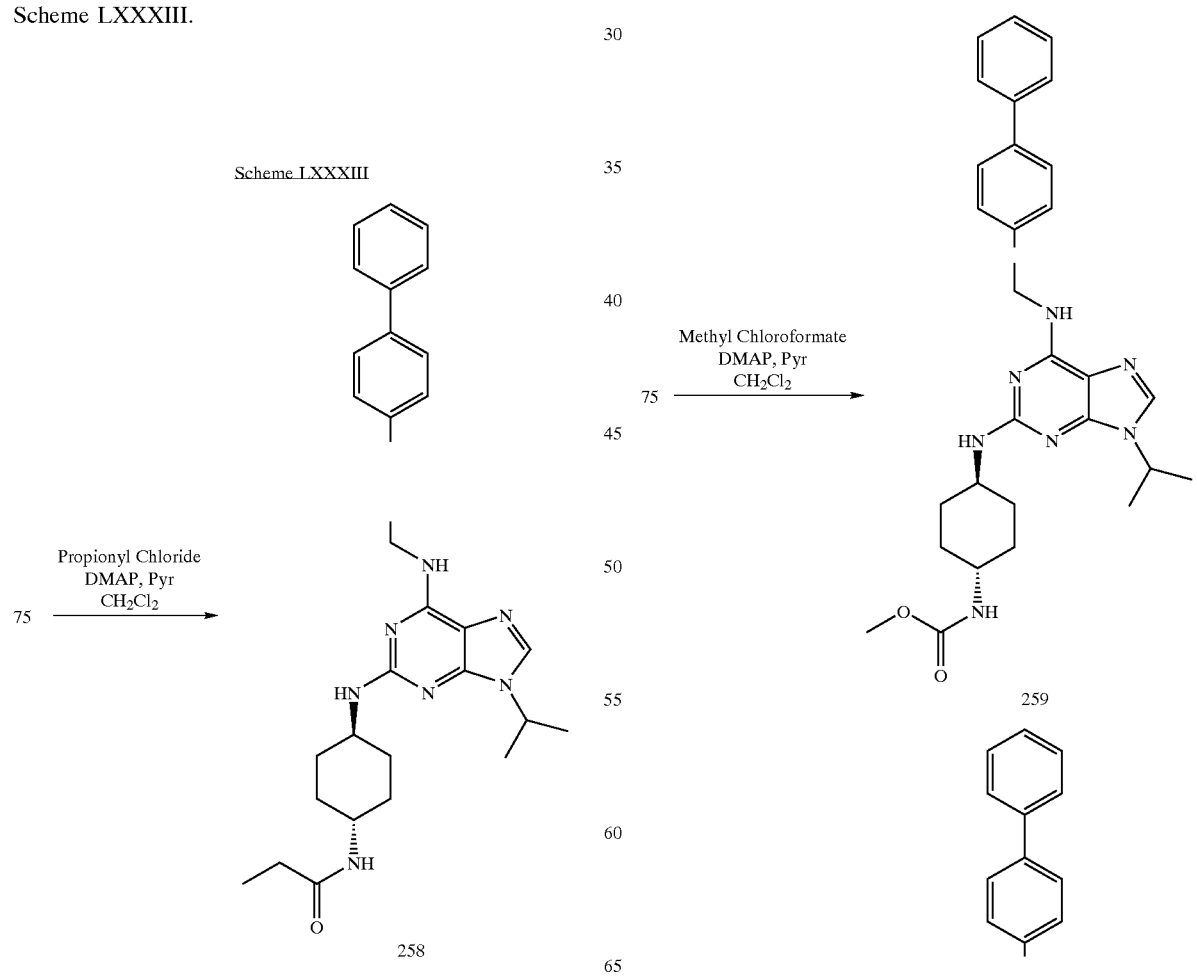

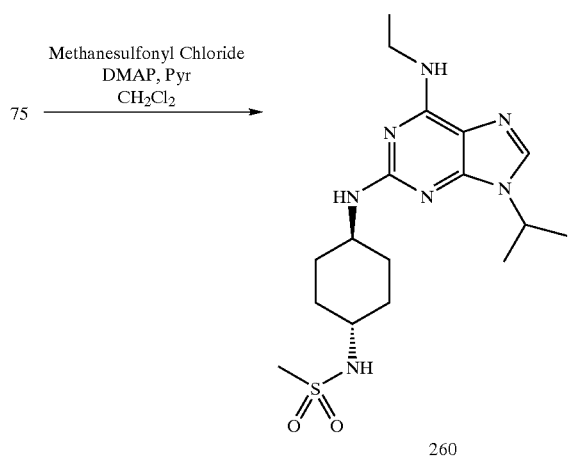
260
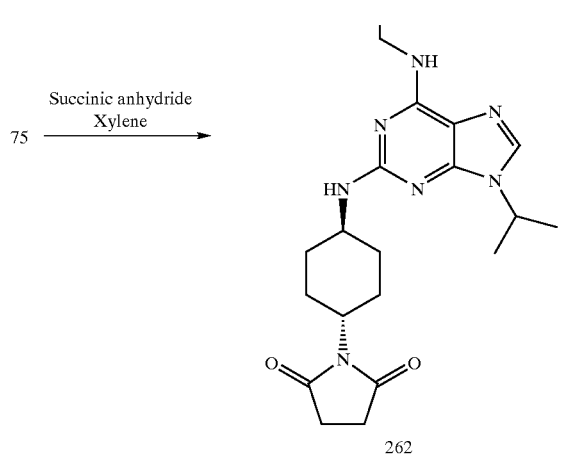
262
The syntheses of compounds 261–263 are shown below in Scheme LXXXIV.
Scheme LXXXIV
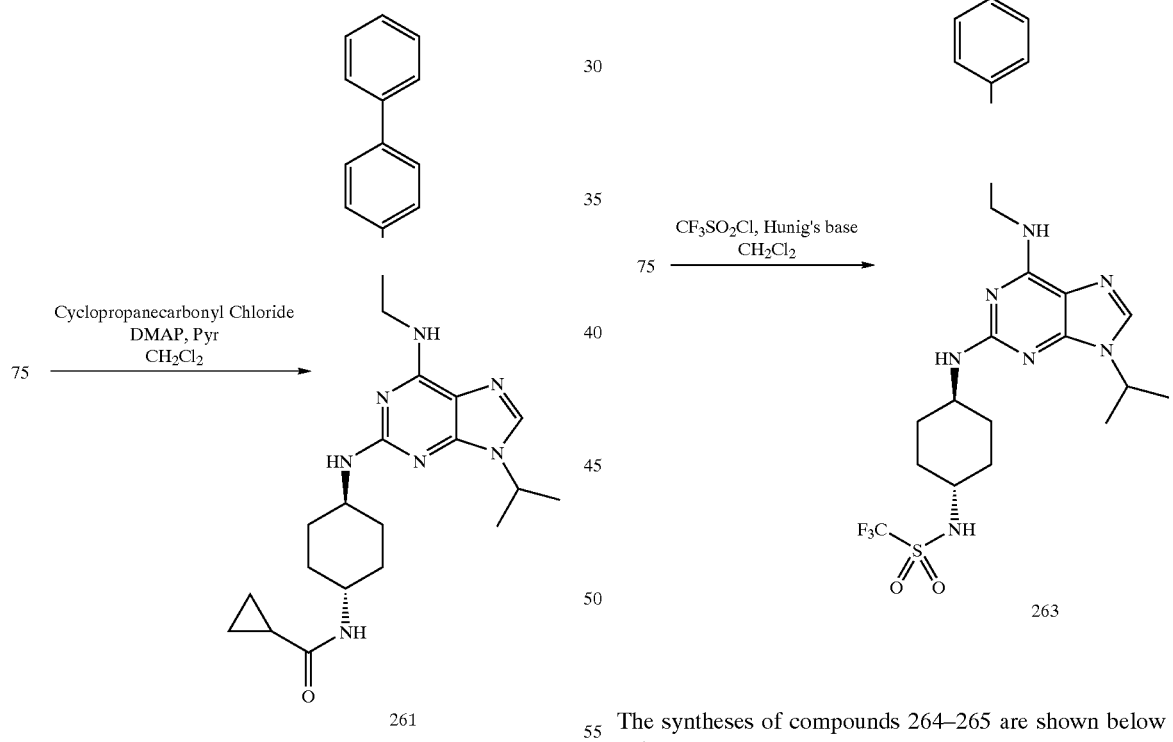
261
263
The syntheses of compounds 264–265 are shown below in Scheme LXXXV.
Scheme LXXXV
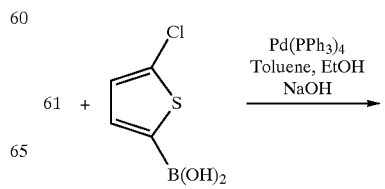

-continued

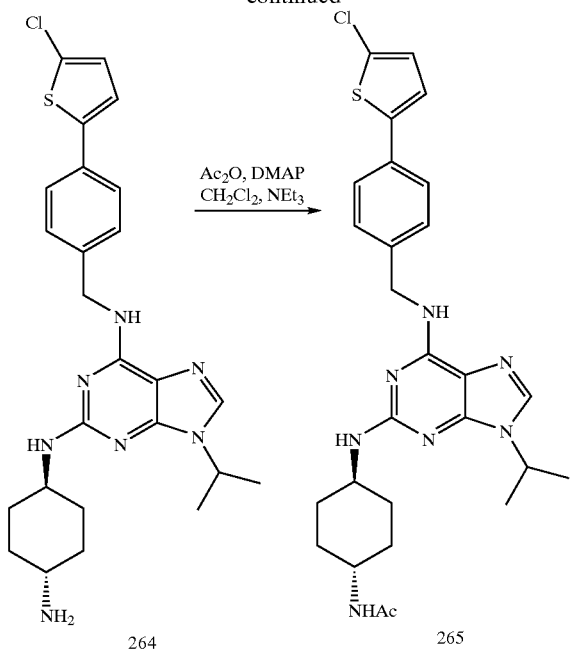

The synthesis of compound 266 is shown below in Scheme LXXXVI.

Scheme LXXXVI

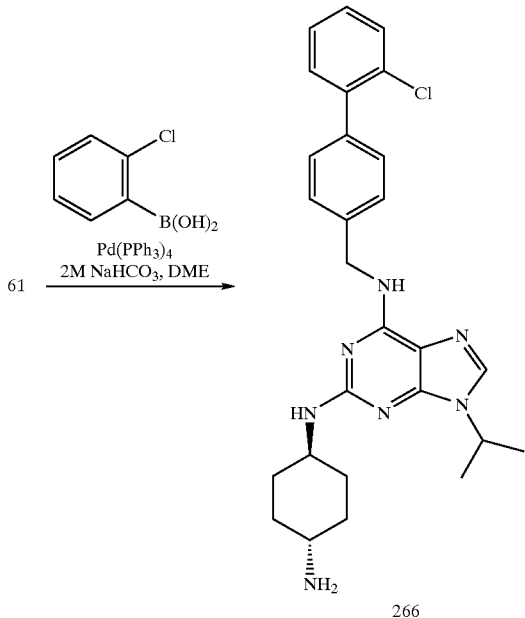

EXAMPLES

Proton NMR spectra were obtained on a Bruker AC 300 spectrometer at 300 MHz or a Bruker 500 MHz spectrometer and were referenced to tetramethylsilane as an internal standard. The IR spectrometer used was a single beam Perkin-Elmer Spectrum 1000 FT-IR. All IR spectra obtained were prepared in a pressed disc of KBr. All IR spectra obtained were acquired with a total of 4 accumulations at a resolution of 4.00 cm$^{-1}$. Melting points were obtained on a Mel-Temp II apparatus and are uncorrected. Mass spectra were obtained on either a Shimadzu QP-5000 or a PE Sciex API 150 Mass Spectrometer.

Example 1

Preparation of Compound 2

To the starting material 1 (1.0 g, 5.29 mmol) was added 4-bromobenzylamine (2.53 g, 11.4 mmol), and EtOH (11 mL). The mixture was stirred and heated at 50° C. in a round-bottomed flask and then H$_2$O (1 mL) and EtOH (10 mL) were added to dissolve the solids. The mixture was refluxed for 1 h. Hünig's base (3.68 mL, 21.2 mmol) was added and refluxed overnight, during which time a precipitate formed. The solution was filtered to provide a light yellow solid. The solid was dried in vacuo (1.08 g, 60%): $^1$H NMR (300 MHz, DMSO-d$_6$) δ 8.75 (bs, 1H), 8.15 (s, 1 H), 7.52 (d, 2H), 7.30 (d, 2H), 4.63 (bs, 2H); CI MS m/z=340 [C$_{12}$H$_9$BrClN$_5$+H]$^+$.

Example 2

Preparation of Compound 3

To the starting material 2 (1.08 g, 3.19 mmol) was added DMSO (11 mL), K$_2$CO$_3$ (2.20 g, 15.95 mmol), and 2-iodopropane (1 mL, 9.57 mmol). The solution was stirred overnight then poured into H$_2$O (75 mL) and stirred. Additional H$_2$O (25–50 mL) was added to the mixture to form a yellow solid. The stirring was continued at 0° C. The solid was filtered in vacuo. The crude product was purified by silica gel chromatography to provide 3 (0.66 g, 50%) as a white solid: mp 136–140° C.; $^1$H NMR (300 MHz, CDCl$_3$) δ 7.78 (s, 1H), 7.49 (d, 2H), 7.28 (d, 2H), 6.12 (bs, 1H), 4.90–4.70 (m, 3H), 1.61 (d, 6H).

Example 3

Preparation of Compound 4

To starting material 3 (1.44 g, 3.78 mmol) was added 2-amino-1-butanol (5.06 g, 56.7 mmol) and ethanol (5 mL) and the mixture was heated in a sealed tube in an oil bath at 150–160° C. for 48 h. The cooled solution was transferred to a round-bottomed flask and the ethanol was removed in vacuo. The crude product was purified by flash column chromatography on silica gel to give 4 (0.90 g, 55%): $^1$H NMR (300 MHz, CDCl$_3$) δ 7.44–7.41 (m, 3H), 7.23 (d, 2H), 6.22 (s, 1H), 5.06 (s, 1H), 4.90 (d, 1H), 4.78–4.68 (m, 2H), 4.65–4.55 (m, 1H), 3.91–3.80 (m, 2H), 3.66–3.60 (m, 1H), 1.66–1.47 (m, 8H), 1.04–0.99 (t, 3H).

Example 4

Preparation of Compound 5

To starting material 4 (0.13 g, 0.29 mmol) was added 3-acetamidophenylboronic acid (0.21 g, 1.19 mmol) and Pd(PPh$_3$)$_4$ (0.08 g, 0.07 mmol), Na$_2$CO$_3$ (2M, 0.60 mL), and toluene (5 mL). The solution was degassed with argon for 10 min then heated at 130° C. for 6 h. The cooled solution was diluted with water and then extracted with CH$_2$Cl$_2$ (3×50 mL). The combined organic phases were washed with brine, dried over anhydrous Na$_2$SO$_4$, filtered, and concentrated to yield a viscous orange oil. The oil was purified by flash column chromatography on silica gel and then the product crystallized upon standing to give 5 (0.06 g, 41%) as a pale yellow solid: $^1$H NMR (300 MHz, CDCl$_3$) δ 8.01–7.21 (m, 9H), 6.48 (s, 1H), 4.97 (d, 1H), 4.82–4.70 (m, 2H), 4.65–4.53 (m, 1H), 3.98–3.25 (m, 2H), 3.20–3.05 (m, 1H), 2.20 (s, 3H), 1.69–1.45 (m, 8H), 1.07–0.98 (t, 3H).

Example 5

Preparation of Compound 7

To 4-iodobenzoic acid (52.2 g, 0.21 mol) was added $CH_2Cl_2$ (500 mL) and DMF (2 drops) at room temperature. Oxalyl chloride (32 g, 0.25 mol) was added dropwise in 0.5 h and stirred for 2 d. The volatiles were removed in vacuo to a volume of 150 mL to give the acid chloride and $CH_2Cl_2$. To a mixture of ice (500 mL) and $NH_4OH$ (29%; 100 mL) was added the $CH_2Cl_2$ solution during 15 min. The resulting solids were collected, washed with $CH_2Cl_2$, and dried in vacuo. The solids were slurried in $H_2O$ for 1 h. The solids were collected by filtration, washed in water and acetone, and dried in vacuo to give 7 (48 g; 92%): mp 213–216° C.

Example 6

Preparation of Compound 8

To a suspension of 7 (11 g, 45 mmol) in THF (50 mL) was added $BH_3$-THF (1M, 22.5 mL, 22.5 mmol). The resulting solution was heated under reflux overnight. The reaction was cooled in an ice bath and MeOH-HCl (60 mL) was slowly added dropwise. The resulting precipitate was filtered and dried to give 8 (10.8 g, 88%) as a white solid: mp 256–262° C. dec.; $^1$H NMR (300 MHz, DMSO-$d_6$) δ 8.55 (bs, 3H), 7.79 (d, 2H), 7.32 (d, 2H), 3.98 (s, 2H).

Example 7

Preparation of Compound 9

To compound 1 (7.63 g, 40.4 mmol) was added compound 8 (10.8 g, 40.4 mmol), water (123 mL), and Hünig's base (14 mL, 81 mmol). The mixture was heated to reflux for 5 h and stirred overnight at room temperature to give a pale yellow solution. An additional quantity of water (150 mL) was added, refluxed for 3 h, then cooled overnight. A pale yellow solid was formed which was filtered, washed with water, rinsed with EtOH (2×), and dried in vacuo to give yield 9 (13.3 g, 80%): $^1$H NMR (300 MHz, DMSO-$d_6$) δ 8.68 (bs, 1H), 8.28 (s, 1H), 7.68 (d, 2H), 7.50 (d, 2H), 5.08 (bs, 1H), 4.50 (d, 2H).

Example 8

Preparation of Compound 10

To compound 9 (12.2 g, 31.7 mmol) was added $K_2CO_3$ (35 g, 0.25 mol), 2-iodopropane (13 g, 0.13 mol) and DMSO (210 mL). The reaction mixture was stirred under $N_2$ at room temperature overnight, then poured into $H_2O$ (1.5 L) and stirred for 2 d. The precipitate was collected as an off-white solid and washed with $Et_2O$. The aqueous layer was extracted with EtOAc (2×) and the combined organic phases were washed with brine, dried over $Na_2SO_4$, filtered, and evaporated to give an off-white foam (6.4 g). This off-white foam was combined with the precipitate and washed with $Et_2O$ to give 10 (11.0 g): $^1$H NMR (300 MHz, DMSO-$d_6$) δ 8.91 (m, 1H), 8.38 (s, 1H), 7.74 (d, 2H), 7.21 (d, 2H), 5.11 (bs, 1H), 4.68 (m, 1H), 4.60 (d, 2H), 1.48 (d, 6H).

Example 9

Preparation of Compound 11

Compound 10 (1.52 g, 3.55 mmol), trans-1,4-diaminocyclohexane (6.35 g, 55.60 mmol), and EtOH (18 mL) were placed in a sealed tube. The reaction mixture was heated at 120–190° C. for 24 h. The reaction was then allowed to cool to room temperature. The reaction mixture was filtered and the filtrate evaporated. The residue was purified by column chromatography, and dried in vacuo for 16 h to yield 11 (1.60 g, 89%) as a yellow sticky oil: $^1$H NMR (300 MHz, CDCl$_3$) δ 7.62 (d, 2H), 7.44 (s, 1H), 7.08 (d, 2H), 6.14 (br, 1H), 4.75–4.63 (m, 2H), 4.63–4.54 (m, 2H), 3.75–3.63 (m, 1H), 2.72–2.57 (m, 2H), 2.18–2.00 (m, 2H), 2.00–1.75 (m, 4H), 1.54 (d, 6H), 1.39–1.00 (m, 3H); API MS m/z=506 $[C_{21}H_{28}IN_7+H]^+$.

Example 10

Preparation of Compound 12

To compound 11 (0.133 g, 0.26 mmol) was added DME (2.5 mL) and 3-thiopheneboronic acid (0.12 g, 0.97 mmol) in a round-bottomed flask and equipped with a condenser purged with argon. To this was added DME (3 mL) followed by tris(dibenzylidoneacetone)dipalladium (0.01 g, 0.01 mmol) and PPh$_3$ (0.04 g, 0.15 mmol). Na$_2$CO$_3$ (2M, 0.6 mL) and DME (1 mL) was added to the reaction mixture and the reaction mixture was allowed to reflux for 18.5 h, then stirred at room temperature under argon for 46 h. The reaction mixture was diluted with $H_2O$ and extracted with $CH_2Cl_2$. The combined organic phases were washed with brine, dried over anhydrous Na$_2$SO$_4$, filtered, and concentrated in vacuo. The residue was purified by column chromatography to yield 12 (0.050 g, 41%) as a tan solid: $^1$H NMR (300 MHz, CDCl$_3$) δ 7.56–7.50 (m, 4H), 7.44–7.35 (m, 3H), 6.02 (br, 1H), 4.78 (d, 2H), 4.69–4.54 (m, 2H), 3.75 (br, 1H), 2.69 (br, 1H), 2.15 (br, 2H), 1.88 (br, 3H), 1.54 (d, 7H), 1.33–0.97 (m, 4H); API MS m/z=462 $[C_{25}H_{31}N_7S+H]^+$.

Example 11

Preparation of Compound 13

DME (3 mL), tris(dibenzylidoneacetone)dipalladium (0.01 g, 0.01 mmol), and PPh$_3$ (0.04 g, 0.15 mmol) were placed in a round-bottomed flask fitted with a condenser and maintained under argon. Compound 11 (0.13 g, 0.26 mmol), and 4-methylbenzeneboronic acid (0.13 g, 0.98 mmol) dissolved in Na$_2$CO$_3$ (2M, 0.6 mL) and DME (1 mL) were added to the reaction mixture. The reaction mixture was refluxed for 19.5 h and stirred at room temperature for 4 h. The reaction mixture was diluted with water and extracted with $CH_2Cl_2$. The combined organic phases were washed with brine, dried over anhydrous Na$_2$SO$_4$, and evaporated. The crude product was purified by column chromatography and dried in vacuo for 22 h to yield the desired product 13 (54 mg, 44%) as an off-white solid: $^1$H NMR (300 MHz, CDCl$_3$) δ 7.56–7.41 (m, 7H), 7.23 (s, 1H), 5.92 (br, 1H), 4.83 (d, 2H), 4.74–4.58 (m, 2H), 3.77 (br, 1H), 2.70 (br, 1H), 2.40 (s, 3H), 2.16 (d, 3H), 1.88 (d, 3H), 1.55 (d, 7H), 1.33–0.97 (m, 4H); API MS m/z=470 $[C_{28}H_{35}N_7+H]^+$.

Example 12

Preparation of Compound 14

DME (3 mL), tris(dibenzylideneacetone)dipalladium (0.01 g, 0.01 mmol), and PPh$_3$ (0.04 g, 0.15 mmol) were placed in a round-bottomed flask with a condenser under argon. Compound 11 (0.13 g, 0.25 mmol) and 3-chloro-4-fluoroboronic acid (0.15 g, 0.88 mmol) were dissolved in Na$_2$CO$_3$ (2M, 0.6 mL) and DME (1 mL) were added to the reaction mixture, refluxed for 19 h then stirred at room temperature for 2 h. The reaction mixture was diluted with water and extracted with $CH_2Cl_2$. The combined organic phases were washed with brine, dried over anhydrous $Na_2SO_4$, and evaporated. The crude product was purified by repeated column chromatography to yield 14 (0.019 g, 15%): $^1$H NMR (300 MHz, $CDCl_3$) δ 7.59–7.53 (m, 1H), 7.47–7.35 (m, 4H), 7.26–7.14 (m, 3H), 5.81 (br, 1H), 4.81 (d, 2H), 4.72–4.54 (m, 2H), 3.72 (br, 1H), 2.69 (br, 1H), 2.21–2.03 (m, 3H), 1.94–1.78 (m, 3H), 1.54 (d, 6H), 1.33–1.12 (m, 4H); API MS m/z=508 $[C_{27}H_{31}ClFN_7+H]^+$.

Example 13

Preparation of Compound 16

A solution of 15 (2.5 g, 15.8 mmol) and ether was cooled to −78° C. In a separate flask, n-BuLi (15.8 mmol) was also cooled to −78° C. The solution of 15 was added to the n-BuLi solution via cannula to give a dark red solution. The reaction mixture was stirred for 5 min prior to the rapid addition of $(n-Bu)_3SnCl$ (6.2 g, 19 mmol). The resulting bright yellow solution was stirred at −78° C. for 2 h, allowed to warm to room temperature, and stirred for another 10 min. The solution was then diluted with $H_2O$ (80 mL) and extracted with ethyl acetate (3×50 mL). The organic extracts were combined, washed with brine, dried over $Na_2SO_4$, filtered, and concentrated in vacuo to yield the crude product as a yellow oil. Purification by column chromatography gave the product 16 (4.89 g, 84%) as a pale yellow liquid: $^1$H NMR (300 MHz, $CDCl_3$) δ 8.72 (d, 1H), 7.48–7.46 (m, 1H), 7.40–7.38 (m, 1H), 7.11–7.09 (m, 1H), 1.61–1.50 (m, 6H), 1.38–1.26 (m, 6H), 1.14–1.09 (m, 6H), 0.97–0.77 (t, 9H).

Example 14

Preparation of Compound 17

To compound 16 (0.18 g, 0.48 mmol) was added compound 4 (0.14 g, 0.33 mmol), $Pd(PPh_3)_4$ (0.05 g, 0.49 mmol), and toluene (10 mL) in a sealed tube under an argon atmosphere. The solution was degassed with argon and heated at 135° C. in an oil bath for 3 h. The solution was cooled to room temperature, diluted with saturated $NaHCO_3$, and extracted with $CH_2Cl_2$ (3×30 mL). The organic layer was washed with brine, dried over $Na_2SO_4$, and concentrated in vacuo to give a light brown oil. The residue was purified by flash column chromatography using $MeOH/CH_2Cl_2$ (10%) to afford 17 as a white solid. The sample was dissolved into hexane/$CH_2Cl_2$/MeOH and then precipitated with diethyl ether, filtered, and rinsed several times with ether to provide in 17 (30.3 mg): mp 95–100° C.; $^1$H NMR (300 MHz, $CDCl_3$) δ 8.68 (d, 1H), 7.96 (d, 2H), 7.77–7.69 (m, 2H), 7.49–7.45 (m, 3H), 7.24–7.20 (m, 1H), 5.99 (s, 1H), 5.11 (s, 1H), 4.88–4.83 (m, 3H), 4.65–4.56 (m, 1H), 3.91–3.80 (m, 2H), 3.65–3.60 (m, 1H), 1.66–1.52 (m, 8H), 1.05–0.99 (t, 3H); IR (KBr) 3411, 2968, 1601, 1489 cm$^{-1}$; CI MS m/z=432 $[C_{24}H_{29}N_7+H]^+$.

Example 15

Preparation of Compound 19

To a solution of n-BuLi (2.5M hexane solution, 10.9 mL, 27.4 mmol) in ethyl ether 28 mL at −78° C. was added 2-bromopyridine (4.33 g, 27.4 mmol) in ethyl ether (15 mL). After stirring for 30 min, a solution of trimethylstannylchloride (6.0 g, 30 mmol) in THF (10 mL) was added. Stirring was continued at −78° C. for 2 h and the mixture was then warmed up to room temperature and filtered. The precipitate was washed with ether and the combined the ether filtrates were concentrated to give the crude product: $^1$H NMR (500 Hz, $CDCl_3$) δ 8.69–8.68 (d, 1H), 7.47–7.07 (m, 3H), 0.30 (s, 9H).

Example 16

Preparation of Compound 21

A mixture of 4-bromobenzonitrile (1.68 g, 9.2 mmol), crude 2-trimethylstannylpyridine (3.33 g, 13.8 mmol), and $PdCl_2(PPh_3)_2$ (321 mg, 0.46 mmol) in DMF (25 mL) was heated at 150–155° C. in pressure tube for 24 h. The DMF was distilled off under reduced pressure and the residue was filtered through a short column of basic alumina and washed with ethyl acetate and then concentrated. Flash chromatography of the residue on silica gel gave the product (41%) as a white solid: mp 99–100° C.; $^1$H NMR (500 Hz, $CDCl_3$) δ 8.74 (dd, $J_1$=1 Hz, $J_2$=1.7 Hz, 1H), 8.12 (d, J=8.6 Hz, 2H), 7.83–7.76 (m, 4H), 7.32 (m, 1H).

Example 17

Preparation of Compound 22

To $LiAlH_4$ (8 mmol) in THF (25 mL) was added 21 (0.96 g, 5.3 mmol) in THF (15 mL) slowly while the flask was cooled with ice. The mixture was stirred at room temperature for 10–30 min then stirred at reflux for 4 h under nitrogen. The mixture was cooled in an ice bath and aqueous sodium hydroxide solution (0.5 mL, 10%) was added. The mixture was stirred until the residue became white and the solid was filtered and washed with methylene chloride (4×5 mL). The methylene chloride solution was dried with anhydrous sodium sulfate, concentrated, and the crude product was chromatographed on silica gel to give the product as a yellow liquid. A small amount of ethanol was added and the pure amine 22 was obtained as a white solid (74%) after filtration: mp 114–117° C.; $^1$H NMR (500 Hz, $CDCl_3$) δ 8.66 (d, J=4.4 Hz, 1H), 7.94 (d, J=8.1 Hz, 2H), 7.70 (m, 2H), 7.39 (d, J=8.0 Hz), 7.19 (m, 1H), 3.90 (s, 2H), 1.98 (s, 2H).

Example 18

Preparation of Compound 23

A mixture of 2,6-dichloropurine (1, 0.19 g, 1 mmol), amine 22 (0.39 g, 2.15 mmol) in ethanol (13 mL), and water (3.4 mL) was heated at 100–110° C. under nitrogen for 24 h and then it was cooled to room temperature. The mixture was concentrated and water (5 mL) was added. A solid was filtered and washed with water (2×5 mL) and dried under vacuum to give the product (93%) as yellow solid: mp 260° C. (dec); $^1$H NMR (500 Hz, DMSO-$d_6$) δ 12.4 (bs, 1H), 8.76 (m, J=1 Hz, 1H), 8.28 (s, 1H), 8.16 (d, J=8.1 Hz, 2H), 8.03 (d, J=7.8 Hz, 1H), 7.97 (m, 1H), 7.58 (d=8.6 Hz, 2H), 7.45 (m, 1H), 4.82 (s, 2H).

Example 19

Preparation of Compound 24

To the solution of compound 23 (0.33 g, 1 mmol) in DMSO (5.2 mL), added potassium carbonate (0.7 g, 5 mmol) and 2-iodopropane (0.5 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (76%) as white crystals: mp 178–179° C.; $^1$H NMR (500 Hz, CDCl$_3$) δ 8.68 (m, 1H), 7.96 (d, J=8 Hz, 2H), 7.76–7.70 (m, 2H), 7.73 (s, 1H), 7.47 (d, J=8 Hz, 2H), 7.22 (m, 1H), 4.89 (s, 1H), 4.79 (m, 1H), 1.54 (d, J=6.8 Hz, 6H); CI MS m/z=379 [C$_{20}$H$_{19}$ClN$_6$+H]$^+$. Anal. Calcd. for C$_{20}$H$_{19}$ClN$_6$: C, 63.41; H, 5.05; N, 22.18. Found: C, 63.07; H, 5.01; N, 22.01.

Example 20

Preparation of Compound 17

To compound 24 (0.7 g, 1.8 mmol) was added (R)-(–)-2 amino-1-butanol (3.5 g, 3.9 mmol) stirred in a sealed tube for 2 h at 190° C. The reaction mixture was allowed to cool and then was partitioned between EtOAc and brine. The EtOAc was separated, washed with saturated brine (4×), dried with Na$_2$SO$_4$, and concentrated. The product was air dried to give an oil, then dissolved in EtOAc. The EtOAc solution was cooled again, and the precipitate collected, washed with cold EtOAc (2×), air dried, and heated in vacuo for 2 h to give 17 (0.54 g, 67%): mp 98–100° C.; $^1$H NMR (300 MHz, CDCl$_3$) δ 8.00–7.85 (m, 2H), 7.75–7.55 (m, 2H), 7.50–7.35 (m, 3H), 7.30–7.15 (m, 1H), 6.40–6.20 (bs, 1H), 5.00–4.82 (m, 1H), 4.80–4.68 (bs, 3H), 4.60 (heptuplet, 1H), 3.98–3.70 (m, 2H), 3.70–3.54 (dd, 1H), 2.10 (bs, 1H), 1.75–1.53 (m, 2H), 1.51 (d, 6H), 1.00 (t, 3H); IR (KBr) 3406, 2969, 1601, 1490, 1389, 1254, 779 cm$^{-1}$; API MS m/z=432 [C$_{24}$H$_{29}$N$_7$O+H]$^+$.

Example 21

Preparation of Compound 25

To compound 4 (0.14 g, 0.33 mmol) was added 3-(tributylstannyl)pyridine (0.15 g, 0.33 mmol), Pd(PPh$_3$)$_4$ (0.06 g, 0.41 mmol), and toluene (10 mL). The solution was degassed with argon for 8 min in a sealed tube, and heated in an oil bath for 3 h at 130° C. The cooled reaction mixture was diluted with saturated NaHCO$_3$ and extracted with CH$_2$Cl$_2$ (3×50 mL). The combined organic extracts were washed with brine and dried over Na$_2$SO$_4$. The reaction mixture was purified by column chromatography on silica gel to give the desired coupling product. The product was dissolved in acetonitrile and washed with hexane (3×10 mL) to remove a portion of the tin contaminants. The reaction mixture was again purified by column chromatography on reversed phase silica gel to give compound 25 (0.04 g): $^1$H NMR (300 MHz, CDCl$_3$) δ 8.83 (s, 1H), 8.58 (d, 1H), 7.88–7.83 (m, 1H), 7.56–7.46 (m, 5H), 7.38–7.33 (m, 1H), 5.99 (s, 1H), 5.11 (s, 1H), 4.90–4.83 (m, 2H), 4.63–4.56 (m, 1H), 3.92–3.81 (m, 2H), 3.67–3.60 (m, 1H), 1.69–1.49 (m, 8H), 1.05–1.00 (t, 3H); CI MS m/z=432 [C$_{24}$H$_{29}$N$_7$O+H]$^+$.

Example 22

Preparation of Compound 27

A mixture of diethyl(3-pyridyl)borane (26, 540 mg, 3.67 mmol), 4-bromobenzonitrile (803 mg, 4.41 mmol) and Pd(PPh$_3$)$_4$ (144 mg, 0.13 mmol) in toluene (9 mL), ethanol (1.3 mL) and 2M aqueous sodium carbonate solution (4.1 mL, 8.2 mmol) was heated at 90–100° C. under nitrogen for 27 h. The mixture was cooled to room temperature and water (10 mL) was added. The organic layer was separated and the aqueous layer was extracted with ethyl acetate (2×20 mL). The combined organic layers were washed with brine (2×15 mL) and dried over anhydrous sodium sulfate. Flash chromatography of the crude product on silica gave the product as a white solid (80%): mp 95–96° C.

Example 23

An Alternative Preparation of 27 is Described Below

A flask charged with 4-bromobenzonitrile (360 mg, 2.0 mmol), bis(pinacolato)diboron (560 mg, 2.2 mmol), potassium acetate (590 mg, 6.0 mmol) and PdCl$_2$(dppf) (49 mg, 0.06 mmol) was flushed with nitrogen and DMF (12 mL) was added. The mixture was heated at 80–85° C. for 4 h and then cooled to room temperature at which time PdCl$_2$(dppf) (49 mg, 0.06 mmol), 3-bromopyridine (385 δL, 3.40 mmol), and 2M aqueous sodium carbonate solution (5 mL, 10 mmol) was added. The mixture was stirred at 80–85° C. for 24 h and extracted with ethyl ether (3×30 mL) and then washed with brine (3×15 mL) and dried with anhydrous sodium sulfate. Flash chromatography of the crude product on silica gel gave the product as white crystals (56%): mp 96–97° C.; $^1$H NMR (500 Hz, CDCl$_3$) δ 8.55 (dd, J$_1$=1 Hz, J$_2$=1.4 Hz, 1H), 8.66 (m, 1H), 7.90–7.87 (m, 1H), 7.77 (d, J=7.8 Hz, 2H), 7.69 (d, J=8.8 Hz, 2H), 7.42 (m, 1H).

Example 24

Preparation of Compound 28

To LiAlH$_4$ (8 mmol) in THF (25 mL) was added 27 (0.96 g, 5.3 mmol) in THF (25 mL) slowly while the flask was cooled with ice. The mixture was stirred at room temperature for 10–30 min then stirred at reflux for 4 h under nitrogen. The mixture was cooled in an ice bath and aqueous sodium hydroxide solution (0.5 mL, 10%) was added. The mixture was stirred until the residue became white and the solid was filtered and washed with methylene chloride (4×5 mL). The methylene chloride solution was dried with anhydrous sodium sulfate, concentrated, and the crude product was chromatographed on silica gel to give the product as a yellow liquid. A small amount of ethanol was added and the pure amine 28 was obtained as a white solid (46%) after filtration: mp 94–96° C.; $^1$H NMR (500 Hz, CDCl$_3$) δ 8.74 (d, J=2.4 Hz, 1H), 8.48 (dd, J$_1$=1.5 Hz, J$_2$=4.7 Hz, 1H), 7.77 (m, 1H), 7.45 (d, J=8.10 Hz, 2H), 7.33 (d, J=8.0 Hz, 2H), 7.25 (m, 1H), 3.83 (s, 2H), 2.25 (s, 2H).

Example 25

Preparation of Compound 29

A mixture of 2,6-dichloropurine (1, 0.19 g, 1 mmol), amine 28 (0.4 g, 2.15 mmol) in ethanol (13 mL), water (3 mL) was heated at 100–110° C. under nitrogen for 24 h and then it was cooled to room temperature. The mixture was concentrated and water (5 mL) was added. A solid was filtered and washed with water (2×5 mL) and dried under vacuum to give the product (92%) as a yellow solid: mp 219° C. (dec); $^1$H NMR (500 Hz, DMSO-d$_6$) δ 13.2 (bs, 1H), 8.99 (s, 1H), 8.66 (d, J=3.5 Hz, 1H), 8.28 (s, 1H), 8.16 (d, J=7.3 Hz, 1H), 7.80 (d, J=7.6 Hz, 2H), 7.60–7.57 (m, 3H).

Example 26

Preparation of Compound 30

To a solution of 29 (0.3 g, 1 mmol) in DMSO (5 mL), was added potassium carbonate (0.7 g, 5 mmol) and 2-iodopropane (0.5 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (76%) as white crystals: mp 178–179° C.; $^1$H NMR (500 Hz, CDCl$_3$) δ 8.82 (d, J=1.3 Hz, 1H), 8.59–8.58 (m, 1H), 7.86–7.84 (m, 1H), 7.72 (s, 1H), 7.56–7.48 (m, 4H), 7.37–7.34 (m, 1H), 4.88 (s, 2H), 4.82 (m, 1H), 1.56 (d, J=0.7 Hz, 3H), 1.55 (d, J=0.8 Hz, 3H); CI MS m/z=379 [C$_{20}$H$_{19}$ClN$_6$+H]$^+$. Anal. Calcd. for C$_{20}$H$_{19}$ClN$_6$: C, 63.41; H, 5.05; N, 22.18. Found: C, 63.24; H, 4.97; N, 21.93.

Example 27

Preparation of Compound 32

To a mixture of 4 (0.05 g, 0.11 mmol) was added 4-(tributylstannyl)pyridine (0.06 g, 0.16 mmol), Pd(PPh$_3$)$_4$ (0.02 g, 0.02 mmol), and toluene (2.5 mL). The reaction mixture was degassed and heated in a sealed tube at 125° C. for 3 h. The reaction mixture was cooled to room temperature then saturated NaHCO$_3$ (30 mL) was added followed by extraction with CH$_2$Cl$_2$ (3×30). The organic layer was washed with brine (50 mL), dried with MgSO$_4$, and concentrated. The reaction mixture was purified by column chromatography on silica gel to give 32: $^1$H NMR (300 MHz, CDCl$_3$) δ 8.65 (s, 2H), 7.60–7.57 (m, 2H), 7.49–7.45 (m, 5H), 6.20 (s, 1H), 4.93 (d, 1H), 4.84 (s, 2H), 4.65–4.57 (m, 1H), 3.92–3.80 (m, 2H), 3.68–3.51 (m, 1H), 1.68–1.58 (m, 2H), 1.52 (d, 6H), 1.05–0.99 (t, 3H).

Example 28

Preparation of Compound 33

To compound 4 (0.18 g, 0.43 mmol) was added 4-vinylphenylboronic acid (0.19 g, 1.28 mmol), Pd(PPh$_3$)$_4$ (0.09 g, 0.08 mmol), Na$_2$CO$_3$ (2M, 0.85 mL), was added toluene (5 mL). The mixture was degassed with argon for 10 min. The resulting solution was heated in a sealed tube at 135° C. for 4.5 h. The cooled solution was diluted with water and extracted with CH$_2$Cl$_2$ (3×50 mL). The combined organic extracts were washed with brine and dried over Na$_2$SO$_4$. The solution was purified by flash column chromatography (2×) on silica gel to give the desired product 33 as a yellow solid (0.09 g): mp 130–131° C.; $^1$H NMR (300 MHz, CDCl$_3$) δ 7.57–7.42 (m, 9H), 6.80–6.70 (dd, 1H), 5.98 (s, 1H), 5.79 (d, 1H), 5.27 (d, 1H), 4.88 (d, 1H), 4.84–4.72 (m, 2H), 4.63–4.56 (m, 1H), 3.92–3.81 (m, 2H), 3.66–3.60 (m, 1H), 1.68–1.52 (m, 8H), 1.05–1.00 (t, 3H); IR (CH$_2$Cl$_2$) 3293, 2968, 1601, 1489, 1390 cm$^{-1}$; CI MS m/z=457 [C$_{27}$H$_{32}$N$_6$O+H]$^+$.

Example 29

Preparation of Compound 34

To compound 33 (0.008 g, 0.016 mmol) was added OsO$_4$ (0.007 g, 0.026 mmol), pyridine (0.08 mL), and toluene (0.75 mL). The reaction mixture was stirred at room temperature in the dark for 1 h, concentrated in vacuo, and then slurried in methanol/water (9:1). Sodium metabisulfite (0.07 g) was added and the reaction was stirred for 1 h. The mixture was washed with brine, extracted with CH$_2$Cl$_2$ (3×10 mL), dried over Na$_2$SO$_4$, and concentrated. The product was purified by column chromatography on silica gel to give compound 34 (0.003 g) as a tan solid: $^1$H NMR (300 MHz, CDCl$_3$) δ 7.51 (s, 1H), 7.43–7.35 (m, 6H), 7.25–7.22 (m, 2H), 6.51 (s, 1H), 4.98 (d, 1H), 4.35–4.25 (m, 2H), 4.64–4.54 (m, 1H), 3.93–3.80 (m, 3H), 3.74–3.59 (m, 3H), 1.68–1.58 (m, 2H), 1.52 (d, 6H), 1.06–0.99 (t, 3H).

Example 30

Preparation of Compound 36

To compound 4 (0.12 g, 0.27 mmol) was added 3-aminophenylboronic acid hydrochloride (0.12 g, 0.69 mmol), and Pd(PPh$_3$)$_4$ (0.09 g, 0.75 mmol) in a sealed tube filled with argon. To this mixture was added toluene (5 mL) and Na$_2$CO$_3$ (2M, 0.55 mL). The resulting solution was degassed with argon for 5 min and placed in a 130° C. oil bath for 6 h. The cooled solution was diluted with water and extracted with CH$_2$Cl$_2$ (3×50 mL). The combined organic layers were washed with brine, dried over Na$_2$SO$_4$, and concentrated. The solution was purified by column chromatography on silica gel to yield 36 (0.04 g, 36%): $^1$H NMR (300 MHz, CDCl$_3$) δ 7.52–7.46 (m, 3H), 7.39 (d, 2H), 7.23–7.18 (m, 1H), 6.96 (d, 1H), 6.88 (t, 1H), 6.68–6.66 (m, 1H), 6.12 (s, 1H), 4.90 (d, 1H), 4.79 (s, 2H), 4.62–4.57 (m, 1H), 3.92–3.76 (m, 4H), 3.66–3.60 (m, 1H), 1.65–1.48 (m, 8H), 1.04–0.99 (t, 3H); CI MS m/z=446 [C$_{25}$H$_{31}$N$_7$O+H]$^+$.

Example 31

Preparation of Compound 38

To a suspension of Pd(PPh$_3$)$_4$ (0.02 g, 0.01 mmol) in anhydrous DME (8 mL) was added 4 (0.12 g, 0.27 mmol) and the mixture stirred at room temperature for 10 min. To this solution was added 3-(trifluoromethyl)phenylboronic acid (37; 0.12 g, 0.65 mmol) in a minimum of EtOH, followed by Na$_2$CO$_3$ (2M, 0.27 mL), and the resulting mixture was heated at reflux for 20 h. The cooled reaction mixture was diluted with water and extracted with CH$_2$Cl$_2$ (3×50 mL). The combined organic layers were washed with brine, dried over Na$_2$SO$_4$, and concentrated. The reaction mixture was purified by column chromatography on normal phase silica gel followed by reversed phase column chromatography to obtain 38 (0.04 g, 33%) as an off white solid: mp 60–67° C.; $^1$H NMR (300 MHz, CDCl$_3$) δ 7.81 (s, 1H), 7.74 (d, 1H), 7.58–7.45 (m, 7H), 5.98 (s, 1H), 4.90–4.83 (m, 3H), 4.63–4.59 (m, 1H), 3.90–3.81 (m, 2H), 3.66–3.60 (m, 1H), 1.68–1.51 (m, 8H), 1.05–1.00 (t, 3H); IR (KBr) 3406, 2969, 1602, 1489, 1335 cm$^{-1}$; CI MS m/z=499 [C$_{26}$H$_{29}$FN$_7$O+H]$^+$.

Example 32

Preparation of Compound 40

A mixture of 4 (0.13 g, 0.31 mmol), 2-naphthaleneboronic acid (39; 0.11 g, 0.62 mmol) and Pd(PPh$_3$)$_4$ (0.09 g, 0.08 mmol) was placed in a sealed tube that was filled with argon. To the mixture was added toluene (5 mL) and Na$_2$CO$_3$ (2M, 0.62 mL). The tube was quickly sealed and heated at 125° C. in an oil bath for 6 h. The cooled solution was diluted with water and extracted with CH$_2$Cl$_2$ (3×50 mL). The organic layers were washed with brine, dried over Na$_2$SO$_4$, and concentrated. The reaction mixture was purified by column chromatography on normal phase silica gel, followed by reversed phase chromatography to give 40 (0.04 g, 28%): mp 70–75° C.; $^1$H NMR (300 MHz, CDCl$_3$) δ 8.02 (s, 1H), 7.92–7.84 (m, 3H), 7.74–7.67 (m, 3H), 7.51–7.44 (m, 5H), 5.96 (s, 1H), 4.89–4.84 (m, 3H), 4.66–4.57 (m, 1H), 3.93–3.82 (m, 2H), 3.67–3.61 (m, 1H), 1.76–1.50 (m, 8H), 1.06–1.01 (t, 3H); IR (KBr) 3422, 2927, 1601, 1491, 1388 cm$^{-1}$.

Example 33

Preparation of Compound 43

To compound 4 (0.14 g, 0.33 mmol) was added 4-methoxyphenylboronic acid (42, 0.11 g, 0.71 mmol), Pd(PPh$_3$)$_4$ (0.10 g, 0.087 mmol), Na$_2$CO$_3$ (2M, 0.66 mL), and toluene (7 mL). The solution was degassed for 8 min with argon and heated in an oil bath at 125° C. for 6 h. The cooled solution was diluted with water and extracted with CH$_2$Cl$_2$ (3×50 mL). The combined organic layers were washed with brine, dried over Na$_2$SO$_4$, filtered, and concentrated. The reaction mixture was purified by normal phase column chromatography followed by reversed phase chromatography to give 43 (0.05 g, 28%) as a white solid: mp 128–130° C.; $^1$H NMR (300 MHz, CDCl$_3$) δ 7.52–7.50 (m, 5H), 7.41 (d, 2H), 6.97 (d, 2H), 5.93 (s, 1H), 4.89–4.79 (m, 3H), 4.63–4.56 (m, 1H), 3.92–3.81 (m, 5H), 3.67–3.60 (m, 1H), 1.68–1.49 (m, 8H), 1.05–1.00 (t, 3H); IR (KBr) 3417, 2931, 1610, 1499, 1389 cm$^{-1}$; CI MS m/z=461 [C$_{26}$H$_{32}$N$_6$O$_2$+H]$^+$.

Example 34

Preparation of Compound 45

To a solution of s-BuLi (5 mL, 6.24 mmol) and TMEDA (1 mL) in anhydrous THF (35 mL) at −75° C. under argon was added dropwise a solution of N,N-diethylbenzamide (0.98 g, 5.57 mmol) in THF (5 mL). The mixture was stirred for 50 min and then treated with trimethylborate (2 mL, 17 mmol). The solution was allowed to warm to room temperature overnight. The colorless solution was cooled to 0° C. and acidified to pH=6 with 2N HCl. The THF was removed in vacuo and the residue was diluted with water. This was extracted with CH$_2$Cl$_2$ (3×50 mL) and the combined organic layers were washed with brine, dried over Na$_2$SO$_4$, concentrated in vacuo, followed by removal of trace solvent on the vacuum pump to give 45 as an off-white foamy solid: $^1$H NMR (300 MHz, CD$_3$OD) δ 7.67–7.39 (m, 4H), 3.88–3.69 (q, 4H), 1.41–1.30 (t, 6H).

Example 35

Preparation of Compound 46

To compound 4 (0.14 g, 0.31 mmol) was added 2-(diethylcarbamoyl)phenylboronic acid (45, 0.29 g, 1.31 mmol), Pd(PPh$_3$)$_4$ (0.1 g, 0.09 mmol), Na$_2$CO$_3$ (2M, 0.63 mL), toluene (5 mL), and the mixture degassed with argon for 10 min. The mixture was heated in an oil bath for 5 h at 135° C. The cooled solution was diluted with water and extracted with CH$_2$Cl$_2$ (3×50 mL). The organic layers were combined, washed with brine, dried over Na$_2$CO$_3$, and concentrated. The reaction mixture was purified by normal phase column chromatography on silica gel, followed by reversed phase chromatography to give 46 (0.03 g, 18%) as a yellow solid: $^1$H NMR (300 MHz, CDCl$_3$) δ 7.49–7.36 (m, 9H), 6.18 (s, 1H), 4.93 (d, 1H), 4.78 (s, 2H), 4.64–4.55 (m, 1H), 3.92–3.60 (m, 4H), 3.06–2.92 (m, 2H), 2.69–2.64 (m, 1H), 1.68–1.51 (m, 8H), 1.04–0.99 (t, 3H), 0.91–0.86 (t, 3H), 0.77–0.72 (t, 3H); CI MS m/z=530 [C$_{30}$H$_{39}$N$_7$O$_2$+H]$^+$.

Example 36

Preparation of Compound 48

To a suspension of Pd(PPh$_3$)$_4$ (0.08 g, 0.69 mmol) in DME was added 4 (0.129 g, 0.30 mmol) and the mixture stirred for 10 min at room temperature. To this was added 3-nitrophenylboronic acid (47, 0.157 g, 0.94 mmol) and Na$_2$CO$_3$ (2 M, 0.59 mL). The solution was heated at reflux under argon overnight. The cooled solution was diluted with water and extracted with CH$_2$Cl$_2$ (3×50 mL). The organic layers were combined, washed with brine, dried over Na$_2$SO$_4$, and concentrated in vacuo. The solution was purified by flash column chromatography on silica gel to give 48 (0.04 g, 29%) as a bright yellow solid: mp 73–77° C.; $^1$H NMR (300 MHz, CDCl$_3$) δ 8.43 (s, 1H), 8.20 (d, 1H), 7.89 (d, 1H), 7.63–7.43 (m, 6H), 6.01 (s, 1H), 4.95–4.76 (m, 3H), 4.68–4.58 (m, 1H), 3.98–3.80 (m, 2H), 3.68–3.60 (m, 1H), 1.71–1.40 (m, 8H), 1.02–0.98 (t, 3H); IR (KBr) 3405, 2930, 1713, 1602, 1490, 1351 cm$^{-1}$; CI MS m/z=476 [C$_{25}$H$_{29}$N$_7$O$_3$+H]$^+$.

Example 37

Preparation of Compound 50

To a suspension of Pd(PPh$_3$)$_4$ (0.09 g, 0.08 mmol) in DME (5 mL) was added 4 (0.14 g, 0.32 mmol) and the mixture stirred at room temperature for 15 min. To this was added benzo[b]furan-2-boronic acid (49, 0.153 g, 0.94 mmol) and Na$_2$CO$_3$ (2 M, 0.63 mL). The solution was heated at reflux under argon overnight. The reaction mixture was cooled, diluted with water, extracted with CH$_2$Cl$_2$ (3×50 mL). The organic layers were combined, washed with brine, dried over Na$_2$SO$_4$, and concentrated in vacuo. The solution was purified by flash column chromatography on silica gel followed by flash column chromatography on reversed phase silica to give 50 (0.09 g, 60%) as a white solid: $^1$H NMR (300 MHz, CDCl$_3$) δ 7.82 (d, 2H), 7.58–7.42 (m, 5H), 7.30–7.19 (m, 2H), 7.01 (s, 1H), 6.11 (s, 1H), 4.91 (d, 1H), 4.81 (s, 2H), 4.62–4.58 (m, 1H), 3.92–3.80 (m, 2H), 3.66–3.60 (m, 1H), 1.66–1.48 (m, 8H), 1.04–0.99 (t, 3H); CI MS m/z=471 [C$_{27}$H$_{30}$N$_6$O$_2$+H]$^+$.

Example 38

Preparation of Compound 52

To compound 4 (0.46 g, 1.20 mmol) was added 1-amino-1-cyclopentanemethanol (51, 1.0 g, 8.61 mmol) and EtOH (2 mL) and the mixture was heated in an oil bath at 150° C. for 60 h. The brown solution was cooled and heated again at 150° C. for 48 h. The reaction mixture was cooled and concentrated in vacuo. The reaction mixture was purified by flash column chromatography on silica gel to give 52 (0.39 g, 71%) as a tan solid: $^1$H NMR (300 MHz, CDCl$_3$) δ 7.48–7.40 (m, 3H), 7.29–7.20 (m, 2H), 6.88 (s, 1H), 6.25 (s, 1H), 5.10 (s, 1H), 4.72 (s, 2H), 4.63–4.51 (m, 1H), 3.78 (s, 2H), 2.10–1.65 (m, 8H), 1.54 (d, 6H); CI MS m/z=459 [C$_{21}$H$_{27}$BrN$_6$O+H]$^+$.

Example 39

Preparation of Compound 53

To a suspension of Pd(PPh$_3$)$_4$ (0.07 g, 0.06 mmol) in DME (5 mL) was added 52 (0.102 g, 0.22 mmol) and stirred at room temperature for 15 min. To this was added phenylboronic acid (0.098 g, 0.80 mmol) and Na$_2$CO$_3$ (2 M, 0.44 mL). The solution was heated at reflux under argon for 18 h. The reaction mixture was diluted with water, extracted with CH$_2$Cl$_2$ (3×50 mL), washed with brine, and dried over Na$_2$SO$_4$. The solution was purified by flash column chromatography on silica gel followed by flash column chromatography on reversed phase silica gel to give 53 (0.02 g, 20%): $^1$H NMR (300 MHz, CDCl$_3$) δ 7.59–7.31 (m, 10H), 6.95 (s, 1H), 5.95 (s, 1H), 5.10 (s, 1H), 4.79 (s, 2H), 4.61–4.52 (m, 1H), 3.76 (s, 2H), 2.01–1.61 (m, 8H), 1.54 (d, 6H); CI MS m/z=457 [$C_{27}H_{32}N_6O+H$]$^+$.

Example 40

Preparation of Compound 54

To compound 3 (0.26 g, 0.67 mmol) was added trans-4-aminocyclohexanol hydrochloride (0.62 g, 4.11 mmol), Et$_3$N (0.58 mL, 4.16 mmol), and ethanol (5 mL). The mixture was heated for 5 h at 135° C. in an oil bath. The temperature increased to 150° C. and heating was continued for a further 48 h. The solution was cooled and evaporated to give a yellow oil: CI MS m/z=459 [$C_{21}H_{27}BrN_6O+H$]$^+$.

Example 41

Preparation of Compound 55

To compound 3 (0.50 g, 1.31 mmol) was added cis-1,2-diaminocyclohexane (1.57 mL, 13.1 mmol) and EtOH (4 mL). The mixture was heated in an oil bath at 150° C. for 6 h. The reaction mixture was concentrated in vacuo. The reaction mixture was purified by column chromatography on silica gel to give 55 (0.49 g, 82%) as a yellow solid: $^1$H NMR (300 MHz, CDCl$_3$) δ 7.43–7.40 (m, 3H), 7.23 (d, 2H), 6.21 (s, 1H), 5.04 (d, 1H), 4.72 (s, 2H), 4.67–4.58 (m, 1H), 4.08–4.05 (m, 1H), 3.17–3.15 (m, 1H), 2.08 (s, 2H), 1.65–1.38 (m, 14H); CI MS m/z=458 [$C_{21}H_{28}BrN_7+H$]$^+$.

Example 42

Preparation of Compound 56

To compound 55 (0.10 g, 0.22 mmol) was added 2-(tributylstannyl)pyridine (0.10 g, 0.27 mmol), Pd(PPh$_3$)$_4$ (0.05 g, 0.04 mmol), and toluene (5 mL). The solution was degassed with argon for 8 min and heated at 135° C. for 3 h. The cooled solution was diluted with water, extracted with CH$_2$Cl$_2$ (3×50 mL), and the combined organic extracts were washed with brine, dried over Na$_2$SO$_4$, filtered, and concentrated. The solution was followed by flash column chromatography (2×) to give the desired product 56 (0.03 g, 36%) yellow crystalline solid: $^1$H NMR (300 MHz, CDCl$_3$) δ 8.68 (d, 1H), 7.96 (d, 2H), 7.78–7.69 (m, 2H), 7.49 (s, 1H), 7.44 (d, 2H), 7.23–7.18 (m, 1H), 6.10 (s, 1H), 5.10–5.00 (m, 1H), 4.83 (s, 2H), 4.69–4.60 (m, 1H), 4.20–4.10 (m, 1H), 3.27–3.13 (m, 1H), 2.48 (s, 2H), 1.78–1.42 (m, 14H); CI MS m/z=457 [$C_{26}H_{32}N_8+H$]$^+$.

Example 43

Preparation of Compound 57

To compound 1 (0.50 g, 1.31 mmol) was added trans-1,2-diaminocyclohexane (2.52 mL, 21 mmol), and EtOH (6 mL). The reaction mixture was placed in an oil bath and heated to 190° C. for 25 h. The reaction mixture was removed from the heat and cooled to room temperature, concentrated for purification. The reaction mixture was purified by column chromatography on silica gel to yield 57 (520 mg, 87%) as an off white foam: $^1$H NMR (300 MHz, DMSO) δ 7.95 (bs, 1H), 7.85 (s, 1H), 7.50 (d, 2H), 7.34 (d, 2H), 6.17 (d, 1H), 4.70–4.40 (m, 1H), 2.00–1.71 (m, 4H), 1.70–1.52 (m, 2H), 1.41 (d, 6H), 1.30–0.92 (m, 4H); API MS m/z=460 [$C_{21}H_{28}N_7Br+H$]$^+$.

Example 44

Preparation of Compound 58

Compound 57 (0.15 g, 0.32 mmol) was added to a suspension of Pd(PPh$_3$)$_4$ (0.11 g, 0.1 mmol) in DME (7 mL) and stirred at room temperature for 15 min. Phenylboronic acid (0.14 g, 1.14 mmol) was added followed by the Na$_2$CO$_3$ (2M, 0.62 mmol). The reaction mixture was refluxed under argon for 18 h and allowed to stir at room temperature for 51 h. It was then diluted with water, extracted with CH$_2$Cl$_2$, washed with brine, and then extracted with CH$_2$Cl$_2$. The organic layer was evaporated, dried over anhydrous Na$_2$SO$_4$, purified by column chromatography, and placed in vacuo for 18 h to give 58 (0.10 g, 72%) as a white solid: $^1$H NMR (300 MHz, CDCl$_3$) δ 7.62–7.35 (m, 10H), 5.92 (br, 1H), 4.83 (br, 2H), 4.74–4.56 (m, 2H), 3.77–3.55 (m, 1H), 2.55–2.43 (m, 1H), 2.16–1.91 (m, 2H), 1.73 (br, 2H), 1.52 (d, 6H), 1.37–1.09 (m, 6H); API MS m/z=456 [$C_{27}H_{33}N_7+H$]$^+$.

Example 45

Preparation of Compound 59

To compound 57 (460 mg, 1.0 mmol) in solution with CH$_2$Cl$_2$ (2 mL) was added acetic anhydride (0.44 mL, 4.6 mmol), catalytic DMAP, and pyridine (0.5 mL). The mixture was stirred at room temperature for 2.5 h. The mixture was diluted with CH$_2$Cl$_2$, washed with 2N HCl, and the combined organics were then washed with NaHCO$_3$. The organics were then washed with brine, dried over Na$_2$SO$_4$, filtered, and concentrated to give 59 (472 mg, 94%) as an off white solid: $^1$H NMR (300 MHz, DMSO-d$_6$) δ 7.76 (s, 1H), 7.42 (d, 2H), 7.29 (d, 2H), 4.68–4.40 (m, 1H), 4.10 (s, 3H), 3.61–3.40 (m, 2H), 2.15–1.80 (m, 2H), 1.74–1.55 (m, 4H), 1.45 (d, 6H), 1.35–1.05 (m, 4H); API MS m/z=500 [$C_{23}H_{30}BrN_7O+H$]$^+$.

Example 46

Preparation of Compound 60

To a suspension of Pd(PPh$_3$)$_4$ (0.11 g, 0.1 mmol) in DME (7 mL) was added compound 59 (0.15 g, 0.3 mmol) and stirred at room temperature for 15 min under argon. Phenylboronic acid (0.13 g, 1.06 mmol) was added, followed by Na$_2$CO$_3$ (2M, 0.62 mL). The reaction mixture was refluxed under argon for 18 h. The reaction mixture was then diluted with H$_2$O, extracted with CH$_2$Cl$_2$, washed with brine, and extracted with CH$_2$Cl$_2$. The organic layer was dried over anhydrous Na$_2$SO$_4$, purified by column chromatography, concentrated in vacuo for 18 h to yield 60 (61 mg, 42%): $^1$H NMR (300 MHz, DMSO-d$_6$) δ 7.96 (s, 1H), 7.72 (s, 1H), 7.51 (t, 3H), 7.40–7.28 (m, 3H), 7.28–7.13 (m, 2H), 5.84 (br, 1H), 4.46 (br, 3H), 3.47 (br, 2H), 1.83 (br, 1H), 1.62 (s, 4H), 1.43 (d, 6H), 0.12 (s, 3H); API MS m/z=498 [$C_{29}H_{35}N_7O+H$]$^+$.

Example 47

Preparation of Compound 61

To compound 3 (0.58 g, 1.53 mmol) was added trans-1,4-diaminocyclohexane (1.78 g, 15.6 mmol), and EtOH (4 mL). The mixture was heated in an oil bath at 150° C. for ca. 60 h. The reaction mixture was purified by column chromatography on silica gel to yield 61 (0.48 g, 68%) as an off white solid: mp 122–125° C.; $^1$H NMR (300 MHz, CDCl$_3$) δ 7.43 (s, 1H), 7.40 (d, 2H), 7.20 (d, 2H), 6.27 (s, 1H), 4.75–4.68 (m, 2H), 4.67–4.58 (m, 2H), 3.81–3.68 (m, 1H), 3.45 (s, 2H), 2.88–2.75 (m, 1H), 2.18–2.05 (m, 2H), 2.05–1.89 (m, 2H), 4.52 (d, 6H), 1.45–1.13 (m, 4H); CI MS m/z=459 [$C_{21}H_{28}BrN_7+H$]$^+$.

Example 48

Preparation of Compound 62

Amine 61 (53 mg, 0.12 mmol) was dissolved in CH$_2$Cl$_2$ (2 mL) and pyridine (5 mL). Acetic anhydride (0.05 g, 0.53 mmol) and DMAP (few crystals) were added. The reaction mixture was allowed to stir at room temperature for 2.25 h. The reaction mixture was diluted with $CH_2Cl_2$, washed with 2N HCl, $NaHCO_3$, dried over $MgSO_4$, filtered, and evaporated to yield 62 (0.05 g, 78%) as a white solid: $^1$H NMR (300 MHz, $CDCl_3$) δ 7.50–7.20 (m, 5H), 6.02 (br, 1H), 5.29–5.20 (m, 1H), 4.72 (d, 2H), 4.66–4.54 (m, 2H), 3.72 (br, 2H), 2.18–2.06 (m, 2H), 2.06–1.91 (m, 2H), 1.97 (s, 3H), 1.54 (d, 6H), 1.36–1.15 (m, 4H); API MS m/z=500 $[C_{23}H_{30}BrN_7O+H]^+$.

Example 49

Preparation of Compound 64

Compound 61 (0.05 g, 0.11 mmol) was dissolved in $CH_2Cl_2$ (3 mL) and $Et_3N$ (2 mL) and placed in an ice bath for 10 min. Compound 63 (0.06 g, 0.22 mmol) was dissolved in $CH_2Cl_2$ (2 mL), added dropwise, and rinsed with $CH_2Cl_2$ (1.5 mL). The ice bath was removed after 20 min and the reaction was allowed to stir for 7 d. The reaction mixture was diluted with $CH_2Cl_2$, washed with 2N HCl until the aqueous layer was acidic, washed with $NaHCO_3$, dried over $MgSO_4$, and evaporated. The desired product was isolated by column chromatography and dried in vacuo to yield 64 (0.04 g, 50%) as a green solid: $^1$H NMR (300 MHz, $CDCl_3$) δ 8.53 (d, 1H), 8.32–8.20 (m, 2H), 7.59–7.35 (m, 4H), 7.23–7.11 (m, 4H), 6.02 (br, 1H), 4.69–4.45 (m, 5H), 3.57 (br, 1H), 3.12 (br, 1H), 2.87 (s, 1H), 1.97 (br, 2H), 1.75 (br, 2H), 1.48 (d, 6H), 1.27–0.97 (m, 4H); API MS m/z=693 $[C_{33}H_{39}BrN_8O_2S+H]^+$.

Example 50

Preparation of Compound 65

Compound 61 (0.05 g, 0.11 mmol) was dissolved in $CH_2Cl_2$ (3 mL) and $Et_3N$ (2 mL) and placed in an MeOH/ice bath. Methanesulfonyl chloride (0.012 mg, 0.11 mmol) in $CH_2Cl_2$ (2.3 mL) was slowly added. The reaction mixture and ice bath was allowed to come to room temperature. After 1.5 h, the reaction mixture was diluted with $CH_2Cl_2$, washed with 2N HCl until the aqueous layer was acidic. The organic layer was washed with $NaHCO_3$, dried over $MgSO_4$, filtered, and evaporated. The product was purified by column chromatography, and dried in vacuo for 14 h to yield 65 (13 mg, 24%) as an off-white solid: $^1$H NMR (300 MHz, $CDCl_3$) δ 7.50–7.17 (m, 5H), 5.90 (br, 1H), 4.75–4.57 (m, 3H), 4.11 (d, 1H), 3.69 (br, 1H), 3.30 (br, 1H), 2.99 (s, 3H), 2.18–2.03 (m, 4H), 1.69 (d, 6H), 1.42–1.15 (m, 5H); API MS m/z=538 $[C_{22}H_{30}BrN_7O_2S+H]^+$.

Example 51

Preparation of Compound 66

Compound 61 (0.05 g, 0.11 mmol) was dissolved in toluene (4 mL). 2-Acetylphenylisocyanate (0.024 g, 0.15 mmol) diluted with toluene (1 mL) and added to compound 61. Toluene (6 mL) was added to the reaction mixture. The reaction mixture was placed under reflux for 19 h. The product was purified by column chromatography, concentrated, and dried in vacuo for 23 h to yield 66 (42 mg, 62%) as an off-white solid: $^1$H NMR (300 MHz, $CDCl_3$) δ 7.87–7.20 (m, 9H), 6.41 (s, 1H), 5.86 (br, 1H), 4.75–4.54 (m, 4H), 3.69 (br, 1H), 2.60 (s, 3H), 2.12 (br, 4H), 1.51 (d, 6H), 1.42–1.15 (m, 5H); API MS m/z=619 $[C_{30}H_{35}BrN_8O_2+H]^+$.

Example 52

Preparation of Compound 67

Compound 61 (0.04 g, 0.10 mmol) was dissolved in $CH_2Cl_2$ (2 mL) and pyridine (0.5 mL). Cyclopropanecarbonyl chloride (0.05 g, 0.44 mmol) was added along with DMAP (small amount). The reaction mixture was allowed to stir at room temperature for 2.25 h. The reaction mixture was diluted with $CH_2Cl_2$, washed with 2N HCl, saturated $NaHCO_3$, dried over $MgSO_4$, filtered, and evaporated. The product was isolated by column chromatography to yield 67 (0.03 g, 63%) as a white solid: $^1$H NMR (300 MHz, $CDCl_3$) δ 7.50–7.20 (m, 5H), 5.96 (br, 1H), 5.41 (d, 1H), 4.72 (d, 2H), 4.66–4.54 (m, 2H), 3.72 (br, 2H), 2.18–1.97 (m, 4H), 1.51 (d, 6H), 1.36–1.15 (m, 5H), 1.06–0.88 (m, 2H), 0.79–0.67 (m, 2H); API MS m/z=526 $[C_{25}H_{32}BrN_7O+H]^+$.

Example 53

Preparation of Compound 69

To a solution of 4-biphenylcarboxaldehyde (1.0 g, 5.49 mmol) in MeOH (20 mL) was added $NaBH_3CN$ (0.69 g, 11.0 mmol), and $NH_4OH$ (15 mL) and the mixture was stirred at room temperature overnight. To this added HCl and extracted with $CHCl_3$. The resulting aqueous layer was brought to pH>7 with sodium bicarbonate and then extracted with $CHCl_3$. The solution was dried with $MgSO_4$, filtered, and evaporated to give 69 (200 mg) as a white solid: EI MS m/z=183 $[C_{13}H_{13}N]^+$.

Example 54

Preparation of Compound 69

To compound 70 (2.75 g, 13.9 mmol) was added anhydrous THF (60 mL), heated to reflux, and kept under nitrogen. 1M Borane-THF (69.7 mL) was added dropwise to 70 through an addition funnel resulting in a homogeneous solution. The solution was refluxed for 18 h. The reaction mixture was cooled in an ice water bath and quenched with $H_2O$, 2N HCl (20 mL), followed by 3N NaOH (60 mL). The reaction mixture was extracted with EtOAc (3×). The organic extracts were washed with brine, and dried over sodium sulfate. The crude product was concentrated, dissolved in MeOH, and HCl gas was bubbled through the solution. The solution was filtered in vacuo to give 69 as a white solid: $^1$H NMR (300 MHz, $CD_3OD$) δ 7.71 (d, 2H), 7.63 (d, 2H), 7.52 (d, 2H), 7.47–7.30 (m, 3H), 4.13 (s, 2H).

Example 55

Preparation of Compound 71

To compound 1 (6.8 g, 36.0 mmol) and 69 (8.0 g, 36.5 mmol) was added $H_2O$ (60 mL) and Hünigs base (9.0 g, 70.0 mmol). The mixture was stirred and heated to reflux for 5 h during which time $H_2O$ (50 mL) was added as the reaction continued to thicken. The crude product was collected by filtration, washed with $H_2O$ (500 mL) and EtOH (2×30 mL), air dried, and dried in vacuo to give 71 (11.1 g, 92%): mp 267–269° C.

Example 56

Preparation of Compound 72

Compound 71 (4.7 g, 14.0 mmol), $K_2CO_3$ (15.0 g, 109 mmol), DMSO (80 mL), and 2-iodopropane (9.4 g, 55.0 mmol) were combined and stirred overnight. $H_2O$ and EtOAc were added. The EtOAc layer was separated and washed with brine (3×). The EtOAc solution was dried with $MgSO_4$, concentrated, and crystallized from EtOAc to give 72 (3.5 g, 66%): mp 139–140° C.

Example 57

Preparation of Compound 73

Compound 72 (2.00 g, 5.30 mmol) and (R)-(−)-2-amino-1-butanol (10.8 g, 121 mmol) were combined in a sealed tube, and heated in an oil bath at 190° C. for 2 h. The solution was cooled to 60° C., diluted in EtOAc, washed with brine (4×), dried with Na$_2$SO$_4$, and concentrated. Purification by column chromatography on SiO$_2$ gave the desired product 73 (1.72 g, 75%) as a foam: $^1$H NMR (300 MHz, CDCl$_3$) δ 7.65–7.10 (m, 9H), 6.40–6.10 (bs, 1H), 5.05–4.85 (m, 1H), 4.85–4.67 (m, 1H), 4.60 (heptuplet, 1H), 4.00–3.70 (dd, 2H), 3.76–3.50 (m, 1H), 1.95 (bs, 1H), 1.80–1.55 (m, 2H), 1.51 (d, 6H), 1.03 (t, 3H); IR (CH$_2$Cl$_2$) 3301, 2969, 1601, 1488, 1389, 1255, 762, 698 cm$^{-1}$; API MS m/z=431 [C$_{25}$H$_{30}$N$_6$O+H]$^+$.

Example 58

Preparation of Compound 74

Compound 72 (0.23 g, 0.60 mmol), cis-1,2-diaminocyclohexane (0.72 mL, 6.0 mmol), and ethanol (2 mL) were combined in a sealed tube and heated in an oil bath at 155° C. for 5 d. The ethanol was removed in vacuo and the crude reaction mixture was filtered through a silica plug. The reaction mixture was chromatographed on silica gel, the resulting orange solid was dissolved in CH$_2$Cl$_2$ and a portion of activated charcoal was added. The solution was filtered through a pad of celite and concentrated to give 74 as a yellow solid (0.04 g, 27%): $^1$H NMR (300 MHz, CDCl$_3$) 7.59–7.31 (m, 10H), 6.00 (s, 1H), 5.09 (d, 1H), 4.83 (s, 2H), 4.68–4.62 (m, 1H), 4.11 (s, 1H), 3.70–3.65 (m, 2H), 3.18–3.16 (m, 1H), 2.02 (s, 2H), 1.67–1.42 (m, 12H); CI MS m/z=456 [C$_{27}$H$_{33}$N$_7$+H]$^+$.

Example 59

Preparation of Compound 75

Compound 72 (0.17 g, 0.45 mmol), trans-1,4-diaminocyclohexane (0.53 g, 4.69 mmol), and EtOH (5 mL) were combined in a sealed tube and heated at 155° C. for 5 d. The EtOH was removed in vacuo and the crude mixture was subjected to flash chromatography on silica gel. Recrystallization from CHCl$_3$/MeOH gave 75 (5.8 mg) as an off-white crystalline solid: mp 110–112° C.; $^1$H NMR (300 MHz, CDCl$_3$) δ 7.58–7.31 (m, 10H), 5.95 (s, 1H), 4.88–4.78 (m, 2H), 4.69–4.60 (m, 2H), 3.88–3.78 (m, 1H), 3.07–2.98 (m, 1H), 2.26–2.10 (m, 4H), 1.62–1.52 (m, 8H), 1.29–1.15 (m, 4H); CI MS m/z=456 [C$_{27}$H$_{33}$N$_7$+H]$^+$.

Example 60

Preparation of Compound 76

Compound 75 (0.05 g, 0.11 mmol) was dissolved in CH$_2$Cl$_2$ and the solution cooled to 0° C. under an argon atmosphere. A catalytic amount of DMAP, triethylamine (50 L, 0.36 mmol), followed by the acetyl chloride (25 L, 0.36 mmol) were added to the reaction mixture. The solution was warmed to room temperature and washed with NaHCO$_3$ (5%), water, and brine. The solution was dried over Na$_2$SO$_4$ and concentrated. Purification by flash chromatography on silica gel gave 76 (0.028 g, 53%) as a pale yellow solid: mp 224–225° C.; $^1$H NMR (300 MHz, CDCl$_3$) δ 7.59–7.31 (m, 10H), 5.93 (s, 1H), 5.26 (d, 1H), 4.81 (s, 2H), 4.65–4.58 (m, 1H), 3.78–3.75 (m, 2H), 2.18–1.99 (m, 4H), 1.95 (s, 3H), 1.77 (s, 1H), 1.53 (d, 6H), 1.32–1.22 (m, 4H); CI MS m/z=498 [C$_{29}$H$_{35}$N$_7$O+H]$^+$.

Example 61

Preparation of Compound 77

Compound 72 (0.15 g, 0.40 mmol), trans-4-aminocyclohexanol hydrochloride (0.31 g, 1.99 mmol), Et$_3$N (0.11 mL, 0.8 mmol), and EtOH (5 mL) were combined and heated in a sealed tube at 155° C. for 4 d. Additional trans-4-aminocyclohexanol hydrochloride (0.34 g, 2.2 mmol) and triethylamine (0.60 mL, 4.3 mmol) were added and the heat was resumed at 155° C. overnight. The crude product was purified by flash column chromatography to give 77 (0.036 g, 20%) as an off-white solid: mp 196–200° C.; $^1$H NMR (300 MHz, CDCl$_3$) δ 7.58–7.30 (m, 10H), 5.97 (s, 1H), 4.83–4.81 (m, 2H), 4.66–4.60 (m, 2H), 3.82–3.77 (m, 1H), 3.69–3.62 (m, 1H), 2.17–2.13 (m, 2H), 2.01–1.97 (m, 2H), 1.68 (s, 1H), 1.53 (d, 6H), 1.49–1.20 (m, 4H); CI MS m/z=457 [C$_{27}$H$_{33}$N$_6$O+H]$^+$.

Example 62

Preparation of Compound 78

To compound 61 (0.12 g, 0.26 mmol), was added compound 16 (0.12 g, 0.33 mmol), and Pd(PPh$_3$)$_4$ (0.06 g, 0.056 mmol) and toluene (5 mL). The resulting mixture was degassed for 10 min with argon. The mixture was heated at 140° C. for 3 h. The cooled solution was diluted with saturated NaHCO$_3$ and extracted with CH$_2$Cl$_2$ (3×50 mL). The combined organic extracts were washed with brine, dried over Na$_2$SO$_4$, filtered, and concentrated to give a pale yellow oil which crystallized upon standing at room temperature. The crude product was purified by column chromatography and concentrated to give a white solid. The solid was precipitated with acetonitrile, filtered, washed with ether and hexane to give 78 (0.02 g, 18%): $^1$H NMR (300 MHz, DMSO-d$_6$) δ 8.63 (d, 1H), 8.01 (d, 1H), 7.93–7.83 (m, 2H), 7.59–7.44 (m, 4H), 7.34–7.29 (m, 1H), 6.25 (s, 1H), 4.70–4.60 (m, 2H), 4.57–4.49 (m, 2H), 3.65–3.52 (m, 1H), 2.98–2.88 (m, 1H), 1.98–1.90 (m, 4H), 1.48 (d, 6H), 1.42–1.18 (m, 6H); CI MS m/z=457 [C$_{26}$H$_{32}$N$_8$+H]$^+$.

Example 63

Preparation of Compound 78

To compound 24 (200 mg, 0.53 mmol) was added trans-1,4-diaminocyclohexane (2.00 g, 17 mmol) and EtOH (4 mL). The reagents were heated in a sealed tube in an oil bath at 170° C. for 18 h. The mixture was cooled to 60° C. and partitioned between EtOAc and brine. The EtOAc layer was separated, washed with brine (3×), dried with Na$_2$SO$_4$, and concentrated to give 78 (0.12 g, 50%): mp 135–138° C.; $^1$H NMR (300 MHz, CDCl$_3$) δ 8.03–7.82 (m, 2H), 7.80–7.58 (m, 3H), 7.57–7.30 (m, 3H), 7.30–7.05 (m, 1H), 6.20 (bs, 1H), 5.95–4.73 (m, 2H), 4.73–4.45 (m, 2H), 3.90–3.60 (m, 1H), 2.80–2.52 (m, 1H), 2.25–1.80 (m, 4H), 1.80–1.60 (bs, 3H), 1.52 (d, 6H), 1.38–1.05 (m, 4H); IR (KBr) 3422, 2927, 1599, 1489, 1253, 779 cm$^{-1}$; API MS m/z=457 [C$_{26}$H$_{32}$N$_8$+H]$^+$.

Example 64

Preparation of Compound 79

Compound 78 (50 mg, 0.11 mmol) was dissolved in CH$_2$Cl$_2$ (2 mL) and stirred at room temperature. Pyridine (0.5 mL), Ac$_2$O (0.5 mL, 4.9 mmol), and DMAP (few crystals) were added to the reaction mixture and stirred for 2 h. The solution was diluted in CH$_2$Cl$_2$ and washed in 2N HCl. The HCl layer was concentrated, CH$_2$Cl$_2$ was added and the aqueous phase neutralized with saturated NaHCO$_3$. The CH$_2$Cl$_2$ layer was separated, dried (MgSO$_4$), and concentrated to give 79 (0.03 g, 55%) as a white solid: $^1$H NMR (300 MHz, CDCl$_3$) δ 8.00–7.80 (m, 2H), 7.81–7.57 (m, 2H), 7.56–7.33 (m, 3H), 7.30–7.05 (m, 2H), 6.15–5.90 (bs, 1H), 5.47–5.28 (m, 1H), 4.96–4.72 (m, 2H), 4.73–4.45 (m, 2H), 2.25–1.82 (m, 4H), 2.00 (s, 3H), 1.54 (d, 6H), 1.40–1.00 (m, 4H); API MS m/z=499 $[C_{28}H_{34}N_8O+H]^+$.

Example 65

Preparation of Compound 80

Compound 74 (0.02 g, 0.05 mmol) was dissolved in dry benzene (5 mL) and stirred under a blanket of argon. The solution was cooled in an ice bath and phenylisocyanate (25 L, 0.23 mmol) was added dropwise. The ice bath was removed and the mixture stirred at room temperature for 0.5 h. The solvent was evaporated in vacuo to give a yellow oil. The crude product was purified by flash column chromatography on silica gel to give 80 (0.008 g): $^1$H NMR (300 MHz, CDCl$_3$) δ 7.53–7.30 (m, 10H), 7.13–7.06 (m, 4H), 6.98–6.88 (m, 1H), 6.62 (s, 1H), 6.02 (s, 1H), 5.65 (s, 1H), 5.02 (d, 1H), 4.85–4.70 (m, 2H), 4.60–4.52 (m, 1H), 4.45–4.40 (m, 1H), 4.36–4.22 (m, 2H), 4.00 (s, 1H), 1.91–1.60 (m, 6H), 1.48–1.43 (m, 6H).

Example 66

Preparation of Compound 82

A mixture of 6-chloronicotinamide (2.96 g, 18.9 mmol), phenylboronic acid (2.54 g, 20.8 mmol), and Pd(PPh$_3$)$_4$ (643 mg, 0.565 mmol) in toluene (47 mL), ethanol (7 mL) and 2M aqueous sodium carbonate solution (21 mL, 43 mmol) was stirred and heated at 90–100° C. under nitrogen for 16 h. The mixture was cooled to room temperature and filtered. The resulting solid was washed with water (2×20 mL) and dried in vacuo. To the dried solid was added methanol (50 mL). The mixture was stirred at reflux, cooled to room temperature, and filtered to give the product (90%) as a powder: mp 218–220° C.; $^1$H NMR (500 Hz, DMSO-d$_6$) δ 9.23 (d, J=2.5 Hz, 1H), 8.41 (dd, J$_1$=2.2 Hz, J$_2$=8.3 Hz, 1H), 8.32 (s, 1H), 8.27 (d, J=7.1 Hz, 2H), 8.20 (d, J=8.5 Hz, 1H), 7.74 (s, 1H), 7.66–7.60 (m, 3H).

Example 67

Preparation of Compound 83

To NaBH$_4$ (0.19 g, 5 mmol) in 1,4-dioxane (4 mL) was added HOAc (0.3 g, 5 mmol) in 1,4-dioxane (2 mL) slowly while the flask was cooled with ice. Compound 82 (0.2 g, 1 mmol) was then added. The mixture was stirred at reflux at 100–110° C. for 4 h and the solvent was evaporated. To this mixture was added water (2 mL) slowly. The mixture was extracted with CH$_2$Cl$_2$ (4×10 mL), washed with water (3×5 mL), dried with anhydrous sodium sulfate, concentrated, and purified by flash chromatography on silica gel to provide the product as a yellow liquid. This was triturated with ethanol (1 mL) to provide a white solid which was collected (60%) and dried: mp 97–99° C.; $^1$H NMR (500 Hz, CDCl$_3$) δ 8.60 (d, J=2 Hz, 1H), 7.97–7.95 (m, 2H), 7.72–7.67 (m, 2H), 7.47–7.37 (m, 3H), 3.90 (s, 2H), 1.77 (bs, 2H).

Example 68

Preparation of Compound 84

A mixture of 2,6-dichloropurine (1, 0.19 g, 1 mmol), amine 83 (0.39 g, 2.15 mmol) in ethanol (13 mL), and water (3 mL) was heated at 100–110° C. under nitrogen for 24 h and then cooled to room temperature. The mixture was concentrated and water (5 mL) was added. A solid was filtered and washed with water (2×5 mL) and dried under vacuum to give the product (80%) as a yellow solid: mp 260° C. (dec); $^1$H NMR (500 Hz, DMSO-d$_6$) δ 13.26 (s, 1H), 8.79 (s, 1H), 8.27 (s, 1H), 8.16 (d, J=7.1 Hz, 2H), 8.34 (d, J=7.3 Hz, 1H), 7.96 (d, J=7.6 Hz, 1H), 7.63–7.52 (m, 3H), 4.81 (s, 2H).

Example 69

Preparation of Compound 85

To a solution of compound 84 (0.34 g, 1 mmol) in DMSO (5 mL), was added potassium carbonate (0.7 g, 5 mmol) and 2-iodopropane (0.5 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (63%) as ivory colored crystals: mp 138–139° C.; $^1$H NMR (500 Hz, CDCl$_3$) δ 8.70 (d, J=1.5 Hz, 1H), 7.97 (m, 2H), 7.79 (dd, J$_1$=1.7 Hz, J$_2$=8.1 Hz, 1H), 7.71 (s, 1H), 7.69 (d, J=8.1 Hz, 1H), 7.48–7.39 (m, 3H), 4.87 (s, 2H), 4.80 (m, 1H), 1.55 (d, J=6.8 Hz, 6H); CI MS m/z=379 $[C_{20}H_{19}ClN_6+H]^+$. Anal. Calcd. for $C_{20}H_{19}ClN_6$: C, 63.41; H, 5.05; N, 22.18. Found: C, 63.75; H, 5.09; N, 21.87.

Example 70

Preparation of Compound 86

To compound 85 (0.1 g, 0.26 mmol) was added trans-1,4-diaminocyclohexane (1 g, 8.8 mmol) and EtOH (2 mL). The reaction mixture was heated in a sealed tube in an oil bath at 120° C. The crude product was purified by column chromatography to give 86 (0.08 g, 67%): $^1$H NMR (300 MHz, CDCl$_3$) δ 8.68 (d, 1H), 7.83–7.97 (m, 2H), 7.70–7.83 (m, 1H), 7.55–7.73 (m, 1H), 7.30–7.55 (m, 4H), 6.35 (bs, 1H), 4.72–4.95 (m, 2H), 4.50–4.72 (m, 2H), 3.63–3.85 (m, 1H), 2.65–2.90 (m, 1H), 2.37–2.63 (bs, 2H), 1.80–2.20 (dd, 4H), 1.53 (d, 6H), 0.72–1.42 (m, 4H); API MS m/z=457 $[C_{26}H_{32}N_8+H]^+$.

Example 71

Preparation of Compound 87

Compound 86 (0.08 g, 0.18 mmol) was stirred at room temperature in CH$_2$Cl$_2$ (3 mL). Pyridine (100 mg, 0.82 mmol) was added followed by Ac$_2$O (100 mg, 0.98 mmol) and DMAP (few crystals). After 2 h, more CH$_2$Cl$_2$ (3 mL) was added and the mixture was washed carefully with 2N HCl (10 drops), and saturated NaHCO$_3$. After separation of the CH$_2$Cl$_2$ layer, the organic phase was then dried with Na$_2$SO$_4$ and concentrated to give 87 (80 mg, 92%): $^1$H NMR (300 MHz, CDCl$_3$) δ 8.72 (s, 1H), 8.30–7.03 (m, 9H), 5.75–5.38 (m, 1H), 5.02 (bs, 1H), 4.83 (bs, 2H), 4.72–4.40 (m, 1H), 3.73 (bs, 2H), 2.52–1.83 (m, 4H), 1.98 (s, 3H), 1.52 (d, 6H), 1.50–1.00 (m, 4H); API MS m/z=499 $[C_{28}H_{34}N_8O+H]^+$.

Example 72

Preparation of Compound 88

Compound 85 (0.05 g, 0.13 mmol) and (R)-(−)-2-amino-1-butanol (0.50 g, 5.6 mmol) were combined in a sealed tube and heated in an oil bath at 190° C. for 2 h then cooled to room temperature. The mixture was partitioned between EtOAc and brine, washed with brine (3×), dried with Na$_2$SO$_4$, and concentrated. The mixture was allowed to stand over the weekend and then purified by column chromatography on SiO$_2$ to give 88 (0.01 g, 17%) as a foam: $^1$H NMR (300 MHz, CDCl$_3$) δ 8.70 (s, 1H), 8.05–7.82 (m, 2H), 7.82–7.55 (m, 2H), 7.57–7.30 (m, 4H), 6.55 (bs, 1H), 5.00–4.88 (s, 1H), 4.78 (s, 2H), 4.60 (heptuplet, 1H), 3.98–3.83 (m, 1H), 3.84–3.70 (m, 1H), 3.70–3.50 (m, 1H), 2.90 (bs, 1H), 1.75–1.55 (m, 2H), 1.53 (d, 6H), 1.00 (t, 3H); API MS m/z=432 [C$_{24}$H$_{29}$N$_7$O+H]$^+$.

Example 73

Preparation of Compound 89

A mixture of 6-chloronicotinamide (2.5 g, 16 mmol), crude 2-trimethylstannylpyridine (5.8 g, 24 mmol), and PdCl$_2$(PPh$_3$)$_2$ (560 mg, 0.8 mmol) in DMF (35 mL) was heated at 150–160° C. in a pressure tube for 17 h. The DMF was distilled off under reduced pressure and the residue was extracted with ethyl acetate (6×30 mL) and concentrated. The residue was treated with methanol (15 mL) and a solid separated which was filtered and dried to give the product (40%) as a powder: mp 237–240° C.; $^1$H NMR (500 Hz, DMSO-d$_6$) 9.22 (d, J=2.2 Hz, 1H), 8.83 (m, 1H) 8.57–8.53 (m, 2H), 8.48–8.46 (m, 1H), 8.38 (s, 1H), 8.11–8.07 (m, 1H), 7.78 (s, 1H), 7.63–7.60 (m, 1H).

Example 74

Preparation of Compound 90

To NaBH$_4$ (0.2 g, 5 mmol) in 1,4-dioxane (4 mL) was added HOAc (0.29 g, 5 mmol) in 1,4-dioxane (2 mL) slowly while the flask was cooled with ice. Compound 89 (0.199 g, 1 mmol) was then added. The mixture was stirred at reflux at 100–110° C. for 4 h and the solvent was evaporated. To this mixture was added water (2 mL) slowly. The mixture was extracted with CH$_2$Cl$_2$ (4×10 mL), washed with water (3×5 mL), dried with anhydrous sodium sulfate, filtered, concentrated, and purified by flash chromatography on silica gel to provide the product as a yellow liquid. This was triturated with ethanol (1 mL) and a white solid (32%) was collected and dried: mp 109–112° C.; $^1$H NMR (500 Hz, CDCl$_3$) δ 8.63 (m, 1H), 8.58 (s, 1H), 8.32 (m, 2H), 7.77 (m, 2H), 7.25 (m, 1H), 3.91 (s, 2H), 1.94 (s, 2H).

Example 75

Preparation of Compound 91

A mixture of 2,6-dichloropurine (1, 0.2 g, 1 mmol), compound 90 (0.4 g, 2.2 mmol) in ethanol (13 mL), and water (3 mL) was heated at 100–110° C. under nitrogen for 24 h and then cooled to room temperature. The mixture was concentrated and water (5 mL) was added. A solid was filtered and washed with water (2×5 mL) and dried under vacuum to give the product (83%) as a yellow solid: mp 248° C. (dec); $^1$H NMR (500 Hz, DMSO-d$_6$) δ 13.27 (s, 1H), 8.81 (s, 1H), 8.78 (d, J=4.1 Hz, 1H), 8.47 (m, 2H), 8.28 (s, 1H), 8.06–8.01 (m, 2H), 7.50 (m, 1H), 4.84 (s, 2H).

Example 76

Preparation of Compound 92

To the solution of compound 91 (0.35 g, 1 mmol) in DMSO (5 mL), added potassium carbonate (0.68 g, 5 mmol) and 2-iodopropane (0.49 g, 3 mmol). The mixture was stirred at ambient temperature under nitrogen for 24 h and poured into ice water (30 mL). After filtration, the solid was washed with water (4×5 mL), dried under vacuum to give the crude product as a yellow solid. Flash column chromatography of the crude product on silica gel and recrystallization provided the pure product (64%) as white crystals: mp 150–151° C.; $^1$H NMR (500 Hz, CDCl$_3$) δ 8.71 (d, J=1.9 Hz, 1H), 8.67 (m, 1H), 8.38–8.36 (m, 2H), 7.86–7.79 (m, 2H), 7.75 (s, 1H), 7.30 (m, 1H), 4.91 (s, 2H), 4.82 (m, 1H), 1.57 (d, J=6.8 Hz, 6H); CI MS m/z=380 [C$_{19}$H$_{18}$ClN$_7$+H]$^+$. Anal. Calcd. for C$_{19}$H$_{18}$ClN$_7$: C, 60.08; H, 4.78; N, 25.81. Found: C, 59.76; H, 4.72; N, 25.57.

Example 77

Preparation of Compound 93

Compound 92 (150 mg, 0.39 mmol), trans-1,4-diaminocyclohexane (1.50 g, 13.1 mmol), and EtOH (30 mL) were heated to 120° C. for 26 h in a sealed tube. The mixture was cooled, additional EtOAc was added, washed with brine, dried over Na$_2$SO$_4$, and concentrated to give 93 (170 mg, 94%) as a waxy solid: $^1$H NMR (300 MHz, CDCl$_3$) δ 8.77–8.60 (m, 1H), 8.44–8.27 (m, 2H), 7.90–7.75 (m, 2H), 7.50 (s, 1H), 7.36–7.22 (m, 2H), 6.27 (bs, 1H), 4.96–4.73 (m, 2H), 4.73–4.52 (m, 2H), 3.84–3.60 (m, 1H), 2.80–2.57 (m, 1H), 2.22–2.00 (m, 2H), 2.00–1.67 (m, 5H), 1.54 (d, 6H), 1.38–1.05 (m, 4H); API MS m/z=458 [C$_{25}$H$_{31}$N$_9$+H]$^+$.

Example 78

Preparation of Compound 94

Compound 93 (0.15 g, 0.33 mmol) was dissolved in CH$_2$Cl$_2$ (6 mL) and then pyridine (0.200 g, 1.64 mmol) followed by Ac$_2$O (0.200 g, 1.96 mmol) and DMAP (few crystals) were added. The reaction mixture was stirred for 2 h, washed with 2N HCl and NaHCO$_3$, extracted with CH$_2$Cl$_2$, dried with Na$_2$SO$_4$, and concentrated to give 94 (0.17 g, 69%) as a solid: mp 141–145° C.; $^1$H NMR (300 MHz, CDCl$_3$) δ 8.80–8.63 (m, 1H), 8.45–8.25 (t, 2H), 7.95–7.73 (m, 1H), 7.52 (s, 1H), 7.35–7.20 (m, 2H), 6.20 (bs, 1H), 5.50–5.30 (m, 1H), 4.98–4.75 (m, 2H), 4.75–4.50 (m, 2H), 3.84–3.60 (m, 2H), 2.27–1.87 (m, 4H), 2.00 (s, 3H), 1.52 (d, 6H), 1.40–1.10 (m, 4H); API MS m/z=499 [C$_{27}$H$_{33}$N$_9$O+H]$^+$.

Example 79

Preparation of Compound 95

DME (3 mL), tris(dibenzylideneacetone)dipalladium (0.01 g, 0.01 mmol), and PPh$_3$ (0.04 g, 0.15 mmol) were added to a round bottomed flask equipped with a condensor and maintained under an argon atmosphere. To the solution was added compound 11 (0.13 g, 0.25 mmol). 3-Fluorobenzene boronic acid (0.123 g, 0.9 mmol) was dissolved in a solution of 2M Na$_2$CO$_3$ (0.6 mL) and DME (1 mL), and added to the reaction mixture. The mixture was stirred under argon and refluxed for 19 h then stirred at room temperature for 22 h. The reaction mixture was diluted with H$_2$O, extracted with CH$_2$Cl$_2$, washed with brine. The organic layer was dried over Na$_2$SO$_4$ and evaporated. The reaction mixture was purified twice by column chromatography and dried under high vacuum to give a white solid (17 mg, 14%): $^1$H NMR (300 MHz, CDCl$_3$) δ 7.56–7.32 (m, 8H), 7.08–6.99 (m, 1H), 5.86 (br, 1H), 4.83 (d, 2H), 4.71–4.56 (m, 1H), 3.77 (br, 2H), 2.70 (br, 1H), 2.12 (d, 1H), 1.88 (d, 1H), 1.51 (d, 6H), 1.22 (d, 5H), 0.94–0.70 (m, 3H); API MS m/z=474 [C$_{27}$H$_{32}$FN$_7$+H]$^+$.

Example 80

Preparation of Compound 96

A stock solution of acetic anhydride was made by mixing CH$_2$Cl$_2$ (16 mL), pyridine (4 mL), and Ac$_2$O (0.16 mL). To this stock solution (1.5 mL) was added compound 95 (0.01 g, 0.02 mmol) followed by DMAP (few crystals). The reaction mixture was allowed to stir at room temperature for 26 h. The reaction mixture was then diluted with $CH_2Cl_2$, washed with 2N HCl until the aqueous layer was acidic, washed with $NaHCO_3$, dried over $MgSO_4$, evaporated, and dried in vacuo for 15 h to give a white solid (11 mg, 92%): $^1$H NMR (300 MHz, $CDCl_3$) δ 8.65 (br, 1H), 7.77–7.17 (m, 8H), 7.11–6.99 (m, 1H), 5.14 (br, 2H), 4.90 (br, 1H), 4.69 (br, 1H), 3.78 (br, 2H), 2.09 (br, 3H), 1.94 (s, 2H), 1.57 (d, 6H), 1.42 (br, 4H), 1.24 (s, 2H), 0.94–0.76 (m, 1H); CI MS m/z=516 $[C_{29}H_{34}FN_7O+H]^+$.

Example 81

Preparation of Compound 97

A stock solution of acetic anhydride was made by mixing $CH_2Cl_2$ (16 mL), pyridine (4 mL), and $Ac_2O$ (0.16 mL). To this stock solution (1.5 mL) was added compound 13 (0.01 g, 0.02 mmol) followed by DMAP (few crystals). The reaction mixture was allowed to stir at room temperature for 2 h. The reaction mixture was then diluted with $CH_2Cl_2$, washed with 2N HCl until it was acidic, washed with $NaHCO_3$, dried over $MgSO_4$, and evaporated to give a white solid (8 mg, 89%): $^1$H NMR (300 MHz, $CDCl_3$) δ 8.78 (d, 1H), 8.44 (t, 1H), 7.95 (t, 2H), 7.69–7.45 (m, 5H), 5.30 (br, 2H), 4.84 (br, 1H), 4.68 (br, 1H), 3.78 (br, 2H), 2.39 (s, 3H), 2.10 (br, 4H), 1.96 (s, 2H), 1.57 (br, 10H), 1.25 (s, 2H), 0.88 (br, 1H); API MS m/z=512 $[C_{30}H_{37}N_7O+H]^+$.

Example 82

Preparation of Compound 98

DME (3 mL), tris(dibenzylideneacetone)dipalladium (0.01 g, 0.01 mmol), and $PPh_3$ (0.04 g, 0.15 mmol) were added to a round bottom flask equipped with condensor and maintained under an argon atmosphere. Iodide 11 (0.13 g, 0.26 mmol), and 3-chlorobenzene boronic acid (0.15 g, 0.93 mmol) was dissolved in 2M $Na_2CO_3$ (0.6 mL) and DME (1 mL). This was then added to the reaction mixture and refluxed for 19.5 h then stirred at room temperature for 30 h. The reaction mixture was then diluted with $H_2O$, extracted with $CH_2Cl_2$, washed with brine, dried over $Na_2SO_4$, filtered, and evaporated. The reaction mixture was purified by column chromatography (3×) and evaporated. The product was triturated in hexanes, filtered, and dried in vacuo for 1 h to give a white solid (16 mg): $^1$H NMR (300 MHz, $CDCl_3$) δ 7.56–7.38 (m, 9H), 6.01 (br, 1H), 4.80 (d, 2H), 4.71–4.62 (m, 1H), 3.77 (br, 2H), 2.73 (br, 1H), 2.19–2.04 (m, 1H), 1.94–1.85 (m, 1H), 1.51 (d, 6H), 1.24 (d, 5H), 0.91–1.76 (m, 3H); API MS m/z=490 $[C_{27}H_{32}ClN_7+H]^+$.

Example 83

Preparation of Compound 99

A stock solution of acetic anhydride was made by mixing $CH_2Cl_2$ (16 mL), pyridine (4 mL), and $Ac_2O$ (0.16 mL). To this solution (1.5 mL) was added compound 98 (0.01 g, 0.02 mmol), followed by DMAP (few crystals). The reaction mixture was allowed to stir at room temperature for 2 h. The reaction mixture was diluted with $CH_2Cl_2$, washed with 2N HCl until the aqueous layer was acidic, washed with $NaHCO_3$, dried over $MgSO_4$, filtered, and evaporated to give a white solid (0.01 g, 83%): $^1$H NMR (300 MHz, $CDCl_3$) δ 7.65–7.35 (m, 8H), 7.26–7.14 (m, 1H), 5.23 (br, 1H), 4.66 (br, 1H), 3.78 (br, 2H), 2.18–2.00 (m, 4H), 1.94 (s, 3H), 1.54 (d, 6H), 1.24 (s, 5H), 0.94–0.69 (m, 3H); API MS m/z=532 $[C_{29}H_{34}ClN_7O+H]^+$.

Example 84

Preparation of Compound 100

A stock solution of acetic anhydride was made by mixing $CH_2Cl_2$ (16 mL), pyridine (4 mL), and $Ac_2O$ (0.16 mL). To compound 14 (0.02 g, 0.03 mmol) was added this solution (2 mL), followed by DMAP (few crystals). The reaction mixture was allowed to stir at room temperature for 3 h. The reaction mixture was diluted with $CH_2Cl_2$, washed with 2N HCl until the aqueous layer was acidic, washed with $NaHCO_3$, filtered, and evaporated to give a white solid (8 mg, 44%): $^1$H NMR (300 MHz, $CDCl_3$) δ 7.41–7.32 (m, 7H), 7.26–7.14 (m, 1H), 5.96 (br, 1H), 5.23 (d, 1H), 4.84 (br, 2H), 4.69–4.54 (m, 1H), 3.75 (br, 1H), 2.21–2.12 (m, 1H), 2.09–1.96 (m, 1H), 1.97 (s, 3H), 1.54 (d, 6H), 1.36–1.15 (m, 5H), 0.85 (br, 3H); API MS m/z=550 $[C_{29}H_{33}ClFN_7O+H]^+$.

Example 85

Preparation of Compound 101

DME (3 mL), tris(dibenzylideneacetone)dipalladium (0.01 g, 0.01 mmol), and $PPh_3$ (0.04 g, 0.15 mmol) were added to a round bottomed flask equipped with a condensor and maintained under an argon atmosphere. Compound 10 (0.13 g, 0.26 mmol) and 4-fluorobenzene boronic acid (0.13 g, 0.95 mmol) was dissolved in 2M $Na_2CO_3$ (0.6 mL) and DME (1 mL). This was then added to the reaction mixture and refluxed for 19 h then stirred at room temperature for 72 h. The reaction mixture was then diluted with $H_2O$, extracted with $CH_2Cl_2$, washed with brine, dried over $Na_2SO_4$, filtered, and evaporated. The reaction mixture was purified by column chromatography on silica gel to give a white solid (17 mg, 14%): $^1$H NMR (300 MHz, $CDCl_3$) δ 7.56–7.38 (m, 8H), 7.11 (t, 1H), 5.81 (br, 1H), 4.81 (d, 2H), 4.69–4.57 (m, 1H), 3.78 (br, 2H), 2.69 (br, 1H), 2.12 (br, 1H), 1.88 (br, 1H), 1.54 (d, 6H), 1.33–1.12 (m, 5H), 0.85 (br, 3H); API MS m/z=474 $[C_{27}H_{32}FN_7+H]^+$.

Example 86

Preparation of Compound 102

A stock solution of acetic anhydride was made by mixing $CH_2Cl_2$ (16 mL), pyridine (4 mL), and $Ac_2O$ (0.16 mL). To the solution (1.4 mL) was added compound 101 (0.01 g, 0.02 mmol), followed by DMAP (few crystals). The reaction mixture was allowed to stir at room temperature for 2.5 h. The reaction mixture was diluted with $CH_2Cl_2$, washed with 2N HCl until the aqueous layer was acidic, and washed with saturated $NaHCO_3$. The organic layer was dried over $MgSO_4$ and evaporated to give a product (3 mg). The $NaHCO_3$ layer was further extracted with EtOAc (2×), the organic layers were combined, dried over $MgSO_4$, evaporated to give product 102 (2 mg). The products were combined using EtOAc, evaporated, and dried in vacuo for 15 h to give product 102 (5 mg, 50%): $^1$H NMR (300 MHz, $CDCl_3$) δ 7.71–7.08 (m, 9H), 5.29 (br, 2H), 4.84 (br, 1H), 4.66 (br, 1H), 3.78 (br, 2H), 2.09 (br, 4H), 1.97 (s, 1H), 1.57 (br, 3H), 1.24 (d, 6H), 0.87 (br, 5H); API MS m/z=516 $[C_{29}H_{34}FN_7O+H]^+$.

Example 87

Preparation of Compound 103

Compound 30 (0.10 g, 0.27 mmol) and trans-1,4-diaminocyclohexane (0.48 g, 4.2 mmol) were combined with EtOH (2 mL) in a sealed tube and heated at 190° C. for 24 h, and then stirred at room temperature for 46 h. The reaction mixture was purified by column chromatography and dried in vacuo to give 103 as a white solid (0.10 g, 81%): $^1$H NMR (300 MHz, CDCl$_3$) δ 8.83 (d, 1H), 8.58 (t, 1H), 7.87–7.83 (m, 1H), 7.55–7.47 (m, 5H), 7.38–7.33 (m, 1H), 5.96 (br, 1H), 4.82 (d, 2H), 4.68–4.59 (m, 1H), 3.75 (br, 2H), 2.69 (br, 1H), 2.14 (d, 2H), 1.86 (d, 2H), 1.54 (d, 6H), 1.31–1.18 (m, 5H); API MS m/z=457 [C$_{26}$H$_{32}$N$_8$+H]$^+$.

Example 88

Preparation of Compound 104

A stock solution of acetic anhydride was made by mixing CH$_2$Cl$_2$ (16 mL), pyridine (4 mL), and Ac$_2$O (0.16 mL). To the solution (3.1 mL) was added compound 103 (0.02 g, 0.04 mmol), followed by DMAP (few crystals). The reaction mixture was allowed to stir at room temperature for 2.5 h. The reaction mixture was evaporated, dried in vacuo for 19 h, and purified by column chromatography to give a white solid (0.02 g): $^1$H NMR (300 MHz, CDCl$_3$) δ 8.83 (d, 1H), 8.59 (t, 1H), 7.85 (d, 1H), 7.55–7.47 (m, 5H), 7.38–7.34 (m, 1H), 5.89 (br, 1H), 5.25 (d, 2H), 4.85 (br, 1H), 4.66–4.61 (m, 1H), 3.77 (br, 2H), 2.15 (br, 2H), 2.05 (br, 2H), 1.97 (s, 2H), 1.54 (d, 6H), 1.33–1.25 (m, 5H), 0.88 (br, 1H); API MS m/z=499 [C$_{28}$H$_{34}$N$_8$O+H]$^+$.

Example 89

Preparation of Compound 106

Compound 72 (0.30 g, 0.80 mmol) and compound 105 (1.15 g, 6.50 mmol) (Gardiner, J. M., et al. *Tetrahedron*, 42(11):515 (1995), which is hereby incorporated by reference, were combined with EtOH (7 mL) and allowed to reflux for 23 h. Triethylamine (1 mL) was added and the reaction was refluxed further for another 21 h. The reaction mixture was then transferred to a sealed tube and EtOH (3 mL) was added. The reaction mixture was heated further at 100° C. for 3 h. The mixture was purified by column chromatography to give 105 (0.13 g): $^1$H NMR (300 MHz, CDCl$_3$) δ 7.57–7.26 (m, 10H) 5.58 (br, 1H), 5.10 (br, 1H), 4.83 (br, 1H), 4.69–4.62 (m, 2H), 3.36–2.91 (m, 5H), 2.82–2.65 (m, 2H), 1.53 (d, 2H), 1.44 (s, 9H), 1.25 (d, 1H), 1.13 (d, 3H); CI MS m/z=416 [C$_{29}$H$_{39}$N$_7$O-Boc+H]$^+$.

Example 90

Preparation of Compound 107

To compound 106 (0.10 g, 0.18 mmol) was added Et$_2$O (2 mL), CH$_2$Cl$_2$ (1 mL) and MeOH (1 mL). During 16 h HCl/ether (1M, 5 mL) was added while stirring. The resulting precipitate was collected by filtration and dried in vacuo for 30 min to provide 106 as an off-white solid (60 mg, 81%): $^1$H NMR (300 MHz, DMSO) δ 8.48 (br, 2H), 8.15 (br, 1H), 7.67–7.27 (m, 10H), 4.79 (br, 1H), 3.60–3.42 (m, 3H), 3.18–3.06 (m, 2H), 3.03–2.91 (m, 2H), 1.52 (d, 2H), 1.27 (d, 6H); CI MS m/z=416 [C$_{24}$H$_{29}$N$_7$+H]$^+$.

Example 91

Preparation of Compound 108

A stock solution of acetic anhydride was made by mixing CH$_2$Cl$_2$ (16 mL), pyridine (4 mL), and Ac$_2$O (0.16 mL). To this solution (5.6 mL) was added compound 107 (0.04 g, 0.09 mmol), followed by DMAP (few crystals). The reaction mixture was allowed to stir at room temperature for 2 h. The reaction mixture was diluted with CH$_2$Cl$_2$, washed with 2N HCl until acidic, the organic layer was washed with NaHCO$_3$, dried over MgSO$_4$, filtered, and evaporated to give a white solid (16 mg). The product was purified by column chromatography to provide 108 as a white solid (0.01 g, 18%): $^1$H NMR (300 MHz, CDCl$_3$) δ 7.58–7.43 (m, 10H), 6.60 (br, 1H), 5.91 (br, 1H), 5.04 (t, 1H), 4.84 (br, 2H), 4.72–4.59 (m, 1H), 4.10–4.02 (m, 1H), 3.59–3.47 (m, 2H), 1.80 (s, 3H), 1.57 (d, 6H), 1.19 (d, 3H); CI MS m/z=458 [C$_{26}$H$_{31}$N$_7$O+H]$^+$.

Example 92

Preparation of Compound 109

Compound 61 (1.0 g, 2.18 mmol), 3-chlorophenylboronic acid (1.3 g, 8.16 mmol), PPh$_3$ (0.3 g, 1.26 mmol), 2M Na$_2$CO$_3$ (5.0 mL), and DME (54 mL) were added to a three-necked round-bottomed flask. The mixture was degassed with argon and heated to reflux for 40 min, cooled to room temperature, and then Pd$_2$(dba)$_3$ (0.08 g, 0.08 mmol) was added. The reaction mixture was heated at reflux for 7 h. 3-Chlorophenylboronic acid (0.6 g) and Pd$_2$(dba)$_3$ (0.08 g) was then added and reflux continued for 12 h. The reaction mixture was cooled to room temperature, diluted with H$_2$O (50 mL), and extracted with CH$_2$Cl$_2$ (3×50 mL). The combined organic phases were washed with H$_2$O (50 mL), brine (50 mL), dried over Na$_2$SO$_4$, filtered, and concentrated in vacuo. The residue was purified by silica gel chromatography and concentrated in vacuo to obtain compound 109 (950 mg, 89%): mp 178–181° C.; $^1$H NMR (500 MHz, CDCl$_3$) δ 7.56 (s, 1H), 7.42–7.54 (m, 6H), 7.26–7.35 (m, 2H), 6.08 (bs, 1H), 4.81 (bs, 2H), 4.5–94.64 (m, 2H), 3.75–3.81 (m, 1H), 2.65–2.72 (m, 1H), 2.12 (d, 2H), 1.88 (d, 2H), 1.53 (d, 6H), 1.18–1.27 (m, 4H); CI MS m/z=490 [C$_{27}$H$_{32}$ClN$_7$+H]$^+$.

Example 93

Preparation of Compound 110

Compound 109 (500 mg, 1.02 mmol) was dissolved in anhydrous CH$_2$Cl$_2$ (30 mL), cooled with an ice-water bath, followed by the addition of DMAP (12.2 mg, 0.1 mmol), pyridine (124 μL, 1.53 mmol), and Ac$_2$O (106 μL, 1.12 mmol). The reaction mixture was stirred for 30 min at 0° C. an ice-water bath then stirred another 2 h at room temperature. The reaction mixture was then concentrated in vacuo and the residue was purified by column chromatography on silica gel. After removal of the solvent, the residue was dried in vacuo to give 110 (339 mg, 63%): mp 198–200° C.; $^1$H NMR (500 MHz, CDCl$_3$) δ 7.57 (s, 1H), 7.39–7.53 (m, 6H), 7.27–7.37 (m, 2H), 6.31 (bs, 1H), 5.28 (d, 1H), 4.78 (bs, 2H), 4.70 (d, 1H), 4.58–4.67 (m, 1H), 3.72–3.83 (m, 1H), 2.18 (d, 2H), 2.00 (d, 2H), 1.90 (s, 3H), 1.51 (d, 6H), 1.18–1.31 (m, 4H); CI MS m/z=532 [C$_{29}$H$_{34}$ClN$_7$O+H]$^+$.

Example 94

Preparation of Compound 111

Compound 61 (1.0 g, 2.18 mmol), 2-thiopheneboronic acid (1.0 g, 8.16 mmol), PPh$_3$ (0.3 g, 1.26 mmol), 2M Na$_2$CO$_3$ (5.0 mL), Pd$_2$(dba)$_3$ (0.08 g, 0.08 mmol), and DME (54 mL) were added to a round-bottomed flask and purged with argon. The reaction mixture was heated at reflux for 24 h. 2-Thiopheneboronic acid (0.5 g), Pd$_2$(dba)$_3$ (0.1 g), and 2M Na$_2$CO$_3$ (2 mL) were added and heated to reflux for another 24 h. The reaction mixture was cooled to room temperature, diluted with H$_2$O (50 mL) and extracted with CH$_2$Cl$_2$ (3×50 mL). The organic phase was washed with H$_2$O (50 mL) and brine (50 mL), dried over Na$_2$SO$_4$, filtered, and concentrated in vacuo. The residue was repeatedly chromatographed on silica gel to obtain 111 (574 mg, 59%): mp 109–110° C.; $^1$H NMR (500 MHz, CDCl$_3$) δ 7.56 (d, 2H), 7.54 (s, 1H), 7.46 (d, 2H), 7.24–7.37 (m, 2H), 7.06 (t, 1H), 6.04 (bs, 1H), 4.78 (bs, 2H), 4.59–4.69 (m, 2H), 3.75–3.81 (m, 1H), 2.67–2.74 (m, 1H), 2.14 (d, 2H), 1.87 (d, 2H), 1.52 (d, 6H), 1.17–1.29 (m, 4H); CI MS m/z=462 [C$_{25}$H$_{31}$N$_7$S+H]$^+$.

Example 95

Preparation of Compound 112

Compound 111 (410.0 mg, 0.89 mmol) was dissolved in anhydrous CH$_2$Cl$_2$ (30 mL) and purged with N$_2$ and cooled with an ice-water bath. Pyridine (108 mg, 1.34 mmol) and DMAP (10.9 mg, 0.09 mmol) followed by Ac$_2$O (92 μL, 0.98 mmol) were added slowly. The reaction mixture was stirred for 30 min in an ice-water bath followed by 2 h at room temperature. The reaction mixture was concentrated in vacuo. The residue was chromatographed on silica gel to give 112 (325 mg, 73%): mp 237–244° C.; $^1$H NMR (500 MHz, CDCl$_3$) δ 7.54 (d, 2H), 7.50 (s, 1H), 7.36 (d, 2H), 7.24–7.37 (m, 2H), 7.08 (t, 1H), 6.06 (bs, 1H), 5.34 (s, 1H), 4.78 (bs, 2H), 4.58–4.70 (m, 2H), 3.78 (bs, 2H), 2.17 (d, 2H), 2.04 (d, 2H), 1.96 (s, 3H), 1.56 (d, 6H), 1.18–1.32 (m, 4H); CI MS m/z=504 [C$_{27}$H$_{33}$N$_7$OS+H]$^+$.

Example 96

Preparation of Compound 113

Compound 12 (600 mg, 1.30 mmol) was dissolved in anhydrous CH$_2$Cl$_2$ (40 mL), purged with N$_2$, and cooled to 0° C. followed by an addition of DMAP (15.9 mg, 0.13 mmol), pyridine (165.3 mg, 1.95 mmol), and Ac$_2$O (135 mg, 1.43 mmol). The mixture was stirred 30 min at 0° C. then 2 h at room temperature. The reaction mixture was concentrated in vacuo. The residue was chromatographed on silica gel to give 113 (495 mg, 76%): mp 248–253° C.; $^1$H NMR (500 MHz, CDCl$_3$) δ 7.54 (d, 2H), 7.46 (s, 1H), 7.35–7.41 (m, 5H), 6.13 (bs, 1H), 5.28 (d, 1H), 4.78 (br, 2H), 4.61–4.63 (m, 2H), 3.75 (bs, 2H), 2.14 (d, 2H), 1.97 (d, 2H), 1.95 (s, 3H), 1.52 (d, 6H), 1.15–1.37 (m, 4H); CI MS m/z=504 [C$_{27}$H$_{33}$N$_7$OS+H]$^+$.

Example 97

Preparation of Compound 114

To compound 61 (1.0 g, 2.18 mmol) was added PPh$_3$ (330 mg, 1.26 mmol), 2M Na$_2$CO$_3$ (5 mL), DME (54 mL), and 4-carboxyphenylboronic acid (1.0 g, 6.03 mmol). The mixture was purged with N$_2$ for 45 min then Pd$_2$(dba)$_3$ (366 mg, 0.4 mmol) was added and the mixture was heated at reflux for 3 d. The reaction mixture was diluted with H$_2$O (100 mL). The aqueous layer was separated, and washed with CH$_2$Cl$_2$ (3×40 mL). The aqueous layer was adjusted the pH to 5.8 by using 1N HCl. Some precipitate appeared. The mixture was stored in a freezer overnight. The precipitate was collected and dried to obtain 114 (450 mg, 41%): mp 246–249° C. (dec.); $^1$H NMR (500 MHz, CD$_3$OD+NaOD) δ 7.84 (s, 2H), 7.64 (s, 1H), 7.54–7.63 (m, 4H), 7.39 (s, 2H), 6.08 (bs, 1H), 4.85 (bs, 2H), 4.73 (s, 1H), 3.76 (m, 1H), 2.74 (m, 1H), 1.99 (s, 2H), 1.88 (s, 2H), 1.63 (d, 6H), 1.21–1.36 (m, 4H); CI MS m/z=500 [C$_{28}$H$_{33}$N$_7$O$_2$+H]$^+$.

Example 98

Preparation of Compound 115

To a cooled MeOH (20 mL) solution was slowly added TMSCl (253 μL, 2.0 mmol). The solution was stirred 20 min, followed by the addition of 114 (100 mg, 0.2 mmol). The reaction mixture was stirred at room temperature for 24 h. The reaction mixture was cooled with an ice-water bath then Et$_3$N (557 mL) was added. The mixture was concentrated in vacuo, to provide the crude product, which was washed with water (2×20 mL). The residue was purified by chromatography on a silica gel. After removal of the solvent and drying in vacuo, the residue was dissolved in MeOH (5 mL), followed by the addition of ether (10 mL). The precipitate was collected and dried to provide 115 (75 mg, 73%): mp194–197° C.; $^1$H NMR (500 MHz, CD$_3$OD) δ 8.07 (d, 2H), 7.80 (s, 1H), 7.72 (d, 2H), 7.63 (d, 2H), 7.46 (d, 2H), 4.63–4.79 (m, 1H), 3.91 (s, 3H), 3.65–3.77 (m, 1H), 3.07 (bs, 1H), 2.12 (d, 2H), 2.01 (d, 2H), 1.55 (d, 6H), 1.29–1.49 (m, 4H); API MS m/z=514 [C$_{29}$H$_{35}$N$_7$O$_2$+H]$^+$.

Example 99

Preparation of Compound 117

To a suspension of compound 114 (250 mg, 0.50 mmol), pyridine (60 μL, 0.75 mmol), and DMAP (6.1 mg, 0.05 mmol) in H$_2$O-dioxane (2:1, 40 mL) was added Ac$_2$O (57 μL, 0.60 mmol). After stirring 4 h at room temperature, K$_2$CO$_3$ (100 mg) was added followed by additional Ac$_2$O (100 μL). The reaction mixture was stirred 2 h at room temperature. Water (50 mL) was added and the pH was adjusted to 5. The precipitate was collected, washed with water and ether, and dried in vacuo. The precipitate (200 mg) was added to a solution of TMSCl (500 μL, 3.94 mmol) in MeOH (25 mL). The reaction mixture was stirred 24 h at room temperature. The mixture was concentrated in vacuo. The product was purified by silical gel chromatography to provide 117 (145 mg, 52%): mp 247–250° C.; $^1$H NMR (500 MHz, CDCl$_3$) δ 8.09 (d, 2H), 7.64 (d, 2H), 7.58 (d, 2H), 7.49 (s, 1H), 7.45 (d, 2H), 5.91 (bs, 1H), 5.18 (d, 1H), 4.83 (bs, 2H), 4.61–4.68 (m, 2H), 3.93 (s, 3H), 3.67–3.78 (m, 2H), 3.07 (bs, 1H), 2.16 (d, 2H), 2.02 (d, 2H), 1.95 (s, 3H), 1.54 (d, 6H), 1.23–1.32 (m, 4H); API MS m/z=556 [C$_{31}$H$_{37}$N$_7$O$_3$+H]$^+$.

Example 100

Preparation of Compound 116

To a solution of compound 117 (90 mg, 0.16 mmol) in MeOH-H$_2$O (6:1, 23 mL) was added KOH (11 mg, 0.19 mmol) in 5 mL MeOH. The reaction mixture was refluxed for 24 h. After removal of the solvent the residue was dissolved in 15 mL of water and washed with CH$_2$Cl$_2$. The aqueous layer was separated and adjusted pH to 4.5 by using 1N HCl. The precipitate was collected and dried to obtain 116 (60 mg, 68%): mp 344–347° C.; $^1$H NMR (500 MHz, DMSO-d$_6$) δ 11.21 (bs, 1H), 8.14 (d, 2H), 7.64–7.88 (m, 6H), 7.47 (d, 2H), 6.06 (bs, 1H), 5.18 (d, 1H), 4.85 (bs, 2H), 4.51–4.66 (m, 1H), 3.62 (bs, 1H), 3.46 (bs, 1H), 1.89 (bs, 2H), 1.77 (bs, 5H), 1.95 (s, 3H), 1.47 (d, 6H), 1.23–1.36 (m, 4H); API MS m/z=542 [C$_{30}$H$_{35}$N$_7$O$_3$+H]$^+$.

Example 101

Preparation of Compound 118

Compound 61 (1.0 g, 2.18 mmol), 3-carboxyphenylboronic acid (1.0 g, 6.03 mmol), 2N Na$_2$CO$_3$ (5 mL), and DME/EtOH (50 mL) were mixed together and degassed with N$_2$ for 1 h. Pd$_2$(dba)$_3$ (366.0 mg, 0.4 mmol) and PPh$_3$ (330.0 mg, 1.26 mmol) were added and the reaction mixture was heated to reflux for 48 h. The reaction mixture was cooled to room temperature, diluted with CH$_2$Cl$_2$ (50 mL), and extracted with aqueous 5% Na$_2$CO$_3$ (3×30 mL). The combined washes were extracted with CH$_2$Cl$_2$ (3×30 mL) and ether (40 mL). The aqueous phase was neutralized to a pH of 5.8 using 1N HCl and kept in a freezer for 1 h. The precipitate was collected, suspended in MeOH (30 mL) and the insolubles were removed by filtration. To the MeOH solution was added ether (20 mL) to precipitate the product. The white solid was collected and dried in vacuo to offer 118 (65 mg, 6%): mp 205–208° C.; $^1$H NMR (500 MHz, CD$_3$OD+NaOD) δ 8.17 (s, 1H), 7.88 (d, 1H), 7.80 (s, 1H), 7.56–7.63 (m, 3H), 7.35–7.41 (m, 3H), 6.08 (bs, 1H), 4.80 (bs, 2H), 4.59–4.75 (m, 1H), 3.72–3.82 (m, 1H), 2.89–3.01 (m, 1H), 1.90–1.99 (m, 4H), 1.51 (d, 6H), 1.29–1.40 (m, 2H), 1.12–1.23 (m, 2H); API MS m/z= 500 [C$_{28}$H$_{33}$N$_7$O$_2$+H]$^+$.

Example 102

Preparation of Compound 119

3-Thiopheneboronic acid (4.5 g, 35.2 mmol) and 6-chloronicotinamide (5.0 g, 32.0 mmol) were dissolved in DMA (150 mL), followed by the addition of 2N Na$_2$CO$_3$ (23 mL). N$_2$ gas was passed through the mixture for 1 h. Pd(PPh$_3$)$_4$ (0.74 g, 0.64 mmol) was added and the reaction mixture was heated to reflux for 24 h. The reaction mixture was cooled to room temperature and poured into an ice-water (1 L) and stirred for 10 min. The precipitate was collected and washed with acetone. The collected solid was suspended in EtOAc (150 mL) and heated to reflux for 5 min. The solid was filtered and collected. After drying in vacuo, 119 (4.5 g, 69%) was obtained: $^1$H NMR (500 MHz, DMSO-d$_6$) δ 9.08 (s, 1H), 8.34 (s, 1H), 8.28 (d, 1H), 8.20 (bs, 1H), 7.99 (d, 1H), 7.81 (d, 1H), 7.71 (d, 1H), 7.60 (bs, 1H).

Example 103

Preparation of Compound 120

To compound 119 (4.08 g, 20.0 mmol) suspended in THF (50 mL), was added 1M BH$_3$-THF (164 mL). The mixture was heated to reflux for 9 h. The mixture was cooled with an ice-water bath and adjusted to a pH of 1–2, and stirred for 1 h at room temperature. The pH was adjusted to 9–10 (2N NaOH) and extracted with EtOAc (3×50 mL). The combined organic phases were washed with H$_2$O (50 mL), brine (50 mL), and dried over Na$_2$SO$_4$. After filtration and removal of the solvent, the residue was dissolved in EtOH (50 mL), followed by the addition of 1M HCl/ether (20 mL). The mixture was concentrated to dryness to provide 120 (2.03 g, 45%): $^1$H NMR (500 MHz, CD$_3$OD) δ 8.93 (s, 1H), 8.61 (d, 1H), 8.51 (s, 1H), 8.43 (d, 1H), 7.81 (d, 1H), 7.70 (d, 1H), 3.30 (t, 2H).

Example 104

Preparation of Compound 121

Compound 120 (2 g, 8.82 mmol), 2,6-dichloropurine (1.5 g, 8.01 mmol), EtOH (50 mL), and (i-Pr)$_2$NEt (3.8 mL, 22 mmol) were heated at reflux for 16 h. The reaction mixture was then cooled with an ice-water bath. The precipitate was collected and washed with EtOH, H$_2$O, and ether. The precipitate was dried in vacuo to obtain 121 (0.84 g, 31%): $^1$H NMR (500 MHz, DMSO-d$_6$) δ 11.02 (bs, 1H), 8.76 (bs, 1H), 8.63 (s, 1H), 8.07 (bs, 2H), 7.79 (bs, 2H), 7.71 (d, 1H), 7.64 (d, 1H), 4.68 (bs, 2H).

Example 105

Preparation of Compound 122

Compound 121 (950 mg, 2.77 mmol) was dissolved in DMSO (50 mL), and then K$_2$CO$_3$ (2.07 g, 15.0 mmol) was added, followed by the addition of 2-iodopropane (830 μL, 8.31 mmol). The reaction mixture then was stirred at room temperature overnight. The reaction mixture was poured into an ice-water bath (400 mL), stirred for 10 min, and extracted with EtOAc (4×50 mL). The combined organic phases were washed with H$_2$O (40 mL), brine (40 mL), and dried over MgSO$_4$. After filtration and removal of the solvent, the residue was dissolved in hot EtOAc (40 mL), followed by the addition of hexanes (80 mL). The precipitate was collected and dried in vacuo to obtain 122 (798 mg, 90%): $^1$H NMR (500 MHz, CDCl$_3$) δ 8.64 (s, 1H), 7.83 (s, 1H), 7.70–7.79 (m, 2H), 7.60 (d, 1H), 7.55 (d, 1H), 7.36 (d, 1H), 6.11 (bs, 1H), 4.77–4.96 (m, 3H), 1.53 (d, 6H).

Example 106

Preparation of Compound 123

Compound 122 (780.0 mg, 2.03 mmol), trans-1,4-diaminocyclohexane (2.3 g, 20.3 mmol), and EtOH (4 mL) were heated in a sealed tube to 150° C. for 20 h. The reaction mixture was poured into ice-water (150 mL) and stirred for 10 min. The resulting precipitate was washed with H$_2$O (2×20 mL) and dried. The solid was chromatographed on a silica gel column. After removal of the solvent and drying in vacuo, 123 (765 mg) was obtained: mp 78–81° C.; $^1$H NMR (500 MHz, CDCl$_3$) δ 8.63 (s, 1H), 7.87 (s, 1H), 7.72 (d, 1H), 7.64 (d, 1H), 7.55 (d, 1H), 7.04–7.09 (m, 1H), 6.92 (s, 1H), 5.95 (bs, 1H), 4.64 (bs, 2H), 4.33–4.45 (m, 2H), 3.74–3.77 (m, 1H), 2.67–2.76 (m, 1H), 2.13 (d, 2H), 1.90 (d, 2H), 1.63 (bs, 2H), 1.54 (d, 6H), 1.19–1.30(m, 4H); $^{13}$C NMR(CDCl$_3$) δ 159.1, 155.0, 152.7, 151.3, 149.3, 143.3, 142.3, 136.2, 134.8, 133.4, 126.4, 126.4, 123.5, 120.2, 114.8, 50.4, 50.3, 46.5, 42.0, 35.7, 32.3, 22.8; API MS m/z=463 [C$_{24}$H$_{30}$N$_8$S+H]$^+$.

Example 107

Preparation of Compound 124

To an ice-cold solution of compound 123 (420 mg, 0.91 mmol) in CH$_2$Cl$_2$ (20 mL) was added pyridine (110 μL, 1.4 mmol), DMAP (11.0 mg, 0.09 mmol) and Ac$_2$O (94.2 μL, 1 mmol). The reaction mixture was stirred for 30 min at 0° C., followed by 2 h at room temperature. After removal of the solvent, the residue was chromatographed on a silica gel column. The resulting solid was recrystallized with EtOAc/MeOH and dried in vacuo to give 124 (350 mg, 79%): mp 249–252° C.; $^1$H NMR (500 MHz, CDCl$_3$) δ 8.61 (s, 1H), 7.85 (s, 1H), 7.70 (d, 1H), 7.62 (d, 1H), 7.53 (d, 1H), 7.48 (s, 1H), 7.38 (d, 1H), 6.00 (bs, 1H), 5.25 (d, 1H), 4.77 (bs, 2H), 4.53–4.72 (m, 2H), 3.68–3.77 (m, 2H), 2.10 (d, 2H), 2.00 (d, 2H), 1.94 (s, 3H), 1.52 (d, 6H), 1.17–1.28 (m, 4H); $^{13}$C NMR (CDCl$_3$) δ 169.4, 159.0, 155.0, 152.8, 149.2, 142.8, 142.3, 136.1, 134.9, 133.4, 126.5, 126.4, 123.5, 120.2, 114.9, 50.1, 48.3, 46.5, 42.2, 32.2, 32.1, 22.8; API MS m/z=505 [C$_{26}$H$_{32}$N$_8$OS+H]$^+$.

Example 108

Alternative Preparation of Compound 71

To a solution of 4-phenylbenzoic acid (5.46 g, 27.6 mmol) in methylene chloride (66 mL) was added 2 drops of DMF and oxalyl chloride (2.80 mL, 30.3 mmol). The reaction mixture was stirred overnight and added to a stirred solution of ice and ammonium hydroxide. The resulting precipitate was filtered, washed with methylene chloride, and triturated with water. The product was collected by filtration and dried in vacuo to yield 4-phenylbenzamide (3.88 g, 71%).

Under a nitrogen atmosphere, 4-phenylbenzamide (2.01 g, 10.2 mmol) was dissolved in THF (50 mL) and heated to reflux. To the mixture was added dropwise 1 M borane in THF (80.0 mL, 80.0 mmol). After refluxing for 18 h, the reaction mixture was cooled to room temperature and treated with 1 N HCl (40 mL). The solution was made basic via addition of 3 N NaOH (60 mL) and extracted with ethyl acetate (3×370 mL). The extract was washed with brine and dried over sodium sulfate. Concentration yielded 4-phenylbenzyl amine as a white solid (1.73 g, 93%).

4-Phenylbenzyl amine (1.73 g, 10.1 mmol) and 2,6-dichloropurine (1.94 g, 10.1 mmol) was dissolved in water (110 mL). To the solution was added N,N-diisopropylethylamine (3.54 mL, 20.2 mmol). The reaction mixture was heated to reflux for 5 h and cooled to room temperature. A precipitate was collected by filtration. The solid was washed with water and ethanol and dried to yield 71 (2.35 g, 69%): $^1$H NMR (300 MHz, (CD$_3$)$_2$SO) δ 8.69 (brs, 1H), 8.15 (s, 1H), 7.57–7.68 (m, 4H), 7.30–7.50 (m, 5H), 4.71 (d, 2H).

Example 109

Preparation of Compound 126

To a stirred solution of 3-iodobenzylamine (5.00 g, 21.4 mmol) in water (100 mL) was added 2,6-dichloropurine (4.04 g, 21.4 mmol) and N,N-diisopropylethylamine (7.47 mL, 42.5 mmol). The mixture was refluxed for 5 h and stored at room temperature overnight. The resulting suspension was filtered. The filter cake was triturated with water (3×25 mL) and ethanol (2×15 mL) and dried under high vacuum to yield 126 (7.49 g, 91%): $^1$H NMR (300 MHz, (CD$_3$)$_2$SO) δ 8.50–8.80 (brs, 1H), 8.17 (s, 1H), 7.75 (s, 1H), 7.61 (d, 1H), 7.37 (d, 1H), 7.14 (t, 1H), 5.14 (brs, 1H), 4.61 (d, 2H).

Example 110

Preparation of Compound 127

The purine derivative 126 (7.00 g, 18.2 mmol) was dissolved in dimethylsulfoxide (120 mL). To this stirred solution was added potassium carbonate (20.0 g, 145 mmol) and 2-iodopropane (7.28 mL, 72.8 mmol). The reaction mixture was stirred under a nitrogen atmosphere for 20 h before being poured into stirred water (600 mL). After 10 min, the resulting mixture was extracted with ethyl acetate (4×95 mL). The combined organic layers were washed with water (25 mL) and brine (3×25 mL), dried over sodium sulfate, and concentrated in vacuo. The resulting material was purified by recrystallization from ethyl acetate in hexanes to yield 127 (7.51 g, 97%): mp 147–152° C.; $^1$H NMR (300 MHz, (CD$_3$)$_2$SO) δ 8.84 (m, 1H), 8.31 (s, 1H), 7.74 (s, 1H), 7.60 (d, 1H), 7.36 (d, 1H), 7.13 (t, 1H), 4.51–4.75 (m, 3H), 1.50 (d, 6H); API MS m/z=429 [C$_{15}$H$_{15}$ClIN$_5$H]$^+$.

Example 111

Preparation of Compound 128

In a sealed tube, 127 (2.57 g, 6.00 mmol), trans-1,4-diaminocyclohexane (6.85 g, 60.0 mmol), and ethanol (10 mL) were combined. The reaction mixture was heated to 160° C. for 24 h. After cooling to room temperature, the mixture was filtered. The filtrate was concentrated and diluted with ethyl acetate (250 mL). The organic solution was washed with water (250 mL) and saturated sodium bicarbonate solution (2×250 mL). The organic layer was dried over sodium sulfate, filtered, and concentrated. A portion of the resulting crude product was purified via silica gel chromatography to yield 128 (181 mg): $^1$H NMR (300 MHz, (CD$_3$)$_2$SO) δ 7.87 (brs, 1H), 7.78 (s, 1H), 7.70 (s, 1H), 7.55 (d, 1H), 7.35 (d, 1H), 7.09 (t, 1H), 6.06 (d, 1H), 4.43–4.70 (m, 3H), 3.58 (brs, 1H), 1.66–1.94 (m, 4H), 1.46 (d, 6H), 1.00–1.30 (m, 4H); ESI MS m/z=506 [C$_{21}$H$_{28}$IN$_7$+H]$^+$.

Example 112

Preparation of Compound 129

The amine 127 (6.06 g, 6.00 mmol) was dissolved in a mixture of tetrahydofuran (45 mL) and water (15 mL). To this stirred mixture were added sodium bicarbonate (2.02 g, 24.0 mmol) and di-tert-butyldicarbonate (2.90 g, 13.3 mmol). After 3.5 h, the solution was extracted with methylene chloride (3×75 mL). The organic extracts were combined, washed with brine (225 mL), and dried over sodium sulfate. The organic liquid was concentrated and the resulting material was purified via silica gel chromatography (33:67 to 50:50 to 60:40 ethyl acetate/hexanes) to yield 129 (4.94 g, 68%): $^1$H NMR (300 MHz, CDCl$_3$) δ 7.72 (s, 1H), 7.58 (d, 1H), 7.46 (s, 1H), 7.30 (d, 1H), 7.02 (t, 1H), 4.50–4.76 (m, 4H), 4.40 (m, 1H), 3.70 (brs, 1H), 3.43 (brs, 1H), 1.90–2.20 (m, 4H), 1.51 (d, 6H), 1.45 (s, 9H), 1.13–1.35 (m, 4H); API MS m/z=607 [C$_{26}$H$_{36}$IN$_7$O$_2$+H]$^+$.

Example 113

Preparation of Compound 130

To a stirred solution of 129 (1.00 g, 1.65 mmol) in ethylene glycol dimethyl ether (40 mL) was added 3-thiopheneboronic acid, triphenylphosphine (250 mg, 0.950 mmol), and 2 M sodium carbonate solution (3.8 mL). The mixture was purged with nitrogen for 10 min and tris(dibenzylideneacetone)dipalladium(0) (64.0 mg, 0.060 mmol) was added. After refluxing overnight under nitrogen, the reaction mixture was cooled to room temperature and diluted with water (100 mL). The resulting solution was extracted with methylene chloride (3×50 mL). The organic extracts were combined, washed with brine (30 mL), and dried over sodium sulfate. The organic liquid was filtered and concentrated in vacuo. Purification via silica gel chromatography (50:50 ethyl acetate/hexanes) yielded 130 (0.87 g, 94%): $^1$H NMR (300 MHz, CDCl$_3$) δ 7.23–7.30 (m, 8H), 6.02 (brs, 1H), 4.78 (d, 2H), 4.53–4.68 (m, 1H), 4.32 (m, 1H), 3.70 (m, 1H), 3.28–3.55 (m, 1H), 1.80–2.19 (m, 4H), 1.53 (d, 6H), 1.45 (s, 9H), 1.05–1.32 (m, 4H); ESI MS m/z=562 [C$_{30}$H$_{39}$N$_7$O$_2$S+H]$^+$.

Example 114

Preparation of Compound 131

To a solution of 130 in EtOAc was added 1 N HCl. After concentration of the solution, isolate 131 (658 mg, 91%): mp 211–216° C.; $^1$H NMR (300 MHz, CD$_3$OD) δ 8.40 (brs, 1H), 7.25–7.85 (m, 7H), 4.60–5.10 (m, 5H), 3.91 (m, 1H), 3.16 (m, 1H), 1.94–2.33 (m, 4H), 1.32–1.79 (m, 10H); ESI MS m/z=462 [C$_{25}$H$_{31}$N$_7$S+H]$^+$.

Example 115

Preparation of Compound 132

Following procedures outlined above for acetylation, prepared 132 from 131 (352 mg, 80%): mp 209–211° C.; $^1$H NMR (300 MHz, CDCl$_3$) δ 7.27–7.67 (m, 8H), 6.25 (brs, 1H), 5.19 (d, 1H), 4.79 (d, 2H), 4.52–4.67 (m, 2H), 3.69 (m, 2H), 2.09 (m, 2H), 1.88–1.98 (m, 5H), 1.50 (d, 6H), 1.06–1.33 (m, 4H); ESI MS m/z=504 [C$_{27}$H$_{33}$N$_7$OS+H]$^+$.

Example 116

Preparation of Compound 133

Following general procedures outlined above for Suzuki Coupling reaction, prepared 133 from 129 (0.61 g, 67%): $^1$H NMR (300 MHz, CDCl$_3$) δ 7.30–7.62 (m, 10H) 6.00 (brs, 1H), 4.83 (d, 2H), 4.54–4.70 (m, 2H), 4.37 (m, 1H), 3.71 (m, 1H), 3.39 (m, 1H), 2.12 (m, 2H), 2.47 (m, 2H), 1.53 (d, 6H), 1.45 (s, 9H), 1.19 (m, 4H); ESI MS m/z=556 [C$_{32}$H$_{41}$N$_7$O$_2$+H]$^+$.

Example 117

Preparation of Compound 134

To a stirred solution of 133 (530 mg, 0.950 mmol) in methanol (3 mL) was added 1 N HCl in diethyl ether (9.50 mL, 9.50 mmol). After stirring for 3.5 h, hydrogen chloride gas was gently bubbled through the solution. After 20 min, the solution was concentrated in vacuo. The resulting material was recrystallized from methanol in ether to afford 134 in quantitative yield: $^1$H NMR (300 MHz, CD$_3$OD) δ 8.33 (brs, 1H), 7.67 (s, 1H), 7.52–7.64 (m, 3H), 7.29–7.50 (m, 5H), 4.80–5.00 (m, 4H), 4.72 (m, 1H), 3.87 (m, 1H), 3.14 (m, 1H), 2.02–2.25 (m, 4H), 1.59 (d, 6H), 1.47 (m, 4H); ESI MS m/z=456 [C$_{27}$H$_{33}$N$_7$+H]$^+$.

Example 118

Preparation of Compound 135

Following procedures outlined above for acetylation, prepared 135 from 134 (195 mg, 82%): mp 183–185° C.; $^1$H NMR (300 MHz, CDCl$_3$) δ 7.30–7.64 (m, 10H), 6.19 (brs, 1H), 5.12 (d, 1H), 4.81 (d, 2H), 4.60 (m, 2H), 3.68 (m, 2H), 2.09 (m, 2H), 1.86–1.99 (m, 5H), 1.51 (d, 5H), 1.04–1.32 (m, 4H); ESI MS m/z=498 [C$_{29}$H$_{35}$N$_7$O+H]$^+$.

Example 119

Preparation of Compound 136

To a mixture of 71 (2.00 g, 5.96 mmol) in dimethylsulfoxide (44 mL) was added potassium carbonate (6.56 g, 47.7 mmol) and iodoethane (2.00 mL, 24.4 mmol). After stirring overnight, the reaction mixture was poured into a stirred solution of water (300 mL). After 2 d, it was filtered. The filtrate was extracted with ethyl acetate (2×180 mL). The organic extracts were combined and washed with brine (150 mL). The organic layer was dried over magnesium sulfate. Concentration afforded 136 (1.90 g, 88%).

Example 120

Preparation of Compound 137

In a sealed tube, 136 (0.60 g, 1.66 mmol), trans-1,4-diaminocyclohexane (1.93 g, 16.8 mmol), and potassium iodide (10 mg), were dissolved in ethanol (18 mL). The mixture was heated to 160° C. After 4 d, the mixture was cooled to room temperature and filtered. The filtrate was dissolved in ethyl acetate and washed with water (2×100 mL) and brine (100 mL). The organic layer was dried over magnesium sulfate, filtered, and concentrated. The material was purified by silica gel chromatography and recrystallization from ethanol in hexanes (1:10) to yield 137 (886 mg, 41%): mp 175–182° C.; $^1$H NMR (500 MHz, CD$_3$OD) δ 7.30–7.75 (m, 10H), 4.55–4.95 (m, 4H), 4.10 (q, 2H), 3.78 (m, 1H), 2.99 (m, 1H), 2.11 (d, 2H), 1.99 (d, 2H), 1.44 (m, 3H), 1.31 (m 4H); ESI MS m/z=442 [C$_{26}$H$_{31}$N$_7$+H]$^+$.

Example 121

Preparation of Compound 138

Compound 71 (2.02 g, 6.02 mmol), iodomethane (1.50 mL, 24.4 mmol), and potassium carbonate were dissolved in dimethylsulfoxide (44 mL) and stirred overnight. The reaction mixture was poured into 150 mL of stirring water. The organic and aqueous layers were separated. The organic layer was washed with brine (3×100 mL) and dried over magnesium sulfate. The solids were removed by filtration and the solution was concentrated in vacuo to afford 138 (1.93 g, 93%).

Example 122

Preparation of Compound 139

In a sealed tube, 138 (1.80 g, 5.15 mmol) and trans-1,4-diaminocyclohexane (5.90 g, 51.7 mmol) were dissolved in ethanol (85 mL). The mixture was heated to 140° C. After heating overnight, the reaction mixture was cooled to room temperature and concentrated. The resulting solid was dissolved in ethyl acetate (160 mL) and washed with water (160 mL) and brine (2×100 mL). The organic layer was dried over magnesium sulfate and filtered. Concentration afforded a solid, which was purified by silica gel chromatography and recrystallization from ethanol in hexanes (1:20) and ethyl acetate in hexanes to yield 139 (850 mg, 38%): mp 182–184° C.; $^1$H NMR (500 MHz, CD$_3$OD) δ 7.25–7.70 (m, 10H), 4.64–4.90 (m, 4H), 3.75 (m, 1H), 3.65 (s, 3H), 2.68 (m, 1H), 2.05 (m, 2H), 1.88 (m, 2H), 1.25 (m, 4H); ESI MS m/z=428 [C$_{25}$H$_{29}$N$_7$+H]$^+$.

Example 123

Preparation of Compound 140

The HCl salt of 139 (86.7 mg, 0.162 mmol) was suspended in methylene chloride (20 mL). The suspension was immersed in an ice bath while triethylamine (0.16 mL, 1.12 mmol) and a catalytic amount of DMAP were added. Acetyl chloride (0.04 mL, 0.560 mmol) was added to the mixture. The reaction was quenched by the addition of 5% aqueous NaHCO$_3$ solution (50 mL). The aqueous layer was extracted with methylene chloride (2×50 mL). The extracts were washed with brine (100 mL), dried over magnesium sulfate, filtered, and concentrated. The resulting solid material was dried in vacuo. Purification by silica gel chromatography and recrystallization from ethyl acetate in hexanes (5:60) afforded 140 (6.4 mg, 8%): $^1$H NMR (300 MHz, CD$_3$OD) δ 7.50–7.68 (m, 5H), 7.25–7.47 (m, 5H), 5.22 (m, 3H), 4.20–5.05 (m, 2H), 3.75 (m, 1H), 3.65 (s, 3H), 3.35–3.47 (m, 1H), 2.78 (m, 1H), 1.95–2.16 (m, 2H), 1.80–1.95 (m, 2H), 1.17–1.40 (m, 4H).

Example 124

Preparation of Compound 144

Compound 71 (2.03 g, 5.96 mmol), 1-iodopropane (2.25 mL, 24.4 mmol), and potassium carbonate (6.61 g, 47.7 mmol) were dissolved in dimethylsulfoxide (44 mL) and allowed to stir overnight. The reaction mixture was added to 300 mL of stirring water and stirred for 2 d. The resulting precipitate was collected by filtration and dried in vacuo to afford 141 (2.07 g, 92%).

Example 125

Preparation of Compound 142

In a sealed tube, 141 (1.82 g, 4.81 mmol) and trans-1,4-diaminocyclohexane (5.67 g, 49.7 mmol) were dissolved in ethanol (53 mL). The mixture was heated to 140° C. for 3 d. After cooling to room temperature, the reaction mixture was concentrated and dissolved in ethyl acetate (100 mL). This solution was washed with water (100 mL) and brine (2×100 mL). The organic layer was dried over magnesium sulfate, filtered, and concentrated. The product was purified by silica gel chromatography and recrystallizations from ethanol in hexanes (1:20) to yield 142 (523 mg, 24%): mp 133–138° C.; $^1$H NMR (500 MHz, CD$_3$OD) δ 7.25–7.70 (m, 10H), 4.65–4.85 (m, 4H), 4.02 (t, 2H), 3.76 (m, 1H), 2.85 (m, 1H), 2.08 (d, 2H), 1.94 (d, 2H), 1.86 (q, 2H), 1.20–1.42 (m, 4H), 0.93 (t, 3H); ESI MS m/z=456 [C$_{27}$H$_{33}$N$_7$+H]$^+$.

Example 126

Preparation of Compound 143

Compound 71 (2.01 g, 5.98 mmol), iodocyclopentane (2.80 mL, 24.2 mmol), and potassium carbonate (6.75 g, 48.9 mmol) were dissolved in dimethylsulfoxide (44 mL) and allowed to stir under nitrogen overnight. The reaction mixture was added to 150 mL of stirring water and diluted with 150 mL ethyl acetate. The organic and aqueous phases were separated. The organic phase was washed with brine (3×100 mL) and dried over magnesium sulfate. After filtering, the organic liquid was concentrated and the resulting solid was dried in vacuo to afford 143 (1.29 g, 55%).

Example 127

Preparation of Compound 144

In a sealed tube, 143 (304 mg, 0.749 mmol) and trans-1,4-diaminocyclohexane (891 mg, 7.80 mmol) were dissolved in ethanol (10 mL). The mixture was heated to 140° C. for 4 d. After cooling to room temperature, the reaction mixture was diluted with ethyl acetate (160 mL). This solution was washed with water (160 mL) and brine (2×100 mL). The organic layer was dried over magnesium sulfate, filtered, and concentrated. The material was purified by silica gel chromatography and recrystallizations from ethanol in hexanes (1:20) to yield 144 (299 mg, 19%): mp 144–146° C.; $^1$H NMR (500 MHz, CD$_3$OD) δ 7.28–7.75 (m, 10H), 4.68–4.85 (m, 4H), 3.75 (m, 1H), 2.82 (m, 1H), 1.70–2.25 (m, 13H), 1.20–1.43 (m, 4H); ESI MS m/z=482 [C$_{29}$H$_{35}$N$_7$+H]$^+$.

Example 128

Preparation of Compound 145

Compound 71 (2.01 g, 5.98 mmol), allylbromide (2.10 mL, 24.4 mmol), and potassium carbonate (6.61 g, 47.8 mmol) were dissolved in dimethylsulfoxide (44 mL) and stirred overnight. The reaction mixture was added to 150 mL of stirring water and diluted with 150 mL ethyl acetate. The organic and aqueous phases were separated. The organic phase was washed with brine (3×100 mL), dried over magnesium sulfate, filtered, and concentrated. The resulting solid was dried in vacuo to afford 145 (1.98 g, 88%).

Example 129

Preparation of Compound 146

In a sealed tube, 145 (1.99 mg, 5.29 mmol), trans-1,4-diaminocyclohexane (6.21 g, 54.3 mmol), and 2,6-di-tert-butylphenol (1.13 g, 5.48 mmol) were dissolved in ethanol (60 mL). The mixture was heated to 140° C. for 4 d. After cooling to room temperature, the reaction was concentrated and diluted with ethyl acetate (175 mL). This organic solution was washed with water (175 mL) and brine (2×100 mL) and concentrated. The product was purified by silica gel chromatography and recrystallizations from ethanol in hexanes (1:20) to yield 146 (432 mg, 18%): mp 111–114° C.; $^1$H NMR (300 MHz, CD$_3$OD) δ 7.25–7.72 (m, 10H), 5.95–6.10 (m, 1H), 5.21 (d, 1H), 5.10 (d, 1H), 4.82 (m, 2H), 4.77 (s, 2H), 4.67 (d, 2H), 3.75 (m, 1H), 2.87 (m, 1H), 2.07 (d, 2H), 1.92 (d, 2H), 1.15–1.47 (m, 4H); ESI MS m/z=454 [C$_{27}$H$_{31}$N$_7$+H]$^+$.

Example 130

Preparation of Compound 147

Compound 71 (2.07 g, 6.17 mmol), 2-iodobutane (3.10 mL, 26.9 mmol), and potassium carbonate (6.78 g, 49.1 mmol) were dissolved in dimethylsulfoxide (44 mL) and allowed to stir under nitrogen overnight. The reaction mixture was diluted with ethyl acetate (300 mL). The organic material was washed with water (200 mL) and brine (300 mL) and dried over magnesium sulfate. After filtration, the material was concentrated and the resulting solid was dried in vacuo to afford 147 (1.29 g, 55%).

Example 131

Preparation of Compound 148

In a sealed tube, 147 (1.29 g, 3.30 mmol) and trans-1,4-diaminocyclohexane (3.80 g, 33.2 mmol) were dissolved in ethanol (70 mL). The mixture was heated to 140° C. After 4 d, the reaction was cooled to room temperature, concentrated, and dissolved in ethyl acetate (160 mL). This solution was washed with water (160 mL) and brine (2×100 mL) and dried over magnesium sulfate. The organic liquid was filtered and concentrated. The resulting solid was dried in vacuo and purified by silica gel chromatography and recrystallizations from ethanol in hexanes (1:40) to yield 148 (229 mg, 15%): mp 146–150° C.; $^1$H NMR (500 MHz, CD$_3$OD) δ 7.70 (s, 1H), 7.25–7.60 (m, 9H), 4.65–4.90 (m, 4H), 4.37 (m, 1H), 3.74 (m, 1H), 2.86 (m, 1H), 1.82–2.15 (m, 6H), 1.50 (d, 3H), 1.20–1.43 (m, 4H), 0.87 (t, 3H).

Example 132

Preparation of Compound 149

To a solution of 61 (0.90 g, 1.96 mmol) in ethylene glycol dimethyl ether (54 mL), were added 3,5-dimethylphenylboronic acid (0.59 g, 3.93 mmol), triphenylphosphine (0.26 g, 0.99 mmol), and 2 M sodium carbonate solution (10 mL). The solution was refluxed for 20 min and cooled to room temperature. Tris(dibenzylideneacetone)dipalladium(0) (0.66 g, 0.072 mmol) was added and the reaction returned to reflux. After refluxing overnight, the reaction mixture was cooled to room temperature and another 100 mg 3,5-dimethylphenylboronic acid were added. After refluxing for another 5 h, the reaction was quenched with 50 mL water. The aqueous solution was extracted with methylene chloride (3×50 mL). The extracts were combined and washed with water (50 mL) and brine (50 mL). The organic solution was dried over sodium sulfate, filtered, and concentrated. The product was purified by silica gel chromatography to yield 149: mp 86–90° C.; $^1$H NMR (300 MHz, CDCl$_3$) δ 7.34–7.58 (m, 5H), 7.20 (s, 2H), 6.97 (s, 1H), 5.93 (brs, 1H), 4.54–4.90 (m, 4H), 3.66–3.85 (m, 1H), 2.70 (m, 1H), 2.37 (s, 6H), 2.05–2.20 (m, 4H), 1.80–1.95 (m, 2H), 1.54 (d, 6H), 1.10–1.35 (m, 4H); API MS m/z=484 $[C_{29}H_{37}N_7+H]^+$.

Example 133

Preparation of Compound 150

To a stirred, 0° C. solution of 149 (500 mg, 0.97 mmol) in methylene chloride (20 mL), were added pyridine (120 μL), DMAP (11.8 mg, 0.097 mmol), and acetic anhydride (91 μL, 0.097 mmol). After 40 min, the reaction mixture was warmed to room temperature and stirred for 3 h. Another 100 μL acetic anhydride was added. After 1 h, the solution was concentrated and dried in vacuo. The resulting material was purified by silica gel chromatography (95:5:1 CH$_2$Cl$_2$/methanol/NH$_4$OH) to yield 150 (400 mg, 80%): mp 207–210° C.; $^1$H NMR (300 MHz, CDCl$_3$) δ 7.46–7.56 (m, 3H), 7.36–7.45 (m, 2H), 7.18 (s, 2H), 6.98 (s, 1H), 5.98 (brs, 1H), 5.27 (d, 1H), 4.80 (d, 2H), 4.56–4.70 (m, 1H), 3.68–3.84 (m, 1H), 2.37 (s, 6H), 1.90–2.23 (m, 7H), 1.54 (d, 6H), 1.15–1.48 (m, 4H); API MS m/z=526 $[C_{31}H_{39}N_7O+H]^+$.

Example 134

Preparation of Compound 152

To a solution of 149 (500 mg, 1.03 mmol) in 1,2-dichloroethane (4 mL) was added propionaldehyde (90 μL, 1.24 mmol). After stirring for 10 min, sodium triacetoxyborohydride (306 mg, 1.44 mmol) was added. The reaction mixture stirred under nitrogen for 1.5 h before being quenched with saturated sodium bicarbonate solution (5 mL). The resulting solution was extracted with ethyl acetate (3×7 mL). The organic extracts were combined and dried over sodium sulfate. The organic liquid was filtered and concentrated. Purification by silica gel chromatography (90:10:1 CH$_2$Cl$_2$/methanol/NH$_4$OH) yielded 152.

Example 135

Preparation of Compound 152.HCl

To a stirred solution of 152 (120 mg, 0.211 mmol) in ethyl acetate (10 mL) was added 2 M HCl in diethyl ether (127 μL). After 20 min, the solution was concentrated and dried in vacuo to yield the HCl salt of 152: $^1$H NMR (300 MHz, CD$_3$OD) δ 8.48 (s, 1H), 7.40–7.68 (m, 4H), 7.20 (s, 2H), 6.98 (s, 1H), 4.66–5.07 (m, 3H), 3.80–4.00 (m, 1H), 2.90–3.50 (m, 5H), 2.01–2.45 (m 10H), 1.36–1.90 (m, 14H), 1.02 (t, 6H); API MS m/z=568 $[C_{35}H_{49}N_7+H]^+$.

Example 136

Preparation of Compound 151

To a solution of 149 (302 mg, 0.624 mmol) in 1,2-dichloroethane (2.5 mL) was added propionaldehyde (36.0 μL, 0.500 mmol). After stirring for 15 min under nitrogen, sodium triacetoxyborohydride (93.0 mg, 0.874 mmol) was added. After 10 min, another 93.0 mg (0.874 mmol) sodium triacetoxyborohydride were added. The reaction mixture stirred under nitrogen for 1.5 h before being quenched with saturated sodium bicarbonate solution (5 mL). The resulting solution was extracted with ethyl acetate (3×7 mL). The organic extracts were combined and dried over sodium sulfate. The organic liquid was filtered and concentrated. Purification by silica gel chromatography (90:10:1 CH$_2$Cl$_2$/methanol/NH$_4$OH) yielded 151.

Example 137

Preparation of Compound 151.HCl

To a stirred solution of 151 (90.0 mg, 0.171 mmol) in ethyl acetate (8 mL) was added 2 M HCl in diethyl ether (103 μL). After 20 min, the solution was concentrated and dried in vacuo to yield the HCl salt of 151: mp 280–290° C.; $^1$H NMR (300 MHz, CD$_3$OD) δ 8.45 (brs, 1H), 7.38–7.67 (m, 4H), 7.29 (s, 2H), 6.97 (s, 1H), 4.63–5.40 (m, 4H), 3.78–3.97 (m, 1H), 2.85–3.23 (m, 3H), 2.07–2.44 (m, 8H), 1.32–1.87 (m, 14H), 1.02 (t, 3H); API MS m/z=526 $[C_{32}H_{43}N_7+H]^+$.

Example 138

Preparation of Compound 153

To a solution of 61 (2.03 g, 4.44 mmol) in ethylene glycol dimethyl ether (100 mL), was added 2,5-dimethoxyphenylboronic acid (2.42 g, 13.3 mmol), tris(dibenzylideneacetone)dipalladium(0) (0.135 g, 0.148 mmol), triphenylphosphine (0.581 g, 2.22 mmol), and 2 M sodium carbonate solution (10 mL). The dispersion was refluxed overnight under nitrogen. After cooling to room temperature, the reaction mixture was diluted with 100 mL water. The aqueous solution was extracted with methylene chloride (3×100 mL). The extracts were combined and washed with water (300 mL) and brine (300 mL). The organic solution was dried over sodium sulfate, filtered, and concentrated. The product was purified by silica gel chromatography (90:10:1 CH$_2$Cl$_2$/methanol/NOH) to yield 153 (900 mg, 39%).

Example 139

Preparation of 153.HCl

To a stirred solution of 153 (100 mg, 0.194 mmol) in ethyl acetate (10 mL), was added 2 M HCl in diethyl ether (116 μL). After 20 min, the solution was concentrated to afford the HCl salt of 153 in quantitative yield: mp 278–288° C.; $^1$H NMR (300 MHz, CD$_3$OD) δ 8.34 (brs, 1H), 7.36–7.53 (m, 4H), 6.77–7.01 (m, 3H), 5.30 (brs, 1H), 4.65–5.20 (m, 4H), 3.80–3.95 (m, 1H), 3.76 (s, 1H), 3.69 (s, 1H), 3.05–3.22 (m, 1H), 2.03–2.30 (m, 4H), 1.35–1.71 (m, 10H); API MS m/z=516 $[C_{29}H_{37}N_7O_2+H]^+$.

Example 140

Preparation of Compound 154

To a 0° C. stirred solution of 153 (300 mg, 0.582 mmol) in methylene chloride (12 mL) was added pyridine (70 μL), acetic anhydride (54.0 μL, 0.582 mmol), and DMAP (7.10 mg, 0.582 mmol). The solution was stirred for 40 min before warming to room temperature. After 3 h, another 100 μL acetic anhydride was added. After stirring for 1 h, the reaction mixture was concentrated and dried in vacuo. The material was purified by silica gel chromatography (90:10:1 CH$_2$Cl$_2$/methanol/NH$_4$OH) to yield 154: mp 185–192° C.; $^1$H NMR (300 MHz, CD$_3$OD) δ 7.78 (s, 1H), 7.29–7.45 (m, 4H), 6.87–6.98 (m, 1H), 6.75–6.86 (m, 2H), 4.75 (s, 2H), 4.55–4.68 (m, 1H), 3.74 (s, 3H), 3.67 (s, 3H), 1.97–2.13 (m, 2H), 1.81–1.96 (m, 5H), 1.53 (d, 6H), 1.21–1.40 (m, 4H); API MS m/z=558 $[C_{31}H_{39}N_7O_3+H]^+$.

Example 141

Preparation of Compound 155

To a solution of 153 (242 mg, 0.469 mmol) in 1,2-dichloroethane (1.5 mL) was added propionaldehyde (27.0 µL, 0.375 mmol). After stirring for 15 min under nitrogen, sodium triacetoxyborohydride (140 mg, 0.657 mmol) was added. The reaction mixture was stirred under nitrogen overnight before being concentrated. Purification by silica gel chromatography (90:10:1 $CH_2Cl_2$/methanol/$NH_4OH$) yielded 155.

Example 142

Preparation of Compound 155.HCl

To a stirred solution of 155 (30.0 mg, 0.054 mmol) in ethyl acetate (6 mL) was added 2 M HCl in diethyl ether (40.0 µL). After 20 min, the solution was concentrated and dried in vacuo to afford the HCl salt of 155 in quantitative yield: mp 264–268° C.; $^1$H NMR (300 MHz, CD$_3$OD) δ 8.41 (brs, 1H), 7.46 (m, 4H), 6.98 (d, 1H), 6.76–6.93 (m, 2H), 4.63–5.07 (m, 4H), 3.89 (m, 1H), 3.77 (s, 3H), 3.71 (s, 3H), 3.13 (m, 1H), 2.97 (m, 2H), 2.10–2.35 (m, 4H), 1.35–1.88 (m, 12H), 1.02 (t, 3H); API MS m/z=558 $[C_{32}H_{43}N_7O_2+H]^+$.

Example 143

Preparation of Compound 156

To a solution of 153 (242 mg, 0.469 mmol) in 1,2-dichloroethane (1.5 mL) was added propionaldehyde (27.0 µL, 0.375 mmol). After stirring for 15 min under nitrogen, sodium triacetoxyborohydride (140 mg, 0.657 mmol) was added. The reaction mixture stirred under nitrogen overnight before being concentrated. Purification by silica gel chromatography (90:10:1 CHCl$_3$/methanol/NH$_4$OH) yielded 156.

Example 144

Preparation of Compound 156.HCl

To a stirred solution of 156 (160 mg, 0.267 mmol) in ethyl acetate (8 mL) was added 2 M HCl in diethyl ether (170 µL). After 20 min, the solution was concentrated and dried in vacuo to afford the HCl salt of 156 in quantitative yield: mp 235–243° C.; $^1$H NMR (300 MHz, CD$_3$OD) δ 8.43 (brs, 1H), 7.47 (m, 4H), 6.94–7.04 (d, 1H), 6.80–6.93 (m, 2H), 4.67–5.10 (m, 4H), 3.81–3.98 (m, 1H), 3.76 (s, 3H), 3.71 (s, 3H), 2.93–3.48 (m, 5H), 2.00–2.35 (m, 4H), 1.36–1.90 (m, 14H), 1.01 (t, 6H); API MS m/z=601 $[C_{35}H_{49}N_7O_2+H]^+$.

Example 145

Preparation of Compound 157

To a solution of 61 (1.50 g, 3.27 mmol) in ethylene glycol dimethyl ether (75 mL), was added 5-methyl-2-thiopheneboronic acid (1.40 g, 9.82 mmol), tris(dibenzylideneacetone)dipalladium(0) (100 mg, 0.109 mmol), triphenylphosphine (430 mg, 1.64 mmol), and 2 M sodium carbonate solution (10 mL). The solution was refluxed under nitrogen for 2 d. After cooling to room temperature, the reaction mixture was diluted with 100 mL water. The aqueous solution was extracted with methylene chloride (3×100 mL). The extracts were combined and washed with water (300 mL) and brine (300 mL). The organic solution was dried over sodium sulfate, filtered, and concentrated. The product was purified by silica gel chromatography (90:10:1 CHCl$_3$/methanol/NH$_4$OH) to yield 157 (1.04 g, 67%).

Example 146

Preparation of Compound 157.HCl

To a stirred solution of 157 (150 mg, 0.269 mmol) in ethyl acetate (10 mL) was added 2 M HCl in diethyl ether (161 µL). After 20 min, the solution was concentrated to afford the HCl salt of 157 in quantitative yield: mp 300° C.; $^1$H NMR (300 MHz, CD$_3$OD) δ 8.35 (brs, 1H), 7.55 (d, 2H), 7.39 (d 2H), 7.17 (d, 1H), 6.74 (d, 1H), 4.62–5.40 (m, 5H), 3.78–3.94 (m, 1H), 3.03–3.20 (m, 1H), 2.47 (s, 3H), 1.98–2.29 (m, 4H), 1.44–1.74 (m, 10H); API MS m/z=476 $[C_{26}H_{33}N_7S+H]^+$.

Example 147

Preparation of Compound 159

To a solution of 157 (300 mg, 0.631 mmol) in 1,2-dichloroethane (2.0 mL) was added propionaldehyde (36.0 µL, 0.505 mmol). After stirring for 30 min under nitrogen, sodium triacetoxyborohydride (190 mg, 0.883 mmol) was added. The reaction mixture stirred under nitrogen for 3 h before being concentrated. Purification by silica gel chromatography (90:10:1 CHCl$_3$/methanol/NH$_4$OH) yielded 159: mp 150–155° C.; $^1$H NMR (300 MHz, CD$_3$OD) δ 7.81 (s, 1H), 7.51 (d, 2H), 7.33 (d, 2H), 7.11 (d, 1H), 6.73 (d, 1H), 4.80–5.05 (m, 1H), 4.55–4.78 (m, 3H), 3.65–3.80 (m, 1H), 3.01 (m, 1H), 2.91 (t, 2H), 2.47 (s, 3H), 2.02–2.19 (m, 4H), 1.60–1.75 (m, 8H), 1.54 (d, 6H), 1.19–1.50 (m, 4H), 1.01 (t, 3H); API MS m/z=518 $[C_{29}H_{39}N_7S+H]^+$.

Example 148

Preparation of Compound 158

To a 0° C. stirred solution of 157 (300 mg, 0.631 mmol) in methylene chloride (12 mL) was added pyridine (76 µL), acetic anhydride (58 µL, 0.631 mmol), and DMAP (7.7 mg, 0.063 mmol). After 20 min, the reaction mixture warmed to room temperature. After mixing overnight, the reaction mixture was concentrated and dried in vacuo. The material was purified by silica gel chromatography (90:10:1 CHCl$_3$/methanol/NH$_4$OH) to yield 158: mp 225–230° C.; $^1$H NMR (300 MHz, CDCl$_3$) δ 7.39–7.51 (m, 3H), 7.32 (d, 2H), 7.07 (d, 1H), 6.71 (m, 1H), 6.14 (brs, 1H), 5.32 (d, 1H), 4.53–4.82 (m, 4H), 3.74 (m, 2H), 2.50 (s, 3H), 1.90–2.23 (m, 7H), 1.51 (d, 6H), 1.12–1.38 (m, 4H); API MS m/z=518 $[C_{28}H_{35}N_7OS+H]^+$.

Example 149

Preparation of Compound 160

To a suspension of 61 (1.00 g, 2.18 mmol) in ethylene glycol dimethyl ether (50 mL), was added 4-methylthiophene-2-boronic acid (0.93 g, 6.54 mmol), tris(dibenzylideneacetone)dipalladium(0) (67.0 mg, 0.073 mmol), triphenylphosphine (287 mg, 1.09 mmol), and 2 M sodium carbonate solution (10 mL). The solution was refluxed under nitrogen for 2 d. After cooling to room temperature, the reaction mixture was diluted with 100 mL water. The aqueous solution was extracted with methylene chloride (3×100 mL). The extracts were combined and washed with water (300 mL) and brine (300 mL). The organic solution was dried over sodium sulfate, filtered, and concentrated. The product was purified by silica gel chromatography (90:10:1 CHCl$_3$/methanol/NH$_4$OH) to yield 160 (450 mg, 44%).

Example 150

Preparation of Compound 160.HCl

To a stirred solution of 160 (50.0 mg, 0.105 mmol) in ethyl acetate (4 mL) was added 2 M HCl in diethyl ether (100 μL). After 20 min, the solution was concentrated to afford the HCl salt of 160 in quantitative yield: mp 308–315° C.; $^1$H NMR (300 MHz, CD$_3$OD) δ 8.31 (brs, 1H), 7.60 (d, 2H), 7.39 (d, 2H), 7.20 (s, 1H), 6.94 (s, 1H), 4.65–5.10 (m, 3H), 3.86 (m, 1H), 3.13 (m, 1H), 2.26 (s, 3H), 2.00–2.12 (m, 4H), 1.32–1.72 (m, 10H); API MS m/z=476 [C$_{26}$H$_{33}$N$_7$S+H]$^+$.

Example 151

Preparation of Compounds 162 and 163

To a stirred solution of 160 (300 mg, 0.631 mmol) in 1,2-dichloromethane (3 mL) was added propionaldehyde (36.0 μL). After stirring under nitrogen for 15 min, sodium triacetoxyborohydride (161 mg, 0.757 mmol) was added. The mixture was stirred overnight. The reaction was concentrated and purified by silica gel chromatography (95:4.5:1 CHCl$_3$/methanol/NH$_4$OH) to yield 162 (80 mg, 31%), and 163(110 mg). For 162: $^1$H NMR (300 MHz, CD$_3$OD) δ7.79 (s, 1H), 7.54 (d, 2H), 7.33 (d, 2H), 7.16 (s, 1H), 6.89 (s, 1H), 4.71 (s, 2H), 4.60 (m, 1H), 3.70 (m, 1H), 3.31 (t, 2H), 2.42–2.62 (m, 3H), 2.23 (s, 3H), 1.87–2.10 (m, 4H), 1.51 (d, 6H), 1.10–1.33 (m, 4H), 0.94 (t, 3H).

Example 152

Preparation of Compound 162.HCl

To a stirred solution of 162 (80.0 mg, 0.155 mmol) in ethyl acetate (6 mL) was added 2 M HCl in diethyl ether (100 μL). After 20 min, the solution was concentrated to afford the HCl salt of 162 in quantitative yield: mp 225–240° C.; $^1$H NMR (300 MHz, CD$_3$OD) δ 8.36 (brs, 1H), 7.62 (d, 2H), 7.42 (d, 2H), 7.22 (s, 1H), 6.95 (s, 1H), 4.65–5.05 (m, 4H), 3.87 (m, 1H), 3.11 (m, 1H), 2.98 (t, 2H), 2.07–2.36 (m, 5H), 1.32–1.85 (m, 14H), 1.04 (t, 3H); API MS m/z=518 [C$_{29}$H$_{39}$N$_7$S+H]$^+$.

Example 153

Preparation of Compound 163.HCl

To a stirred solution of 163 (110 mg, 0.196 mmol) in ethyl acetate (8 mL) was added 2 M HCl in diethyl ether (120 μL). After 20 min, the solution was concentrated to afford the HCl salt of 163 in quantitative yield: mp 227–229° C.; $^1$H NMR (300 MHz, CD$_3$OD) δ 8.39 (brs, 1H), 7.60 (d, 2H), 7.41 (d, 2H), 7.22 (s, 1H), 6.94 (s,1H), 4.63–5.10 (m, 3H), 3.85 (m, 1H), 2.93–3.47 (m, 5H), 1.92–2.40 (m, 7H), 1.32–1.90 (m, 14H), 1.04 (t, 6H); API MS m/z=560 [C$_{32}$H$_{45}$N$_7$S+H]$^+$.

Example 154

Preparation of Compound 161

To a 0° C. stirred solution of 160 (100 mg, 0.210 mmol) in methylene chloride (5 mL) were added pyridine (26.0 μL), acetic anhydride (20.0 μL, 0.210 mmol), and DMAP (3.0 mg, 0.021 mmol). After 40 min, the reaction mixture warmed to room temperature. The reaction mixture was concentrated and dried in vacuo. The material was purified by silica gel chromatography (90:10:1 CHCl$_3$/methanol/NH$_4$OH) to yield 161: mp 222–223° C.; $^1$H NMR (300 MHz, CD$_3$OD) δ 7.78 (s, 1H), 7.52 (d, 2H), 7.35 (d, 2H), 7.16 (s, 1H), 6.89 (s, 1H), 4.83–5.05 (m, 1H), 4.72 (s, 2H), 4.64 (m, 1H), 3.73 (m, 1H), 3.61 (m, 1H), 2.25 (s, 3H), 1.97–2.13 (m, 2H), 1.81–1.96 (m, 5H), 1.54 (d, 6H), 1.19–1.40 (m, 4H); API MS m/z=518 [C$_{28}$H$_{35}$N$_7$OS+H]$^+$.

Example 155

Preparation of Compound 164

To a solution of 61 (1.20 g, 2.62 mmol) in ethylene glycol dimethyl ether (75 mL), was added furan-3-boronic acid (0.88 g, 7.85 mmol), tris(dibenzylideneacetone)dipalladium (0) (80.0 mg, 0.087 mmol), triphenylphosphine (343 mg, 1.31 mmol), and 2 M sodium carbonate solution (10 mL). The solution was refluxed under nitrogen overnight. After cooling to room temperature, the reaction mixture was diluted with 100 mL water. The aqueous solution was extracted with methylene chloride (3×150 mL). The extracts were combined and washed with water (450 mL) and brine (450 mL). The organic solution was dried over sodium sulfate, filtered, and concentrated. The product was purified by silica gel chromatography (90:10:1 CHCl$_3$/methanol/NH$_4$OH) to yield 164 (700 mg, 60%).

Example 156

Preparation of Compound 164.HCl

To a stirred solution of 164 (100 mg, 0.224 mmol) in ethyl acetate (6 mL) was added 2 M HCl in diethyl ether (135 μL). After 20 min, the solution was concentrated to afford the HCl salt of 164 in quantitative yield: mp 320–330° C.; $^1$H NMR (300 MHz, CD$_3$OD) δ 8.35 (brs, 1H), 7.90 (s, 1H), 7.57 (m, 3H), 7.42 (d, 2H), 6.79 (s, 1H), 4.65–5.07 (m, 5H), 3.87 (m, 1H), 3.13 (m, 1H), 2.00–2.30 (m, 4H), 1.35–1.75 (m, 10H); API MS m/z=446 [C$_{25}$H$_{31}$N$_7$O+H]$^+$.

Example 157

Preparation of Compound 166

To a stirred solution of 164 (200 mg, 0.449 mmol) in 1,2-dichloromethane (2 mL) was added propionaldehyde (26.0 μL). After stirring under nitrogen for 20 min, sodium triacetoxyborohydride (114 mg, 0.539 mmol) was added. The mixture was stirred overnight. The reaction was concentrated and purified by silica gel chromatography (90:10:1 CHCl$_3$/methanol/NH$_4$OH) to yield 166.

Example 158

Preparation of Compound 166.HCl

To a stirred solution of 166 (120 mg, 0.227 mmol) in ethyl acetate (7 mL) was added 2 M HCl in diethyl ether (150 μL). After 20 min, the solution was concentrated to afford the HCl salt of 166 in quantitative yield: mp 285–286° C.; $^1$H NMR (300 MHz, CD$_3$OD) δ 8.42 (brs, 1H), 7.90 (s, 1H), 7.49–7.62 (m, 3H), 7.43 (d, 2H), 6.80 (s, 1H), 4.76–5.10 (m, 3H), 3.91 (m, 1H), 2.93–3.49 (m, 5H), 2.00–2.40 (m, 4H), 1.35–1.95 (m, 14H), 1.03 (t, 6H); API MS m/z=530 [C$_{31}$H$_{43}$N$_7$O+H]$^+$.

Example 159

Preparation of Compound 165

To a 0° C. stirred solution of 164 (200 mg, 0.449 mmol) in methylene chloride (8 mL) was added pyridine (55.0 μL),

193 acetic anhydride (46.0 μL, 0.449 mmol), and DMAP (6.0 mg, 0.045 mmol). After 40 min, the reaction mixture warmed to room temperature. After stirring overnight, the reaction mixture was concentrated and dried in vacuo. The material was purified by silica gel chromatography (90:10:1 CHCl$_3$/methanol/NH$_4$OH) to yield 165 (190 mg, 87%): mp 241–243° C.; $^1$H NMR (300 MHz, CD$_3$OD) δ 7.86 (s, 1H), 7.80 (s, 1H), 7.45–7.54 (m, 3H), 7.32–7.40 (m, 2H), 6.76 (s, 1H), 4.71 (s, 2H), 4.62 (m, 1H), 3.74 (m, 1H), 3.61 (m, 1H), 1.73–2.11 (m, 7H), 1.54 (d, 6H), 1.20–1.40 (m, 4H); API MS m/z=488 [C$_{27}$H$_{33}$N$_7$O$_2$+H]$^+$.

Example 160

Preparation of Compounds 167 and 168

Compound 75 (0.500 g, 1.10 mmol) was dissolved in 1,2-dichloroethane (10 mL). To this stirred solution was added acetaldehyde (0.054 g, 1.22 mmol) and sodium triacetoxyborohydride (0.360 g, 1.71 mmol). After 1.5 h, the reaction was quenched with saturated sodium bicarbonate solution (10 mL). The mixture was extracted with ethyl acetate (10 mL). The organic layers were combined, dried over sodium sulfate, and concentrated. The resulting material was purified via silica gel chromatography (60:1:1 CH$_2$Cl$_2$/methanol/triethylamine) to yield 167 (213 mg, 40%), and 168 (109 mg, 19%).

Example 161

Preparation of Compound 167.HCl

To a stirred solution of 167 (213 mg, 0.440 mmol) in ethyl acetate (10 mL) was added 2 M HCl in diethyl ether (0.264 mL). The organic liquid was concentrated to afford the HCl salt of 167 in quantitative yield: $^1$H NMR (300 MHz, CD$_3$OD) δ 8.30 (brs, 1H), 7.30–7.63 (m, 10H), 4.71–4.80 (m, 3H), 3.65–3.72 (m, 1H), 3.48 (q, 2H), 3.10 (brs, 2H), 2.10–2.20 (m, 4H), 1.60 (d, 6H), 1.30–1.59 (m, 7H); API MS m/z=484 [C$_{29}$H$_{37}$N$_7$+H]$^+$.

Example 162

Preparation of Compound 168.HCl

To a stirred solution of 168 (109 mg, 0.213 mmol) in ethyl acetate (10 mL) was added 2 M HCl in diethyl ether (0.128 mL). The organic liquid was concentrated to afford the HCl salt of 168 in quantitative yield: $^1$H NMR (300 MHz, CD$_3$OD) δ 7.25–7.67 (m, 10H), 4.60–4.80 (m, 3H), 3.68–3.80 (m, 1H), 3.48 (q, 4H), 2.78–2.95 (m, 4H), 2.02–2.17 (m, 2H), 1.10–1.59 (m, 10H), 1.35 (t, 6H); API MS m/z=512 [C$_{31}$H$_{41}$N$_7$+H]$^+$.

Example 163

Preparation of Compounds 169 and 170

Compound 75 (0.500 g, 1.10 mmol) was dissolved in 1,2-dichloroethane (10 mL). To this stirred solution was added butyraldehyde (0.072 g, 1.00 mmol) and sodium triacetoxyborohydride (0.297 g, 1.40 mmol). After 2.5 h, the reaction was quenched with saturated sodium bicarbonate solution (10 mL). The mixture was extracted with ethyl acetate (10 mL). The organic layers were combined, dried over sodium sulfate, and concentrated. The resulting material was purified via silica gel chromatography (200:10:1 CH$_2$Cl$_2$/methanol/NH$_4$OH) to yield 169 (180 mg, 32%), and 170 (160 mg, 26%).

Example 164

Preparation of Compound 169.HCl

To a stirred solution of 169 (170 mg, 0.332 mmol) in ethyl acetate (10 mL) was added 2 M HCl in diethyl ether (0.199 mL). The organic liquid was concentrated to afford the HCl salt of 169 in quantitative yield: $^1$H NMR (300 MHz, CD$_3$OD) δ 8.30–8.34 (m, 1H), 7.30–7.68 (m, 10H), 5.30 (brs, 1H), 4.654.90 (m, 4H), 3.80–3.92 (m, 2H), 2.94–3.35 (m, 4H), 2.15–2.32 (m, 4H), 1.41–1.75 (m, 12H), 1.00 (t, 3H).

Example 165

Preparation of Compound 171

To a stirred, 0° C. solution of 169 (125 mg, 0.228 mmol) in methylene chloride (10 mL), was added pyridine (46 μL), DMAP (6.0 mg, 0.046 mmol), and acetic anhydride (24.0 μL, 0.251 mmol). After 1 h under a nitrogen atmosphere, the reaction mixture was warmed to room temperature. After stirring overnight, another 2.2 equivalents of acetic anhydride and 0.2 equivalents of DMAP were added and the mixture was heated to reflux. Following concentration, the material was diluted with ethyl acetate (20 mL) and saturated sodium bicarbonate solution (20 mL). The organic layer was concentrated and dried in vacuo. The resulting material was purified via silica gel chromatography (90:10:1 CH$_2$Cl$_2$/methanol/NH$_4$OH) and trituration with hexanes to yield 171 (26 mg): API MS m/z=554 [C$_{33}$H$_{43}$N$_7$O+H]$^+$.

Example 166

Preparation of Compound 170.HCl

To a stirred solution of 170 (150 mg, 0.264 mmol) in ethyl acetate (10 mL) was added 2 M HCl in diethyl ether (0.158 mL). The organic liquid was concentrated to afford the HCl salt of 170 in quantitative yield: $^1$H NMR (300 MHz, CD$_3$OD) δ 8.15–8.25 (m, 1H), 7.31–7.68 (m, 10H), 4.65–4.90 (m, 3H), 3.70–3.95 (m, 1H), 2.95–3.41 (m, 6H), 2.05–2.32 (m, 4H), 1.31–1.79 (m, 18H), 1.00 (t, 6H).

Example 167

Preparation of Compounds 172 and 173

Compound 75 (0.500 g, 1.10 mmol) was dissolved in 1,2-dichloroethane (10 mL). To this stirred solution was added cyclopropanecarboxaldehyde (0.070 g, 1.00 mmol) and sodium triacetoxyborohydride (0.297 g, 1.40 mmol). After 3 h, the reaction was quenched with saturated sodium bicarbonate solution (10 mL). The mixture was extracted with ethyl acetate (10 mL). The organic layers were combined, dried over sodium sulfate, and concentrated. The resulting material was purified via silica gel chromatography (200:10:1 CH$_2$Cl$_2$/methanol/NH$_4$OH) to yield 172 (103 mg, 18%), and 173 (160 mg, 26%).

Example 168

Preparation of Compound 172.HCl

To a stirred solution of 172 (103 mg, 0.202 mmol) in ethyl acetate (10 mL) was added 2 M HCl in diethyl ether (0.121 mL). The organic liquid was concentrated to afford the HCl salt of 172 in quantitative yield: $^1$H NMR (300 MHz, CD$_3$OD) δ 8.30 (brs, 1H), 7.30–7.69 (m, 10H), 4.69–4.92 (m, 4H), 3.80–3.92 (m, 1H), 2.84–3.19 (m, 3H), 2.11–2.28 (m, 4H), 1.37–1.72 (m, 10H), 1.05–1.15 (m, 1H), 0.68–0.74 (m, 2H), 0.38–0.42 (m, 2H).

Example 169

Preparation of Compound 173.HCl

To a stirred solution of 173 (160 mg, 0.284 mmol) in ethyl acetate (10 mL) was added 2 M HCl in diethyl ether (0.170 mL). The organic liquid was concentrated to afford the HCl salt of 173 in quantitative yield: $^1$H NMR (300 MHz, CD$_3$OD) δ 8.30–8.41 (m, 1H), 7.30–7.68 (m, 10H), 5.30 (brs, 1H), 4.68–4.90 (m, 4H), 3.55–3.95 (m, 2H), 3.05–3.20 (m, 4H), 2.00–2.32 (m, 4H), 1.10–1.90 (m, 10H), 0.75–0.80 (m, 4H), 0.35–0.50 (m, 4H).

Example 170

Preparation of Compounds 174 and 175

Compound 75 (1.50 g, 3.29 mmol) was dissolved in 1,2-dichloroethane (30 mL). To this stirred solution was added propionaldehyde (0.174 g, 2.99 mmol) and sodium triacetoxyborohydride (0.888 g, 4.19 mmol). After 1.5 h, the reaction was quenched with saturated sodium bicarbonate solution (30 mL). The mixture was extracted with ethyl acetate (30 mL). The organic layers were combined, dried over sodium sulfate, and concentrated. The resulting material was purified via silica gel chromatography (200:10:1 CH$_2$Cl$_2$/methanol/NH$_4$OH) to yield 174 (317 mg, 19%): $^1$H NMR (300 MHz, CD$_3$OD) δ 7.26–7.80 (m, 10H), 4.62–4.81 (m, 3H), 3.74 (brs, 1H), 2.41–2.62 (m, 3H), 1.90–2.11 (m, 4H), 1.52 (d, 6H), 1.12–1.52 (m, 8H), 0.92 (t, 3H), and 175 (320 mg, 18%): $^1$H NMR (300 MHz, CD$_3$OD) δ 8.18–8.28 (m, 1H), 7.28–7.68 (m, 10H), 4.65–4.90 (m, 3H), 3.81–3.94 (m, 1H), 2.94–3.25 (m, 4H), 2.02–2.31 (m, 6H), 1.40–1.81 (m, 14H), 1.05 (t, 6H).

Example 171

Preparation of Compound 267

The HCl salt of 167 (10 mg, 0.037 mmol), was dispersed in ethyl acetate and neutralized with sodium bicarbonate. The organic material was dried over magnesium sulfate and concentrated. The solid was dissolved in dry CH$_2$Cl$_2$ (10 mL) and cooled to 0° C. To the solution was added DMAP (9 mg), pyridine (0.074 mL) and acetic anhydride (0.037 mL). The ice bath was removed after 1 h. After being stirred overnight, additional DMAP and Ac$_2$O was added in portions to consume starting material by TLC analysis. The mixture was heated to reflux for 2 d. Upon cooling, the mixture was concentrated in vacuo, then neutralized with aqueous sodium bicarbonate, extracted with ethyl acetate, dried and concentrated. The residue was purified by chromatography to provide 267: API MS m/z=526 [C$_{31}$H$_{39}$N$_7$O+H]$^+$.

Example 172

Preparation of Compound 177

To a solution of 61 (1.00 g, 2.21 mmol) and 3-tolylboronic acid (0.33 g, 2.43 mmol) in tetrahydrofuran (5 mL) was added tris(dibenzylideneacetone)dipalladium(0) (0.010 g, 0.011 mmol), tri-tert-butylphosphine (5.5 mg, 0.027 mmol), and potassium fluoride (0.42 g, 7.29 mmol). After mixing overnight at room temperature, the reaction mixture was refluxed for 24 h and cooled to room temperature. The reaction mixture was diluted with ether (50 mL) and filtered through Celite. The organic liquid was concentrated and the resulting material was purified via silica gel chromatography (90:10:1 CH$_2$Cl$_2$/methanol/NH$_4$OH) to yield 177 (0.70 g, 71%).

Example 173

Preparation of Compound 177.HCl

To a stirred solution of 177 (449 mg, 0.956 mmol) in ethyl acetate (10 mL) was added 2 M HCl in diethyl ether (575 μL). The organic liquid was concentrated to afford the HCl salt of 177 in quantitative yield: mp 186–195° C.; $^1$H NMR (300 MHz, CD$_3$OD) δ 7.82 (s, 1H), 7.54 (d, 2H), 7.20–7.48 (m, 5H), 7.12 (d, 1H), 4.83–5.10 (m, 2H), 4.77 (s, 2H), 4.64 (m, 1H), 3.77 (m, 1H), 3.03 (m, 1H), 2.38 (s, 3H), 1.93–2.20 (m, 4H), 1.19–1.70 (m, 10H); API MS m/z=470 [C$_{28}$H$_{35}$N$_7$+H]$^+$.

Example 174

Preparation of Compound 178

To a stirred solution of 177 (219 mg, 0.466 mmol) in methylene chloride (25 mL) was added acetic anhydride (48 μL, 0.513 mmol), DMAP (5.7 mg, 0.047 mmol), and pyridine (57.0 μL, 0.699 mmol). The mixture was placed under a nitrogen atmosphere and immersed in an ice water bath. After 30 min, the reaction mixture was warmed to room temperature and stirred for another 1.5 h. The solution was concentrated and the resulting material was purified via silica gel chromatography (95:5:1 CH$_2$Cl$_2$/methanol/NH$_4$OH) to afford 178.

Example 175

Preparation of Compound 178.HCl

To a stirred solution of 178 (50.0 mg, 0.098 mmol) in ethyl acetate (5 mL) was added 2 M HCl in diethyl ether (59.0 μL). The organic liquid was concentrated to afford the HCl salt of 178 in quantitative yield: mp 165–174° C.; $^1$H NMR (300 MHz, CD$_3$OD) δ 8.26 (brs, 1H), 7.61 (d, 2H), 7.47 (d, 2H), 7.24–7.41 (m, 3H), 7.15 (d, 1H), 4.62–5.08 (m, 4H), 3.83 (m, 1H), 3.67 (m, 1H), 2.39 (s, 3H), 1.87–2.20 (m, 7H), 1.60 (d, 6H), 1.40 (m, 4H); API MS m/z=512 [C$_{30}$H$_{37}$N$_7$O+H]$^+$.

Example 176

Preparation of Compound 179

To a solution of 61 (2.00 g, 4.36 mmol) and 3-methoxyphenyl boronic acid (0.73 g, 4.79 mmol) in tetrahydrofuran (10 mL) was added tris(dibenzylideneacetone) dipalladium(0) (20 mg, 0.022 mmol), tri-tert-butylphosphine (10.0 mg, 0.052 mmol), and potassium fluoride (0.84 g, 14.39 mmol). After refluxing overnight, the reaction mixture was diluted with ether (50 mL) and filtered through Celite. The organic liquid was concentrated and the resulting material was purified via silica gel chromatography (95:5:1 CH$_2$Cl$_2$/methanol/NH$_4$OH) to yield 179 (1.18 g, 56%).

Example 177

Preparation of Compound 179.HCl

To a stirred solution of 179 (980 mg, 2.02 mmol) in ethyl acetate (10 mL) was added 2 M HCl in diethyl ether (1.21 mL). The organic liquid was concentrated to afford the HCl salt of 179 in quantitative yield: mp 182–189° C.; $^1$H NMR (300 MHz, CD$_3$OD) δ 7.80 (s, 1H), 7.54 (d, 2H), 7.40 (d, 2H), 7.30 (t, 1H), 7.12 (m, 2H), 6.87 (m, 1H), 4.76 (s, 2H), 4.62 (m, 1H), 3.67–3.90 (m, 4H), 2.94 (m, 1H), 1.90–2.20 (m, 4H), 1.17–1.65 (m, 10H); API MS m/z=486 [C$_{28}$H$_{35}$N$_7$O+H]$^+$.

Example 178

Preparation of Compound 180

To a stirred solution of 179 (200 mg, 0.412 mmol) in methylene chloride (25 mL) was added acetic anhydride (43

μL, 0.450 mmol), DMAP (5.0 mg, 0.041 mmol), and pyridine (50.0 μL, 0.618 mmol). The mixture was placed under a nitrogen atmosphere and immersed in an ice water bath. After 30 min, the reaction mixture was warmed to room temperature and stirred for another 1.5 h. The solution was concentrated and the resulting material was purified via silica gel chromatography (95:5:1 $CH_2Cl_2$/methanol/$NH_4OH$) to afford 180.

Example 179

Preparation of Compound 180.HCl

To a stirred solution of 180 (60.0 mg, 0.114 mmol) in ethyl acetate (5 mL) was added 2 M HCl in diethyl ether (68.0 μL). The organic liquid was concentrated to afford the HCl salt of 180 in quantitative yield: $^1$H NMR (300 MHz, $CD_3OD$) δ 8.20 (brs, 1H), 7.62 (d, 2H), 7.46 (d, 2H), 7.34 (t, 1H), 7.10–7.20 (m, 2H), 6.90 (1H), 4.60–5.10 (m, 4H), 3.83 (s, 3H), 3.64 (m, 1H), 3.20–3.42 (m, 1H), 1.87–2.18 (m, 7H), 1.60 (d, 6H), 1.22–1.50 (m, 4H); API MS m/z=528 $[C_{30}H_{37}N_7O_2+H]^+$.

Example 180

Preparation of Compound 181

To a solution of 61 (2.00 g, 4.36 mmol) and furan-2-boronic acid (1.50 g, 13.1 mmol) in ethylene glycol dimethyl ether (150 mL) was added tris(dibenzylideneacetone)dipalladium(0) (120 mg, 0.130 mmol), tri-tert-butylphosphine (570 mg, 2.18 mmol), and 2 M sodium carbonate solution (12.5 mL, 25.3 mmol). After refluxing overnight, 2 more equivalents of furan-2-boronic acid were added. The reaction was refluxed for 24 h, cooled to room temperature, and diluted with water (50 mL). The aqueous mixture was extracted with methylene chloride (3×80 mL). The extracts were combined and washed with water (250 mL) and brine (250 mL). The organic phase was dried over sodium sulfate and filtered. The organic liquid was concentrated and the resulting material was purified via silica gel chromatography (95:5:1 $CH_2Cl_2$/methanol/$NH_4OH$) to yield 181.

Example 181

Preparation of Compound 181.HCl

To a stirred solution of 181 (600 mg, 1.35 mmol) in ethyl acetate (10 mL) was added 2 M HCl in diethyl ether (0.810 mL). The organic liquid was concentrated to afford the HCl salt of 181 (406 mg, 68%): $^1$H NMR (300 MHz, $CD_3OD$) δ 8.06 (s, 1H), 7.66 (d, 2H), 7.53 (s, 1H), 7.41 (d, 2H), 6.74 (m, 1H), 6.49 (m, 1H), 4.60–5.00 (m, 5H), 3.82 (m, 1H), 3.10 (m, 1H), 1.95–2.20 (m, 4H), 1.20–1.61 (m, 10H); API MS m/z=446 $[C_{25}H_{31}N_7O+H]^+$.

Example 182

Preparation of Compound 182

To a stirred solution of 181 (750 mg, 1.68 mmol) in methylene chloride (30 mL) was added acetic anhydride (0.18 mL, 1.85 mmol), DMAP (20.8 mg, 0.17 mmol), and pyridine (0.20 mL, 2.52 mmol). The mixture was placed under a nitrogen atmosphere and immersed in an ice water bath. After 30 min, the reaction mixture was warmed to room temperature and stirred for another 1.5 h. The solution was concentrated and the resulting material was purified via silica gel chromatography (95:5:1 $CH_2Cl_2$/methanol/$NH_4OH$) to afford 182 (530 mg, 65%).

Example 183

Preparation of Compound 182.HCl

To a stirred solution of 182 (300 mg, 0.620 mmol) in ethyl acetate (10 mL) was added 2 M HCl in diethyl ether (0.370 mL). The organic liquid was concentrated to afford the HCl salt of 182 in quantitative yield: $^1$H NMR (300 MHz, $CD_3OD$) δ 8.25 (brs, 1H), 7.56–7.73 (m, 2H), 7.54 (s, 1H), 7.30–7.47 (m, 2H), 6.75 (m, 1H), 6.49 (m, 1H), 4.60–5.05 (m, 4H), 3.73–3.90 (m, 1H), 3.55–3.73 (m, 1H), 1.82–2.23 (m, 7H), 1.15–1.70 (m, 10H); API MS m/z=488 $[C_{27}H_{33}N_7O_2+H]^+$.

Example 184

Preparation of Compound 183

To a stirred mixture of 6-chloronicotinamide (5.00 g, 31.9 mmol) in ethanol (13 mL) and toluene (80 mL) was added 3-fluorobenzeneboronic acid (4.92 g, 35.1 mmol) and 2 M sodium carbonate solution (32 mL). The suspension was heated to 80° C. and degassed with argon for 1 h. After cooling to room temperature, tetrakis(triphenylphophine)palladium(0) (1.11 g, 0.958 mmol) was added. The reaction mixture was refluxed under argon for 3 h. After cooling to room temperature, the mixture was diluted with water (100 mL) and filtered. The filter cake was washed with water and dried in vacuo to afford 183 (6.38 g, 92%).

Example 185

Preparation of Compound 184

To a stirred suspension of 183 (3.00 g, 13.9 mmol) in tetrahydrofuran (25 mL) was added dropwise 1 M borane in THF (97.0 mL, 97.0 mmol). After refluxing for 2 h, the reaction mixture was cooled in an ice bath. The mixture was acidified to pH 1 with 2 N HCl and stirred for 1 h. The pH was raised to a value of 10 by adding 6 N NaOH and the resulting solution was extracted with ethyl acetate (3×50 mL). The extractions were combined, washed with brine (150 mL), and dried over sodium sulfate. The suspension was filtered and concentrated. The resulting material was purified by precipitation as the HCl salt from an ethanol solution. The product was recovered by filtration and dried in vacuo to yield 184 (1.69 g, 51%): $^1$H NMR (300 MHz, $CD_3OD$) δ 8.92 (s, 1H), 8.41 (d, 1H), 8.27 (d, 1H), 7.77–7.90 (m, 2H), 7.35–7.70 (m, 2H), 4.36 (s, 2H).

Example 186

Preparation of Compound 185

The amine 184 (1.84 g, 7.69 mmol), 2,6-dichloropurine (1.31 g, 6.99 mmol), and N,N-diisopropylethylamine (2.68 mL, 15.4 mmol) were dissolved in ethanol (65 mL). After refluxing overnight, the solution was immersed in an ice water bath for 20 min. The mixture was filtered and cake was washed with water. The cake was triturated with ethanol and diethyl ether and dried in vacuo to afford 185 (1.12 g, 47%).

Example 187

Preparation of Compound 186

To a stirred solution of 185 (1.00 g, 2.94 mmol) in dimethylsulfoxide (100 mL) was added potassium carbonate (2.19 g, 15.9 mmol) and 2-iodopropane (0.88 mL, 8.81 mmol). The mixture was placed under an argon atmosphere and stirred overnight. The reaction mixture was poured into stirred water (300 mL) and the resulting solution was extracted with ethyl acetate (3×300 mL). The extractions were combined, washed with water (900 mL) and brine (900 mL), and dried over magnesium sulfate. Following filtration, the organic liquid was concentrated. The material was purified by recrystallization from ethyl acetate in hexanes to yield 186 (0.92 g, 82%).

Example 188

Preparation of Compound 187

In a sealed tube were combined 186 (640 mg, 1.67 mmol), trans-1,4-diaminocyclohexane (0.96 g, 8.36 mmol), and ethanol (3.5 mL). The reaction mixture was heated to 150° C. for 4 d and cooled to room temperature. The solution was poured into stirred ice water (5 mL) and the resulting mixture was extracted with methylene chloride (3×5 mL). The extractions were combined, washed with water (15 mL) and brine (15 mL), and dried over sodium sulfate. The organic liquid was concentrated. Purification by column chromatography (97:3 $CH_2Cl_2$/methanol) and trituration with hexanes yielded the free base, 187: $^1$H NMR (300 MHz, $CDCl_3$) δ 8.68 (s, 1H), 7.60–7.82 (m, 4H), 7.50 (s, 1H), 7.42 (q, 1H), 7.11 (m, 1H), 6.07 (m, 1H), 4.85 (d, 2H), 4.60 (m, 2H), 3.74 (m, 1H), 2.69 (m, 1H), 2.02–2.19 (m, 2H), 1.78–1.96 (m, 2H), 1.52 (d, 6H), 1.10–1.36 (m, 4H); API MS m/z=475 $[C_{26}H_{31}FN_8+H]^+$.

Example 189

Preparation of Compound 188

The free amine 187 (80.0 mg, 0.170 mmol) was dissolved in methylene chloride (4 mL). The solution was immersed in an ice water bath and acetic anhydride (17.5 μL, 0.185 mmol), DMAP (2.0 mg, 0.017 mmol), and pyridine (20.0 μL, 0.252 mmol) were added. After stirring for 30 min, the solution was warmed to room temperature and concentrated. Purification via silica gel chromatography and trituration with hexanes yielded 188 (67 mg, 78%): mp 199–230° C.; $^1$H NMR (300 MHz, $CDCl_3$) δ 8.71 (s, 1H), 7.62–7.85 (m, 4H), 7.52 (s, 1H), 7.42 (m, 1H), 7.10 (m, 1H), 6.01 (m, 1H), 5.28 (d, 1H), 4.81 (d, 2H), 4.62 (m, 2H), 3.72 (m, 2H), 1.90–2.27 (m, 7H), 1.53 (d, 6H), 1.24 (m, 4H); API MS m/z=517 $[C_{28}H_{33}FN_8O+H]^+$.

Example 190

Preparation of Compound 189

To a stirred mixture of 6-chloronicotinamide (3.00 g, 19.2 mmol) in ethanol (7.6 mL) and toluene (48 mL) were added 3-methoxyphenylboronic acid (3.20 g, 21.1 mmol) and 2 M sodium carbonate solution (19 mL). The suspension was heated to 80° C. and degassed with argon for 1 h. After cooling to room temperature, tetrakis(triphenylphophine)palladium(0) (664 mg, 0.575 mmol) was added. The reaction mixture was refluxed under argon for 3 h. After cooling to room temperature, the mixture was diluted with water (100 mL) and filtered. The filter cake was washed with water and dried in vacuo to afford 189 (3.62 g, 83%).

Example 191

Preparation of Compound 190

To a stirred solution of 189 (3.00 g, 13.1 mmol) in tetrahydrofuran (25 mL) was added dropwise 1 M borane in THF (92.0 mL, 92.0 mmol). After refluxing for 4 h, the reaction mixture was cooled in an ice bath. The mixture was acidified to pH 1 with 2 N HCl and stirred for 1 h. The pH was raised to a value of 10 by adding 6 N NaOH and the resulting solution was extracted with ethyl acetate (3×50 mL). The extractions were combined, washed with brine (150 mL), and dried over sodium sulfate. The suspension was filtered and concentrated. The resulting material was purified by precipitation as the HCl salt from an ethanol solution. The product was recovered by filtration and dried in vacuo to yield 190 (1.81 g, 55%).

Example 192

Preparation of Compound 191

The amine 190 (1.80 g, 7.18 mmol), 2,6-dichloropurine (1.22 g, 6.53 mmol), and N,N-diisopropylethylamine (1.86 g, 6.53 mmol) were dissolved in ethanol (82 mL). After refluxing overnight, the dispersion was immersed in an ice water bath for 60 min. The mixture was filtered and cake was washed with water. The cake was triturated with ethanol and diethyl ether and dried in vacuo to afford 191 (1.04 g, 44%).

Example 193

Preparation of Compound 192

To a stirred solution of 191 (1.04 g, 2.84 mmol) in dimethylsulfoxide (60 mL) was added potassium carbonate (2.12 g, 15.3 mmol) and 2-iodopropane (0.85 mL, 8.52 mmol). The mixture was placed under an argon atmosphere and stirred overnight. The reaction mixture was poured into stirred water (60 mL) and the resulting solution was extracted with ethyl acetate (3×60 mL). The extractions were combined, washed with water (180 mL) and brine (180 mL), and dried over magnesium sulfate. Following filtration, the organic liquid was concentrated. The material was purified by recrystallization from ethyl acetate in hexanes (1:40) to yield 192.

Example 194

Preparation of Compound 193

In a sealed tube were combined 192 (400 mg, 1.09 mmol), trans-1,4-diaminocyclohexane (1.25 g, 10.9 mmol), and ethanol (4.0 mL). The reaction mixture was heated to 150° C. for 24 h and cooled to room temperature. The solution was filtered and the filtrate was concentrated. Purification by column chromatography (97:3 $CH_2Cl_2$/methanol) yielded the free base, 193 (240 mg, 45%).

Example 195

Preparation of Compound 194

The free amine 193 (130 mg, 0.27 mmol) was dissolved in methylene chloride (6 mL). The solution was immersed in an ice water bath and acetic anhydride (28.0 μL, 0.294 mmol), DMAP (3.2 mg, 0.026 mmol), and pyridine (33.0 μL, 0.401 mmol) were added. After stirring for 30 min, the solution was warmed to room temperature and concentrated. Purification via prep-TLC (9:1 $CH_2Cl_2$/methanol) and trituration with ethyl acetate yielded 194: mp 161–163° C.; $^1$H NMR (300 MHz, $CDCl_3$) δ 8.76 (s, 1H), 7.77 (d, 1H), 7.64 (d, 1H), 7.50 (m, 3H), 7.35 (t, 1H), 6.73–7.00 (m, 2H), 5.33 (d, 1H), 4.50–4.92 (m, 4H), 3.56–4.00 (m, 5H), 1.84–2.22 (m, 7H), 1.55 (d, 6H), 1.25 (m, 4H); API MS m/z=529 $[C_{29}H_{36}N_8O_2+H]^+$.

Example 196

Preparation of Compound 195

To a stirred mixture of 6-chloronicotinamide (2.00 g, 12.8 mmol) in ethanol (5.0 mL) and toluene (32 mL) was added thiophene-2-boronic acid (1.80 g, 14.1 mmol) and 2 M sodium carbonate solution (13 mL). The suspension was heated to 80° C. and degassed with argon for 1 h. After cooling to room temperature, tetrakis(triphenylphophine) palladium(0) (443 mg, 0.383 mmol) was added. The reaction mixture was refluxed under argon for 3 h. After cooling to room temperature, another 0.950 g thiophene-2-boronic acid and 280 mg tetrakis(triphenylphophine)palladium(0) were added to the reaction mixture. It was refluxed for 4 h and cooled to room temperature. The mixture was diluted with water (50 mL) and filtered. The filter cake was washed with water and dried in vacuo to afford 195 (1.65 g, 63%).

Example 197

Preparation of Compound 196

To a stirred solution of 195 (1.40 g, 6.86 mmol) in tetrahydrofuran (23 mL) was added dropwise 1 M borane in THF (48.0 mL, 48.0 mmol). After refluxing for 1 h, the reaction mixture was cooled in an ice bath. The mixture was acidified to pH 1 with 2 N HCl and stirred for 1 h. The pH was raised to a value of 10 by adding 6 N NaOH and the resulting solution was extracted with ethyl acetate (3×50 mL). The extractions were combined, washed with brine (150 mL), and dried over sodium sulfate. The suspension was filtered and concentrated. The resulting material was purified by precipitation as the HCl salt from an ethanol solution. The product was recovered by filtration and dried in vacuo to yield 196 (0.87 g, 56%).

Example 198

Preparation of Compound 197

The amine 196 (210 mg, 1.10 mmol), 2,6-dichloropurine (188 mg, 1.00 mmol), and N,N-diisopropylethylamine (286 g, 2.21 mmol) were dissolved in ethanol (12 mL). After refluxing overnight, the suspension was immersed in an ice water bath for 60 min. The mixture was filtered and cake was washed with water. The cake was triturated with ethanol and diethyl ether and dried in vacuo to afford 197 (206 mg, 60%).

Example 199

Preparation of Compound 198

To a stirred solution of 197 (200 mg, 0.583 mmol) in dimethylsulfoxide (12 mL) was added potassium carbonate (435 mg, 3.15 mmol) and 2-iodopropane (0.18 mL, 1.75 mmol). The mixture was placed under an argon atmosphere and stirred overnight. The reaction mixture was poured into stirred water (15 mL) and the resulting solution was extracted with ethyl acetate (3×30 mL). The extractions were combined, washed with water (90 mL) and brine (90 mL), and dried over magnesium sulfate. Following filtration, the organic liquid was concentrated to yield 198 (200 mg, 89%).

Example 200

Preparation of Compound 199

In a sealed tube were combined 198 (100 mg, 0.260 mmol), trans-1,4-diaminocyclohexane (297 mg, 2.60 mmol), and ethanol (2.0 mL). The reaction mixture was heated to 150° C. for 2 d and cooled to room temperature. The solution was filtered and diluted with ethanol. The filtrate was concentrated, and converted to its HCl salt to afford 199: $^1$H NMR (300 MHz, CD$_3$OD) δ 9.00 (s, 1H), 8.72 (d, 2H), 8.46 (d, 1H), 8.27 (m, 1H), 8.15 (d, 1H), 7.54 (m, 1H), 4.89–5.35 (3H), 4.04 (m, 1H), 3.35 (m, 1H), 2.20–2.50 (m, 4H), 1.55–1.90 (m, 10H); ESI MS m/z=463 $[C_{24}H_{30}N_8S+H]^+$.

Example 201

Preparation of Compound 200

The free amine 199 (100 mg, 0.216 mmol) was dissolved in methylene chloride (5 mL). The solution was immersed in an ice water bath and acetic anhydride (20.0 μL, 0.216 mmol), DMAP (2.6 mg, 0.021 mmol), and pyridine (33.0 μL, 0.324 mmol) were added. After stirring for 30 min, the solution was warmed to room temperature and concentrated. Purification via prep-TLC (10:1 CH$_2$Cl$_2$/methanol) yielded 200 (20 mg): mp 206–208° C.; $^1$H NMR (300 MHz, CDCl$_3$) δ 8.56 (s, 1H), 7.70 (d, 1H), 7.58 (d, 1H), 7.53 (m, 2H), 7.37 (m, 1H), 7.10 (m, 1H), 6.15 (brs, 1H), 5.33 (d, 1H), 4.76 (d, 2H), 4.61 (m, 2H), 3.70 (m, 2H), 1.75–2.15 (m, 7H), 1.52 (d, 6H), 1.23 (m, 4H); API MS m/z=505 $[C_{26}H_{32}N_8OS+H]^+$.

Example 202

Preparation of Compound 201

To a stirred solution of 6-chloronicotinamide (2.80 g, 17.9 mmol) in ethanol (7.5 mL) and toluene (48 mL) was added furan-2-boronic acid (3.00 g, 26.8 mmol) and 2 M sodium carbonate solution (18 mL). The suspension was heated to 80° C. and degassed with argon for 1 h. After cooling to room temperature, tetrakis(triphenylphophine)palladium(0) (619 mg, 0.536 mmol) was added. The reaction mixture was refluxed under argon for 2 d then cooled to room temperature. The mixture was diluted with water (75 mL) and filtered. The filter cake was washed with water and dried in vacuo to afford 201 (1.95 g, 58%).

Example 203

Preparation of Compound 202

To a stirred solution of 201 (1.69 g, 8.98 mmol) in tetrahydrofuran (34 mL) was added dropwise 1 M borane in THF (50.0 mL, 50.0 mmol). After refluxing for 2 h, the reaction mixture was cooled in an ice bath. The mixture was acidified to pH 1 with 2 N HCl and stirred for 1 h. The pH was raised to a value of 10 by adding 6 N NaOH and the resulting solution was extracted with ethyl acetate (3×50 mL). The extractions were combined, washed with brine (150 mL), and dried over sodium sulfate. The suspension was filtered and concentrated. The resulting material was purified by precipitation as the HCl salt from an ethanol solution. The product was recovered by filtration and dried in vacuo to yield 202 (1.12 g, 50%).

Example 204

Preparation of Compound 203

The amine 202 (177 mg, 1.02 mmol), 2,6-dichloropurine (173 mg, 0.920 mmol), and N,N-diisopropylethylamine (267 g, 2.07 mmol) were dissolved in ethanol (11 mL). After refluxing overnight, the suspension was immersed in an ice water bath for 60 min. The mixture was filtered and cake was washed with water. The cake was triturated with ethanol and diethyl ether and dried in vacuo to afford 203 (166 mg, 54%).

Example 205

Preparation of Compound 204

To a stirred solution of 203 (166 mg, 0.508 mmol) in dimethylsulfoxide (11 mL) was added potassium carbonate (379 mg, 2.74 mmol) and 2-iodopropane (0.150 mL, 1.52 mmol). The mixture was placed under an argon atmosphere and stirred overnight. The reaction mixture was poured into stirred water (15 mL) and the resulting solution was extracted with ethyl acetate (3×30 mL). The extractions were combined, washed with water (90 mL) and brine (90 mL), and dried over magnesium sulfate. Following filtration, the organic liquid was concentrated to yield 204 (178 mg, 95%).

Example 206

Preparation of Compound 205

In a sealed tube were combined 204 (170 mg, 0.461 mmol), trans-1,4-diaminocyclohexane (526 mg, 4.61 mmol), and ethanol (2.5 mL). The reaction mixture was heated to 150° C. for 4 d and cooled to room temperature. The solution was filtered and concentrated to afford 205.

Example 207

Preparation of Compound 206

The free amine 205 (100 mg, 0.224 mmol) was dissolved in methylene chloride (5 mL). The solution was immersed in an ice water bath and acetic anhydride (21.0 µL, 0.224 mmol), DMAP (2.7 mg, 0.022 mmol), and pyridine (34.0 µL, 0.336 mmol) were added. After stirring for 30 min, the solution was stored at 0° C. overnight. Purification via prep-TLC (9:1 $CH_2Cl_2$/methanol) yielded 206 (43 mg): mp 216–218° C.; $^1$H NMR (300 MHz, $CDCl_3$) δ 8.63 (s, 1H), 7.72 (d, 1H), 7.61 (d, 1H), 7.50 (m, 2H), 6.99 (m, 1H), 6.50 (m, 1H), 6.15 (brs, 1H), 5.36 (d, 1H), 4.79 (d, 2H), 4.62 (m, 2H), 3.68 (m, 2H), 1.78–2.20 (m, 7H), 1.54 (d, 6H), 1.22 (m, 4H); API MS m/z=489 $[C_{26}H_{32}N_8O_2+H]^+$.

Example 208

Preparation of Compound 207

Prepared by reaction of 72 with ethylene diamine by general methods described above (91%): $^1$H NMR (300 MHz, $(CD_3)_2SO$) δ 8.06 (brs, 3H), 7.65 (d, 4H), 7.31–7.52 (m, 6H), 4.68–4.90 (m, 3H), 3.61 (m, 2H), 3.01 (m, 2H), 1.54 (d, 6H); ESI MS m/z=402 $[C_{23}H_{27}N_7+H]^+$.

Example 209

Preparation of Compound 208

Prepared by reaction of 207 under standard acetylation conditions (35%): $^1$H NMR (300 MHz, $CDCl_3$) δ 7.49–7.62 (m, 5H), 7.30–7.48 (m, 5H), 6.44 (brs, 1H), 6.13 (brs, 1H), 5.05 (t, 1H), 4.82 (d, 2H), 4.65 (m, 1H), 3.58 (m, 2H), 3.45 (m, 2H), 1.87 (s, 3H), 1.54 (d, 6H); ESI MS m/z=444 $[C_{25}H_{29}N_7O+H]^+$.

Example 210

Preparation of Compound 211

Prepared by reaction of 72 and 1,3-propanediamine (28%): $^1$H NMR (300 MHz, $(CD_3)_2SO$) δ 8.00–8.22 (m, 3H), 7.63–7.70 (d, 4H), 7.32–7.59 (m, 6H), 4.84 (m, 2H), 4.70 (m, 1H), 4.43 (m, 2H), 2.88 (m, 2H), 1.88 (m, 2H), 1.52 (d, 6H); ESI MS m/z=416 $[C_{24}H_{29}N_7+H]^+$.

Example 211

Preparation of Compound 212

Prepared by reaction of 211 with acetic anhydride under standard conditions (44%): mp 106–107° C.; $^1$H NMR (300 MHz, $CDCl_3$) δ 7.50–7.62 (m, 5H), 7.28–7.50 (m, 5H), 5.87 (brs, 2H), 4.93 (m, 1H), 4.84 (m, 2H), 4.66 (m, 1H), 3.49 (m, 2H), 3.33 (m, 2H), 1.91 (s, 3H), 1.74 (m, 2H), 1.55 (d, 6H); ESI MS m/z=458 $[C_{26}H_{31}N_7O+H]^+$.

Example 212

Preparation of Compound 213

Prepared by the general methods described above (48%): $^1$H NMR (300 MHz, $CDCl_3$) δ 7.29–7.66 (m, 10H), 6.40 (brs, 1H), 4.71–5.03 (m, 3H), 4.61 (m, 1H), 3.30–3.55 (m, 2H), 2.73 (m, 2H), 2.32 (m, 2H), 1.38–1.85 (m, 10H); ESI MS m/z=430 $[C_{25}H_{31}N_7+H]^+$.

Example 213

Preparation of Compound 214

Prepared by the general methods described above (45%): $^1$H NMR (300 MHz, $CDCl_3$) δ 7.27–7.65 (m, 10H), 5.92 (m, 1H), 5.43 (m, 1H), 4.83 (m, 3H), 4.66 (m, 1H), 3.46 (m, 2H), 3.25 (m, 2H), 1.93 (s, 3H), 1.76 (m, 3H), 1.40–1.70 (m, 8H); ESI MS m/z=472 $[C_{27}H_{33}N_7O+H]^+$.

Example 214

Preparation of Compounds 209 and 210

Prepared by the general methods described above. For 210 (17%): $^1$H NMR (300 MHz, $(CD_3)_2SO$) δ 7.31–7.72 (m, 10H), 4.64–4.92 (m, 3H), 3.73 (m, 4H), 2.84–3.33 (m, 6H), 1.43–1.79 (m, 10H), 0.85 (m, 6H); ESI MS m/z=486 $[C_{29}H_{39}N_7+H]^+$. For 209: $^1$H NMR (300 MHz, $CDCl_3$) δ 7.26–7.63 (m, 10H), 6.46 (brs, 1H), 5.83 (brs, 1H), 4.85 (m, 2H), 4.66 (m, 1H), 3.79 (d, 2H), 3.11 (m, 2H), 2.76 (m, 2H), 1.76 (m, 2H), 1.50 (d, 6H), 0.84 (m, 3H); ESI MS m/z=444 $[C_{26}H_{33}N_7+H]^+$.

Example 215

Preparation of Compound 215

Prepared by the general methods described above: $^1$H NMR (300 MHz, $CDCl_3$) δ 7.22–7.60 (m, 10H), 6.18 (brs, 1H), 5.11 (brs, 1H), 4.81 (m, 2H), 4.64 (m, 1H), 3.40 (m, 2H), 2.87 (m, 2H), 2.77 (m, 2H), 1.70–2.00 (m, 4H), 1.55–1.70 (m, 2H), 1.51 (m, 6H), 0.92 (t, 3H); ESI MS m/z=472 $[C_{28}H_{37}N_7+H]^+$.

Example 216

Preparation of Compound 216

Prepared by the general methods described above (71%): $^1$H NMR (300 MHz, $CDCl_3$) δ 7.28–7.61 (m, 10H), 6.01 (brs, 1H), 4.86 (d, 2H), 4.66 (m, 1H), 3.79–3.89 (m, 1H), 3.70–3.79 (m, 1H), 3.57–3.70 (m, 2H), 3.27–3.37 (m, 1H), 2.10–2.23 (m, 1H), 1.68–1.82 (m, 1H), 1.55 (d, 6H); ESI MS m/z=428 $[C_{25}H_{29}N_7+H]^+$.

Example 217

Preparation of Compound 217

Prepared by the general methods described above: TLC silica gel $R_f$=0.52 (20:1:0.01-$CH_2Cl_2$/MeOH/$NH_4OH$).

Example 218

Preparation of Compound 218

Prepared by the general methods described above: $^1$H NMR (300 MHz, $(CD_3)_2SO$) δ 8.02 (brs, 1H), 7.88 (s, 1H), 7.54–7.68 (m, 4H), 7.40–7.50 (m, 3H), 7.30–7.40 (m, 1H), 7.26 (s, 1H), 6.77 (s, 1H), 4.50–4.72 (m, 4H), 2.78 (t, 2H), 2.31 (m, 1H), 1.68 (d, 2H), 1.49 (d, 6H); ESI MS m/z=470 $[C_{27}H_{31}N_7O+H]^+$.

Example 219

Preparation of Compound 219

Prepared by the general methods described above (66%): $^1$H NMR (300 MHz, $CDCl_3$) δ 7.28–7.62 (m, 10H), 5.89 (brs, 1H), 4.86 (d, 4H), 4.67 (m, 1H), 2.81 (t, 2H), 2.58 (d, 2H), 1.77 (d, 2H), 1.40–1.69 (m, 10H), 1.06–1.31 (m, 2H); ESI MS m/z=456 $[C_{27}H_{33}N_7+H]^+$.

Example 220

Preparation of Compound 221

The compound 220 (100 mg, 0.170 mmol) was dissolved in methanol (25 mL). To the stirred solution was added ammonium formate (100 mg), and Pd/C (10.0 mg). After refluxing for 2 h, more ammonium formate (100 mg) and Pd/C (10.0 mg) were added. The reaction was cooled to room temperature and filtered through Celite. The filtrate was concentrated in vacuo. The resulting material was purified via silica gel chromatography (3:1:0.01 $CH_2Cl_2$/MeOH/$NH_4OH$) to yield 221 (26.9 mg, 34%): $^1$H NMR (300 MHz, $CDCl_3$) δ 7.29–7.63 (m, 10H), 5.95 (brs, 1H), 4.73–4.93 (m, 3H), 4.64 (m, 1H), 3.32 (t, 2H), 3.10 (d, 2H), 2.59 (t, 2H), 1.76 (m, 2H), 1.54 (d, 6H), 1.28 (m, 3H), 0.90 (m, 1H); ESI MS m/z=456 $[C_{27}H_{33}N_7+H]^+$.

Example 221

Preparation of Compound 222

Prepared by the general methods described above: $^1$H NMR (300 MHz, $CDCl_3$) δ 7.28–7.61 (m, 10H), 6.20 (brs, 1H), 4.70–4.91 (m, 3H), 4.54–4.70 (m, 1H), 4.28 (brs, 1H), 3.75–3.90 (m, 1H), 3.08–3.11 (m, 1H), 2.80–2.93 (m, 1H), 2.28–2.41 (d, 1H), 1.95–2.10 (m, 1H), 1.84–1.95 (m, 1H), 1.70–1.84 (m, 1H), 1.60–1.70 (m, 1H), 1.52 (d, 6H), 1.22–1.41 (m, 2H), 0.94–1.22 (m, 2H), 0.89 (t, 1H); ESI MS m/z=456 $[C_{27}H_{33}N_7+H]^+$.

Example 222

Preparation of Compound 223

Prepared by the general Suzuki coupling conditions of 62 with boronic ester as shown in Scheme LXXV (58%): mp 200–206° C.; $^1$H NMR (300 MHz, $(CD_3)_2SO$) δ 7.22–8.00 (m, 9H), 6.10 (m, 2H), 4.40–4.76 (m, 4H), 3.63 (m, 1H), 1.62–2.01 (m, 7H), 1.35–1.60 (d, 6H), 1.08–1.35 (m, 4H); ESI MS m/z=527 $[C_{30}H_{38}N_8O+H]^+$.

Example 223

Preparation of Compound 224

Prepared by the general Suzuki coupling conditions of 61 and 3,4-dimethylbenzeneboronic acid: $^1$H NMR (300 MHz, $CDCl_3$) δ 7.53 (m, 3H), 7.41 (d, 2H), 7.26–7.38 (m, 2H), 7.19 (d, 1H), 4.79 (s, 2H), 4.64 (m, 1H), 3.80 (m, 1H), 3.12 (m, 1H), 2.10–2.36 (m, 10H), 1.43–1.72 (m, 8H), 1.27 (m, 4H); ESI MS m/z=484 $[C_{29}H_{37}N_7+H]^+$.

Example 224

Preparation of 5-Bromo-2-cyanopyridine 2,5-Dibromopyridine (20.0 g, 84.4 mmol) was dissolved in dimethylformamide (422 mL). To the stirred solution was added copper(I) cyanide. After refluxing for 5 h, the mixture was cooled to room temperature and stored overnight. The reaction mixture was diluted with ethyl acetate (1200 mL) and filtered through a Buchner funnel containing sand, Celite, and silica gel layers. The filtrate was concentrated to a volume of 400 mL. This organic liquid was diluted with water (300 mL) and the resulting liquid was extracted with ethyl acetate (2×200 mL). The organic extracts were combined, washed with water (2×300 mL) and brine (1×250 mL), and dried over magnesium sulfate. After concentration, the product was purified via silica gel chromatography (50:50 ethyl acetate/$CH_2Cl_2$) to afford the title compound (9.79 g).

Example 225

Preparation of Compound 225

Prepared by reation of 5-bromo-2-cyanopyridine with benzeneboronic acid under standard Suzuki conditions (68%).

Example 226

Preparation of Compound 226

In a Parr shaker vessel were combined 225 (300 mg, 1.67 mmol), glacial acetic acid (25 mL), and 10% palladium on carbon catalyst (177 mg, 0.167 mmol). The solution was agitated under 45 psig hydrogen gas for 2 h. The resulting dispersion was filtered through a Buchner funnel. The filtrate was concentrated. Purification by acid/base extraction yielded 226 (240 mg, 78%).

Example 227

Preparation of Compound 229

Following the general schemes outlined above, compound 226 was transformed into 227 (57% yield). Compound 227 was then transformed into 228 in 83% yield. Compound 228 was then converted into compound 229 and then its HCl salt (75%): $^1$H NMR (300 MHz, $CD_3OD$) δ 9.11 (s, 1H), 8.90 (d, 2H), 8.23 (d, 1H), 7.83 (m, 2H), 7.58 (m, 3H), 5.23 (m, 2H), 4.70–5.01 (m, 1H), 3.72 (m, 1H), 3.09 (m, 1H), 1.80–2.15 (m, 4H), 1.20–1.80 (m, 10H); ESI MS m/z=457 $[C_{26}H_{32}N_8+H]^+$.

Example 228

Preparation of Compound 230

In a flask immersed in an ice water bath were combined 187 (30.0 mg, 0.055 mmol), BOC-L-alanine (10.4 mg, 0.055 mmol), HATU (25.0 mg, 0.066 mmol), N,N-diisopropylethylamine (0.050 mL, 0.274 mmol), and dimethylformamide (0.500 mL) for 10 min then warmed to room temperature. After stirring overnight, the reaction mixture was diluted with methylene chloride (50 mL). The organic material was washed with 1 M citric acid (2×50 mL), saturated sodium bicarbonate solution (50 mL), and brine (50 mL). The organic layer was dried over magnesium sulfate, filtered, and concentrated in vacuo. To remove remaining dimethylformamide, the resulting material was dissolved in ethyl acetate (50 mL) and rinsed with 5% lithium chloride solution (3×50 mL). The organic layer was dried over magnesium sulfate, filtered, and concentrated in vacuo to yield 230 (28.0 mg, 79%): $^1$H NMR (300 MHz, CDCl$_3$) δ 8.71 (s, 1H), 7.62–7.83 (m, 4H), 7.37–7.60 (m, 2H), 7.11 (m, 1H), 6.11 (brs, 1H), 6.00 (d, 1H), 5.01 (brs, 1H), 4.81 (d, 2H), 4.64 (m, 2H), 4.08 (m, 1H), 3.72 (m, 2H), 2.12 (m, 2H), 2.00 (m, 2H), 1.54 (d, 6H), 1.43 (s, 9H), 1.15–1.38 (m, 7H); ESI MS m/z=646 [C$_{34}$H$_{44}$FN$_9$O$_3$+H]$^+$.

Example 229

Preparation of Compound 231

To a stirred solution of 230 in methylene chloride (2 mL) was added HCl in ethanol (2 mL). After stirring for 10 min, the solution was concentrated in vacuo to yield 231 (15.4 mg): $^1$H NMR (300 MHz, CD$_3$OD) δ 8.92 (s, 1H), 8.35–8.67 (m, 2H), 8.32 (d, 1H), 7.83 (t, 2H), 7.69 (m, 1H), 7.40 (m, 1H), 4.65–5.20 (m, 3H), 3.60–4.00 (m, 2H), 1.80–2.30 (m, 4H), 2.65 (d, 3H), 1.08–1.58 (m, 12H); ESI MS m/z=546 [C$_{29}$H$_{36}$FN$_9$O+H]$^+$.

Example 230

Preparation of Compound 232

In a flask immersed in an ice water bath were combined 187 (30.0 mg, 0.055 mmol), BOC-glycine (9.6 mg, 0.055 mmol), HATU (25.0 mg, 0.066 mmol), N,N-diisopropylethylamine (0.05 mL, 0.274 mmol), and dimethylformamide (0.50 mL) for 10 min then warmed to room temperature. After stirring overnight, the reaction mixture was diluted with methylene chloride (50 mL). The organic material was washed with 1 M citric acid (2×50 mL), saturated sodium bicarbonate solution (50 mL), and brine (50 mL). The organic layer was dried over magnesium sulfate, filtered, and concentrated in vacuo. To remove remaining dimethylformamide, the resulting material was dissolved in ethyl acetate (50 mL) and rinsed with 5% lithium chloride solution (3×50 mL). The organic layer was dried over magnesium sulfate, filtered, and concentrated in vacuo to yield 232 (33.0 mg): $^1$H NMR (300 MHz, CDCl$_3$) δ 8.65 (s, 1H), 7.52–7.75 (m, 4H), 7.44 (s, 1H), 7.35 (q, 1H), 7.01 (t, 1H), 6.05 (brs, 1H), 4.75 (d, 2H), 4.57 (m, 2H), 3.70 (m, 2H), 2.05 (m, 2H), 1.92 (m, 2H), 1.46 (d, 6H), 1.40 (s, 9H), 1.20 (m, 6H); ESI MS m/z=632 [C$_{33}$H$_{42}$FN$_9$O$_3$+H]$^+$.

Example 231

Preparation of Compound 233

To a stirred solution of 232 in methylene chloride (2 mL) was added HCl in ethanol (2 mL). After stirring for 10 min, the solution was concentrated in vacuo to yield 233 (10.6 mg): $^1$H NMR (300 MHz, CD$_3$OD) δ 8.95 (s, 1H), 8.28–8.75 (m, 3H), 7.79 (t, 2H), 7.69 (m, 1H), 7.46 (t, 1H), 4.63–5.20 (m, 3H), 3.59–3.92 (m, 2H), 1.96–2.24 (m, 4H), 1.62 (d, 6H), 1.05–1.52 (m, 8H); ESI MS m/z=532 [C$_{28}$H$_{34}$FN$_9$O+H]$^+$.

Example 232

Preparation of Compound 239

Reaction of 234 with 1 under standard conditions provides 236 (90%). Reaction of 236 with trans-1,4-cyclohexanediamine provides 237 (95%). Boc protection of 237 followed by Suzuki coupling provides 238 in 50% yield. Compound 238 was added to a 1:1 mixture of methylene chloride and trifluroacetic acid. After stirring for 2 h, the solution was concentrated in vacuo. The resulting material was purified via silica gel chromatography (94:5:1 CH$_2$Cl$_2$:MeOH:NH$_4$OH) to afford 239: $^1$H NMR (300 MHz, CDCl$_3$) δ 7.51–7.61 (m, 4H), 7.48 (s, 1H), 7.41 (t, 2H), 7.31 (m, 3H), 5.61 (m, 1H), 4.63 (m, 2H), 3.87 (m, 2H), 3.18 (m, 1H), 3.00 (t, 2H), 2.20–2.35 (m, 3H), 1.72 (m, 4H), 1.52 (d, 6H), 1.25 (m, 4H).

Example 233

Preparation of Compound 240

Compound 239 was acetylated under the general conditions described above to provide 240 (73%). Salt formation occurred in 71% yield: $^1$H NMR (300 MHz, CDCl$_3$) δ 7.28–7.62 (m, 10H), 5.67 (m, 1H), 4.64 (m, 2H), 3.68–3.97 (m, 3H), 3.00 (t, 2H), 2.23 (m, 2H), 1.84–2.11 (m, 7H), 1.53 (d, 6H), 1.30 (m, 4H).

Example 234

Preparation of Compound 241

Reductive amination of 239 with propionaldehyde followed by salt formation provided 241: ESI MS m/z=512 [C$_{31}$H$_{41}$N$_7$+H]$^+$.

Example 235

Preparation of Compound 242

Compound 237 was Boc-protected and then treated with 3-thiopheneboronic acid under standard Suzuki condition to prepare 242: $^1$H NMR (300 MHz, CDCl$_3$) δ 7.33–7.76 (m, 6H), 7.28 (m, 2H), 5.72 (brs, 1H), 4.64 (m, 1H), 4.43 (m, 1H), 3.83 (m, 2H), 3.47 (m, 1H), 2.97 (t, 2H), 2.21 (m, 2H), 2.08 (m, 2H), 1.53 (d, 6H), 1.46 (s, 9H), 1.29 (m, 4H); ESI MS m/z=576 [C$_{31}$H$_{41}$N$_7$O$_2$S+H]$^+$.

Example 236

Preparation of Compound 243

Compound 242 was deprotected with HCl in methanol to provide 243: $^1$H NMR (500 MHz, CDCl$_3$) δ 7.68 (m, 1H), 7.54 (d, 2H), 7.47 (s, 1H), 7.42 (s, 1H), 7.37 (s, 1H), 7.28 (m, 2H), 5.68 (brs, 1H), 4.63 (m, 2H), 3.85 (m, 3H), 2.99 (t, 2H), 2.71 (m, 1H), 2.18 (d, 2H), 1.90 (d, 2H), 1.52 (d, 6H), 1.25 (m, 4H).

Example 237

Preparation of Compound 245

To a stirred solution of sodium hydride (423 mg, 17.6 mmol) in tetrahydrofuran (12 mL), was added 4-phenylphenol (2.00 g, 11.8 mmol). After 1 h, BOC-2-aminoethylbromide (3.90 g, 17.6 mmol) was added to the solution. After stirring overnight, the reaction mixture was quenched with 2 N potassium hydroxide solution (10 mL). The resulting mixture was extracted with methylene chloride (12 mL). The organic layer was concentrated and the crude material was purified via silica gel chromatography to yield 245.

Example 238

Preparation of Compound 246

The protected amine 245 was added to 10 mL of an 1:1 mixture of methylene chloride and trifluoroacetic acid. After concentration, the material was diluted with 2 N potassium hydroxide solution (10 mL). The aqueous layer was extracted with methylene chloride (2×10 mL). The organic extracts were combined, dried over magnesium sulfate, and concentrated in vacuo to afford the product (400 mg). Reaction with 1 under standard conditions provided 246 (91%).

Example 239

Preparation of Compound 248

Compound 246 was transformed into 247 under standard conditions (80%). Reaction of 247 with trans-1,4-cyclohexanediamine provided 248. Salt formation provided the target compound (68%): $^1$H NMR (500 MHz, CDCl$_3$) δ 7.53 (m, 4H), 7.40 (m, 2H), 7.29 (m, 2H), 7.00 (d, 2H), 5.93 (brs, 1H), 4.61 (m, 2H), 4.22 (t, 2H), 4.02 (m, 2H), 3.78 (m, 1H), 2.70 (m, 1H), 2.18 (d, 2H), 1.90 (d, 2H), 1.53 (d, 6H), 1.25 (m, 4H).

Example 240

Preparation of Compound 250

Reductive amination of 248 with propionaldehyde and salt formation under standard conditions described above provided 250: ESI MS m/z=528 [C$_{31}$H$_{41}$N$_7$O+H]$^+$.

Example 241

Preparation of Compound 249

N-Acetylation of 248 and salt formation under standard conditions provided 249: $^1$H NMR (300 MHz, CDCl$_3$) δ 6.95–7.60 (m, 10H), 5.97 (brs, 1H), 5.24 (d, 1H), 4.63 (m, 2H), 4.23 (t, 2H), 4.02 (m, 2H), 3.78 (m, 2H), 2.21 (m, 2H), 2.04 (m, 2H), 1.94 (s, 3H), 1.55 (d, 6H), 1.30 (m, 4H).

Example 242

Preparation of Compound 255

Utilizing reaction conditions described in general above, 251 was converted to 252 (100%). Compound 252 was converted to 253 then 254 and then Boc-protected to make 255 (21%).

Example 243

Preparation of Compound 256

Compound 255 was treated with phenylboronic acid under standard Suzuki condions. The product was dissolved in methanol and immersed in an ice water bath. Hydrogen chloride gas was bubbled through the solution. The solution was concentrated in vacuo and the resulting material was purified via preparatory HPLC (acetonitrile/water/trifluoroacetic acid) to yield 256 (8 mg).

Example 244

Preparation of Compound 257

Compound 255 was treated with 3-thiopheneboronic acid under standard Suzuki conditions. The product was dissolved in methanol and immersed in an ice water bath. Hydrogen chloride gas was bubbled through the solution. The solution was concentrated in vacuo and the resulting material was purified via preparatory HPLC (acetonitrile/water/trifluoroacetic acid) to yield 257: $^1$H NMR (300 MHz, CDCl$_3$) δ 7.31–7.58 (m, 8H), 5.99 (brs, 1H), 5.10–5.50 (m, 1H), 4.49–4.69 (m, 2H), 3.67 (m 1H), 2.67 (m, 1H), 2.13 (m, 2H), 1.90 (m, 2H), 1.62 (d, 3H), 1.53 (d, 6H), 1.21 (m, 4H).

Example 245

Preparation of Compound 258

Reaction of 75 with propionoyl chloride under standard conditions provides 258 (89%): mp 182–183° C.

Example 246

Preparation of Compound 259

Reaction of 75 with methyl chloroformate under standard conditions provides 259 (68%): mp 148–150° C.

Example 247

Preparation of Compound 260

Reaction of 75 with methanesulfonyl chloride under standard conditions provides 260 (56%): mp 143–145° C.

Example 248

Preparation of Compound 261

Reaction of 75 with cyclopropanecarbonyl chloride under standard conditions provides 261 (87%): mp 196–204° C.

Example 249

Preparation of Compound 262

Compound 75 (250 mg, 0.549 mmol) and succinic anhydride (60.0 mg, 0.600 mmol) were dissolved in xylene (30 mL). A few drops of dimethylformamide were added to the solution. After refluxing for 48 h, the mixture was concentrated in vacuo. The resulting material was purified via silica gel chromatography (99.5:0.5 CH$_2$Cl$_2$/MeOH) and recrystallized from CH$_2$Cl$_2$ in hexanes (1:10) to yield 262 (30.0 mg, 10%): mp 141–147° C.

Example 250

Preparation of Compound 263

The amine 75 (200 mg, 0.439 mmol) was dissolved in methylene chloride (15 mL). The stirred solution was cooled to −78° C. and N,N-diisopropylethylamine (113 mg, 0.878 mmol) and trifluromethylsulfonylchloride (81.4 mg, 0.483 mmol) were added. After 30 min, the solution was warmed to room temperature. The mixture was cooled to −78° C. and another 1.10 equivalents of trifluoromethylsulfonylchloride and 1.50 equivalents of N,N-diisopropylethylamine were added. After warming to room temperature, the solution was concentrated. The resulting material was purified via silica gel chromatography (99:1 CH$_2$Cl$_2$/MeOH) and recrystallization from ether in hexanes to afford 263 (60 mg, 23%): mp 131–136° C.

Example 251

Preparation of Compound 264

Prepared by standard Suzuki coupling of 61 to provide 264 (65%): mp 186–190° C.

Example 252

Preparation of Compound 265

N-Acetylation of 264 under standard conditions provides 265 (37%): mp 241–246° C.

Example 253

Preparation of Compound 266

Suzuki coupling of 61 with 2-chlorobenzeneboronic acid provides 266 (13%): API MS m/z=490 [C$_{27}$H$_{32}$ClN$_7$+H]$^+$.

Example 254

Description of Biological Assays

A. Immunopurification of CyctinA/cdk2 and CyclinE/cdk2 Complexes.

CyclinA/cdk2 and cyclinE/cdk2 assays were carried out with cyclin/cdk complexes isolated from HeLa S-3 suspension cultures. HeLa cells were grown in spinner flasks at 37° C. in Joklik's modified minimum essential media (MEM) supplemented with 7% horse serum. After growing in medium supplemented with 2 mM thymidine for 16–18 h, cultures were arrested at the G1/S border and cyclinA/cdk2 and cyclinE/cdk2 were isolated from cell lysates by immunoprecipitation with antibodies specifically directed against each cyclin subunit. Rabbit anti-cyclinA (H-432) and the mouse monoclonal antibody against cyclinE (HE111) were purchased from Santa Cruz Biotechnology. Cells blocked at the appropriate stage of the cell cycle were disrupted in lysis buffer (50 mM Tris, pH 8.0, 250 mM NaCl, 0.5% NP-40 plus protease and phosphatase inhibitors) and centrifuged at 10,000×g to remove insoluble material. To isolate cyclin/cdk complexes, 1 μg of anti-cyclin antibody was incubated with lysate from 1×10$^7$ cells for 0.1 h at 4° C. Protein A-coated agarose beads were then added for 1 h to collect antibody-bound immune complexes. The immobilized cyclin/cdk complexes were then washed 4× with lysis buffer to reduce nonspecific protein binding. The complexes were then washed 1× in kinase assay buffer (50 mM Tris-HCl, pH 7.4, 10 mM MgCl$_2$, 1 mM DTT) and aliquoted into individual assay tubes.

B. Immunopurification of CyclinB/cdk1 Complex.

HeLa cells are blocked at the G1/S border by culturing in the presence of 2 mM thymidine for 20 h. The cells are then rinsed 3× in phosphate buffered saline and resuspended in regular medium. After 4 h of culture, the mitotic blocker, nocodazole is added to a final concentration of 75 ng/ml. Sixteen hours later, the cells are harvested by centrifugation, washed in PBS, and lysed in cold Lysis Buffer (50 mM Tris pH 8.0, 250 mM NaCl, 0.5% NP-40, 1 mM DTT, 25 μg/ml leupeptin, 25 μg/ml aprotinin, 15 μg/ml benzamidine, 1 mM PMSF, 50 mM sodium fluoride, 1 mM sodium orthovanadate) for 15 min at 1×10$^7$ cells/ml. The lysate is then clarified by centrifugation at 10,000×g for 10 min. The supernatant is collected and diluted 1:5 with Lysis Buffer. Monoclonal antibody against cyclinB (GNS1) is added to the supernatant to a final concentration of 5 μg/ml and shaken at 4° C. for 2 h. The immune complexes are then collected by the addition of 200 μl of protein agarose beads for 1 h. The beads are washed 4×in lysis buffer and 1× in kinase assay buffer.

C. Protein Kinase Assays and Determination of IC$_{50}$ Values.

CyclinA/cdk2 assays were carried out with complexes isolated from 0.5×10$^6$ cells. CyclinE/cdk2 assays were carried out with complexes isolated from 4×10$^6$ cells. CyclinB/cdk1 assays were carried out with complexes isolated from 4×10$^4$ cells. After centrifugation, the wash buffer was removed and the complexes resuspended in 15 μl of kinase assay buffer (kinase wash buffer+167 μg/ml histone H1). Compounds being tested for inhibition were added prior to the addition of [γ $^{32}$P] ATP to a final concentration of 15 μM. The tubes were incubated at 30° C. for 5 min and the reactions were stopped by the addition of an equal volume of 2×SDS-PAGE sample buffer. The samples were then subjected to electrophoresis on 10% SDS-PAGE to resolve the histone H1 from other reaction components. The amount of radioactive phosphate transferred to histone H1 was quantified on a Storm Phosphorimager (Molecular Dynamics).

Prior to the protein kinase assay, test compounds were dissolved in DMSO at a concentration of 25 mM and were diluted to produce final concentrations of 0.1, 1.0, and 10.0 μM in the kinase assays. To eliminate possible effects of differences in DMSO concentration, the DMSO was kept constant at 0.04%, including the control reaction. Duplicate assays were performed at each concentration. The activity was plotted as the percent of activity in the absence of added test compound versus test compound concentration. IC$_{50}$ values were calculated using GraphPad Prism data analysis software.

D. Measuring the Inhibition of Cell Growth.

Growth inhibition (GI$_{50}$) values were measured with HeLa S-3 cells selected for growth on plastic. The procedure was based on the protocol of Skehan et al. (Skehan, P., et al., J. Natl. Cancer Inst., 82:1107–1112 (1990), which is hereby incorporated by reference) HeLa cells were plated at 2×10$^4$ cells/well in 96 well plates. One day later, a control plate was fixed by addition of TCA to 5%. After five rinses with tap water the plate was air dried and stored at 4° C. Test compounds were added to the remaining plates at 10-fold dilutions between 0.01 and 100 μM. Two days later all plates were fixed as described above. Cells were then stained by the addition of 100 μl per well of 0.4% sulforhodamine B (SRB) in 1% acetic acid for 30 min at 4° C. Wells were then quickly rinsed 5× with acetic acid (1%) and allowed to air dry. The SRB was then solubilized by the addition of 100 μl per well of unbuffered 10 mM Tris base. Dye was quantified by measuring absorbance at 490 nm on a Molecular Devices kinetic microplate reader. Growth at each inhibitor concentration relative to the untreated control was calculated according to the following equation: percent growth=100× (T-T$_0$)/(C-T$_0$), where T was the average optical density (OD) of the test wells after 2 days of treatment, T$_0$ was the average OD of the wells in the control plate on day 0 and C was the average OD of untreated wells. Plots of percent growth versus inhibitor concentration were used to determine the GI$_{50}$.

The data below shown in Table 2 summarizes the in vitro cyclin/cdk inhibition constants (IC$_{50}$) and growth inhibition constants (GI$_{50}$) of HeLa Cells for the compounds of the current invention. Replicate experimental results are summarized below.

TABLE 2

In Vitro Cyclin/cdk Inhibition (IC$_{50}$) and Growth Inhibition (GI$_{50}$) of HeLa Cells For Compounds of the Current Invention.

| Compound | IC$_{50}$ CyclinA/cdk2 (μM) | IC$_{50}$ CyclinE/cdk2 (μM) | IC$_{50}$ CyclinB/cdk1 (μM) | GI$_{50}$ HeLa Cells (μM) |
|---|---|---|---|---|
| 5 | >10 | 12 | 7 | 5 |
|   | 0.4 | 0.6 |   | >10 |
| 12 | 2 | 1 | 3 | 0.06 |
|   | 0.7 | 3 |   | 0.003 |
|   | 0.9 | 0.5 |   | 0.001 |
|   | 0.2 | 0.1 |   | 0.02 |
|   |   |   |   | 0.0001 |
| 13 | 4 | 2 | 4 | 3 |
|   | 1 | 0.3 |   | 2 |
|   | 0.8 | 0.9 |   |   |
| 14 | 3 | 0.4 | 7 | 0.4 |
|   | 3 | 2 |   | 0.03 |
|   |   |   |   | 0.03 |
| 17 | 1 | 1 | 10 | 0.4 |
|   | 2 | 0.9 | 3 | 0.6 |
|   | 1 | 0.2 | 11 | 0.25 |
|   | >10 | 9 |   | 0.4 |
|   | 10 | 2 |   | 0.3 |
|   |   |   |   | 0.4 |
| 25 | 1 | 4 | >10 | 2 |
|   | 6 | 1 | >10 | 0.4 |
|   | >10 | 9 |   | >1 |
| 32 | 2 | 3 | — | 5 |
|   | 5 | 0.9 |   | 0.7 |

TABLE 2-continued

In Vitro Cyclin/cdk Inhibition (IC$_{50}$) and Growth Inhibition (GI$_{50}$) of HeLa Cells For Compounds of the Current Invention.

| Compound | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|
| 33 | >10 | 4 | >10 | 1 |
|  | 13 | 6 |  | 2 |
|  | 8 |  |  | 0.9 |
| 34 | 12 | 5 | >10 | 7 |
|  | 13 | 2 |  | 6 |
|  |  |  |  | 7 |
| 36 | >10 | >10 | >10 | 20 |
|  | >10 | >10 |  | 20 |
|  | >10 |  |  | >10 |
| 38 | >10 | >10 | >10 | 0.6 |
|  | >10 | >10 |  | 1 |
|  |  |  |  | 0.6 |
| 40 | >10 | >10 | >10 | 9 |
|  | >10 | >10 |  | 25 |
|  |  |  |  | >10 |
| 43 | >10 | >10 | >10 | 4 |
|  | >10 | >10 |  | 4 |
|  |  |  |  | 8 |
| 46 | >10 | 6 | >10 | 25 |
|  | 8 | 3 |  | >10 |
| 48 | 22 | 1 | >10 | 0.3 |
|  | 6 | 5 |  | 0.6 |
|  |  |  |  | 0.5 |
| 50 | >10 | >10 | >10 | 3 |
|  | 7 | 9 |  | >10 |
| 53 | >10 | 15 | >10 | 0.2 |
|  | >10 | 4 |  | 0.3 |
|  |  |  |  | 0.5 |
| 58 | 11 | 2 | 12 | 2 |
|  | 4 | 4 |  | 0.5 |
|  |  |  |  | 0.7 |
| 60 | >10 | 12 | >10 | 7 |
|  | 0.4 | >10 |  | 6 |
| 73 | >50 | 4 | >10 | 0.3 |
|  | 14 | 12 |  | 0.5 |
|  | >10 | >10 |  | 0.3 |
|  | >10 | >10 |  | 0.5 |
| 74 | 5 | 2 | 6 | 0.2 |
|  | 2 | 3 |  | 0.01 |
|  | 1 | 2 |  | 0.05 |
|  |  |  |  | 0.03 |
|  |  |  |  | 0.05 |
| 75 | 3 | 3 | 6 | 0.09 |
|  |  |  |  | 0.02 |
|  |  |  |  | 0.005 |
| 76 | 12 | 3 | 6 | 0.07 |
|  | 11 | 5 |  | 0.01 |
|  | 3 | 2 |  | 0.06 |
|  |  |  |  | 0.2 |
|  |  |  |  | 0.04 |
| 77 | >10 | 4 | >10 | 0.15 |
|  | >10 | 14 |  | 0.5 |
|  |  |  |  | 0.3 |
| 78 | 0.9 | 0.6 | 0.8 | 0.05 |
|  | 0.9 | 0.3 | 0.8 | 0.025 |
|  | 0.7 | 0.2 |  | 0.08 |
|  |  |  |  | 0.002 |
| 79 | 10 | 2 | 3 | 0.07 |
|  | 0.5 | 0.1 |  | 0.007 |
|  | 1 | 0.08 |  | 0.004 |
|  |  |  |  | 0.4 |
| 80 | >10 | >10 | >10 | >100 |
|  | >10 | 4 |  | >10 |
|  |  | 2 |  |  |
| 86 | 0.9 | 0.4 | 2 | 0.2 |
|  | 0.7 | 0.2 |  | 0.03 |
|  | 0.4 | 0.4 |  | 0.01 |
|  | 0.6 | 0.03 |  | 0.01 |
|  |  |  |  | 0.2 |
| 87 | 4 | 1 | 5 | 0.07 |
|  | 2 | 0.3 |  | 0.01 |
|  | 0.5 | 0.1 |  | 0.004 |
|  |  |  |  | 0.006 |
|  |  |  |  | 0.03 |
|  |  |  |  | 0.006 |
|  |  |  |  | 0.001 |
|  |  |  |  | 0.0001 |
| 88 | 3 | 4 | >10 | 0.1 |
|  | >10 | >10 |  | 0.05 |
|  | 2 | 5 |  | 0.04 |
|  |  |  |  | 0.005 |
| 93 | 0.2 | 0.09 | 0.9 | 0.3 |
|  | 0.3 | 0.1 |  | 0.08 |
|  |  |  |  | 0.3 |
| 94 | 0.6 | 0.3 | 0.4 | 0.1 |
|  | 0.2 | 0.3 |  | 0.07 |
|  |  |  |  | 0.4 |
| 95 | 1 | 1 | 4 | 0.08 |
|  | 2 | 0.7 |  | 0.003 |
|  |  |  |  | 0.0005 |
| 96 | 8 | 4 | 6 | 0.04 |
|  |  |  |  | 0.01 |
| 97 | >10 | 3 | 10 | 3 |
| 98 | 6 | 2 | >10 | >10 |
| 99 | 2 | 2 |  | 11 |
|  | >10 | 9 | >10 | 5 |
| 100 | >10 | 4 | >10 | 0.6 |
| 101 | 3 | 1 | 4 | 1 |
|  | 0.9 | 0.7 |  | 1 |
| 102 | >10 | 4 |  | 4 |
| 103 | 0.6 | 0.2 | 1 | 0.03 |
|  | 0.7 | 0.2 |  | 0.008 |
|  |  |  |  | 0.02 |
|  |  |  |  | 0.01 |
| 104 | 7 | 1 | 2 | 0.4 |
|  | 8 | 1 |  | 0.2 |
| 106 | 11 | 3 | — | 0.3 |
|  | 4 | 1 |  | 0.1 |
| 107 | 1 | 2 | — | 0.4 |
|  | 4 |  |  | 0.3 |
| 108 | 10 | >10 | — | 3 |
|  | >10 | >10 |  | 5 |
| 109 | 0.6 | 0.1 | — | 0.04 |
|  |  |  |  | <0.0001 |
| 110 | 0.6 | 2 |  | 0.02 |
|  |  |  |  | 0.03 |
|  |  |  |  | 0.02 |
|  |  |  |  | 0.01 |
| 111 | 0.2 | 0.07 |  | 0.02 |
|  |  |  |  | 0.0006 |
| 112 | 2 | 2 | — | <0.001 |
|  |  |  |  | 0.002 |
|  |  |  |  | 0.02 |
|  |  |  |  | 0.006 |
|  |  |  |  | 0.0006 |
| 113 | 0.4 | 0.3 | — | <0.001 |
|  |  |  |  | 0.00001 |
|  |  |  |  | 0.03 |
|  |  |  |  | 0.001 |
|  |  |  |  | 0.02 |
| 114 | 3 | 0.7 | — | >10 |
| 115 | 3 | 0.4 | — | 3 |
| 116 | >10 | >10 | — | >10 |
|  |  |  |  | >10 |
| 117 | >10 | 3 | — | 3 |
| 118 | 6 | 1 | — | >10 |
|  |  |  |  | >10 |
| 123 | 0.2 | 0.04 | — | <0.001 |
|  |  |  |  | <0.001 |
|  |  |  |  | 0.0001 |

TABLE 2-continued

In Vitro Cyclin/cdk Inhibition (IC$_{50}$) and Growth Inhibition (GI$_{50}$) of HeLa Cells For Compounds of the Current Invention.

| Compound | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|
| 124 | 2 | 0.8 | — | 0.003 |
|  |  |  |  | <0.001 |
|  |  |  |  | <0.0001 |
| 130 | — | — | — | >10 |
|  |  |  |  | >10 |
| 131 | — | — | — | 3 |
|  |  |  |  | 2 |
| 132 | — | — | — | 4 |
|  |  |  |  | 3 |
| 133 | — | — | — | >10 |
|  |  |  |  | >10 |
| 134 | — | — | — | 2 |
|  |  |  |  | 3 |
| 135 | — | — | — | 4 |
|  |  |  |  | 3 |
| 137 | — | — | — | 0.05 |
|  |  |  |  | 0.06 |
|  |  |  |  | 0.05 |
| 139 | — | — | — | 0.2 |
|  |  |  |  | 0.07 |
| 140 | — | — | — | 1 |
|  |  |  |  | 2 |
| 142 | — | — | — | 0.4 |
|  |  |  |  | 0.5 |
| 144 | — | — | — | 0.4 |
|  |  |  |  | 0.4 |
| 146 | — | — | — | 0.7 |
|  |  |  |  | 0.3 |
| 148 | — | — | — | 1 |
|  |  |  |  | 1 |
| 149 | — | — | — | 0.3 |
|  |  |  |  | 0.2 |
| 150 | — | — | — | 0.3 |
|  |  |  |  | 0.2 |
| 151 | — | — | — | 0.8 |
|  |  |  |  | 0.6 |
| 152 | — | — | — | 0.7 |
|  |  |  |  | 0.3 |
| 153 | — | — | — | 3 |
|  |  |  |  | 2 |
| 154 | — | — | — | 0.6 |
|  |  |  |  | 0.9 |
| 155 | — | — | — | 0.5 |
|  |  |  |  | 0.8 |
| 156 | — | — | — | 3 |
|  |  |  |  | 2 |
| 157 | — | — | — | 0.4 |
|  |  |  |  | 0.5 |
| 158 | — | — | — | 0.6 |
|  |  |  |  | 0.4 |
| 159 | — | — | — | 4 |
|  |  |  |  | 3 |
| 160 | — | — | — | 0.2 |
|  |  |  |  | 0.3 |
| 161 | — | — | — | 0.2 |
|  |  |  |  | 0.4 |
| 162 | — | — | — | 0.2 |
|  |  |  |  | 0.3 |
| 163 | — | — | — | 2 |
|  |  |  |  | 3 |
| 164 | — | — | — | 0.2 |
|  |  |  |  | 0.1 |
| 165 | — | — | — | 0.2 |
|  |  |  |  | 0.1 |
| 166 | — | — | — | 4 |
|  |  |  |  | 2 |
| 167 | — | — | — | 2 |
|  |  |  |  | 0.9 |
| 168 | — | — | — | 4 |
|  |  |  |  | 3 |
| 169 | — | — | — | 0.5 |
|  |  |  |  | 0.3 |
| 170 | — | — | — | 4 |
|  |  |  |  | 2 |
| 171 | — | — | — | 3 |
|  |  |  |  | 3 |
| 172 | — | — | — | 0.3 |
|  |  |  |  | 0.3 |
| 173 | — | — | — | 3 |
|  |  |  |  | 3 |
| 174 | — | — | — | 0.04 |
|  |  |  |  | 0.03 |
|  |  |  |  | 0.1 |
|  |  |  |  | 0.06 |
|  |  |  |  | 0.4 |
|  |  |  |  | 0.4 |
| 175 | — | — | — | 0.6 |
|  |  |  |  | 0.3 |
| 177 | — | — | — | 0.2 |
|  |  |  |  | 0.06 |
|  |  |  |  | 0.06 |
| 178 | — | — | — | 0.4 |
|  |  |  |  | 0.2 |
| 179 | — | — | — | 0.1 |
|  |  |  |  | 0.05 |
|  |  |  |  | 0.05 |
| 180 | — | — | — | 0.4 |
|  |  |  |  | 0.3 |
| 181 | — | — | — | 0.04 |
| 182 | — | — | — | 0.3 |
|  |  |  |  | 0.3 |
| 187 | — | — | — | 0.05 |
|  |  |  |  | 0.03 |
| 188 | — | — | — | 0.2 |
|  |  |  |  | 0.07 |
| 194 | — | — | — | 0.06 |
|  |  |  |  | 0.04 |
| 199 | — | — | — | 0.2 |
|  |  |  |  | 0.09 |
| 200 | — | — | — | 0.3 |
|  |  |  |  | 0.2 |
| 206 | — | — | — | 0.2 |
|  |  |  |  | 0.2 |
| 207 | — | — | — | 0.4 |
|  |  |  |  | 0.2 |
| 208 | — | — | — | 4 |
|  |  |  |  | 3 |
| 209 | — | — | — | 2 |
|  |  |  |  | 2 |
| 210 | — | — | — | 3 |
|  |  |  |  | 4 |
| 211 | — | — | — | 0.6 |
|  |  |  |  | 0.3 |
| 212 | — | — | — | 5 |
|  |  |  |  | 3 |
| 213 | — | — | — | 3 |
|  |  |  |  | 2 |
| 214 | — | — | — | 5 |
|  |  |  |  | 5 |
| 215 | — | — | — | 2 |
|  |  |  |  | 3 |
| 216 | — | — | — | 0.5 |
|  |  |  |  | 0.5 |
| 217 | — | — | — | 4 |
|  |  |  |  | 4 |
| 218 | — | — | — | 3 |
|  |  |  |  | 5 |
| 219 | — | — | — | 0.4 |
|  |  |  |  | 0.6 |
| 221 | — | — | — | 2 |
|  |  |  |  | 2 |

TABLE 2-continued

In Vitro Cyclin/cdk Inhibition (IC$_{50}$) and Growth Inhibition (GI$_{50}$) of HeLa Cells For Compounds of the Current Invention.

| Compound | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|
| 222 | — | — | — | 1 |
|  |  |  |  | 2 |
| 223 | — | — | — | 0.04 |
|  |  |  |  | 0.1 |
| 224 | — | — | — | 2 |
|  |  |  |  | 2 |
| 229 | — | — | — | 0.4 |
| 230 | — | — | — | 0.3 |
| 231 | — | — | — | 0.04 |
| 232 | — | — | — | 0.3 |
| 233 | — | — | — | 0.5 |
| 239 | — | — | — | 4 |
|  |  |  |  | 6 |
| 240 | — | — | — | 8 |
|  |  |  |  | 8 |
| 241 | — | — | — | 7 |
|  |  |  |  | 4 |
| 242 | — | — | — | 7 |
|  |  |  |  | >10 |
| 243 | — | — | — | 3 |
|  |  |  |  | 3 |
| 248 | — | — | — | 3 |
|  |  |  |  | 4 |
| 249 | — | — | — | >10 |
|  |  |  |  | >10 |
| 250 | — | — | — | 3 |
|  |  |  |  | 6 |
| 256 | — | — | — | 4 |
|  |  |  |  | 3 |
| 257 | — | — | — | 3 |
|  |  |  |  | 3 |
| 258 | — | — | — | 0.2 |
|  |  |  |  | 0.3 |
|  |  |  |  | 0.4 |
| 259 | — | — | — | 0.3 |
|  |  |  |  | 0.4 |
|  |  |  |  | 0.7 |
| 260 | — | — | — | 0.2 |
|  |  |  |  | 0.1 |
|  |  |  |  | 0.2 |
| 261 | — | — | — | 0.3 |
|  |  |  |  | 0.3 |
|  |  |  |  | 0.3 |
| 262 | — | — | — | 0.3 |
|  |  |  |  | 0.2 |
|  |  |  |  | 0.5 |
| 263 | — | — | — | 2 |
|  |  |  |  | 3 |
|  |  |  |  | 4 |
| 264 | — | — | — | 0.3 |
|  |  |  |  | 0.3 |
|  |  |  |  | 0.5 |
| 265 | — | — | — | 0.3 |
|  |  |  |  | 0.3 |
|  |  |  |  | 0.4 |
| 266 | — | — | — | 0.3 |
|  |  |  |  | 0.3 |
|  |  |  |  | 0.5 |
| 267 | — | — | — | 0.8 |
|  |  |  |  | 0.6 |

The data below shown in Table 3 summarizes the in vitro cyclin/cdk inhibition (IC$_{50}$) and growth inhibition (GI$_{50}$) of HeLa Cells for several reference compounds in comparison to several compounds of the current invention. The chemical structures are provided.

TABLE 3

In Vitro cyclin/cdk Inhibition (IC$_{50}$) and Growth Inhibition (GI$_{50}$) of HeLa Cells For Reference Compounds in Comparison to Several Compounds of the Current Invention.

| Compound | Structure | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|---|
| Olomoucine | 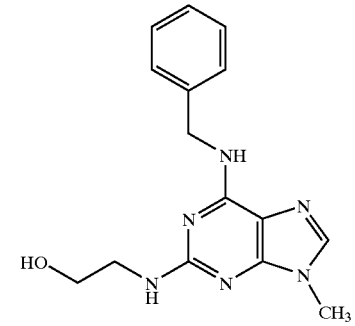 | 0.5–24 (n > 10) | 1–14 (n > 10) | 7–23 (n > 10) | 75 |

TABLE 3-continued

In Vitro cyclin/cdk Inhibition (IC$_{50}$) and Growth Inhibition (GI$_{50}$) of HeLa Cells For Reference Compounds in Comparison to Several Compounds of the Current Invention.

| Compound | Structure | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|---|
| Roscovitine | 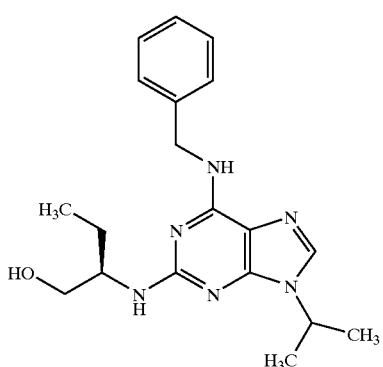 | 2.1<br>4<br>3 | 0.04<br>0.7 | — | 30<br>25<br>30<br>>10<br>25 |
| Flavopiridol | 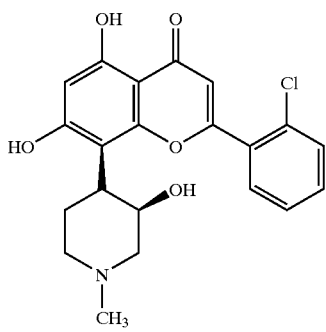 | 0.06<br>0.2 | 0.6<br>0.04 | 0.06<br>(n = 2) | 0.18 |
| 125 | 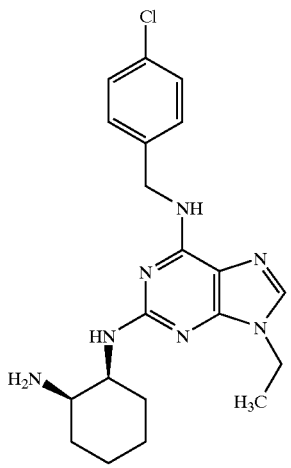 | 1 | 0.1 | 0.6 | 3 |

TABLE 3-continued

In Vitro cyclin/cdk Inhibition (IC$_{50}$) and Growth Inhibition (GI$_{50}$) of HeLa Cells For Reference Compounds in Comparison to Several Compounds of the Current Invention.

| Compound | Structure | IC$_{50}$ CyclinA/cdk2 (μM) | IC$_{50}$ CyclinE/cdk2 (μM) | IC$_{50}$ CyclinB/cdk1 (μM) | GI$_{50}$ HeLa Cells (μM) |
|---|---|---|---|---|---|
| 126 | 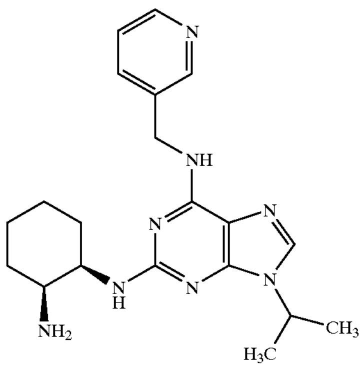 | 0.6<br>0.8 | 0.06<br>0.06 | 2<br>0.2 | 2<br>4<br>6 |
| 74 | 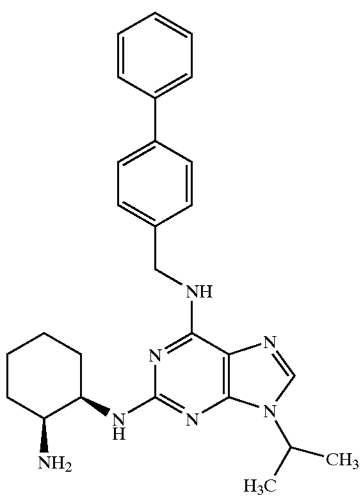 | 5 | 2 | 6 | 0.2<br>0.01<br>0.05 |
| 127 | 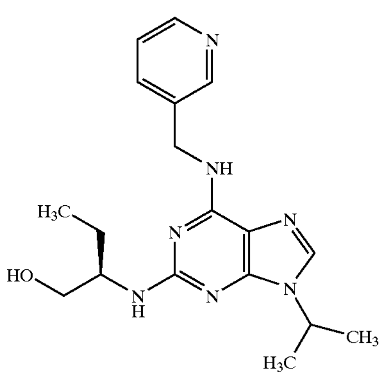 | 0.3–2<br>(n > 15) | 0.04–0.07<br>(n > 15) | 0.5–2<br>(n > 15) | 7–15<br>(n > 5) |

TABLE 3-continued

In Vitro cyclin/cdk Inhibition (IC$_{50}$) and Growth Inhibition (GI$_{50}$) of HeLa Cells For Reference Compounds in Comparison to Several Compounds of the Current Invention.

| Compound | Structure | IC$_{50}$ CyclinA/cdk2 ($\mu$M) | IC$_{50}$ CyclinE/cdk2 ($\mu$M) | IC$_{50}$ CyclinB/cdk1 ($\mu$M) | GI$_{50}$ HeLa Cells ($\mu$M) |
|---|---|---|---|---|---|
| 88 | 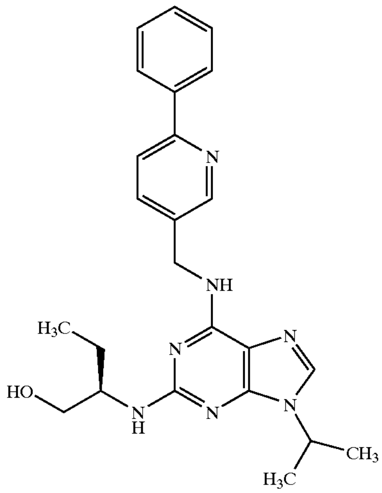 | 3 | 4 | >10 | 0.1<br>0.05<br>0.04 |

The following data in Tables 4, 5, 6, and 7 summarize the growth inhibition properties of several compounds of the current invention and olomoucine against 60-human transformed cell lines. These data were cooperatively obtained at the National Cancer Institute in their 60-cell line growth inhibition assay according to published procedures (Boyd, M. R., "Anticancer Drug Development Guide," *Preclinical Screening Clinical Trials, and Approval*; Teicher, B. Ed.; Humana Press; Totowa, N.J., 23–42 (1997), which is hereby incorporated by reference).

TABLE 4

In Vitro Growth Inhibition (GI$_{50}$) of NCI Human Transformed Cell Lines of Several Compounds of the Current Invention.

| Cancer Type | Cell Line | 73 GI$_{50}$ ($\mu$M) | 17 GI$_{50}$ ($\mu$M) | 33 GI$_{50}$ ($\mu$M) | 38 GI$_{50}$ ($\mu$M) |
|---|---|---|---|---|---|
| Breast | BT-549 | 0.25 | 0.40 | 51.3 | 0.32 |
| Breast | HS 578T | 0.10 | 6.31 | — | — |
| Breast | MCF7 | 0.16 | 0.16 | 5.2 | 0.20 |
| Breast | MDA-MB-231/ATCC | 0.50 | — | — | 0.06 |
| Breast | MDA-MB-435 | 0.25 | 0.20 | 4.9 | 0.05 |
| Breast | MDA-N | 0.13 | 0.11 | — | — |
| Breast | NCI/ADR-RES | 0.40 | 0.28 | 6.3 | 0.32 |
| Breast | T-47D | 0.25 | 0.13 | 3.9 | 0.25 |
| CNS | SF-268 | 0.16 | 0.04 | 6.3 | 0.20 |
| CNS | SF-295 | 0.25 | 0.19 | 7.8 | 0.50 |
| CNS | SF-539 | 0.76 | 0.40 | 89.1 | 1.26 |
| CNS | SNB-19 | 0.43 | 0.14 | 38.0 | 0.50 |
| CNS | SNB-75 | 0.02 | 0.02 | — | — |
| CNS | U251 | 0.32 | 0.40 | 3.7 | 0.20 |
| Colon | COLO 205 | 0.28 | 0.05 | 7.8 | 0.16 |
| Colon | HCC-2998 | 0.20 | 0.03 | >1000 | 7.94 |
| Colon | HCT-116 | 0.20 | 0.16 | 6.2 | 0.32 |
| Colon | HCT-15 | 0.18 | 0.04 | 8.9 | 0.25 |
| Colon | HT29 | — | 0.10 | 8.9 | 0.25 |
| Colon | KM12 | 0.13 | 0.03 | 4.1 | 0.16 |
| Colon | SW-620 | — | 0.01 | 2.9 | 0.03 |
| Leukemia | CCRF-CEM | 0.25 | 0.16 | 4.6 | 0.20 |

TABLE 4-continued

In Vitro Growth Inhibition (GI$_{50}$) of NCI Human Transformed Cell Lines of Several Compounds of the Current Invention.

| Cancer Type | Cell Line | 73 GI$_{50}$ ($\mu$M) | 17 GI$_{50}$ ($\mu$M) | 33 GI$_{50}$ ($\mu$M) | 38 GI$_{50}$ ($\mu$M) |
|---|---|---|---|---|---|
| Leukemia | HL-60(TB) | — | — | 3.2 | 0.04 |
| Leukemia | K-562 | 0.16 | 0.16 | 3.1 | 0.25 |
| Leukemia | MOLT-4 | 0.32 | 0.25 | 3.8 | 0.25 |
| Leukemia | RPMI-8226 | 0.03 | 0.03 | 1.5 | — |
| Leukemia | SR | — | 0.50 | 4.5 | 3.98 |
| Melanoma | LOX IMVI | — | 0.32 | 16.6 | 0.40 |
| Melanoma | M14 | 0.03 | 0.03 | 7.8 | 0.05 |
| Melanoma | MALME-3M | 0.27 | 19.95 | 11.7 | 0.25 |
| Melanoma | SK-MEL-2 | 0.63 | 1.00 | >1000 | 2.00 |
| Melanoma | SK-MEL-28 | 0.45 | 0.12 | 5.9 | 0.03 |
| Melanoma | SK-MEL-5 | 0.25 | 0.32 | 16.2 | 0.32 |
| Melanoma | UACC-257 | 0.16 | 0.20 | 75.9 | 0.50 |
| Melanoma | UACC-62 | 0.30 | 0.27 | 8.3 | 1.00 |
| Non-Small Cell Lung | A549/ATCC | 0.03 | 0.03 | 4.6 | 0.13 |
| Non-Small Cell Lung | EKVX | 0.25 | 2.51 | 6.9 | 0.20 |
| Non-Small Cell Lung | HOP-62 | 0.06 | 0.20 | >1000 | 0.32 |
| Non-Small Cell Lung | HOP-92 | 1.00 | 1.58 | — | 0.32 |
| Non-Small Cell Lung | NCI-H226 | 0.22 | 0.11 | — | — |
| Non-Small Cell Lung | NCI-H23 | 0.32 | 0.16 | 26.3 | 0.32 |
| Non-Small Cell Lung | NCI-H322M | 0.16 | >1000 | 38.9 | 0.40 |
| Non-Small Cell Lung | NCI-H460 | 0.40 | 0.41 | 25.7 | 3.16 |
| Non-Small Cell Lung | NCI-H522 | — | — | 4.2 | — |
| Ovarian | IGROV1 | 0.32 | 0.20 | 10.0 | 0.16 |
| Ovarian | OVCAR-3 | 0.30 | 0.65 | >1000 | 1.00 |
| Ovarian | OVCAR-4 | 0.32 | 0.32 | 31.6 | 1.26 |
| Ovarian | OVCAR-5 | 0.25 | 0.26 | >1000 | 0.40 |

TABLE 4-continued

In Vitro Growth Inhibition (GI$_{50}$) of NCI Human Transformed Cell Lines of Several Compounds of the Current Invention.

| Cancer Type | Cell Line | 73 GI$_{50}$ ($\mu$M) | 17 GI$_{50}$ ($\mu$M) | 33 GI$_{50}$ ($\mu$M) | 38 GI$_{50}$ ($\mu$M) |
|---|---|---|---|---|---|
| Ovarian | OVCAR-8 | — | 0.13 | 6.6 | 0.25 |
| Ovarian | SK-OV-3 | 0.95 | 0.40 | >1000 | 3.98 |
| Prostate | DU-145 | 7.08 | 0.63 | 17.8 | 1.26 |
| Prostate | PC-3 | 0.35 | 0.20 | >1000 | 0.40 |
| Renal | 786-0 | 0.20 | 0.25 | 18.6 | 0.32 |
| Renal | A498 | 2.88 | 1.58 | — | 1.26 |
| Renal | ACHN | 0.32 | 0.40 | 5.2 | 2.00 |
| Renal | CAKI-1 | 1.66 | 0.13 | 4.4 | 0.20 |
| Renal | RXF 393 | 0.09 | 0.02 | 13.2 | 0.13 |
| Renal | SN12C | — | 0.56 | — | — |
| Renal | TK-10 | — | — | 8.3 | 0.40 |
| Renal | UO-31 | 0.06 | 0.10 | 8.1 | 0.13 |

TABLE 5

In Vitro Growth Inhibition (GI$_{50}$) of NCI Human Transformed Cell Lines of Several Compounds of the Current Invention.

| Cancer Type | Cell Line | 43 GI$_{50}$ ($\mu$M) | 48 GI$_{50}$ ($\mu$M) | 75 GI$_{50}$ ($\mu$M) | 76 GI$_{50}$ ($\mu$M) |
|---|---|---|---|---|---|
| Breast | BT-549 | 4.0 | 0.01 | <0.01 | <0.01 |
| Breast | HS 578T | — | 0.03 | <0.01 | <0.01 |
| Breast | MCF7 | 2.7 | 0.25 | <0.01 | <0.01 |
| Breast | MDA-MB-231/ATCC | 3.2 | 0.09 | <0.01 | <0.01 |
| Breast | MDA-MB-435 | 2.1 | — | — | — |
| Breast | MDA-N | — | 0.02 | <0.01 | <0.01 |
| Breast | NCI/ADR-RES | 5.2 | 0.12 | 0.48 | 0.015 |
| Breast | T-47D | 2.2 | 0.15 | <0.01 | <0.01 |
| CNS | SF-268 | 3.0 | <0.01 | <0.01 | <0.01 |
| CNS | SF-295 | 4.0 | 0.24 | <0.01 | <0.01 |
| CNS | SF-539 | 3.4 | 0.38 | 0.02 | 0.054 |
| CNS | SNB-19 | 5.0 | 0.02 | <0.01 | <0.01 |
| CNS | SNB-75 | — | <0.01 | <0.01 | <0.01 |
| CNS | U251 | 2.3 | 0.17 | <0.01 | 0.020 |
| Colon | COLO 205 | 1.6 | 0.03 | <0.01 | <0.01 |
| Colon | HCC-2998 | 3.4 | — | — | — |
| Colon | HCT-116 | 2.1 | 0.19 | <0.01 | 0.014 |
| Colon | HCT-15 | 3.9 | 0.02 | 0.03 | <0.01 |
| Colon | HT29 | 3.6 | <0.01 | <0.01 | <0.01 |
| Colon | KM12 | 2.3 | 0.02 | <0.01 | <0.01 |
| Colon | SW-620 | 1.6 | <0.01 | <0.01 | <0.01 |
| Leukemia | CCRF-CEM | 2.8 | 0.03 | <0.01 | <0.01 |
| Leukemia | HL-60(TB) | 2.1 | — | — | — |
| Leukemia | K-562 | 3.1 | 0.16 | <0.01 | <0.01 |
| Leukemia | MOLT-4 | 2.0 | 0.05 | <0.01 | <0.01 |
| Leukemia | RPMI-8226 | — | <0.01 | <0.01 | <0.01 |
| Leukemia | SR | 2.2 | 0.16 | <0.01 | <0.01 |
| Melanoma | LOX IMVI | 3.4 | 0.19 | <0.01 | <0.01 |
| Melanoma | M14 | 2.2 | <0.01 | <0.01 | <0.01 |
| Melanoma | MALME-3M | 3.0 | 0.13 | <0.01 | <0.01 |
| Melanoma | SK-MEL-2 | 61.7 | 0.48 | 0.02 | 0.112 |
| Melanoma | SK-MEL-28 | 2.3 | <0.01 | <0.01 | <0.01 |
| Melanoma | SK-MEL-5 | 2.1 | 0.17 | 0.01 | 0.013 |
| Melanoma | UACC-257 | 4.8 | 0.04 | <0.01 | <0.01 |
| Melanoma | UACC-62 | 3.3 | 0.10 | 0.01 | 0.018 |
| Non-Small Cell Lung | A549/ATCC | 4.1 | <0.01 | <0.01 | <0.01 |
| Non-Small Cell Lung | EKVX | 2.8 | — | — | — |
| Non-Small Cell Lung | HOP-62 | 3.3 | 0.03 | <0.01 | <0.01 |
| Non-Small Cell Lung | HOP-92 | 2.6 | 0.46 | <0.01 | 0.017 |
| Non-Small Cell Lung | NCI-H226 | — | — | — | — |
| Non-Small Cell Lung | NCI-H23 | 4.3 | 0.07 | <0.01 | <0.01 |
| Non-Small Cell Lung | NCI-H322M | 3.5 | 0.03 | <0.01 | <0.01 |
| Non-Small Cell Lung | NCI-H460 | 3.2 | 0.25 | <0.01 | 0.047 |
| Non-Small Cell Lung | NCI-H522 | — | <0.01 | <0.01 | <0.01 |
| Ovarian | IGROV1 | 3.4 | 0.23 | <0.01 | <0.01 |
| Ovarian | OVCAR-3 | 9.3 | 0.17 | <0.01 | <0.01 |
| Ovarian | OVCAR-4 | 8.9 | 0.20 | <0.01 | <0.01 |
| Ovarian | OVCAR-5 | 3.6 | 0.16 | <0.01 | <0.01 |
| Ovarian | OVCAR-8 | 3.9 | 0.10 | <0.01 | <0.01 |
| Ovarian | SK-OV-3 | 72.4 | 1.38 | 0.03 | 0.051 |
| Prostate | DU-145 | 2.6 | 0.55 | <0.01 | 0.043 |
| Prostate | PC-3 | 38.9 | 0.23 | <0.01 | <0.01 |
| Renal | 786-0 | 3.1 | 0.25 | <0.01 | <0.01 |
| Renal | A498 | 3.0 | 0.39 | 0.01 | <0.01 |
| Renal | ACHN | 3.1 | 0.25 | 0.02 | 0.025 |
| Renal | CAKI-1 | 3.0 | — | — | — |
| Renal | RXF 393 | 1.9 | <0.01 | <0.01 | <0.01 |
| Renal | SN12C | — | 0.03 | <0.01 | <0.01 |
| Renal | TK-10 | 3.2 | 0.37 | <0.01 | 0.013 |
| Renal | UO-31 | 2.8 | <0.01 | 0.03 | <0.01 |

TABLE 6

In Vitro Growth Inhibition (GI$_{50}$) of NCI Human Transformed Cell Lines of Several Compounds of the Current Invention.

| Cancer Type | Cell Line | 79 GI$_{50}$ ($\mu$M) | 87 GI$_{50}$ ($\mu$M) | 12 GI$_{50}$ ($\mu$M) |
|---|---|---|---|---|
| Breast | BT-549 | <0.01 | 0.02 | 0.041 |
| Breast | HS 578T | <0.01 | <0.01 | <0.005 |
| Breast | MCF7 | <0.01 | 0.04 | <0.005 |
| Breast | MDA-MB-231/ATCC | <0.01 | <0.01 | <0.005 |
| Breast | MDA-MB-435 | <0.01 | <0.01 | <0.005 |
| Breast | MDA-N | <0.01 | 0.014 | <0.005 |
| Breast | NCI/ADR-RES | 0.86 | 0.28 | 1.26 |

TABLE 6-continued

In Vitro Growth Inhibition (GI$_{50}$) of NCI Human Transformed Cell Lines of Several Compounds of the Current Invention.

| Cancer Type | Cell Line | 79 GI$_{50}$ ($\mu$M) | 87 GI$_{50}$ ($\mu$M) | 12 GI$_{50}$ ($\mu$M) |
|---|---|---|---|---|
| Breast | T-47D | <0.01 | 0.048 | 0.0088 |
| CNS | SF-268 | <0.01 | <0.01 | <0.005 |
| CNS | SF-295 | <0.01 | 0.047 | 0.018 |
| CNS | SF-539 | <0.01 | 0.081 | 0.022 |
| CNS | SNB-19 | <0.01 | 0.038 | 0.016 |
| CNS | SNB-75 | <0.01 | 0.012 | <0.005 |
| CNS | U251 | <0.01 | 0.028 | 0.0078 |
| Colon | COLO 205 | <0.01 | <0.01 | <0.005 |
| Colon | HCC-2998 | <0.01 | <0.01 | <0.005 |
| Colon | HCT-116 | <0.01 | 0.037 | 0.0089 |
| Colon | HCT-15 | <0.01 | 0.066 | 0.17 |
| Colon | HT29 | <0.01 | <0.01 | <0.005 |
| Colon | KM12 | <0.01 | <0.01 | <0.005 |
| Colon | SW-620 | <0.01 | <0.01 | <0.005 |
| Leukemia | CCRF-CEM | <0.01 | <0.01 | <0.005 |
| Leukemia | HL-60(TB) | <0.01 | <0.01 | <0.005 |
| Leukemia | K-562 | <0.01 | 0.024 | <0.005 |
| Leukemia | MOLT-4 | <0.01 | 0.02 | <0.005 |
| Leukemia | RPMI-8226 | <0.01 | <0.01 | <0.005 |
| Leukemia | SR | <0.01 | 0.032 | <0.005 |
| Melanoma | LOX IMVI | <0.01 | 0.027 | <0.005 |
| Melanoma | M14 | <0.01 | <0.01 | <0.005 |
| Melanoma | MALME-3M | <0.01 | 0.024 | 0.010 |
| Melanoma | SK-MEL-2 | <0.01 | 0.056 | 0.0096 |
| Melanoma | SK-MEL-28 | <0.01 | <0.01 | 0.01 |
| Melanoma | SK-MEL-5 | <0.01 | 0.028 | 0.014 |
| Melanoma | UACC-257 | <0.01 | 0.017 | 0.008 |
| Melanoma | UACC-62 | <0.01 | 0.045 | 0.027 |
| Non-Small Cell Lung | A549/ATCC | <0.01 | <0.01 | <0.005 |
| Non-Small Cell Lung | EKVX | <0.01 | 0.081 | 0.023 |
| Non-Small Cell Lung | HOP-62 | <0.01 | 0.01 | <0.005 |
| Non-Small Cell Lung | HOP-92 | <0.01 | 0.088 | 0.011 |
| Non-Small Cell Lung | NCI-H226 | <0.01 | 0.0.052 | 0.021 |
| Non-Small Cell Lung | NCI-H23 | <0.01 | 0.022 | <0.005 |
| Non-Small Cell Lung | NCI-H322M | <0.01 | 0.021 | <0.005 |
| Non-Small Cell Lung | NCI-H460 | <0.01 | 0.22 | 0.015 |
| Non-Small Cell Lung | NCI-H522 | <0.01 | <0.01 | <0.005 |
| Ovarian | IGROV1 | <0.01 | 0.052 | 0.013 |
| Ovarian | OVCAR-3 | <0.01 | 0.05 | 0.012 |
| Ovarian | OVCAR-4 | <0.01 | 0.048 | <0.005 |
| Ovarian | OVCAR-5 | <0.01 | 0.051 | 0.017 |
| Ovarian | OVCAR-8 | <0.01 | 0.033 | 0.0076 |
| Ovarian | SK-OV-3 | <0.01 | 0.35 | 0.018 |
| Prostate | DU-145 | <0.01 | 0.22 | 0.017 |
| Prostate | PC-3 | <0.01 | 0.018 | <0.005 |
| Renal | 786-0 | <0.01 | 0.047 | 0.0065 |
| Renal | A498 | <0.01 | 0.10 | 0.016 |
| Renal | ACHN | <0.01 | 0.19 | 0.039 |
| Renal | CAKI-1 | <0.01 | 0.064 | 0.038 |
| Renal | RXF 393 | <0.01 | 0.011 | <0.005 |
| Renal | SN12C | <0.01 | <0.01 | <0.005 |
| Renal | TK-10 | <0.01 | 0.029 | 0.01 |
| Renal | UO-31 | <0.01 | 0.016 | 0.063 |

TABLE 7

In Vitro Growth Inhibition (GI$_{50}$) of NCI Human Transformed Cell Lines of Several Compounds of the Current Invention and Olomoucine.

| Cancer Type | Cell Line | 74 GI$_{50}$ ($\mu$M) | 78 GI$_{50}$ ($\mu$M) | 77 GI$_{50}$ ($\mu$M) | Olomoucine GI$_{50}$ ($\mu$M) |
|---|---|---|---|---|---|
| Breast | BT-549 | 0.16 | 0.04 | <0.01 | 79 |
| Breast | HS 578T | <0.01 | — | <0.01 | 63 |
| Breast | MCF7 | <0.01 | — | 0.03 | 50 |
| Breast | MDA-MB-231/ATCC | <0.01 | <0.01 | 0.04 | 100 |
| Breast | MDA-MB-435 | — | — | — | 63 |
| Breast | MDA-N | <0.01 | <0.01 | 0.01 | 79 |
| Breast | NCI/ADR-RES | 0.24 | 14.45 | 0.03 | 100 |
| Breast | T-47D | <0.01 | 0.03 | 0.01 | 63 |
| CNS | SF-268 | <0.01 | — | <0.01 | 50 |
| CNS | SF-295 | <0.01 | 0.21 | 0.04 | 79 |
| CNS | SF-539 | 0.07 | — | 0.22 | 32 |
| CNS | SNB-19 | <0.01 | <0.01 | 0.03 | 63 |
| CNS | SNB-75 | <0.01 | <0.01 | <0.01 | 25 |
| CNS | U251 | <0.01 | 0.02 | 0.09 | 50 |
| Colon | COLO 205 | <0.01 | <0.01 | 0.02 | 32 |

TABLE 7-continued

In Vitro Growth Inhibition (GI₅₀) of NCI Human Transformed Cell Lines of Several Compounds of the Current Invention and Olomoucine.

| Cancer Type | Cell Line | 74 GI$_{50}$ ($\mu$M) | 78 GI$_{50}$ ($\mu$M) | 77 GI$_{50}$ ($\mu$M) | Olomoucine GI$_{50}$ ($\mu$M) |
|---|---|---|---|---|---|
| Colon | HCC-2998 | — | <0.01 | — | 63 |
| Colon | HCT-116 | <0.01 | 0.03 | 0.05 | 40 |
| Colon | HCT-15 | <0.01 | 1.48 | <0.01 | 40 |
| Colon | HT29 | <0.01 | <0.01 | <0.01 | 63 |
| Colon | KM12 | <0.01 | <0.01 | <0.01 | 40 |
| Colon | SW-620 | <0.01 | <0.01 | <0.01 | 40 |
| Leukemia | CCRF-CEM | <0.01 | — | <0.01 | 40 |
| Leukemia | HL-60(TB) | — | <0.01 | — | 40 |
| Leukemia | K-562 | <0.01 | 0.02 | 0.02 | 100 |
| Leukemia | MOLT-4 | <0.01 | <0.01 | 0.01 | 63 |
| Leukemia | RPMI-8226 | <0.01 | <0.01 | <0.01 | 50 |
| Leukemia | SR | <0.01 | — | 0.02 | 25 |
| Melanoma | LOX IMVI | <0.01 | — | 0.04 | 32 |
| Melanoma | M14 | <0.01 | <0.01 | <0.01 | 100 |
| Melanoma | MALME-3M | 0.01 | 0.01 | 0.05 | 100 |
| Melanoma | SK-MEL-2 | 0.06 | 0.02 | 0.51 | 100 |
| Melanoma | SK-MEL-28 | <0.01 | 0.01 | <0.01 | 50 |
| Melanoma | SK-MEL-5 | 0.06 | 0.10 | 0.08 | 40 |
| Melanoma | UACC-257 | <0.01 | 0.02 | 0.02 | 79 |
| Melanoma | UACC-62 | 0.04 | 0.03 | 0.12 | 32 |
| Non-Small Cell Lung | A549/ATCC | <0.01 | <0.01 | <0.01 | 50 |
| Non-Small Cell Lung | EKVX | — | 0.05 | — | 100 |
| Non-Small Cell Lung | HOP-62 | <0.01 | 0.02 | <0.01 | 32 |
| Non-Small Cell Lung | HOP-92 | 0.03 | — | 0.13 | 50 |
| Non-Small Cell Lung | NCI-H226 | — | 0.02 | — | 50 |
| Non-Small Cell Lung | NCI-H23 | <0.01 | 0.01 | 0.01 | 79 |
| Non-Small Cell Lung | NCI-H322M | <0.01 | <0.01 | <0.01 | 63 |
| Non-Small Cell Lung | NCI-H460 | <0.01 | 0.05 | 0.22 | 63 |
| Non-Small Cell Lung | NCI-H522 | <0.01 | <0.01 | <0.01 | 40 |
| Ovarian | IGROV1 | <0.01 | <0.01 | 0.09 | 40 |
| Ovarian | OVCAR-3 | <0.01 | 0.03 | 0.02 | 79 |
| Ovarian | OVCAR-4 | <0.01 | 0.02 | <0.01 | 100 |
| Ovarian | OVCAR-5 | 0.03 | <0.01 | 0.04 | 40 |
| Ovarian | OVCAR-8 | <0.01 | 0.02 | 0.02 | 63 |
| Ovarian | SK-OV-3 | 0.22 | 0.06 | 0.19 | 100 |
| Prostate | DU-145 | 0.02 | 0.06 | 0.13 | 40 |
| Prostate | PC-3 | <0.01 | <0.01 | 0.02 | 100 |
| Renal | 786-0 | <0.01 | 0.04 | 0.03 | 63 |
| Renal | A498 | 0.03 | 0.03 | 0.03 | 32 |
| Renal | ACHN | 0.03 | 0.32 | 0.11 | 25 |
| Renal | CAKI-1 | — | 0.79 | — | 32 |
| Renal | RXF 393 | <0.01 | <0.01 | <0.01 | 20 |
| Renal | SN12C | <0.01 | <0.01 | <0.01 | 100 |
| Renal | TK-10 | <0.01 | 0.07 | 0.05 | 63 |
| Renal | UO-31 | 0.01 | 0.17 | <0.01 | 32 |

The following data in Table 8 summarize the in vivo properties of several compounds of the current invention. These data were cooperatively obtained at the National Cancer Institute in their Hollow Fiber Assay according to published procedures (Hollingshead, M. G., et al "In Vivo Cultivation of Tumor Cells in Hollow Fibers," *Life Sciences*, 1995, 57(2), 131–141 which is hereby incorporated by reference).

TABLE 8

In Vivo Evaluation of Several Compounds of the Current Invention.

| Compound | MTD (mg/kg) | IP Score | SC score | Cell Kill | Cell Types Killed |
|---|---|---|---|---|---|
| 73 | 100 | 2 | 0 | N | — |
| 17 | 100 | 8 | 0 | Y | H522 |
| 38 | 100 | 0 | 4 | N | — |
| 78 | 6.3 | 34 | 0 | Y | H23, H522, OVCAR3, SF29 |
| 79 | 6.3 | 26 | 6 | N | — |
| 86 | 6.3 | 38 | 0 | Y | OVCAR 3, OVCAR 5, H522 |
| 87 | 25 | 30 | 2 | Y | H522 |
| 12 | 3.1 | 26 | 4 | Y | H522, MDA-MB-435 |
| 93 | 25 | 22 | 8 | Y | OVCAR-3 |
| 94 | 50 | 22 | 2 | Y | COLO205, OVCAR-3, H522 |
| 103 | 6.3 | 38 | 6 | Y | OVCAR 3, OVCAR 5, H522, MDA-MB-435, SF295 |
| 109 | 400 | 18 | 10 | Y | H522 |
| 112 | 50 | 18 | 2 | Y | OVCAR-3 |
| 113 | 200 | 18 | 4 | Y | H23, H522, OVCAR-3 |
| 110 | 50 | 14 | 0 | Y | OVCAR-3 |
| 124 | 25 | 28 | 0 | Y | H23, H522, OVCAR-3, MDA-MB-435 |

The following data in Table 9 summarize the in vivo properties of several compounds of the current invention. The protocol for the experiment is as follows. The dose-range finding study consists of four groups of three athymic mice each (four dose levels.) The compound is administered on the basis of individual animal body weight. The route is intraperitoneal (IP) and the treatment schedule is daily for 14 days (qd×14) or once every 4 days for 12 days (q4d×3). The mice were observed for survival, and body weights recorded weekly.

The efficacy study consists of three compound-treated groups (six mice/group), a positive control-treated group (six mice), and a vehicle-treated control group of 12 mice. Test compounds were administered IP under the treatment schedules listed above (qd×14 or q4d×3), whereas the positive control agent (Taxol) was administered intravenously (IV) at a dosage level of 15 mg/1 g/dose for five consecutive days (qd×5). All agents were administered on the basis of individual animal body weight. Treatment began when the implanted tumors were approximately 100 mg in size (range of 65 to 200 mg). The mice were observed daily for survival. Each tumor was measured by caliper in two dimensions and converted to tumor mass using the formula for a prolate ellipsoid (a×b²/2) and assuming unit density. Tumor measurements and animal body weights were recorded twice weekly. Antitumor activity was assessed by the delay in tumor growth of the treated groups in comparison to the vehicle-treated control group, partial and complete regressions, and tumor-free survivors.

TABLE 9

In Vivo Evaluation of Several Compounds of the Current Invention.

| Compound | Dose (mg/kg) | Route | Schedule | Tumor free/total | T-C (days) |
|---|---|---|---|---|---|
| 78 | 0.5 | IP | qd × 14 | 0/6 | 0.8 |
| 78 | 0.33 | IP | qd × 14 | 0/6 | 1.8 |
| 78 | 0.22 | IP | qd × 14 | 0/6 | -0.8 |
| 78 | 1.5 | IP | q4d × 3 | 0/6 | 2.5 |
| 78 | 1.0 | IP | q4d × 3 | 0/6 | 1.1 |
| 78 | 0.67 | IP | q4d × 3 | 0/6 | 2.0 |
| 12 | 0.6 | IP | q4d × 3 | 0/6 | 0.3 |

TABLE 9-continued

In Vivo Evaluation of Several Compounds of the Current Invention.

| Compound | Dose (mg/kg) | Route | Schedule | Tumor free/total | T-C (days) |
|---|---|---|---|---|---|
| 12 | 0.4 | IP | q4d × 3 | 0/6 | 0.2 |
| 12 | 0.27 | IP | q4d × 3 | 0/6 | 1.2 |
| 87 | 15 | IP | q4d × 3 | 0/6 | 2.5 |
| 87 | 10 | IP | q4d × 3 | 0/6 | 2.9 |
| 87 | 6.7 | IP | q4d × 3 | 0/6 | 1.4 |

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A compound of the following formula:

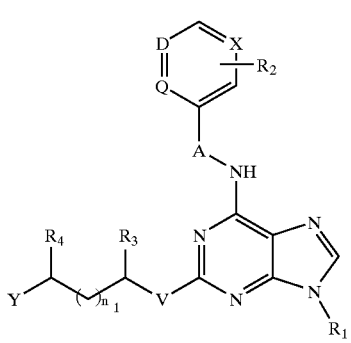

Formula I wherein:

$R_1$ are the same or different and independently selected from the group consisting of:
H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—($C_3$–$C_7$-cycloalkyl);
$CH_2CF_3$;
$CH_2CH_2CF_3$; and
$CH(CF_3)_2$;

Q=N and D=X=CH;

V=NH;
O;
S; or
$CH_2$;

$R_2$=phenyl;
substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
1-naphthyl;
2-naphthyl;
heterocycles selected from the group consisting of:
2-pyridyl;
3-pyridyl;
4-pyridyl;
2-pyrimidyl;
4-pyrimidyl;
5-pyrimidyl;
thiophene-2-yl;
thiophene-3-yl;
2-furanyl;
3-furanyl;
oxazol-2-yl;
oxazol-4-yl;
oxazol-5-yl;
thiazol-2-yl;
thiazol-4-yl;
thiazol-5-yl;
imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;

$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n$Ph; and
$(CH_2)_n$-substituted phenyl, wherein the phenyl substituents are as defined above in $R_2$;

$R_4$=H;
$C_1$–$C_4$-straight chain alkyl; or
$C_3$–$C_4$-branched chain alkyl;

$R_3$ and $R_4$ can be linked together by a carbon chain to form with intervening atoms a 5–8-membered saturated or unsaturated ring;

$n_1$=0–3;

n=0–3;

A=$CH_2$;
$(CH_2)_2$;
$(CH_2)_3$;
$OCH_2CH_2$; or
$CHCH_3$;

Y=H;
OR$_1$;
N(R$_1$)$_2$;
N(R$_1$)C(O)R$_3$;
N(R$_1$)C(O)R$_5$;
N(R$_1$)C(O)CH(R$_6$)NH$_2$;
N(R$_1$)SO$_2$R$_3$;
N(R$_1$)C(O)NHR$_3$; or
N(R$_1$)C(O)OR$_6$;
R$_5$=C$_3$–C$_7$-cycloalkyl;
R$_6$=C$_1$–C$_4$-straight chain alkyl;
C$_3$–C$_4$-branched chain alkyl;
C$_2$–C$_4$-alkenyl chain;
(CH$_2$)$_n$Ph; or
(CH$_2$)$_n$-substituted phenyl, wherein the phenyl substituents are as defined above in R$_2$;
or a pharmaceutically acceptable salt thereof.

2. A compound according to claim 1, wherein
R$_3$ are the same or different and independently selected from the group consisting of:
H;
C$_1$–C$_4$-straight chain alkyl; and
C$_3$–C$_4$-branched chain alkyl;
Y=H;
OR$_1$;
N(R$_1$)$_2$;
N(R$_1$)C(O)R$_3$;
N(R$_1$)SO$_2$R$_3$; or
N(R$_1$)C(O)NHR$_3$.

3. A compound of the following formula:

Formula III

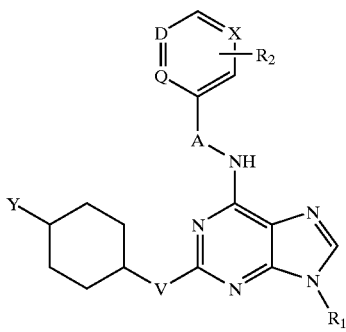

wherein:
R$_1$ are the same or different and independently selected from the group consisting of:
H;
C$_1$–C$_6$-straight chain alkyl;
C$_2$–C$_6$-straight alkenyl chain;
C$_3$–C$_6$-branched alkyl chain;
C$_3$–C$_6$-branched alkenyl chain;
C$_3$–C$_7$-cycloalkyl;
CH$_2$—(C$_3$–C$_7$-cycloalkyl);
CH$_2$CF$_3$;
CH$_2$CH$_2$CF$_3$; and
CH(CF$_3$)$_2$;
Q=N and D=X=CH;
V=NH;
O;
S; or
CH$_2$;
R$_2$=phenyl;
substituted phenyl, wherein the substituents (1–2 in number) are in any position and are independently selected from the group consisting of R$_1$, OR$_1$, SR$_1$, S(O)R$_1$, S(O$_2$)R$_1$, NHR$_1$, NO$_2$, OC(O)CH$_3$, NHC(O)CH$_3$, F, Cl, Br, CF$_3$, C(O)R$_1$, C(O)NHR$_1$, phenyl, and C(O)NHCHR$_1$CH$_2$OH;
1-naphthyl;
2-naphthyl;
heterocycles selected from the group consisting of:
2-pyridyl;
3-pyridyl;
4-pyridyl;
2-pyrimidyl;
4-pyrimidyl;
5-pyrimidyl;
thiophene-2-yl;
thiophene-3-yl;
2-furanyl;
3-furanyl;
oxazol-2-yl;
oxazol-4-yl;
oxazol-5-yl;
thiazol-2-yl;
thiazol-4-yl;
thiazol-5-yl;
imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, R$_1$, and C(O)CH$_3$;
n=0–3;
A=CH$_2$;
(CH$_2$)$_2$;
(CH$_2$)$_3$;
OCH$_2$CH$_2$; or
CHCH$_3$;
Y=H;
OR$_1$;
N(R$_1$)$_2$;
N(R$_1$)C(O)R$_3$;
N(R$_1$)C(O)R$_5$;
N(R$_1$)C(O)CH(R$_6$)NH$_2$;
N(R$_1$)SO$_2$R$_3$;
N(R$_1$)C(O)NHR$_3$; or
N(R$_1$)C(O)OR$_6$;

$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n$Ph; and
$(CH_2)_n$-substituted phenyl, wherein the phenyl substituents are as defined above in $R_2$;
$R_5 = C_3$–$C_7$-cycloalkyl;
$R_6 = C_1$–$C_4$-straight chain alkyl;
$C_3$–$C_4$-branched chain alkyl; or
$C_2$–$C_4$-alkenyl chain;
or a pharmaceutically acceptable salt thereof.

4. A pharmaceutical composition of matter comprising the compound of claim 1 and one or more pharmaceutical excipients.

5. A pharmaceutical composition of matter comprising the compound of claim 3 and one or more pharmaceutical excipients.

6. A process for preparation of a purine derivative compound of the formula:

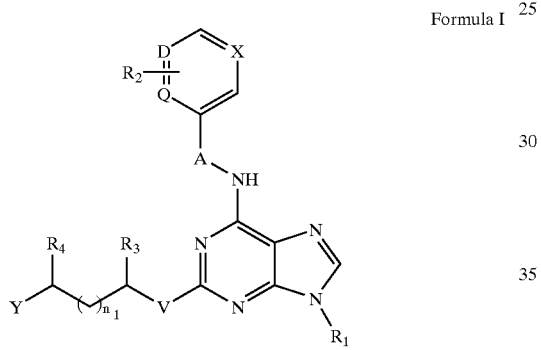

Formula I wherein:
$R_1$ are the same or different and independently selected from the group consisting of:
H;
$C_1$–$C_6$-straight chain alkyl;
$C_2$–$C_6$-straight alkenyl chain;
$C_3$–$C_6$-branched alkyl chain;
$C_3$–$C_6$-branched alkenyl chain;
$C_3$–$C_7$-cycloalkyl;
$CH_2$—($C_3$–$C_7$-cycloalkyl);
$CH_2CF_3$;
$CH_2CH_2CF_3$; and
$CH(CF_3)_2$;
Q=N and D=X=CH;
V=NH;
O;
S; or
$CH_2$;
$R_2$=phenyl;
substituted phenyl, wherein the substituents (1–2 in number) are in any position and are independently selected from the group consisting of $R_1$, $OR_1$, $SR_1$, $S(O)R_1$, $S(O_2)R_1$, $NHR_1$, $NO_2$, $OC(O)CH_3$, $NHC(O)CH_3$, F, Cl, Br, $CF_3$, $C(O)R_1$, $C(O)NHR_1$, phenyl, and $C(O)NHCHR_1CH_2OH$;
1-naphthyl;
2-naphthyl;
heterocycles selected from the group consisting of:
2-pyridyl;
3-pyridyl;
4-pyridyl;
2-pyrimidyl;
4-pyrimidyl;
5-pyrimidyl;
thiophene-2-yl;
thiophene-3-yl;
2-furanyl;
3-furanyl;
oxazol-2-yl;
oxazol-4-yl;
oxazol-5-yl;
thiazol-2-yl;
thiazol-4-yl;
thiazol-5-yl;
imidazol-2-yl;
imidazol-4-yl;
pyrazol-3-yl;
pyrazol-4-yl;
isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n$Ph; and
$(CH_2)_n$-substituted phenyl, wherein the phenyl substituents are as defined above in $R_2$;
$R_4$=H;
$C_1$–$C_4$-straight chain alkyl; or
$C_3$–$C_4$-branched chain alkyl;
$R_3$ and $R_4$ can be linked together by a carbon chain to form with intervening atoms a 5–8-membered saturated or unsaturated ring;
$n_1$=0–3;
n=0–3;
A=$CH_2$;
$(CH_2)_2$;
$(CH_2)_3$;

OCH₂CH₂; or

CHCH₃;

Y=H;

OR₁;

N(R₁)₂;

N(R₁)C(O)R₃;

N(R₁)C(O)R₅;

N(R₁)C(O)CH(R₆)NH₂;

N(R₁)SO₂R₃;

N(R₁)C(O)NHR₃; or

N(R₁)C(O)OR₃(;

R₅=C₃–C₇-cycloalkyl;

R₆=C₁–C₄-straight chain alkyl;

C₃–C₄-branched chain alkyl;

C₂–C₄-alkenyl chain;

(CH₂)ₙPh; or (CH₂)ₙ-substituted phenyl, wherein the phenyl substituents are as defined above in R₂;

or a pharmaceutically acceptable salt thereof;

said process comprising:

reacting a first intermediate compound of the formula:

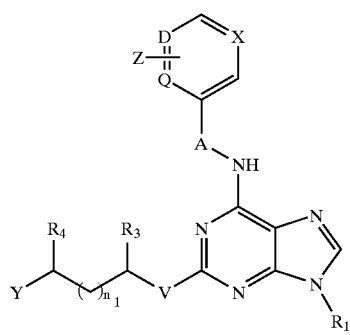

Formula IX where Z=Br or I with a compound of the formula: R₂—B(OH)₂, R₂—Sn(n-Bu)₃, or R₂—Sn(Me)₃, or mixtures thereof, under conditions effective to form the purine derivative compound.

7. A process according to claim 6, wherein if Y is NHR₁, said process further comprises:

reacting the purine derivative compound with R₃C(O)C₁ or R₅C(O)C₁ or R₃SO₂C₁ or R₃NCO or R₆OC(O)Cl under conditions effective to form a final product having the same formula as the purine derivative compound except that Y is NR₁C(O)R₃ or NR₁C(O)R₅ or NR₁SO₂R₃ or NR₁C(O)NHR₃ or NR₁C(O)OR₆.

8. A process for preparation of a purine derivative compound of the formula:

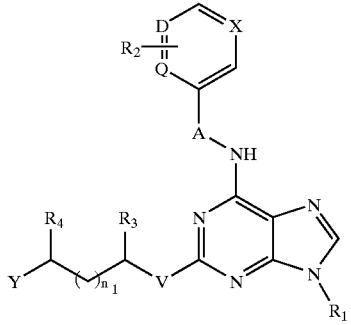

Formula I wherein:

R₁ are the same or different and independently selected from the group consisting of:

H;

C₁–C₆-straight chain alkyl;

C₂–C₆-straight alkenyl chain;

C₃–C₆-branched alkyl chain;

C₃–C₆-branched alkenyl chain;

C₃–C₇-cycloalkyl;

CH₂—(C₃–C₇-cycloalkyl);

CH₂CF₃;

CH₂CH₂CF₃; and

CH(CF₃)₂;

Q=N, and D=X=CH;

V=NH;

O; or

S;

R₂=phenyl;

substituted phenyl, wherein the substituents (1–2 in number) are in any position and are independently selected from the group consisting of R₁, OR₁, SR₁, S(O)R₁, S(O₂)R₁, NHR₁, NO₂, OC(O)CH₃, NHC(O)CH₃, F, Cl, Br, CF₃, C(O)R₁, C(O)NHR₁, phenyl, and C(O)NHCHR₁CH₂OH;

1-naphthyl;

2-naphthyl;

heterocycles selected from the group consisting of:

2-pyridyl;

3-pyridyl;

4-pyridyl;

2-pyrimidyl;

4-pyrimidyl;

5-pyrimidyl;

thiophene-2-yl;

thiophene-3-yl;

2-furanyl;

3-furanyl;

oxazol-2-yl;

oxazol-4-yl;

oxazol-5-yl;

thiazol-2-yl;

thiazol-4-yl;

thiazol-5-yl;

imidazol-2-yl;

imidazol-4-yl;

pyrazol-3-yl;

pyrazol-4-yl;

isoxazol-3-yl;
isoxazol-4-yl;
isoxazol-5-yl;
isothiazol-3-yl;
isothiazol-4-yl;
isothiazol-5-yl;
1,3,4-thiadiazol-2-yl;
benzo[b]furan-2-yl;
benzo[b]thiophene-2-yl;
2-pyrrolyl;
3-pyrrolyl;
1,3,5-triazin-2-yl;
pyrazin-2-yl;
pyridazin-3-yl;
pyridazin-4-yl;
2-quinolinyl;
3-quinolinyl;
4-quinolinyl;
1-isoquinolinyl;
3-isoquinolinyl; and
4-isoquinolinyl; or
substituted heterocycle, wherein the substituents (1–2 in number) are in any position and are independently selected from the group consisting of Br, Cl, F, $R_1$, and $C(O)CH_3$;
$R_3$ are the same or different and independently selected from the group consisting of:
H;
$C_1$–$C_4$-straight chain alkyl;
$C_3$–$C_4$-branched chain alkyl;
$C_2$–$C_4$-alkenyl chain;
$(CH_2)_n Ph$; and
$(CH_2)_n$-substituted phenyl, wherein the phenyl substituents are as defined above in $R_2$;
$R_4$=H;
$C_1$–$C_4$-straight chain alkyl; or
$C_3$–$C_4$-branched chain alkyl;
$R_3$ and $R_4$ can be linked together by a carbon chain to form with intervening atoms a 5–8-membered saturated or unsaturated ring;
n1=0–3;
n=0–3;
A=$CH_2$;
$(CH_2)_2$;
$(CH_2)_3$;
$OCH_2CH_2$; or
$CHCH_3$;
Y=H;
$OR_1$;
$N(R_1)_2$;
$N(R_1)C(O)R_3$;
$N(R_1)C(O)R_5$;
$N(R_1)C(O)CH(R_6)NH_2$;
$N(R_1)SO_2R_3$;
$N(R_1)C(O)NHR_3$; or
$N(R_1)C(O)OR_6$;
$R_5$=$C_3$–$C_7$-cycloalkyl;
$R_6$=$C_1$–$C_4$-straight chain alkyl;
$C_3$–$C_4$-branched chain alkyl;
$C_2$–$C_4$-alkenyl chain;
$(CH_2)_n Ph$; or $(CH_2)_n$-substituted phenyl, wherein the phenyl substituents are as defined above in $R_2$;
or a pharmaceutically acceptable salt thereof; said process comprising:
reacting a first intermediate compound of the formula:

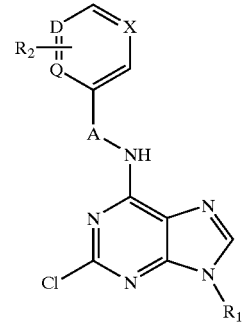

Formula XIV with a compound of the formula:

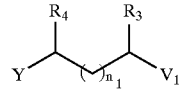

Formula VIII where $V_1$=$NH_2$;
OH; or
SH;

under conditions effective to form the purine derivative compound.

9. A process according to claim 8, wherein if Y is $NHR_1$, said process further comprises:

reacting the purine derivative compound with $R_3C(O)C_1$ or $R_5C(O)C_1$ or $R_3SO_2C_1$ or $R_3NCO$ or $R_6OC(O)C1$ under conditions effective to form a final product having the same formula as the purine derivative compound except that Y is $NR_1C(O)R_3$ or $NR_1C(O)R_5$ or $NR_1SO_2R_3$ or $NR_1C(O)NHR_3$ or $NR_1C(O)OR_6$.

10. A process according to claim 8 further comprising:
reacting a second intermediate compound of the formula:

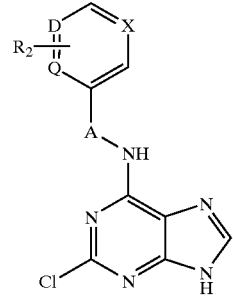

Formula XVIII with a compound of the formula $R_1$-Z under conditions effective to form the first intermediate compound.

11. A process according to claim 10 further comprising: reacting a third intermediate compound of the formula:

Formula XVII

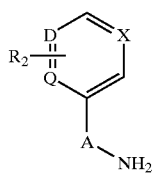

with a compound of the formula 2,6-dichloropurine under conditions effective to form the second intermediate compound.

12. A process according to claim 11 further comprising: reacting a fourth intermediate compound of the formula:

Formula V

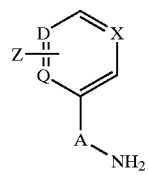

with a compound of the formula: $R_2$—B(OH)$_2$, $R_2$—Sn(n-Bu)$_3$, or $R_2$—Sn(Me)$_3$, or mixtures thereof, under conditions effective to form the third intermediate compound.

13. A process according to claim 8, wherein the purine derivative compound has the formula:

Formula III

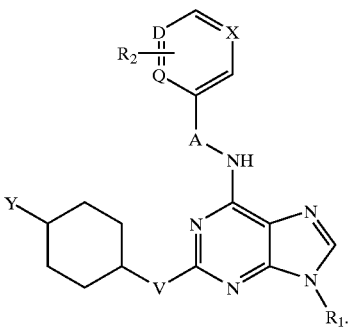

* * * * *